US008163289B2

(12) United States Patent
Arnason et al.

(10) Patent No.: US 8,163,289 B2
(45) Date of Patent: Apr. 24, 2012

(54) METHODS AND COMPOSITIONS INVOLVING POLYMERIC IMMUNOGLOBULIN FUSION PROTEINS

(75) Inventors: Barry G. W. Arnason, Chicago, IL (US); Mark A. Jensen, Chicago, IL (US); David M. White, Chicago, IL (US)

(73) Assignee: Iterative Therapeutics, Inc., Chicago, IL (US)

( * ) Notice: Subject to any disclaimer, the term of this patent is extended or adjusted under 35 U.S.C. 154(b) by 0 days.

(21) Appl. No.: 12/043,769

(22) Filed: Mar. 6, 2008

(65) Prior Publication Data

US 2008/0292704 A1    Nov. 27, 2008

Related U.S. Application Data

(63) Continuation-in-part of application No. 10/096,521, filed on Mar. 11, 2002, now Pat. No. 7,511,121.

(60) Provisional application No. 60/893,318, filed on Mar. 6, 2007, provisional application No. 60/274,392, filed on Mar. 9, 2001.

(51) Int. Cl.
*A61K 39/00* (2006.01)
*A61K 39/38* (2006.01)
*A61K 39/385* (2006.01)

(52) U.S. Cl. ............... 424/184.1; 424/185.1; 424/192.1; 424/193.1

(58) Field of Classification Search .......................... None
See application file for complete search history.

(56) References Cited

U.S. PATENT DOCUMENTS

| | | | |
|---|---|---|---|
| 4,196,265 A | 4/1980 | Koprowski et al. |
| 4,340,535 A | 7/1982 | Voisin et al. |
| 4,554,101 A | 11/1985 | Hopp |
| 4,559,230 A | 12/1985 | David et al. |
| 4,559,231 A | 12/1985 | Bjerre et al. |
| 4,578,770 A | 3/1986 | Mitani |
| 4,596,792 A | 6/1986 | Vyas |
| 4,599,230 A | 7/1986 | Milich et al. |
| 4,601,903 A | 7/1986 | Frasch |
| 4,608,251 A | 8/1986 | Mia |
| 4,658,019 A | 4/1987 | Kung et al. |
| 5,440,013 A | 8/1995 | Kahn |
| 5,446,128 A | 8/1995 | Kahn |
| 5,455,165 A | 10/1995 | Capon et al. |
| 5,475,085 A | 12/1995 | Kahn |
| 5,554,372 A | 9/1996 | Hunter |
| 5,618,914 A | 4/1997 | Kahn |
| 5,670,155 A | 9/1997 | Kahn |
| 5,672,681 A | 9/1997 | Kahn |
| 5,674,976 A | 10/1997 | Kahn |
| 5,679,354 A | 10/1997 | Morein et al. |
| 5,710,245 A | 1/1998 | Kahn |
| 5,714,147 A | 2/1998 | Capon et al. |
| 5,830,731 A | 11/1998 | Seed et al. |
| 5,840,833 A | 11/1998 | Kahn |
| 5,859,184 A | 1/1999 | Kahn et al. |
| 5,922,845 A | 7/1999 | Deo et al. |
| 5,929,237 A | 7/1999 | Kahn |
| 5,998,166 A | 12/1999 | Luo |
| 6,046,310 A | 4/2000 | Queen et al. |
| 6,165,745 A | 12/2000 | Ward et al. |
| 6,262,029 B1 | 7/2001 | Press et al. |
| 7,511,121 B2 | 3/2009 | Arnason et al. |
| 7,897,729 B2 | 3/2011 | Arnason et al. |
| 2003/0161826 A1 | 8/2003 | Arnason et al. |
| 2009/0117133 A1* | 5/2009 | Arnason et al. ............ 424/178.1 |

FOREIGN PATENT DOCUMENTS

| | | |
|---|---|---|
| EP | 0044167 | 1/1982 |
| JP | 5-503009 | 5/1993 |
| WO | 91/08298 | 6/1991 |
| WO | 92/10591 | 6/1992 |
| WO | 99/42077 | 8/1999 |
| WO | 99/58572 | 11/1999 |

OTHER PUBLICATIONS

Wang et al. JBC, 2001 276:49213-49220.*
Mikayama et al. PNAS, 1993. 90: 10056-10060.*
Burgess et al J Cell Biol. 111:2129-2138, 1990.*
Miller, M. L., "Treatment of systemic lupus erythematosus" Curr. Opin. Rheum., 4:693-699 (1992).
Minghetti et al., "Molecular Structure of the Human Albumin Gene is Revealed by Nucleotide Sequence within 911-22 of Chromosome 4" J. Biol. Chem., 261:6747-6757 (1986).
Miyagi, et al., "Fc portion of intravenous immunoglobulin suppresses the induction of experimental allergic neuritis," J. Neuroimmunol., 78:127-131 (1997).
Moingeon, et al., "CD3 zeta dependence of the CD2 pathway of activation in T lymphocytes and natural killer cells," Proc Natl Acad Sci USA, 89:1492-1496 (1992).
Morgan, B. P. "The complement system: an overview" Mol Biol Methods 150, 1-13 (2000).
Morgan, et al., "The N-terminal end of the CH2 domain of chimeric human IgG1 anti-HLA-DR is necessary for C1q, Fc gamma RI and Fc gamma RIII binding," Immunology 86:319-324 (1995).
Morrison, S. L., et al., "Production of novel immunoglobulin molecules by gene transfection" Mt Sinai J Med 53, 175-80 (1986).
Nagler, et al., "Constitutive expression of high affinity interleukin 2 receptors on human CD16-natural killer cells in vivo," J. Exp. Med., 171:1527-1533 (1990).
Needleman et al., "A General Method Applicable to the Search for Similarities in the Amino Acid Sequence of Two Proteins" J. Mol. Biol., 48:443-453 (1970).

(Continued)

*Primary Examiner* — Michail Belyavskyi
(74) *Attorney, Agent, or Firm* — Stipkala LLC; Harry J. Guttman

(57) ABSTRACT

The present invention concerns inventive polypeptides. The present invention also concerns compositions and vaccines comprising the inventive polypeptides. In other embodiments of the invention, the inventive polypeptides are provided to a subject, used to vaccinate, or used to induce immunity. Other embodiments include methods for making the inventive polypeptides and nucleic acids used to encode the inventive polypeptides.

97 Claims, 18 Drawing Sheets

OTHER PUBLICATIONS

Nelson, H. "Targeted cellular immunotherapy with bifunctional antibodies" Cancer Cells 3, 163-72 (1991).

Ngo et al, The Protein Folding Problem and Tertiary Structure Prediction, Birkhauser, Boston, MA, pp. 433-506 (see pp. 433 and 492-495) (1994).

Nitta, T., et al., "Induction of cytotoxicity in human T cells coated with anti-gliomxanti-CD3 bispecific antibody against human glioma cells" J Neurosurg 72, 476-81 (1990).

Nolan, O., et al., "Bifunctional antibodies: concept, production and applications" Biochim Biophys Acta 1040, 1-11 (1990).

Norderhaug, L., et al., "Versatile vectors for transient and stable expression of recombinant antibody molecules in mammalian cells" J. Immun. Meth. 204, 77-87 (1997).

Ober et al, "Exocytosis of IgG as mediated by the receptor, FcRn: an analysis at the single-molecule level" The National Academy of Sciences of the United States of America, 101:11076-11081 (2004).

Ogata, M., et al., "Processing of Pseudomonas exotoxin by a cellular protease results in the generation of a 37,000-Da toxin fragment that is translocated to the cytosol" J Biol Chem 265, 20678-85 (1990).

Ohtsuka, et al., "Decreased production of TGF-beta by lymphocytes from patients with systemic lupus erythematosus," J Immunol, 160:2539-2545 (1998).

Oshima et al., "Antibodies and T cells against synthetic peptides of the C-terminal domain (Hc) of botulinum neurotoxin type A and their cross-reaction with Hc," Immunology Letters, vol. 60, pp. 7-12 (1998).

Oshima et al., "Immune Recognition of Botulinum Neurotoxin Type A: Regions Recognized by T Cells and Antibodies Against the Protective Hc Fragment (Residues 855-1296) of the Toxin," Molecular Immunology, vol. 34, pp. 1031-1040 (1997).
Paoletti and McInnes, Vaccines: From concept to clinic, CRC Press (1999).
Passwell, et al., "Increased prostaglandin production by human monocytes after membrane receptor activation," J Immunol, 123:115-120 (1979).
Perez, P. et al., "Specific targeting of human peripheral blood t cells by heteroaggregates containing anti-t3 crosslinked to anti-target cell antibodies" Journal of Experimental Medicine, vol. 163, 166-178 (1986b).
Perez, P., et al., "Specific targeting of cytotoxic T cells by anti-T3 linked to anti-target cell antibody" Nature 316, 354-6 (1985).
Perez, P., et al., "Specific lysis of human tumor cells by T cells coated with anti-T3 cross-linked to anti-tumor antibody" J Immunol 137, 2069-72 (1986a).
Pfeifer, T. A. "Expression of heterologous proteins in stable insect cell culture" Curr. Opin. Biotechnol. 9, 518-21 (1998).
Pietersz, G. A., et al., "Immunochemotherapy of a murine thymoma with the use of idarubicin monoclonal antibody conjugates" Cancer Res 48, 926-31 (1988a).
Pietersz, G. A., et al., "Specific in vitro anti-tumour activity of methotrexate-monoclonal antibody conjugates prepared using human serum albumin as an intermediary" Immunol Cell Biol 66, 43-9 (1988b).
Plotkin and Orenstein, Vaccines, 4th Ed., Saunders press (2004).
Ptak, et al., "Heat-aggregated immunoglobulins increase in vivo immunogenicity of mouse hapten (TNP)-derivatized macrophages by upregulation of interleukin-12 secretion and expression of B7-1 and B7-2 costimulatory molecules," Scand. J. Immunol, 51:479-484 (2000).
Radaev et al., "The Structure of Human Type III Fcg Receptor in Complex with Fc," The Journal of Biological Chemistry, vol. 276, No. 19, pp. 16469-16477 (May 11, 2001).
Raghavan and Bjorkman, "Fc receptors and their interactions with immunoglobulins," Ann. Rev. Cell. Dev. Biol., 12:181-220 (1996).
Regnault et al., "Fcγ Receptor-mediated Induction of Dendritic Cell Maturation and Major Histocompatibility Complex Class I-restricted Antigen Presentation after Immune Complex Internalization," J. Exp. Med., vol. 189, pp. 371-380 (Jan. 1999).
Remington's Pharmaceutical Sciences, 14th Ed., Mack Printing Company (1970).
Remington's Pharmaceutical Sciences, 18th Ed., Mack Printing Company (1990) (e.g., pp. 1289-1329).
Roopenian et al., "The MHC class I-like IgG receptor controls perinatal IgG transport, IgG homeostasis, and fate of IgG-Fc-coupled drugs" J. of Immunology, 170:3528-3533 (2003).
Rosebaum J.T., R.K. George & C. Gordon "The treatment of refractory uveitis with intravenous immunoglobulin" Am. J. Ophthalmol. 127, 545-9 (1999).
Rosenstein, et al., "Lymphokine-activated killer cells: lysis of fresh synergic natural killer-resistant murine tumor cells by lymphocytes cultured in interleukin-2," Cancer Res., 44:1946-1953 (1984).
Rubin B.K. "Emerging therapies for cystic fibrosis lung disease" Chest 115, 1120-6 (1999).
Sambrook, J., Fritsch, E. F., and Maniatis, T., Molecular Cloning: A Laboratory Manual, vol. 3, Chapter 16, Cold Spring Harbor Laboratory, Cold Spring Harbor, NY (1989).
Scallon et al., "Addition of an extra immunoglobulin domain to two anti-rodent TNF monoclonal antibodies substantially increased their potency," Molecular Immunology, 41:73-80 (2004).
Schwartz and Dayhoff, "Matrices for detecting distant relationships" In: Atlas of Protein Sequence and Structure, National Biomedical Research Foundation, 353 358 (1978).
Segal et al., "Targeting of antitumor responses with bispecific antibodies" Immunobiology, 185(2-4):390-402 (1992).
Semple et al. "Increased Antiplatelet T Helper Lymphocyte Reactivity in Patients With Autoimmune Thrombocytopenia" Blood, 78(10):2619-2625 (1991).
Shields, et al., "High resolution mapping of the binding site on human IgG1 for FcγRI, FcγRII, FcγRIII, and FcRn and design of IgG1 variants with improved binding to the FcγR," J. Biol. Chem., 276:6591-6604 (2001).
Silman et al., "Lymphoproliferative cancer and other malignancy in patients with rheumatoid arthritis treated with azathioprine: a 20 year follow up study" Ann. Rheum. Dis., 47:988-92 (1988).
Smith and Morrison, "Recombinant polymeric IgG: an approach to engineering more potent antibodies," Bio/Technology, 12:683-688 (1994).
Smith and Waterman "Comparison of Biosequences" Adv. Appl. Math 2:482 (1981).
Snider et al., "Enhanced Antigen Immunogenicity Induced by Bispecific Antibodies," J. Exp. Med., vol. 171, pp. 1957-1963 (Jun. 1990).
Sondemann et al., "Crystal structure of the soluble form of the human Fcg-receptor IIb: a new member of the immunoglobulin superfamily at 1.7 A resolution," The EMBO Journal, vol. 18, No. 5, pp. 1095-1103 (1999).
Sondermann, et al, "The 3.2-A crystal structure of the human IgG1 Fc fragment-FcγRIII complex," Nature, 406:267-273, (2000).
Sorensen, et al., "Intravenous immunoglobulin G reduces MRI activity in relapsing multiple sclerosis," Neurology, 50:1273-1281, (1998).
Staerz, U. D., et al., "Hybrid antibodies can target sites for attack by T cells" Nature 314, 628-31 (1985).
Steinberg and Steinber, "Long-term preservation of renal function in patients with lupus nephritis receiving treatment that includes cyclophosphamide versus those treated with prednisone only" Arthritis. Rheum., 34:945-950 (1991).
Stevenson et al.,"Role of Endogenous Gamma Interferon in Host Response to Infection with Blood-Stage *Plasmodium chabaudi* AS" Infect Immun., 58(10):3225-32 (1990).
Swain, S. L., et al. "The role of IL4 and IL5: characterization of a distinct helper T cell subset that makes 1L4 and 1L5 (Th2) and requires priming before induction of lymphokine secretion" Immunol Rev 102, 77-105 (1988).
Takai, "Roles of Fc Receptors in Autoimmunity," Nature Reviews Immunology, vol. 2, pp. 580-592 (Aug. 2002).
Ting, C. C., et al., "Augmentation by anti-T3 antibody of the lymphokine-activated killer cell-mediated cytotoxicity" J Immunol 141, 741-8 (1988).
Traunecker, et al., "Highly efficient neutralization of HIV with recombinant CD4-immunoglobulin molecules," Nature, 339:68-70 (1989).
Trombetta et al., "Cell Biology of Antigen Processing in Vitro and in Vivo," Annu.Rev.Immunol, vol. 23, pp. 975-1028 (2005).

Vaickus, L., et al., "Overview of monoclonal antibodies in the diagnosis and therapy of cancer" Cancer Invest 9, 195-209 (1991).
Venables, P. J. W., "Diagnosis and treatment of systemic lupus erythematosus" British Medical Journal, 307:663-666 (1993).
Vita et al., "Novel miniproteins engineered by the transfer of active sites to small natural scaffolds." Biopolymers 47:93-100 (1998).
Vivier, et al., "CD2 is functionally linked to the zeta-natural killer receptor complex," Eur J Immunol, 21:1077-1080 (1991).
Volk, H. D., et al., "Suppression of the local graft-vs.-host reaction in rats by treatment with a monoclonal antibody specific for the interleukin 2 receptor" Eur J Immunol 16, 1309-12 (1986).
Vyse and Walport, "Connective tissue diseases" Br. F Hosp. Med., 50:121-132 (1993).
Wallace, D. J., et al., "The relevance of antimalarial therapy with regard to thrombosis, hypercholesterolemia and cytokines in SLE" Lupus 2 Suppl 1, S13-5 (1993).
Wang et al. "A Single Amino Acid Determines Lysophospholipid Specificity of the S1P1 (EDG1) and LPA1 (EDG2) Phospholipid Growth Factor Receptors," J. Biol. Chem, vol. 276:49213-49220 (2001).
Weisshoff et al., "Mimicry of beta II'-turns of proteins in cyclic pentapeptides with one and without D-amino acids." Eur. J. Biochem. 259:776-788 (1999).
Wemersson et al., "Immune Complex-Mediated Enhancement of Antibody Responses without Induction of Delayed-Type Hypersensitivity" Scand. J. Immunol., 52:563-569 (2000).
Wernersson et al., "IgG-Mediated Enhancement of Antibody Responses is Low in Fc Receptor y Chain-Deficient Mice and Increased in FcyRII-Deficient Mice," J. Immunol. vol. 163, pp. 618-622 (1999).
Whisstock et al. "Prediction of protein function from protein sequence and structure," Quarterly Review of Biophysics, 36, pp. 307-340. (2003).
White, et al., "Design and Expression of Polymeric Immunoglobulin Fusion Proteins: A Strategy for Targeting Low-Affinity Fc Receptors," Protein Expression and Purification, 21:446-455 (2001).
Wiesenhutter, et al., "IgG aggregates of different sizes stimulate or suppress Ig secretion by human lymphocytes in vitro," J. Clin. Immunol., 4:124-133 (1984).
Wilke et al., "Methotrexate for systemic lupus erythematosus" Clin. Exp. Rheumatol, 9:581-587 (1991).
Winter, G., et al., "Man-made antibodies", Nature, 349, 293-9 (1991).
Woof et al., "Human Antibody-FC Receptor Interactions Illuminated by Crystal Structures," Nature Reviews Immunology, vol. 4, pp. 1-11 (Feb. 2004).
Wu, J., et al., "A novel polymorphism of FcgammaRIIIa (CD16) alters receptor function and predisposes to autoimmune disease" J Clin Invest, 100, 1059-70 (1997).
Wunderlich, J. R., et al., "Bispecific antibodies and retargeted cellular cytotoxicity: novel approaches to cancer therapy" Int J Clin Lab Res, 22, 17-20 (1992).
Young, et al., "Influence of immunoglobulin heavy- and light-chain expression on B-cell differentiation," Genes Develop., 8:1043-1057 (1994).
Yu et al. "Mechanism of intravenous immuneglobulin therapy in antibody-mediated autoimmune diseases" New Eng. J. Med. vol. 340 pp. 227-228 (1999).
Zaghouani et al., "Presentation of a Viral T Cell Epitope Expressed in the CDR3 Region of a Self Immunoglobulin Molecule," Science, vol. 259, pp. 224-227 (1993).
Zanetti, M., et al., "Theoretical and practical aspects of antigenized antibodies" Immunol Rev, 130, 125-50 (1992).
Ismaili et al., "Monophosphoryl Lipid A Activates Both Human Dendritic Cells and T Cells" J. Immunol., 168:926-932 (2002).
Jarvis, D. L., et al., "Immediate-early baculovirus vectors for foreign gene expression in transformed or infected insect cells." Protein Exp. Purif. 8, 191-203 (1996).
Jensen et al., "A novel Fcgamma receptor ligand augments humoral responses by targeting antigen to Fc gamma receptors." Eur. J. Immunol., vol. 37, pp. 1139-1148 (2007).

Jiang et al., "Polymorphisms in IgG Fc receptor IIb regulatory regions associated with autoimmune suspectibility," Immunogenetics, vol. 51, pp. 429-435 (2000).
Johannesson et al., "Bicyclic tripeptide mimetics with reverse turn inducing properties." J. Med. Chem. 42:601-608 (1999).
Johnson et al., "Peptide Turn Mimetics," In: Biotechnology and Pharmacy, Pezzuto et al., eds., Chapman and Hall, New York (1993).
Johnson, P., and Glennie, M. "Rituximab: mechanisms and applications." Brit. J Cancer 85, 1619-1623 (2001).
Keler, T., et al., "Targeting weak antigens to CD64 elicits potent humoral responses in human CD64 transgenic mice" J Immunol, 165, 6738-42 (Dec. 15, 2000).
Kenney et al., "Influence of adjuvants on the quantity, affinity, isotype and epitope specificity of murine antibodies" J. Immunol. Methods, 121:157-166 (1989).
Kimberly, "Treatment: Corticosteroids and Anti-Inflammatory Drugs" Rheum. Dis. Clin. North Am., 14(1):203-21, (1988).
Kimura et al., "In Vivo Antitumor Activity of Neocarzinostatin (NCS)-Tumor Antibody Conjugate against a Transplantable Human Leukemia Cell Line (BALL-1)" Jpn J. Clin. Oncol., 13(2):425-33 (1983).
Kon O.M & N. Barnes "Immunosuppressive treatment in asthma" Br. J. Hospital. Med. 57, 383-386 (1997).
Kroesen, B. J., et al., "Approaches to lung cancer treatment using the CD3×EGP-2-directed bispecific monoclonal antibody BIS-1" Cancer Immunol Immunother 45, 203-6 (1997).
Kurosaki, et al., "A subunit common to an IgG Fc receptor and the T-cell receptor mediates assembly through different interactions," Proc Natl Acad Sci USA, 88: 3837-3841 (1991). ##.
Kyte and Doolittle, "A simple method for displaying the hydropathic character of a protein," J. Mol. Biol., 157 (1):105-132 (1982).
Laemmli, U. K. "Cleavage of structural proteins during the assembly of the head of bacteriophage T4" Nature 227, 680-5 (1970).
Lanier, et al., "Co-association of CD3 zeta with a receptor (CD16) for IgG Fc on human natural killer cells," Nature, 342:803-805 (1989).
Lanier, et al., "Molecular and functional analysis of human natural killer cell-associated neural cell adhesion molecule (N-CAM/CD56),"J Immunol, 146:4421-4426 (1991).
LaSalle, J. M., et al. "T cell anergy" FASEB J, 8, 601-8 (1994).
Lazar et al., "Transforming Growth Factor a: Mutation of Aspartic Acid 47 and Leucine 48 Results in Different Biological Activities," Mol Cell Biol. 8:1247-1252 (1988).
Legge, et al., "Coupling of peripheral tolerance to endogenous interleukin 10 promotes effective modulation of myelin-activated T cells and ameliorates experimental allergic encephalomyelitis," J. Exp. Med., 191:2039-2051 (2000).
Levine D.S., S.H. Fischer, D.L. Christie, R.C. Haggitt & disease H.D. Ochs: "Intravenous immunoglobulin therapy for active, extensive, and medically refractory idiopathic ulcerative or Crohn's colitis" Am. J. Gastroenterol. 87, 91-100 (1992).
Liao et al., "Tyrosine phosphorylation of phospholipase C-yi induced by cross-linking of the high-affinity or low-affinity Fc receptor for IgG in U937 cells" Proc. Natl. Acad. Sci. USA, 89:3659-3663 (1992).
Lieberman, J. D., "Disease modifying therapies" Rheum. Dis. Clin. North. Am., 14:223-243 (1988).
Lisak R.P. "Intravenous immunoglobulin in multiple sclerosis" Neurology 51 (Suppl 5), S25-29 (1998).
Liu, C., et al., "F(c)gammaRI-targeted fusion proteins result in efficient presentation by human monocytes of antigenic and antagonist" T cell epitopes, J Clin Invest, 98, 2001-7 (1996a).
Liu, C., et al., "Fc gamma RII on human B cells can mediate enhanced antigen presentation" Cell Immunol, 167, 188-94 (1996b).
Lord, J. M., et al., "Cell surface and intracellular functions for galactose binding in ricin cytotoxicity" Biochem Soc Trans, 20, 734-8 (1992a).
Lord, J. M., et al., "Chimeric proteins containing ricin A chain" Targeted Diagn Ther, 7, 183-90 (1992b).
Lubbe et al., "Fetal survival after prednisone suppression of maternal lupus-anticoagulant" Lancet, 1361-1363 (Jun. 18, 1983).
Lund, et al. "Human Fc gamma RI and Fc gamma RII interact with distinct but overlapping sites on human IgG," J. Immunol., 147:2657-2662 (1991).

Majeau, et al., "Mechanism of lymphocyte function-associated molecule 3-Ig fusion proteins inhibition of T cell responses. Structure/function analysis in vitro and in human CD2 transgenic mice," J Immunol, 152:2753-2767 (1994).

Makela et al., "Animals models for vaccines to prevent infectious diseases" Vaccine, vol. 14, Issue 7, pp. 717-732 (May 1996).

Manabe, Y., et al., "Production of a monoclonal antibody-methotrexate conjugate utilizing dextran T-40 and its biologic activity" J Lab Clin Med 104, 445-54 (1984).

Manca et al., "Effect of Antigen/Antibody Ratio on Macrophage Uptake, Processing, and Presentation to T Cells of Antigen Complexed with Polyclonal Antibodies," J. Exp. Med., pp. 37-48 (1991).

Marks et al., "By-passing Immunization Human Antibodies from V-gene Libraries Displayed on Phage" J. Mol. Biol., 222:581-97 (1991).

Martin et al.,"Role of Innate Immune Factors in the Adjuvant Activity of Monophosphoryl Lipid A" Infect. Immun., 71:2498-2507 (2003).

Martin et al.,"The need for IgG2c specific antiserum when isotyping antibodies from C57BLr6 and NOD mice" J. Immunol Methods, 212: 187-192 (1998).

Marusic-Galesic et al., "Cellular immune response to the antigen administered as an immune complex" Immunology, 72:526-531 (1991).

Marusic-Galesic et al., "Cellular immune response to the antigen administered as an immune complex in vivo" Immunology, 75:325-329 (1992).

Maxwell et al., "Crystal structure of the human leukocyte Fc receptor FcgRIIa" Nature Structural Biology, vol. 6, No. 5, pp. 437-442 (May 1999).

McCarroll et al., "Stable insect cell cultures for recombinant protein production" Curr. Opin. Biotechnol. 8, 590-4 (1997).

McLean, G., et al., "Human and murine immunoglobulin expression vector cassettes." Mol. Immunol., 837-845 (2000).

Medesan et al., "Delineation of the amino acid residues involved in transcytosis and catabolism of mouse IgG1," Journal of Immunology, 158:2211-2217 (1997).

Menard et al., "Hybrid antibodies in cancer diagnosis and therapy" Int J Biol Markers 4, 131-4 (1989).

Methods in Enzymology, Recombinant DNA Part G, edited by Ray Wu, vol. 216, pp. 3-689 (1992).

Methods in Enzymology, Recombinant DNA Part I, edited by Ray Wu, vol. 218, pp. 3-806 (1993).

Meyerson, et al., "Functional dissociation of CD8 alpha's Ig homologue and connecting peptide domains," J. Immunol., 156:574-584 (1996).

Mikayama et al. "Molecular cloning and functional expression of a cDNA encoding glycosylation-inhibiting factor," PNAS, 90:10056-10060 (1993).

Miller, K. L., et al., "A novel role for the Fc receptor gamma subunit: enhancement of Fc gamma R ligand affinity" J Exp Med 183, 2227-33 (1996).

Canadian Examiner's Report dated Apr. 13, 2010 for Canadian Application No. 2,437,958, 4 pp.

U.S. Appl. No. 12/212,776, Office action dated Jul. 8, 2010, 14 pp.

European App. No. 02719196, Office action dated Feb. 16, 2011, 7 pp.

U.S. Appl. No. 12/212,776, Office action dated Feb. 26, 2010, 14 pp.

Watarai et al., "Posttranslational modification of the glycosylation inhibiting factor (GIF) gene product generates bioactive GIF" PNAS, vol. 97, No. 24, pp. 13251-13256 (Nov. 21, 2000).

U.S. Appl. No. 13/027,207, Office action dated Oct. 19, 2011, 13 pp.

Byrne et al., "Development of vaccines for prevention of botulism" Biochimie, vol. 82, pp. 955-966 (2000).

Cochlovius et al., "Therapeutic Antibodies—After years of promise, magic bullets appear to be on the upswing" Modern Drug Discovery, pp. 33, 34, 37, and 38 (Oct. 2003).

Feldman et al., "Anti-TNFalpha Therapy is Useful in Rheumatoid Arthritis and Crohn's Disease: Analysis of the mechanism of action predicts utility in other diseases" Transplantation Proceedings, vol. 30, pp. 4126-4127 (1998).

Mestas et al., "Of Mice and Not Men: Differences between mouse and human immunology" The Journal of Immunology, vol. 172, pp. 2731-2738 (2004).

Smith, "Development of recombinant vaccines for Botulinum Neurotoxin" Toxicon, vol. 36, No. 11, pp. 1539-1548, (1998).
Smith et al., "Roads from vaccines to therapies" Movement Disorders, vol. 19, Suppl. 8, pp. S48-S52 (2004).
Duncan, et al., "Localization of the binding site for the human high-affinity Fc receptor on IgG," Nature, 332:563-564 (1988).
Dunkel I.J. & J.B. Bussel: "New developments in the treatment of neutropenia". Am. J. Dis. Children 147,994-1000 (1993).
Dupond JL., H. Gil, B. de Wazieres "Five-year efficacy of intravenous gamma globulin to treat dysautonomia in Sjogren's syndrome" Am. J. Medicine. 106,125 (1999).
Durandy, et al., "Dysfunctions of pokeweed mitogen-stimulated T and B lymphocyte responses induced by gammaglobulin therapy," J. Clin. Invest., 67, 867-877 (1981).
Durez P., L. Tourne, W. Feremans, F. Mascart-Lemone, M. Heenen & T. Appelboom: "Dramatic response to intravenous high dose gamma-globulin in refractory vasculitis of the skin associated with Sjogren's syndrome" J. Rheumatology 25, 1032-1033, (1998).
Dwyer J. M.: "Manipulating the immune system with immune globulins" New Engl. J. Med. 326, 107-16 (1992).
Edberg and Kimberly, "Cell type-specific glycoforms of Fc gamma RIIIa (CD16): differential ligand binding," J Immunol, 159:3849-3857 (1997).
Edberg, et al., "Analysis of FcgammaRII gene polymorphisms in Wegener's granulomatosis," Exp Clin Immunogenet, 14:183-195 (1997).
Edwards et al.,"A double blind controlled trial of methylprednisolone infusions in systemic lupus erythematosus using individualised outcome assessment" Ann. Rheum. Dis., 46:773-6 (1987).
Eilat, et al., "Secretion of a soluble, chimeric gamma delta T-cell receptor-immunoglobulin heterodimer," Proc Natl Acad Sci USA, 89:6871-6875 (1992).
Fanger, M. W., et al., "Bispecific antibodies" Crit Rev Immunol vol. 12, 101-24 (1992).
Fazekas, et al., "Randomised placebo-controlled trial of monthly intravenous immunoglobulin therapy in relapsing-remitting multiple sclerosis," Lancet, 349:589-593 (1997).
Ferreri, et al., "Release of leukotrienes C4 and B4 and prostaglandin E2 from human monocytes stimulated with aggregated IgG, IgA, and IgE," J Immunol, 136:4188-4193 (1986).
Fortis, et al., "Dual role of TNF-a in NK/LAK cell-mediated lysis of chronically HIV-infected U1 cells. Concomitant enhancement of HIV expression and sensitization of cell-mediated lysis," Eur. J. Immunol., 29:3654-3662 (1999).
Galfre, G., et al., "Preparation of monoclonal antibodies: strategies and procedures" Methods Enzymol 73, 3-46 (1981).
Galon, et al, "Affinity of the interaction between Fc gamma receptor type III (Fc gammaRIII) and monomeric human IgG subclasses. Role of Fc gammaRIII glycosylation," Eur J Immunol, 27:1928-1932 (1997).
Geha and Rosen, "Intravenous Immunoglobulin Therapy" In: Therapeutic Immunology (Eds. Austen et al.) Blackwell Science, Cambridge, Mass., 280-296 (1996).
GenBank Accession No. BC012299, 2000.
GenBank Accession No. BC057090, 2000.
GenBank Accession No. BC089421, 2000.
GenBank Accession No. J02132, 2000.
GenBank Accession No. M12824, 2000.
GenBank Accession No. M14923, 2000.
GenBank Accession No. M19197, 2000.
GenBank Accession No. M81899, 1998.
GenBank Accession No. V00494, 1998.
GenBank Accession No. Z17370, 1999.
GenBank Accession No. Z33429, 2000.
Gessner, et al., "The IgG Fc receptor family," Ann. Hematol., 76:231-248 (1998).
Getahun et al., "IgG2a-Mediated Enhancement of Antibody and T Cell Responses and its Relation to Inhibitory and Activating Fc Receptors" J. Immunol., 172:5269-5276 (2004).

Ghose, T., et al., "Inhibition of a mouse hepatoma by the alkylating agent Trenimon linked to immunoglobulins" Cancer Immunol Immunother 13, 185-9 (1982).

Ghose, T., et al., "The design of cytotoxic-agent-antibody conjugates" Crit Rev Ther Drug Carrier Syst 3, 263-359 (1987).

Glennie, M. J., et al., "Preparation and performance of bispecific F(ab' gamma)2 antibody containing thioether-linked Fab' gamma fragments" J Immunol 139, 2367-75 (1987).

Goldstein, "Overview of the development of Orthoclone OKT3: monoclonal antibody for therapeutic use in transplanation," Transplant Proc, 19: 1-6 (1987).

Gomez-Guerrero, et al., "Administration of IgG Fc fragments prevents glomerular injury in experimental immune complex nephritis," J. Immunol, 164: 2092-2101 (2000).

Gosselin et al., "Enhanced antigen presentation using human fcγ receptor (monocyte/macrophage)-specificim munogens" J. Immunol., 149:3477-3481 (1992).

Gray, et al., "The role of transforming growth factor beta in the generation of suppression: an interaction between CD8 + T and NK cells," J Exp Med, 180:1937-1942 (1994).

Greenwood et al., "Engineering multiple-domain forms of the therapeutic antibody CAMPATH-IH: effects on complement lysis," Therapeutic Immunology, 1:247-255 (1994).

Greenwood et al., "Structural motifs involved in human IgG antibody effector functions," Eur. J. Immunol., 23:1098-1104 (1993).

Gribskov et al., "Sigma factors from E. coli, B. subtils, phage SPOI, and phage T4 are homologous proteins" Nucl. Acids Res., 14:6745-6763 (1986).

Gupta A.K., N.H. Shear & D.N. Sauder: "Efficacy of human intravenous immune globulin in pyoderma gangrenosum" J. Am. Acad. Dermatol. 32, 140-142 (1995).

Guyre, P. M., et al., "Increased potency of Fc-receptor-targeted antigens" Cancer Immunol Immunother 45, 146-8 (1997).

Harjunpaa et al., "Rituximab (Anti-CD20) Therapy of B-Cell Lymphomas: Direct Complement Killing is Superior to Cellular Effector Mechanisms" Scand. J. Immunol., 51(6):634-41 (2000).

Harlow and Lane, Antibodies: A Laboratory Manual, Cold Spring Harbor Laboratory (1988).

Harris, et al., "Induction of activation antigens on human natural killer cells mediated through the Fc-gamma receptor," J. Immunol., 143:2401-2406 (1989).

Hayes et al., "Adoptive cellular immunotherapy for the treatment of malignant gliomas," Crit. Rev. Oncology/Hematology, 39:31-42 (2001).

Heijnen et al., "Antigen targeting to Myeloid-specific Human FcγRI/CD64 Triggers Enhanced Antibody Responses in Transgenic Mice," J. Clinical Invest. vol. 97,pp. 331-338 ( Jan. 1996).

Hinton et al.,"An Engineered Human IgG1 Antibody with Longer Serum Half-Life" J. Immunol., 176: 346-356 (2006).

Hudson, P. J. "Recombinant antibodies: a novel approach to cancer diagnosis and therapy" Expert Opin Investig Drugs, 9, 1231-42 (2000).

Hulett and Hogarth, "Molecular basis for Fc receptor function," Adv in Immunol., 57:1-127 (1994).

Australian App. No. 2002250293, Office action dated Aug. 16, 2006, 2 pp.

European App. No. 02719196, Office action dated Mar. 31, 2009, 5 pp.

Japanese App. No. 2002-571521, Office action dated Feb. 4, 2009, 6 pp. (translation).

Japanese App. No. 2002-571521, Office action dated Jan. 17, 2008, 6 pp. (translation).

PCT/US02/07365, International Preliminary Examination Report, dated Jun. 11, 2004, 6 pp.

PCT/US02/07365, International Search Report, dated Mar. 13, 2003, 4 pp.

PCT/US08/56066, International Search Report, mailed Oct. 6, 2008, 7 pp.

PCT/US08/56066, Written Opinion, mailed Oct. 6, 2008, 6 pp.

U.S. Appl. No. 10/096,521, Office action dated Feb. 28, 2005, 13 pp.

U.S. Appl. No. 10/096,521, Office action dated Jun. 28, 2007, 18 pp.

U.S. Appl. No. 10/096,521, Office action dated Nov. 1, 2006, 15 pp.

U.S. Appl. No. 10/096,521, Office action dated Nov. 13, 2007, 11 pp.

U.S. Appl. No. 10/096,521, Office action dated Dec. 21, 2005, 12 pp.

Achiron et al., "Intravenous immunoglobulin treatment in multiple sclerosis. Effect on relapses," Neurology, 50:398-402 (1998).

Alcover et al., "A soluble form of the human CD8 alpha chain expressed in the baculovirus system; biochemical characterization and binding to MHC class I" Mol. Immunol., 30:55-67 (1993).

Anegon et al., "Interaction of Fc receptor (CD16) ligands induces transcription of interleukin 2 receptor (CD25) and lymphokine genes and expression of their products in human natural killer cells" J. Exp. Med., 167:452-472 (1988).

Antel et al., "Generation of suppressor cells by aggregated human globulin" Clin. Exp. Immunol., 43:351-356 (1981).

Armour et al., "Recombinant human IgG molecules lacking Fcγ receptor I binding and monocyte triggering activities" Eur.J. Immunol., vol. 29, pp. 2613-2624 (1999).

Asghar, "Pharmacological Manipulation of the complement system in human diseases." Front. Bioscience (On Line) 1, e15-26 (1996).

Ashkenazi and Chamow, "Immunoadhesins as research tools and therapeutic agents" Curr. Opin. Immunol., 9:195-200 (1997).

Balfour-Lynn I. "Difficult asthma. Beyond the guidelines" Arch. Dis. Childhood 80, 201-206 (1999).

Ballester O.F., H.I. Saba, L.C. Moscinski, R. Nelson & P. Foulis P: "Pure red cell aplasia: treatment with intravenous immunoglobulin concentrate" Semin. Hematol. 29(Suppl 2),106-8 (1992).

Baschieri L., A. Antonelli, S. Nardi, B. Alberti, A. Lepri, R. Canapicchi & P. Fallahi "Intravenous immunoglobulin versus corticosteroid in treatment of Graves' ophthalmopathy" Thyroid 7, 579-85, (1997).

Berger et al., "Immune complexes are potent inhibitors of interleukin-12 secretion by human monocytes," Eur. J. Immunol., 27:2994-3000 (1997).

Berger et al., "Immune complex-induced interleukin-6, interleukin-10 and prostaglandin secretion by human monocytes: a network of pro- and anti-inflammatory cytokines dependent on the antigen: antibody ratio," Eur. J. Immunol., 26:1297-1301 (1996).

Bjorkholm M.: "Intravenous immunoglobulin treatment in cytopenic haematological disorders." J. Intern. Medicine. 234, 119-26 (1993).

Bolhuis et al., "Adoptive immunotherapy of ovarian carcinoma with bs-MAb-targeted lymphocytes: a multicenter study" Int J Cancer Suppl 7, 78-81 (1992).

Brittenden et al., "Natural Killer Cells and Cancer," Cancer, 77:1226-1243 (1996).

Brumeanu et al., "Engineering of doubly antigenized immunoglobulins expressing T & B viral epitopes," Immunotechnology vol. 2, pp. 85-95 (1996).

Brumeanu et al., "Efficient Loading of Identical Viral Peptide Onto Class II Molecules by Antigenized Immunoglobulin and Influenza Virus" J. Exp. Med., 178:1795-1799 (1993).

Burgess et al., "Possible dissociation of the heparin-binding and mitogenic activities of heparin-binding (acid fibroblast) growth factor-1 from its receptor-binding activities by site-directed mutagenesis of a single lysine residue," J Cell Biol., 111:2129-2138 (1990).

Capon et al., "Designing CD4 immunoadhesins for AIDS therapy," Nature, 337:525-531 (1989).

Cartron et al., "Therapeutic activity of humanized anti-CD20 monoclonal antibody and polymorphism in IgG Fc receptor Fc.gamma.RIIIa gene" Blood 99, 754-758 (2002).

Chamow and Ashkenazi, "Immunoadhesins: principles and applications," Trends Biotechnol., 14:52-60 (1996).

Chomczynski and Sacchi, "Single-Step Method of RNA Isolation by Acid Guanidinium Thiocyanate-Phenol-Chloroform Extraction" Anal. Biochem., 162:156-159 (1987).

Clark et al., "The potential of hybrid antibodies secreted by hybrid-hybridomas in tumour therapy" Int J Cancer Suppl 2, 15-7 (1988).

Clarkson et al. "Treatment of Refractory Immune Thrombocytopenic Purpura with Anti-Fc gamma Receptor Antibody" N. Engl. J. Med., 314(19):1236-9 (1986).

Clynes et al., "Inhibitory Fc receptors modulate in vivo cytotoxicity against tumor targets" Nat. Med. 6, 443-446 (2000).

Clynes et al., "Uncoupling of immune complex formation and kidney damage in autoimmune glomerulonephritis," Science, 279:1052-1054 (1998).

Cohen et al., "Preliminary Criteria for the Classification of Systemic Lupus Erythematosis" Bull. Rheum. Dis., 21:643 (1971).

Curnow, "Clinical experience with CD64-directed immunotherapy. An overview" Cancer Immunol Immunother., 45 (3-4):210-5 (1997).

Current Protocol in Molecular Biology found at <<http://mrw.interscience.wiley.com/emrw/0471-142727/home/archive.htm#Core>>, 2005.

Daeron, "FC Receptor Biology" Annu. Rev. Immunol., 15:203-234 (1997).

Davis, M. T., et al., "A conjugate of alpha-amanitin and monoclonal immunoglobulin G to Thy 1.2 antigen is selectively toxic to T lymphoma cells" Science 213, 1385-8 (1981).

Deane et al., "IgG-assisted age-dependent clearance of alzheimer's amyloid beta peptide by the blood-brain barrier neonatal Fc receptor," J. of Neuroscience, 25:11495-11503 (2005).

Devereux et al., "A comprehensive set of sequence analysis programs for the VAX" Nucl. Acids Res., 12:387-395 (1984).

Dillman, R. O., et al., "Superiority of an acid-labile daunorubicin-monoclonal antibody immunoconjugate compared to free drug" Cancer Res 48, 6097-102 (1988).

Dockal et al., "The Three Recombinant Domains of Human Serum Albumin," The Journal of Biological Chemistry, vol. 274, No. 41, pp. 29303-29310 (1999).

Dong et al., "Binding and Uptake of Agalactosyl IgG by Mannose Receptor on Macrophages and Dendritic Cells" J. Immunol., 163:5427-5434 (1999).

Duan et al. "Antitumor activities of TEM8-Fc: an engineered antibody-like molecule targeting tumor endothelial marker 8." J. Natl. Cancer Inst., vol. 99, pp. 1551-1555 (2007).

* cited by examiner

FIG 13

Light Chain (Catalytic)

```
437  LC  1 —NH₂
  S
  S
       Heavy Chain
448  Hₙ  872 | 873  HcN  1078 | 1090  HcC  1295 —COO⁻
  Hₙ (Translocation)              Hc (Binding)
```

METHODS AND COMPOSITIONS INVOLVING POLYMERIC IMMUNOGLOBULIN FUSION PROTEINS

CROSS REFERENCE TO RELATED APPLICATIONS

This application claims benefit to U.S. Provisional Application No. 60/893,318, filed Mar. 6, 2007, which is incorporated by reference in its entirety. This application is also a continuation-in-part of co-pending U.S. application Ser. No. 10/096,521, filed Mar. 11, 2002, which is incorporated by reference in its entirety, which claims benefit to U.S. Provisional Application No. 60/274,392, filed Mar. 9, 2001, which is incorporated by reference in its entirety.

GOVERNMENT RIGHTS

This invention was made with government support under 1R21A1058003, awarded by NIH/NIAID and under RG 2978-A-201 awarded by National Multiple Sclerosis Society. The U.S. Government may have certain rights in the invention.

BACKGROUND

The present invention relates generally to the field of immunology.

Induction of immunity to pathogens, toxins, and peptides expressed by tumor cells, requires the coordinated participation of the innate and adaptive immune systems. An early step is Ag internalization by APCs of the innate immune system, notably by dendritic cells (DCs), the most potent APC type, and the one best able to present Ag to naïve T cells (Trombetta and Mellman, 2005). Internalized Ag is processed through the endosomal/lysosomal path. Processed peptides, bound to MHC molecules, are then delivered to the cell surface. Those T cells with appropriate receptors respond to such peptides provided co-stimulatory molecules are expressed by the DC. A second signal is often required to drive DC maturation and efficient co-stimulatory molecule expression. Ag activates B cells bearing appropriate surface immunoglobulin directly to produce IgM. CD4$^+$ T cells, having responded to processed Ag, induce immunoglobulin class-switching from IgM to IgG.

Limited uptake of soluble antigenic peptide by DCs constrains subsequent Ag processing and presentation. Immune responses increase when Ag uptake is facilitated. IgG-immune complexes (ICs) bind to FcγRs expressed on DCs and this is followed by internalization of ICs with their captured Ags. Thus, stronger Ab responses may occur when soluble Ag is complexed to IgG, than when Ag alone is administered (Wemersson et al., 1999). ICs in antibody excess can be more effective at Ag presentation than ICs at equivalence or in Ag excess (Manca et al., 1991). IC driven, FcγR-mediated, Ag internalization favors DC maturation and hence expression by them of costimulatory molecules (Regnault et al., 1999). Other means to target Ag to Fcγ receptors on APCs have been employed in order to elicit strong immune responses against otherwise weak immunogens. Early studies, that documented the potential of this approach, employed Ag-containing anti-FcγR monoclonal antibodies as a means to facilitate delivery of Ag to APCs and hence increase Ag-specific T cell responses and Ag-specific humoral responses (Snider et al., 1990; Heijnen et al., 1996; Gosselin et al., 1992; Keler et al., 2000). Modification of Ig by introduction of epitopes within the CDR region (i.e., antigenized Ig) may also enhance immune responses compared to Ag alone (Zaghouani et al., 1993, Brummeanu et al., 1996).

Immune complexes (IC) exhibit diverse biological activities; some that contribute to disease whereas others ameliorate disease. Deposition of IgG containing IC on tissue surfaces, as for example in glomeruli, can contribute to the pathogenesis of antibody-mediated autoimmune diseases. On the other hand, IC can favorably modulate T- and B-cell activation pathways via binding to Fc receptors expressed on immunocytes. Aggregated IgG (AIG) shares some features and biological activities with IC. Both modulate T-cell suppressor function (Antel et al., 1981; Durandy et al., 1981), cytokine synthesis, IgG secretion, and lymphocyte proliferation (Berger et al., 1997; Wiesenhutter et al., 1984; Ptak et al., 2000).

Monomeric IgG, or the Fc fragment thereof, can ameliorate disease progression in animal models of autoimmune disease (Miyagi et al., 1997; Gomez-Guerrero et al., 2000). Monomeric IgG can be used therapeutically, usually in massive doses, to treat antibody-mediated diseases in man. The protective effect in antibody-mediated diseases may be achieved in part through blockade of FcγRs such that binding of IC to them is impeded (Clynes et al., 1998). IgG administration also favorably affects the course of T-cell mediated autoimmune diseases such as multiple sclerosis (Fazekas et al. 1997; Sorensen et al., 1998; Achiron et al., 1998). Here the basis for benefit is poorly understood though it is postulated to involve the increased production of anti-inflammatory cytokines initiated by binding of IV IgG, or complexes derived therefrom, to FcγR. In both antibody and T-cell mediated processes the mechanisms and consequences of FcγR engagement are fundamental to the understanding and treatment of autoimmune diseases.

Aggregated IgG has been proposed as a treatment for autoimmune diseases of humans. The use of aggregated IgG has been studied as a treatment for multiple sclerosis and other autoimmune diseases. However, aggregated IgG has major limitations. IgG is commonly aggregated by exposure to heat; the resultant aggregates are bound together in a random fashion limiting reproducibility from one preparation to the next. Preparations contain a heterogeneous collection of aggregates of varying size in diverse conformations.

U.S. Pat. Nos. 5,714,147 and 5,455,165 disclose some hybrid immunoglobulin molecules and the expression vectors encoding them. These chimeric molecules can improve the circulating plasma half-life of ligand binding molecules, and can comprise a lymphocyte homing receptor fused to an immunoglobulin constant region. Homo or hetero-dimers or tetramer hybrid immunoglobulins containing predominantly the heavy and light constant regions of immunoglobulin have been used. U.S. Pat. No. 6,046,310 discloses FAS ligand fusion proteins comprising a polypeptide capable of specifically binding an antigen or cell surface marker for use in treatment of autoimmune disorders. The fusion protein preferably comprises IgG2 or IgG4 isotype, and may comprise antibodies with one or more domains, such as the CH2, CH1 or hinge deleted. Majeau et al. (1994) discusses Ig fusion proteins used for the inhibition of T cell responses. These fusion proteins comprise IgG1 and LFA-3. Eilat et al. (1992) disclose a soluble chimeric Ig heterodimer produced by fusing TCR chains to the hinge region, CH2, and CH3 domains of human IgG1.

Immunoglobulin fusion proteins can be employed to express proteins in mammalian and insect cells (Ashkenazi, et al., 1997). Fusion protein platforms can permit the introduction of additional functions, for example, inclusion of the amino-terminal CD8α domain may result in the co-ligation of FcR on lymphocytes to MHC I on antigen presenting cells (Alcover, et al., 1993; Meyerson, et al., 1996).

Other Ig proteins and variants have also been studied for their therapeutic effect on autoimmune diseases, including a recombinant polymeric IgG that mimics the complement activity of IgM (Smith and Morrison, 1994) where the polymeric IgG is formed by the polymerization of $H_2L_2$ subunits. Greenwood et al. (1993) discusses therapeutic potency relative to the structural motifs involving the human IgG antibodies, IgG1, IgG3, and IgG4. U.S. Pat. No. 5,998,166 discloses human FcγR-III variants, which can be used in the therapy or diagnosis of autoimmune diseases. U.S. Pat. No. 5,830,731 discloses novel expression vectors in which cell surface antigens cloned according to that invention appear to have diagnostic and therapeutic utility in immune-mediated infections. Cell surface antigens that are used to regulate lymphocyte activation, appear to achieve antigen aggregation in vitro by incubating lymphocytes with immobilized ligands or antibodies or their fragments (WO9942077). However, the aggregated IgG and Fc aggregates have limited reproducibility, containing a random and heterogeneous mixture of protein thereby limiting their effectiveness as therapeutic agents. Other problems include a lack of an ability to target a number of cell types with a single agent and size limitations.

SUMMARY OF THE INVENTION

In some embodiments, the inventive polypeptide has an immunoglobulin framework and consists of an Fc region linked to two arms. The Fc region consists of two Fc amino acid chains and each Fc amino acid chain is linked to one of the two arms. Each arm consists of an HCH2 polymer linked to an antigen portion, the HCH2 polymer consists of two to six linear copies of an HCH2 monomer, and the HCH2 monomer consists of at least a fragment of an HCH2 region. At least a fragment of an HCH2 region includes a hinge region; and at least one hinge region cysteine of the HCH2 monomer is mutated to serine.

In exemplary embodiments, the inventive polypeptide can consist of two amino acid chains where each amino acid chain consists of (a) an Fc portion which includes the C-terminus of the amino acid chain; (b) a polymer portion consisting of two to six linear copies of an HCH2 monomer; and (c) an antigen portion which includes the N-terminus of the amino acid chain. The N-terminus of the Fc portion is linked to the C-terminus of the polymer portion, and the N-terminus of the polymer portion is linked to the C-terminus of the antigen portion. The two amino acid chains are linked using one or more disulfide bonds located in the Fc portion of each amino acid chain. The HCH2 monomer can consist of at least a fragment of an HCH2 region, wherein the at least a fragment of an HCH2 region includes a hinge region.

In some embodiments, the inventive polypeptide has Fc amino acid chains selected from the group consisting of: an amino acid chain of the IgG1 Fc region, an amino acid chain of the IgG3 Fc region, an amino acid chain of the IgG2a Fc region, SEQ ID NO: 47, SEQ ID NO: 48, and fragments thereof.

In some embodiments, the inventive polypeptide is capable of binding to FcγR or of targeting cells expressing FcγR.

In some embodiments, the inventive polypeptide has the HCH2 region selected from the group consisting of: a human IgG1 HCH2 region, a human IgG2 HCH2 region, a human IgG3 HCH2 region, a human IgG4 HCH2 region, a mouse IgG2a, SEQ ID NO: 9, SEQ ID NO: 10, SEQ ID NO: 50, SEQ ID NO: 51, and fragments thereof.

In some embodiments, the inventive polypeptide has three hinge region cysteines of the HCH2 monomer mutated to serine.

In some embodiments, the antigen portion is an antigen or an epitope, which can be a protein or protein fragment, a Botulinum neurotoxin protein or fragment thereof, BoNT/A Hc, BoNT/A HcN, BoNT/A HcC, HSA1, CD8α, FABP7, PLP, MBP, PLP-MBP, PLP-PLP, SEQ ID NO: 23, SEQ ID NO: 25, SEQ ID NO: 27, SEQ ID NO: 29, SEQ ID NO: 34, SEQ ID NO: 40, SEQ ID NO: 43, or fragments thereof.

In some embodiments, a composition or vaccine comprises the inventive polypeptide.

In other embodiments, the inventive polypeptide is provided to a subject, used in a vaccine, or used to induce immunity.

Other embodiments include methods for making the inventive polypeptides or the nucleic acids used to encode the inventive polypeptides.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A. Recombinant proteins were separated on 7% SDS-PAGE gels and stained with Coomassie brilliant blue dye to reveal protein. FIG. 3B. Recombinant proteins were transferred to nitrocellulose membrane and stained with antibodies directed against human Fc. Note that the human IgG control and the fusion proteins are recognized by anti-Fc antibody.

FIG. 7A. Pre-incubation with antibody to FcγRI (clone 10.1) partially blocks binding of HSA1R4 to U937 cells (gray). FIG. 7B. Preincubation with antibody to FcγRII (clone FLI8.26) partially blocks binding of HSA1R4 to U937 cells (gray). FIG. 7C. Preincubation with antibody to both FcγRI and FcγRII completely blocks binding of HSA1R4 to U937 cells (gray).

FIG. 10A. Mice were immunized with 50 ug of HSA1R4 (n=6), HSA1Fc (n=4), or HSA1 (n=5) subcutaneously. Sera were obtained two wk later. Titers of total IgG reactive with HSA are shown as a mean ±SEM as are $IgG_1$ and $IgG_{2c}$, HSA-specific titers. HSA-specific Ab titers are higher in mice receiving HSA1R4 than in mice receiving HSA1Fc ($p=0.01$) or HSA1 ($p<0.001$). FIG. 10B. Mice were immunized with 250 ng of HSA1R4 (n=8) or HSA1Fc (n=7) subcutaneously in Ribi adjuvant. Anti-HSA Ab titers are higher in mice given HSA1R4 than in mice receiving HSA1Fc ($p<0.001$).

FIG. 12A. HSA1-induced T cell proliferation is higher in splenocytes from mice immunized with HSA1R4 than in splenocytes from mice immunized with HSA1Fc ($p<0.004$). Shown are proliferative responses of cells from mice immunized 2 wk previously with HSA1R4 or HSA1Fc in Ribi adjuvant, and challenged in vitro with HSA1. Data shown are the mean ±SEM of four experiments. FIG. 12B. HSA1R4 augments presentation of HSA1 to HSA-reactive T cells. Shown are proliferative responses of cells isolated from spleens of mice immunized 14 days previously with HSA in CFA following in vitro challenge with HSA1R4, HSA1Fc, or HSA1($1.6 \times 10^{-9}$ M for each). HSA1R4 leads to greater T cell reactivity ($p<0.008$ vs HSA1Fc; $p<0.001$ vs HSA1). Data shown are the mean ±SEM of four experiments.

FIG. 13. Schematic of BoNT/A toxin organization. BoNT is expressed as a single chain 150 kD polypeptide which following proteolytic cleavage results in a light chain (~50 kD) linked by disulphide bonds to a heavy chain (~100 kD). BoNT activities map to discrete regions within the polypeptide chains: Endoprotease activity resides within the light chain. The heavy chain is responsible for receptor binding and translocation. The heavy chain can be further subdivided both functionally and proteolytically into an amino-terminal fragment (HN), involved in ion-channel formation and light chain translocation, and a carboxyl-terminal fragment (Hc) involved in receptor binding. The Hc fragment is composed of two ~200 amino acid sub-domains that are structurally distinct; the amino-terminal portion, HcN (residues 871 to 1078 of the holotoxin) and the carboxyl-terminal portion, HcC (residues 1090 to 1296 of the holotoxin).

HcR4 was incubated with immobilized receptors at the indicated concentrations. Plates were washed and bound ligand was detected as described. Results shown are from a representative assay of three performed.

Figure 15:
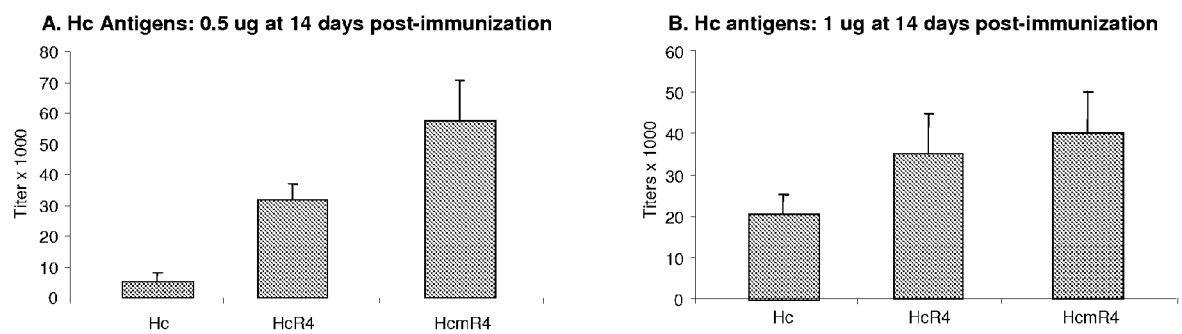

FIG. 15. HcR4 and HcmR4 increased Hc-specific antibody responses in high responder SJL mice. SJL mice were immunized with a single 1.0 ug or 0.5 ug dose of Hc, HcR4, or HcmR4. Serum was collected 14 days after immunization and the Hc-specific antibody titers were determined. HcmR4 and HcR4 induced higher antibody responses than Hc alone at both the 1.0 ug and 0.5 ug doses.

Figure 16:
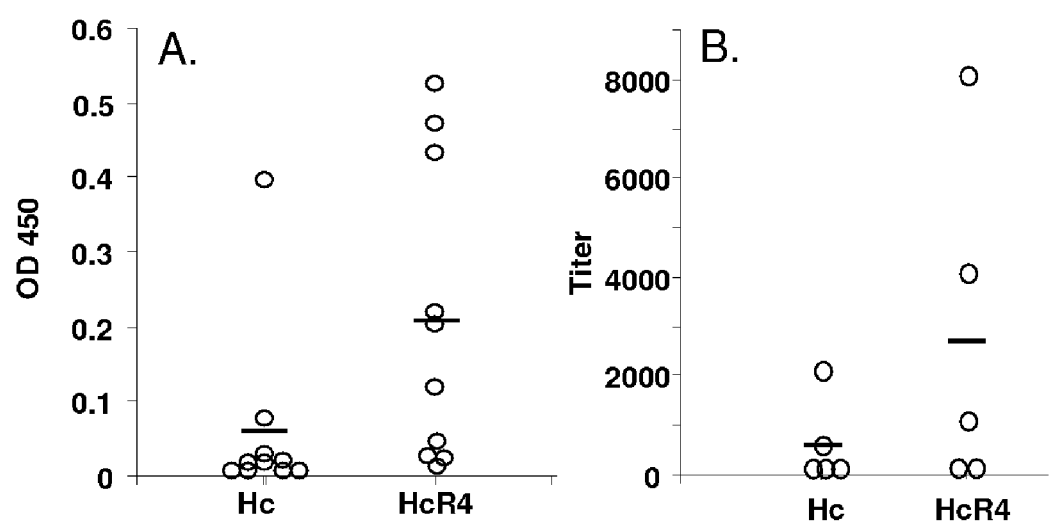

FIG. 16. HcR4 increased Hc-specific antibody responses in low responder C57BL/6 mice. A. Mice were immunized with 5 μg of Hc or HcR4 SC in Ribi adjuvant (10 mice per group). Sera were obtained 14 days later and anti-Hc titers were determined using ELISA. Shown are the results from a 1:250 dilution of sera. The means are marked by a line. The difference between the means is significant ($p<0.03$). B. Mice were immunized with 10 μg of Hc or HcR4 SC as described and Hc-specific titers were determined 14 days later. The means are marked by a line.

Figure 17:
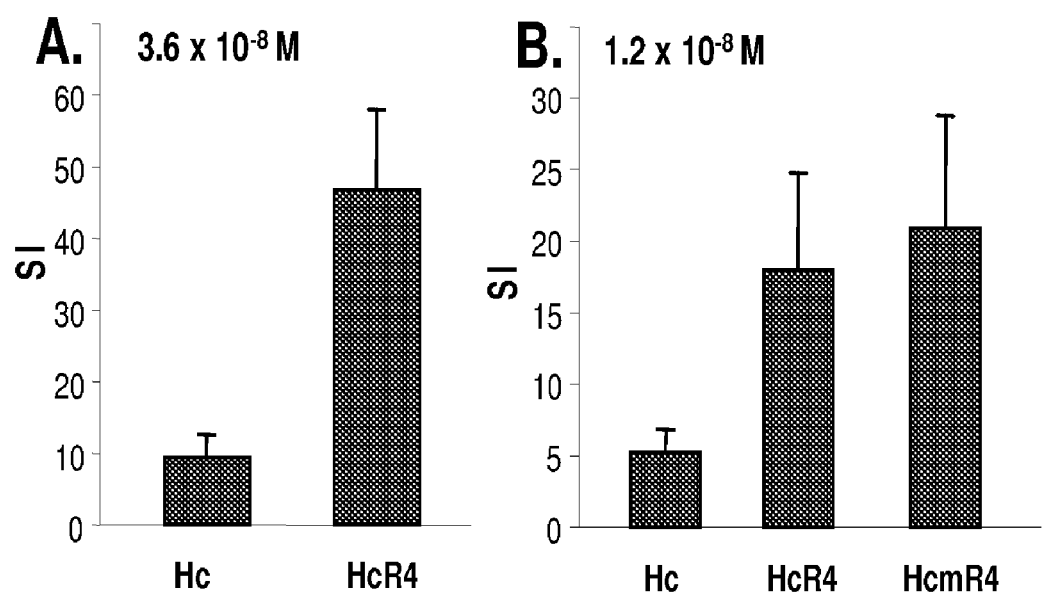

FIG. 17. HcR4 leads to greater induction of secondary T cell responses to recall antigens. LN cells were isolated from SJL mice 14 days post immunization with Hc. LN cells were challenged in vitro with Hc, HcR4, or HcmR4 as indicated. A. HcR4 leads to greater T cell reactivity at $3.6 \times 10^{-8}$ M vs Hc ($p<0.03$). B. Priming at the lower $1.2 \times 10^{-8}$ M dose produces a similar trend. Mean ±SEM of results from 4 mice.

Figure 18:
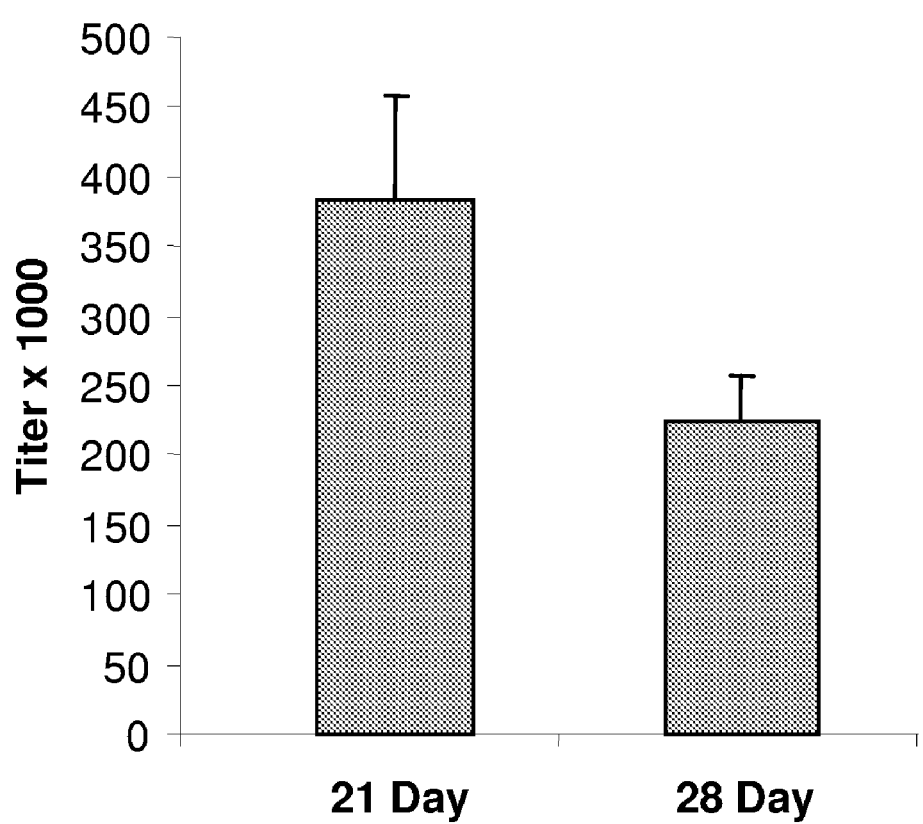

FIG. 18. Intranasal delivery of HcR4 results in large and rapid Hc-specific antibody responses: SJL mice (n=5) received 25 μg of HcR4 in 10 μL PBS instilled into each nostril on days 0, 7, and 14. Serum was obtained at days 21 and 28 and Hc specific IgG titers were determined.

DETAILED DESCRIPTION

The present invention concerns inventive polypeptides. The present invention also concerns compositions and vaccines comprising the inventive polypeptides. This invention describes vaccines and methods of inducing immunity against an antigen using inventive polypeptides described herein. The present invention provides for improved vaccine efficacy by targeting Ag to Fcγ receptors using multiple copies of HCH2 of a human IgG. The vaccines of the present invention can be applied, for example, in the induction of immunity to pathogens, toxins, and peptides expressed by tumor cells. In other embodiments of the invention, the inventive polypeptides are provided to a subject. Still other embodiments include methods for making the inventive polypeptides and nucleic acids used to encode the inventive polypeptides.

A. Antibody Structure

Antibodies comprise a large family of glycoproteins with common structural features. An antibody is comprised of four polypeptides that form a three dimensional structure which resembles the letter Y. Typically, an antibody is comprised of two different polypeptides, termed the heavy chain and the light chain.

An antibody molecule typically consists of three functional regions: the Fc, Fab, and antigen-binding site. The Fc region is located at the base of the Y. The arms of the Y comprise the Fab region. The antigen-binding site is located at the end of each arm of the Y. The area at the fulcrum of the arms of the Y is the hinge region.

There are five different types of heavy chain polypeptides designated as α, δ, ϵ, γ, and μ. There are two different types of light chain polypeptides designated κ and λ. An antibody typically contains only one type of heavy chain and only one type of light chain, although any light chain can associate with any heavy chain.

Antibody molecules are categorized into five classes, IgG, IgM, IgA, IgE, and IgD. The IgG class is further divided into subclasses including IgG1, IgG2, IgG3, and IgG4 for human IgG. An antibody molecule is comprised of one or more Y-units, each Y comprising two heavy chains and two light chains. For example IgG consists of a single Y-unit IgM is comprised of 5 Y-like units.

Amino acids toward the carboxyl terminal of each heavy chain polypeptide make up a constant region. Amino acids toward the amino terminal of each heavy and light chain polypeptide make up a variable (V) region. Within the variable region are hypervariable regions known as complementarity determining regions (CDRs). One heavy chain and one light chain associate to form an antigen-binding site. Each heavy chain and each light chain includes three CDRs. The six CDRs of an antigen-binding site define the amino acid residues that form the actual binding site for the antigen. CDR variability accounts for the diversity of antigen recognition.

The mature human IgG1 heavy (H) chain can span 447 amino acid residues. The Fc region of the H chain is essentially the same for all IgG1 heavy chain molecules. The Fc region is the portion of the IgG1 polypeptide that interacts with Fc receptors. The Fc region can be further subdivided into three consecutive parts, the hinge region, the CH2 domain, and the CH3 domain. For human IgG1, the binding site for Fc receptors is found within the hinge and $CH_2$ (HCH2) region. The HCH2 region encompasses amino acid residues 216 to 340 of the human IgG1 H chain (Eu numbering). The hinge region spans residues 216 to 237 whereas the CH2 domain encompasses residues 238 to 340.

B. Some Exemplary Embodiments of Inventive Polypeptides and Exemplary Methods of Making Capon, et al., 1989, Traunecker, et al., 1989, Chamow, et al., 1996, and Ashkenazi, et al., 1997 disclose some examples of fusion proteins related to immunology. A recombinant immunoglobulin fusion protein can have an amino-terminus composed of a ligand-binding domain fused to a carboxyl-terminus composed of the hinge, $C_H2$, and $C_H3$ regions of Ig. The Ig class sometimes used is IgG1. The hinge, $C_H2$, and $C_H3$ regions of IgG are collectively referred to as the Fc region of IgG. The hinge region can provide a flexible linker between the Fc region and the ligand binding domain. It also is the site of inter-chain disulphide bond formation, i.e., the covalent linking of one antibody amino acid chain to another to make the familiar dimeric structure. The hinge region (e.g., the part nearest to the CH2 domain, known as the hinge proximal region) is associated with molecular recognition and binding to Fcγ receptors and complement components. Thus, some recombinant immunoglobulin fusion proteins are similar to Ig but lack the variable regions and the CH1 domain, which have been replaced by the ligand-binding domain. Sometimes, the recombinant molecule is generated at the cDNA level using recombinant DNA techniques and expressed in cell culture. In some instances, the recombinant immunoglobulin fusion protein is a disulfide-linked homodimer. There have been some variations on the above described fusion proteins. For example, in addition to ligand-binding domains, other fusion partners have been placed at the amino-terminus, such as ligands, enzymes, and peptide epitopes.

The term "amino acid chain" includes a linear chain of amino acids. The amino acid chain can be chemically or biochemically modified (such as, but not limited to, glycosylation or phosphorylation) or derivatized amino acids, and can have a modified peptide backbone.

The term "polypeptide" refers to a polymeric form of amino acids of any length, and includes chemically or biochemically modified or derivatized amino acids, as well as amino acid chains having modified peptide backbones. The term includes amino acid chains that are linked, for example, by one or more disulfide bonds, proteins, amino acid chains, saccharides, or polysaccharides.

A "fragment" of a polypeptide or protein refers to a polypeptide that is shorter than the reference polypeptide or protein, but that can retain a biological function or activity that is recognized to be the same as the reference polypeptide or protein. Such an activity may include, for example, the ability to stimulate an immune response. A fragment may retain at least one epitope of the reference polypeptide or protein. The shorter polypeptide may retain all or part of a modification (e.g., by glycosylation or phosphorylation) of the reference polypeptide or protein.

"Immunological framework" refers to a molecule that comprises two arms attached to an Fc region. The Fc region has the primary structural components of an antibody Fc region, but the arms can be comprised of any molecule and thus are not limited to the Fab-antigen structures of an antibody.

In exemplary embodiments, the inventive polypeptide can consist of two amino acid chains where each amino acid chain consists of (a) an Fc portion which includes the C-terminus of the amino acid chain; (b) a polymer portion consisting of two to six linear copies of an HCH2 monomer; and (c) an antigen portion which includes the N-terminus of the amino acid chain. The N-terminus of the Fc portion is linked to the C-terminus of the polymer portion, and the N-terminus of the polymer portion is linked to the C-terminus of the antigen portion. The two amino acid chains are linked using one or more disulfide bonds located in the Fc portion of each amino acid chain. The HCH2 monomer can consist of at least a fragment of an HCH2 region, wherein the at least fragment of an HCH2 region includes a hinge region. In some embodiments, at least one hinge region cysteine of the HCH2 monomer is mutated to serine. The Fc portion can comprise, for example, SEQ ID NO: 47 or SEQ ID NO: 48.

In other exemplary embodiments, the inventive polypeptide has an immunoglobulin framework consisting of an Fc region consisting of two amino acid chains wherein each amino acid chain is linked to an arm. Each arm can consist of an HCH2 polymer linked to an antigen portion. The HCH2 polymer can consist of two to six linear copies of an HCH2 monomer, which consists of at least a fragment of an HCH2 region. In some embodiments at least one hinge region cysteine of the HCH2 monomer is mutated to serine, or another non-cysteine amino acid. Sometimes all the hinge region cysteines are mutated. In some embodiments, the Fc region comprises the linked Fc portions.

The inventive polypeptide can, for example, bind to FcγR, target cells expressing FcγR, or complement components.

The Fc region can be selected or derived from any animal, mammalian, mouse, or human antibody. For example, the Fc region can combine polypeptides of Fc regions from IgG1, IgG2, IgG3, IgG4, IgA, IgD, IgM, IgE, IgG2a, or fragments thereof. In some embodiments, the combined polypeptides are identical. Some embodiments of the fragments include fragments comprising a hinge region, a CH2 domain, and a CH3 domain. Exemplary embodiments of sequences that can be used to form the amino acid chain of the Fc region can include, but are not limited to SEQ ID NO: 47 and SEQ ID NO: 48.

Linkers can include, but are not limited to, amino acid chains, disulfide bonds, saccharides, polysaccharides, or any known linkers. For example, amino acid chains up to 1, 2, 3, 4, 5, 6, 7, 8, 9, 10, 12, 15, 18, or 20 amino acids can be used as linkers.

In some embodiments, the HCH2 monomer can be selected or derived from an Fc region of any animal, mammalian, mouse, or human antibody. It can be a polypeptide from the Fc regions of, for example, but not limited to, IgG1, IgG2, IgG3, IgG4, IgA, IgD, IgM, IgE, IgG2a, or fragments thereof. For example, the HCH2 region can be selected from the group consisting of: a human IgG 1 HCH2 region, a human IgG2 HCH2 region, a human IgG3HCH2 region, a human IgG4 HCH2 region, a mouse IgG2a region, and fragments thereof. Exemplary embodiments of sequences that can be used in an HCH2 monomer include, but are not limited to, SEQ ID NO: 9, SEQ ID NO: 10, SEQ ID NO: 50, and SEQ ID NO: 51.

The HCH2 polymer can be made from, for example, 1, 2, 3, 4, 5, 6, 7, or 8 linear copies of an HCH2 monomer.

The antigen portion includes, but is not limited to, antigens, polypeptides, proteins protein fragments, or any combination thereof. For example, the antigen portion can include proteins or protein fragments linked together in a serial fashion, such as PLP linked to PLP, a fragment of PLP linked to PLP, a fragment of PLP linked to another fragment of PLP, a fragment of PLP linked to a fragment of MBP, MBP linked to a fragment of PLP. In some embodiments, the antigen portion is a Botulinum neurotoxin protein, including for example, BoNT/A, BoNT/B, BoNT/C, BoNT/D, BoNT/E, BoNT/F, BoNT/G, BoNT/A Hc, BoNT/A HcN, BoNT/A HcC, or portions, fragments, or variants thereof. In some embodiments, the antigen portion can contain at least one antigenic domain or epitope of an infectious agent, microorganism, tumor antigen, or self protein, including for example, cancer antigens (such as, sarcoma, lymphoma, leukemia, melanoma, carcinoma of the breast, colon carcinoma, carcinoma of the lung, glioblastoma, astrocytoma, carcinoma of the cervix, uterine carcinoma, carcinoma of the prostate, ovarian carcinoma, or portions, fragments, or variants thereof), antigenic domains of infectious agents, antigenic domains of viruses (such as, papilloma virus, Epstein Barr virus, herpes virus, retrovirus, hepatitis virus, influenza virus, herpes zoster virus, herpes simplex virus, human immunodeficiency virus 1, human immunodeficiency virus 2, adenovirus, cytomegalovirus, respiratory syncytial virus, rhinovirus, or portions or variants thereof), antigenic domains of a bacteria (from bacteria such as, *Salmonella, Staphylococcus, Streptococcus, Enterococcus, Clostridium, Escherichia, Klebsiella, Vibrio, Mycobacterium, Mycoplasma pneumoniae*, or portions or variants thereof), toxin polypeptides (such as, abrin, a conotoxin, diacetoxyscirpenol, ricin, saxitoxin, a Shiga-like ribosome inactivating protein, flexal, guanarito, junin, machupo, sabia, tetrodotoxin, a Botulinum neurotoxin, *Clostridium perfringens* epsilon toxin, a Shigatoxin, Staphylococcal enterotoxin, T-2 toxin, Bovine spongiform encephalopathy agent, epsilon toxin, ricin toxin, Staphylococcal enterotoxin B, influenza virus hemagglutinin, toxoids, or portions, fragments, or variants thereof), tumor antigens (such as, KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA), bladder tumor oncofetal antigen, differentiation antigen such as human lung carcinoma antigen L6, L20, an antigen of fibrosarcoma, human leukemia T cell antigen-Gp37, neoglycoprotein, a sphingolipid, EGFR, EGFRvIII, FABP7, doublecortin, brevican, HER2 antigen, polymorphic epithelial mucin (PEM), malignant human lymphocyte antigen-APO-1, an I antigen, M18, M39, SSEA-1, VEP8, VEP9, Myl, VIM-D5, $D_{156-22}$, TRA-1-85, C14, F3, AH6, Y hapten, Le$^y$, TL5, EGF receptor, FC10.2, gastric adenocarcinoma antigen, CO-514, NS-10, CO-43, G49, MH2, a gastric cancer mucin, $T_{5A7}$, $R_{24}$, 4.2, $G_D3$, D1.1, OFA-1, $G_M2$, OFA-2, $G_D2$, M1:22:25:8, SSEA-3, SSEA-4, or portions, fragment, or variants thereof), autoantigens from a mammal (such as, myelin basic protein (MBP), proteolipid protein (PLP), myelin-associated glycoprotein (MAG), myelin oligodendrocyte glycoprotein (MOG), collagens, insulin, proinsulin, glutamic acid decarboxylase 65 (GAD65), an islet cell antigen, portions, fragments, or variants thereof). Other examples of antigen portions include, for example, HSA, HSA1 (HSA domain 1), HSA2 (HSA domain 2), HSA3 (HSA domain 3), Fatty Acid Binding Proteins (FABP) such as FABP1, FABP2, FABP3, FABP4, FABP5, FABP6, FABP7, FABP8, FABP9 including FABP5-like 1-7; other examples of antigen portions can be found throughout the application.

While not being by any particular theory, the immunoglobulin Fc region appears to provide some features of the IgG fusion proteins such as stability, covalent dimerization, single-step purification, and ease of detection. The intervening HCH2 polymer appears to confer increased effector function, including, for example, targeting to subsets of cells expressing FcγR, increased capacity to ligate FcγR, and to bind complement components. The amino-terminal domain can deliver a second signal. Thus, multiple molecular signals can be integrated into a single molecule with the potential for synergistic interaction between the domains.

The inventive polypeptide comprises multiple HCH2 regions. The polymers were developed using a cloning system that can result in the rapid addition of HCH2 units into a human IgG$_1$ Fc region expression vector. Each HCH2 region can be composed of the hinge and CH$_2$ domain from an Ig such as IgG$_1$, which encompasses the region that can bind FcγR and complement. In some embodiments, to prevent inter-chain disulfide bond formation between the HCH2 region of the polymer, hinge region cysteines of the HCH2 monomer unit were mutated to serines. These mutations can leave intact those hinge residues that interact with FcR and complement. The hinge within the Fc vector was not mutated thus retaining the dimeric structure of IgG. Several unique restriction sites on the 5' end can allow for the directional cloning of amino-terminal domains into the polymer expression constructs.

In some embodiments of the invention, it is not necessary for the entirety of the HCH2 region to be employed in making the HCH2 monomer. As described above, the entire human IgG1 HCH2 encompasses amino acid residues 216 to 340 of the human IgG1 H chain (Eu numbering), with the hinge region spaning residues 216 to 237 and the CH2 domain encompassing residues 238 to 340. The interactions between IgG and Fc receptors have been analyzed in biochemical and structural studies using wild type and mutated Fc. One consensus indicates that some regions for binding to Fc receptors are located in the part of the hinge region closest to the CH2 domain and in the amino-terminus of the CH2 domain that is adjacent to the hinge, including for example residues 233-239 (Glu-Leu-Leu-Gly-Gly-Pro-Ser). Mutations within this region can result in altered binding to Fc receptors. This region appears to be responsible for some of the direct interactions with Fc receptors. Further into the CH2 domain, and away from the hinge, are other residues that may, at least in some contexts, contribute to Fc receptor binding, including for example, Pro-329 which appears involved in direct contact with the Fc receptor and Asn-297 which appears to be the sole site for N-linked glycosylation within the Fc region. The presence of carbohydrate at this residue may contribute to the binding to Fc receptors. Peptides spanning residues 233-239 of IgG1 Fc may bind to FcγRIII poorly.

In the examples presented below the HCH2 polymers were constructed using the human IgG1 HCH2 region that encompasses amino acid residues 216 to 340 of the human IgG1 H chain. This region contains the sequences that may contribute to Fc receptor binding as well as additional flanking residues. The flanking residues provide structural stability and spacing between the HCH2 regions. In some embodiments it can be advantageous to construct HCH2 polymers comprised of fragments within the HCH2 region instead of the entire HCH2 region. This may be done for example to reduce the size of the HCH2 monomer and hence the HCH2 polymer. One way that this could be achieved is through the deletion of flanking residues on either side of the region that has been identified with Fc receptor binding. For instance the hinge could be truncated to span residues 233 to 237 instead of residues 216 to 237 as used in the examples presented herein. Similar considerations apply to the CH2 region that spans residues 238-340 and to the hinge and CH2 regions of other Ig's including IgA, IgD, IgG2, IgG3, IgG4, and IgE. Other embodiments include different configurations of portions of HCH2 regions.

The HCH2 polymers can bind to low affinity FcR. In some instances the HCH2 polymers can bind the high affinity FcR receptors, for instance the FcγRI receptor. This is a natural consequence of the high binding affinity of the high affinity FcR receptors for the HCH2 region.

In some instances it can be advantageous to construct HCH2 polymers that bind all forms of the low affinity FcγR receptors such as, for example, FcγRIIa, FcγRIIb, FcγRIIc, FcγRIIIa, and FcγRIIIb. In other embodiments the number and spacing of HCH2 monomers comprising the polymer are varied to increase the binding to one type of FcR receptor or conversely to decrease binding to another type of FcR receptor. In yet other embodiments alterations to the HCH2 monomer can be made to increase specificity of the polymer for one type of FcγR receptor or to decrease specific binding to another type of FcγR receptor. Such alterations are achieved by mutating certain amino acid residues within the HCH2 sequence to other amino acid residues. The choice of residues to mutate within the HCH2 unit can be informed by choice of target receptor specificity. In other embodiments the specific binding of the HCH2 polymers to different FcγR receptors can be enhanced by the presence of and type of glycosylation of the HCH2 polymer. Choice of expression system in which to produce the HCH2 polymers in part determines the extent and type of glycosylation.

In the examples presented herein the HCH2 polymers were constructed using DNA sequences from human IgG1. In some instances it can be advantageous to construct HCH2 polymers comprised solely of human sequences to use as immunotherapeutic agents in humans. However in some embodiments the polymers are assembled from sequences of other Ig's including IgA, IgD, IgG, IgM, and IgE. In other embodiments the HCH2 polymers are assembled from sequences of more than one type of Ig, for example a polymer containing HCH2 monomers derived from IgG sequences are linked to HCH2 monomers derived from IgE sequences. In other embodiments the HCH2 polymers are comprised of non-human sequences. The choice of sequences can be determined by the target receptor and host identity (human or non-human). In yet other embodiments the hinge region cysteines are mutated to amino acid residues other than serine. In some embodiments the HCH2 monomer may be altered or mutated to bind complement components and not to bind to FcR. In other embodiments the HCH2 monomer may be altered or mutated to bind FcR and to not bind complement.

In some examples presented herein the HCH2 polymers were constructed using DNA sequences from human IgG1. The expressed proteins have been evaluated for their interactions with low affinity FcγR receptors. However in some embodiments the HCH2 polymers are assembled from sequences of other Ig's including IgA, IgD, IgG, IgM, and IgE and these polymers may bind to and interact with the FcR for other Ig's including FcαR, FcεR, FcμR, FcδR, and FcRn. In other embodiments the polymers are assembled from sequences of more than one type of Ig, for example a polymer protein containing HCH2 units derived from IgG sequences and IgE sequences will interact and bind with the FcR for more than one type of Ig.

In the examples presented herein the HCH2 polymers are constructed from HCH2 monomers consisting of full length HCH2 regions. In some embodiments it may be advantageous to construct HCH2 polymers that contain HCH2 monomers that are smaller than full length HCH2 regions. HCH2 polymers derived from a smaller HCH2 monomer would have a smaller size and mass and yet still retain the ability to effectively bind to and activate FcR or complement. The reduction in the size of the HCH2 monomer is achieved by the removal of sequences that have diminished involvement in the binding to FcR or complement. In some embodiments, the identities of these sequences are known, as are the methods for their removal from the HCH2 monomer unit. The removal of these sequences could maintain the desired binding but yield a polymer of smaller mass.

Recombinant HCH2 polymer constructs can mimic the biological activity and functions of immune complexes (ICs), of aggregated IgG (AIG), and of aggregated Fc. The use of recombinant HCH2 polymer construct can offer several advantages over AIG or Fc aggregates. The number and construction of HCH2 monomers can be altered to hone interaction with FcR's. Aggregates are by nature heterogeneous with considerable variation between batches whereas inventive polypeptides are precisely defined.

The receptors can be specifically activated with constructs containing different numbers of HCH2 monomers. As shown herein, the number of repeating HCH2 monomers available to bind receptor can influence cell function. Cell function can be changed with insertion of additional HCH2 monomers. The constructs of the present invention allow for the measurement of change in receptor function based on IC size. The number of repeating HCH2 monomers included within the polymer construct is variable and can be selected to optimize biological activity. In one embodiment the HCH2 polymers are assembled as disulfide-linked homodimers. In some embodiments the HCH2 polymers are assembled as monomers (e.g., a single chain polypeptide of HCH2 monomers), or hetero- or homo-multimers, and particularly as dimers, tetramers, and pentamers.

A nonlimiting list of proteins or protein fragments are found throughout the application and include, for example, ligand-binding domains, extracellular domains of receptors, enzymes, adhesion molecules, cytokines, peptide hormones, immunoglobulin fragments (Fab'), ligands, antigens, and fragments thereof. The site of the fusion of the protein or protein fragment connecting it to the linker or HCH2 polymer may be selected to optimize biological activity, stability, secretion, avidity, and binding specificity.

HCH2 polymers using IgG1 were designed using sequence data from the human IgG1 constant region gene as a guide (accession # Z17370). Several amino terminal domains have been expressed fused to the HCH2 polymers: the extracellular domain of human CD8α (accession # M12824), domain I of human serum albumin (accession # V00494), murine fatty acid binding protein 7 (accession # BC057090), human fatty acid binding protein (accession # BC012299), the Hc, HcN, HcC fragments of Botulinum neurotoxin subtype A as well as antigen portions and combinations of PLP and MBP. For some uses it may be advantageous to construct HCH2 polymers composed of the HCH2 polymer region unfused to additional protein domains or Fc or framework sequences.

In certain embodiments, the inventive polypeptides are produced by the insertion of the HCH2 polymeric region into an existing antibody sequence or the sequence of a recombinant protein. This process can be advantageous because of its simplicity. The HCH2 polymeric region is a discrete, modular DNA element designed for easy transfer from one cDNA construct to another. A modular DNA element is sometimes referred to as a 'cloning cassette.' The HCH2 polymeric region can be used as a cloning cassette and simply spliced into the existing cDNA for any protein, thus removing several steps from the formation process. In certain circumstances the precise site of insertion within a protein sequence can be determined by experimentation. Using the approach presented in this application, existing monoclonal antibodies and recombinant immunoglobulin fusion proteins can be modified through the addition of the HCH2 polymer region.

Of course, any of the mentioned polypeptides (e.g., those specifically or generally described herein) that are used to construct the inventive polypeptide or parts or portions thereof, can be made from polypeptides that are substantially similar (as defined herein) to the mentioned polypeptides.

The inventive polypeptide may be an ingredient or component of a composition, including, for example, a vaccine, emulsion, solution, pill, or any other liquid or solid composition that may be administered to any organism including, for example, plant, animal, mammal, mouse or human. The inventive polypeptide may be glycosylated or free from glycosylation.

In some embodiments the invention includes methods for producing an inventive polypeptide comprising (1) preparing a vector comprising the nucleic acid sequence encoding the polypeptide; (2) transfecting a host cell with the vector; (3) culturing the host cell to provide expression; and (4) recovering the polypeptide.

The vector can be prepared by any known method, including but not limited to cDNA obtained from reverse transcription, de novo gene synthesis, or obtaining a cDNA template from government or commercial sources.

For example, one can isolate RNA from a cell that expresses the immunoglobulin heavy chain. The RNA can then be used to produce a cDNA using reverse transcription. An example of an expressing cell would be a cell line expressing an antibody of the Ig class of interest. Many monoclonal antibodies are expressed in SP0 mouse myeloma cells. Another example is a myeloma cell line of any species that has aberrant expression of Ig heavy chains. ARH-77 (ATCC #: CRL-162) is an example of a human myeloma cell line that produces IgG1 heavy chains.

In de novo gene synthesis, cDNA sequences can be built up from smaller DNA sequences, such as oligonucleotides. The advantage of de novo synthesis is that it can provide complete control over the design of the sequences employed to construct the cDNA. This strategy can permit the removal of unwanted restriction sites while introducing others that are more desirable. The codons used in the wild-type gene can be altered to remove a codon bias and thereby improve yields of the expressed protein from the cell of choice.

A government source of cDNA template includes obtaining a cDNA clone for the proper Ig type from the IMAGE clone consortium (<<http://image.llnl.gov/>>). The IMAGE consortium or Integrated Molecular Analysis of Genomes and their Expression Consortium, serves as a repository for mammalian cDNAs for expressed genes. The IMAGE consortium has a full-length cDNA clone for nearly every human and mouse gene. In addition to these government sources, commercial sources such as OpenBiosystems are available.

Once the vector is prepared, it can be amplified by any known method including, for example, PCR.

Suitable cells for transfecting and culturing include, but are not limited to insect cells (such as, SF9 cells), mammalian cells (such as, human embryonic kidney cells, HEK 293 cells).

There are numerous resources that provide details and alternative means for the procedures that can be incorporated or used to make the inventive polypeptide. These include, for example (1) Sambrook, J., Fritsch, E. F., and Maniatis, T. (1989) Molecular Cloning: A Laboratory Manual, Vol. 3, p. 16.66, Cold Spring Harbor Laboratory, Cold Spring Harbor, N.Y.; (2) Methods in Enzymology, Vol 216, pp 3-689, 1992, Recombinant DNA Part G; (3) Methods in Enzymology, Vol 218, pp 3-806, 1993, Recombinant DNA Part I; and (4) Current Protocols in Molecular Biology found at <<http://mrw.interscience.wiley.com/emrw/0471-142727/home/archive.htm#Core>>

C. Antigens and Vaccines

Certain embodiments of the present invention involve the use of polypeptides disclosed herein to immunize subjects or as vaccines. As used herein, "immunization" or "vaccination" means increasing or activating an immune response against an antigen. It does not require elimination or eradication of a condition but rather contemplates the clinically favorable enhancement of an immune response toward an antigen. The vaccine may be a prophylactic vaccine or a therapeutic vaccine. A prophylactic vaccine comprises one or more epitopes associated with a disorder for which the individual may be at risk (e.g., Botulinum Neurotoxin antigens as a vaccine for prevention of Botulinum intoxication). Therapeutic vaccines comprise one or more epitopes associated with a particular disorder affecting the individual, such as tumor associated antigens in cancer patients.

As used herein, "vaccine" means an organism or material that contains an antigen in an innocuous form. The vaccine is designed to trigger an immunoprotective response. The vaccine may be recombinant or non-recombinant. When inoculated into a non-immune host, the vaccine will provoke active immunity to the organism or material, but will not cause disease. Vaccines may take the form, for example, of a toxoid, which is defined as a toxin that has been detoxified but that still retains its major immunogenic determinants; or a killed organism, such as typhoid, cholera and poliomyelitis; or attenuated organisms, that are the live, but non-virulent, forms of pathogens, or it may be antigen encoded by such organism, or it may be a live tumor cell or an antigen present on a tumor cell.

"Epitope" refers to an antigenic determinant of a peptide, polypeptide, or protein; an epitope comprises three or more amino acids in a spatial conformation unique to the epitope. Generally, an epitope consists of at least 5 such amino acids and more usually consists of at least 8 to 10 amino acids. Methods of determining spatial conformation of amino acids include, for example, x-ray crystallography and 2-dimensional nuclear magnetic resonance. Antibodies that recognize the same epitope can be identified in a simple immunoassay showing the ability of one antibody to block the binding of another antibody to a target antigen.

Certain embodiments of the present invention pertain to methods of inducing an immune response to an antigen in a subject. The term "antigen" means a substance that is recognized and bound specifically by an antibody or by a T cell antigen receptor. Antigens can include polypeptides, peptides, proteins, glycoproteins, polysaccharides, complex carbohydrates, sugars, gangliosides, lipids and phospholipids, fragments thereof, portions thereof and combinations thereof. The antigens can be those found in nature or can be synthetic. Antigens can elicit an antibody response specific for the antigen. Haptens are included within the scope of "antigen." A hapten is a low molecular weight compound that is not immunogenic by itself but is rendered immunogenic when conjugated with an immunogenic molecule containing antigenic determinants. Small molecules may need to be haptenized in order to be rendered antigenic. In some embodiments, antigens of the present invention include peptides and polypeptides. In this regard, the immunogenic polypeptides set forth herein include an antigen polypeptide. Antigen polypeptides that may be used in the immunogenic polypeptides of the present methods include antigens from an animal, a plant, a bacteria, a protozoan, a parasite, a virus, fragments thereof or a combination thereof.

An antigen polypeptide is an amino acid sequence that under appropriate conditions results in an immune response in a subject. The immune response may be an antibody response. For example, the antibody response can be measured as an increase in antibody production, as measured by any number of techniques (e.g., ELISA). The immune response may also be a T cell response, such as increased antigen presentation to T cells, or increased proliferation of T cells.

The antigen polypeptide may be any polypeptide derived from a virus. For example, the polypeptide may be derived from adenoviridiae (e.g., mastadenovirus and aviadenovirus), herpesviridae (e.g., herpes simplex virus 1, herpes simplex virus 2, Epstein-Barr virus, herpes simplex virus 5, and herpes simplex virus 6), leviviridae (e.g., levivirus, enterobacteria phase MS2, allolevirus), poxyiridae (e.g., chordopoxyirinae, parapoxvirus, avipoxvirus, capripoxvirus, leporipoxvirus, suipoxvirus, molluscipoxvirus, and entomopoxyirinae), papovaviridae (e.g., polyomavirus and papillomavirus), paramyxoviridae (e.g., paramyxovirus, parainfluenza virus 1, mobillivirus (e.g., measles virus), rubulavirus (e.g., mumps virus), pneumonoviridae (e.g., pneumovirus, human respiratory syncytial virus), and metapneumovirus (e.g., avian pneumovirus and human metapneumovirus), picornaviridae (e.g., enterovirus, rhinovirus, hepatovirus (e.g., human hepatitis A virus), cardiovirus, and apthovirus, reoviridae (e.g., orthoreovirus, orbivirus, rotavirus, cypovirus, fijivirus, phytoreovirus, and oryzavirus), retroviridae (e.g., mammalian type B retroviruses, mammalian type C retroviruses, avian type C retroviruses, type D retrovirus group, BLV-HTLV retroviruses, lentivirus (e.g. human immunodeficiency virus 1 and human immunodeficiency virus 2), spumavirus), flaviviridae (e.g., hepatitis C virus), hepadnaviridae (e.g., hepatitis B virus), togaviridae (e.g., alphavirus, e.g., sindbis virus) and rubivirus (e.g., rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, lassa virus), coronaviridae (e.g., coronavirus and torovirus), influenza virus hemagglutinin (Genbank Accession No. J02132), human respiratory syncytial virus G glycoprotein (Genbank Accession No. Z33429), core protein, matrix protein or any other protein of Dengue virus (Genbank Accession No. M19197), measles virus hemagglutinin (Genbank Accession No. M81899), herpes simplex virus type 2 glycoprotein gB (Genbank Accession No. M14923), poliovirus I VP1, envelope glycoproteins of HIV I, hepatitis B surface antigen, diptheria toxin, *streptococcus* 24M epitope, gonococcal pilin, pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulina hydrodysenteriae protective antigen, bovine viral diarrhea glycoprotein 55, Newcastle disease virus hemagglutinin-neuraminidase, swine flu hemagglutinin, swine flu neuraminidase, foot and mouth disease virus, hog cholera virus, swine influenza virus, African swine fever virus, *Mycoplasma* hyopneumoniae, infectious bovine rhinotracheitis virus (e.g., infectious bovine rhinotracheitis virus glycoprotein E or glycoprotein G), infectious laryngotracheitis virus (e.g., infectious laryngotracheitis virus glycoprotein G or glycoprotein I), a glycoprotein of La Crosse virus, neonatal calf diarrhea virus, Venezuelan equine encephalomyelitis virus, punta toro virus, murine leukemia virus, mouse mammary tumor virus, hepatitis B virus core protein or hepatitis B virus surface antigen or a fragment or derivative thereof, antigen of equine influenza virus or equine herpesvirus (e.g., equine influenza virus type A/Alaska 91 neuraminidase, equine influenza virus type A/Miami 63 neuraminidase, equine influenza virus type A/Kentucky 81 neuraminidase equine herpesvirus type 1 glycoprotein B, and equine herpesvirus type 1 glycoprotein D, antigen of bovine respiratory syncytial virus or bovine parainfluenza virus (e.g., bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase), bovine viral diarrhea virus glycoprotein 48 or glycoprotein 53, Cercopithecine herpesvirus (Herpes B virus), *Coccidioides* posadasii, Crimean-Congo haemorrhagic fever virus, Ebola Viruses, Lassa fever virus, Marburg virus, Monkeypox virus, a reconstructed replication competent forms of the 1918 pandemic influenza virus containing any portion of the coding regions of all eight gene segments (Reconstructed 1918 Influenza virus), *Rickettsia prowazekii, Rickettsia rickettsii*, a South American haemorrhagic fever virus, tick-borne encephalitis complex (flavi) viruses, Central European tick-borne encephalitis, Far Eastern tick-borne encephalitis, Variola major virus (Smallpox virus), Variola minor virus (Alastrim), *Yersinia pestis, Bacilius anthracis*, a Botulinum neurotoxin producing species of *Clostridium, Brucella abortus, Brucella melitensis, Brucella suis, Burkholderia mallei* (formerly *Pseudomonas mallei*), *Burkholderia mallei* (formerly *Pseudomonas mallei*), *Burkholderia pseudomallei* (formerly *Pseudomonas pseudomallei*), *Coccidiodes immitis, Coxiella burnetii, Eastern Equine Encephalitis virus, Francisella tularensis*, Hendra virus, Nipah Virus, Rift Valley fever virus, Venezuelan Equine Encephalitis virus, African horse sickness virus, African swine fever virus, Akabane virus, Avian influenza virus, Bluetongue virus, Camel pox virus, Classical swine fever virus, Foot-and-mouth disease virus, Goat pox virus, Japanese encephalitis virus, Lumpy skin disease virus, Malignant catarrhal fever virus, Menangle virus, Mycoplasma capricolum, Mycoplasma mycoides, Newcastle disease virus, Peste des petits ruminants virus, Rinderpest virus, Sheep pox virus, Swine vesicular disease virus, Vesicular stomatitis virus, *bacillus anthracis*, arenavirus, *Brucella* sp., *Burkholderia mallei, Burkholeria pseuomalei, chlamydia psittaci, vibrio cholerae, Coxiella burnetii*, ebola virus, *E. coli, clostridium perfringens, Salmonella* sp., *Shigella* sp., or a variant thereof.

Antigen polypeptides useful in the present invention may also be a cancer antigen or a tumor antigen. Any cancer or tumor antigen may be used in accordance with the immunogenic compositions of the invention including, but not limited to, KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen, differentiation antigen such as human lung carcinoma antigen L6, L20, antigens of fibrosarcoma, human leukemia T cell antigen-Gp37, neoglycoprotein, sphingolipids, breast cancer antigen such as EGFR, EGFRvIII, FABP7, doublecortin, brevican, HER2 antigen, polymorphic epithelial mucin (PEM), malignant human lymphocyte antigen-APO-1, differentiation antigen such as I antigen found in fetal erythrocytes, primary endoderm, I antigen found in adult erythrocytes, preimplantation embryos, I (Ma) found in gastric adenocarcinomas, M18, M39 found in breast epithelium, SSEA-1 found in myeloid cells, VEP8, VEP9, Myl, VIM-D5, $D_{156-22}$ found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 found in Adenocarcinoma, NS-10 found in adenocarcinomas, CO-43, G49 found in EGF receptor of A431 cells, MH2 found in colonic adenocarcinoma, 19.9 found in colon cancer, gastric cancer mucins, $T_{5A7}$ found in myeloid cells, $R_{24}$ found in melanoma, 4.2, $G_D3$, D1.1, OFA-1, $G_M2$, OFA-2, $G_D2$, and M1:22:25:8 found in embryonal carcinoma cells, SSEA-3 and SSEA-4 found in 4 to 8-cell stage embryos, a T cell receptor derived peptide from a Cutaneous T cell Lymphoma, and variants thereof.

Antigen polypeptides useful in the present invention may also be an autoantigen. Autoantigens known to be associated with autoimmune disease have been described. Included are myelin proteins associated with demyelinating diseases, e.g. multiple sclerosis and experimental autoimmune encephalomyelitis; collagens and rheumatoid arthritis; acetylcholine receptor with myasthenia gravis; insulin, proinsulin, glutamic acid decarboxylase 65 (GAD65), islet cell antigen (ICA512; ICA12) with insulin dependent diabetes. Disease associated myelin proteins include myelin basic protein (MBP), proteolipid protein (PLP), myelin-associated glycoprotein (MAG) and myelin oligodendrocyte glycoprotein (MOG).

In some embodiments, the antigen polypeptide can be, but is not limited to, abrin, a conotoxin, diacetoxyscirpenol, ricin, saxitoxin, a Shiga-like ribosome inactivating protein, flexal, guanarito, junin, machupo, sabia, tetrodotoxin, a Botulinum neurotoxin, Clostridium perfringens epsilon toxin, a Shigatoxin, Staphylococcal enterotoxin, T-2 toxin, Bovine spongiform encephalopathy agent, epsilon toxin, ricin toxin, Staphylococcal enterotoxin B, or a variant thereof.

In some embodiments, the antigen polypeptide is administered with the intent of inducing an immune response. Depending on the intended mode of administration, the compounds of the present invention can be in various pharmaceutical compositions. The compositions will include a unit dose of the selected polypeptide in combination with a pharmaceutically acceptable carrier and, in addition, can include other medicinal agents, pharmaceutical agents, carriers, adjuvants, diluents, and excipients. “Pharmaceutically acceptable” means a material that is not biologically or otherwise undesirable, i.e., the material can be administered to an individual along with the fusion protein or other composition without causing any undesirable biological effects or interacting in a deleterious manner with any of the other components of the pharmaceutical composition in which it is contained.

Any method of preparation of vaccines and immunizing agents can be used, as exemplified by U.S. Pat. Nos. 4,608,251; 4,601,903; 4,599,231; 4,599,230; 4,596,792; and 4,578,770. Typically, such vaccines are prepared as injectables either as liquid solutions or suspensions; solid forms suitable for solution in, or suspension in, liquid prior to injection may also be prepared. The preparation may also be emulsified. In addition, if desired, the vaccine may contain minor amounts of auxiliary substances such as wetting or emulsifying agents, pH buffering agents, or adjuvants that enhance the effectiveness of the vaccines.

Examples of physiologically acceptable carriers include saline solutions such as normal saline, Ringer’s solution, PBS (phosphate-buffered saline), and generally mixtures of various salts including potassium and phosphate salts with or without sugar additives such as glucose. The active immunogenic ingredient is often mixed with excipients that are pharmaceutically acceptable and compatible with the active ingredient. Suitable excipients are, for example, water, saline, dextrose, glycerol, ethanol, or the like, and combinations thereof. Nontoxic auxiliary substances, such as wetting agents, buffers, or emulsifiers may also be added to the composition. Oral formulations include such normally employed excipients as, for example, pharmaceutical grades of mannitol, lactose, starch, magnesium stearate, sodium saccharine, cellulose, magnesium carbonate, and the like. In one embodiment of the invention, adjuvants are not required for immunization.

Parenteral administration, if used, is generally characterized by injection. Sterile injectables can be prepared in conventional forms, either as liquid solutions or suspensions, solid forms suitable for solution or suspension in liquid prior to injection, or as emulsions.

The vaccine compositions set forth herein may comprise an adjuvant or a carrier. Adjuvants are any substance whose admixture into the vaccine composition increases or otherwise modifies the immune response to an antigen.

Adjuvants can include but are not limited to $AlK(SO_4)_2$, $AlNa(SO_4)_2$, $AlNH(SO_4)_4$, silica, alum, $Al(OH)_3$, $Ca_3(PO_4)_2$, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyl-L-alanyl-D-isoglutaminyl-L-alanine-2-(1'2'-dipalmitoyl-s-n-glycero-3-hydroxphosphoryloxy)-ethylamine (CGP 19835A, also referred to as MTP-PE), RIBI (MPL+TDM+CWS) in a 2% squalene/Tween-80® emulsion, lipopolysaccharides and its various derivatives, including lipid A, Freund’s Complete Adjuvant (FCA), Freund’s Incomplete Adjuvants, Merck Adjuvant 65, polynucleotides (for example, poly IC and poly AU acids), wax D from *Mycobacterium*, tuberculosis, substances found in *Corynebacterium parvum*, *Bordetella pertussis*, and members of the genus *Brucella*, liposomes or other lipid emulsions, Titermax, ISCOMS, Quil A, ALUN (see U.S. Pat. Nos. 58,767 and 5,554,372), Lipid A derivatives, choleratoxin derivatives, HSP derivatives, LPS derivatives, synthetic peptide matrixes or GMDP, Interleukin 1, Interleukin 2, Montanide ISA-51 and QS-21.

Additional adjuvants or compounds that may be used to modify or stimulate the immune response include ligands for Toll-like receptors (TLRs). In mammals, TLRs are a family of receptors expressed on DCs that recognize and respond to molecular patterns associated with microbial pathogens. Several TLR ligands have been intensively investigated as vaccine adjuvants. Bacterial lipopolysaccharide (LPS) is the TLR4 ligand and its detoxified variant mono-phosphoryl lipid A (MPL) is an approved adjuvant for use in humans. TLR5 is expressed on monocytes and DCs and responds to flagellin whereas TLR9 recognizes bacterial DNA containing CpG motifs. Oligonucleotides (OLGs) containing CpG motifs are potent ligands for, and agonists of, TLR9 and have been intensively investigated for their adjuvant properties.

Other agents that stimulate the immune response can also be administered to the subject. For example, other cytokines are also useful in vaccination protocols as a result of their lymphocyte regulatory properties. Many other cytokines useful for such purposes are known, including interleukin-12 (IL-12) that has been shown to enhance the protective effects of vaccines, GM-CSF and IL-18. Thus cytokines can be administered in conjunction with antigens and adjuvants to increase the immune response to the antigens.

A vaccine composition according to the present invention may comprise more than one different adjuvant. Furthermore, the invention encompasses a therapeutic composition further comprising any adjuvant substance including any of the above or combinations thereof. It is also contemplated that ML-IAP, or one or more fragments thereof, and the adjuvant can be administered separately in any appropriate sequence.

In certain embodiments, the vaccine composition includes a carrier. The carrier may be any suitable carrier, for example a protein or an antigen presenting cell. Examples include serum proteins such as transferrin, bovine serum albumin, human serum albumin, thyroglobulin or ovalbumin, immunoglobulins, or hormones, such as insulin or palmitic acid. For immunization of humans, the carrier should be a physiologically acceptable carrier acceptable to humans and safe. Tetanus toxoid or diptheria toxoid are suitable carriers in one embodiment of the invention. Alternatively, the carrier may be dextrans for example sepharose.

The timing of administration of the vaccine and the number of doses required for immunization can be determined from standard vaccine administration protocols. In some instances, a vaccine composition will be administered in two doses. The first dose will be administered at the elected date and a second dose will follow at one month from the first dose. A third dose may be administered if necessary, and desired time intervals for delivery of multiple doses of a particular antigen containing HCH2 polymer can be determined. In another embodiment, the antigen containing HCH2 polymer may be given as a single dose.

For each recipient, the total vaccine amount necessary can be deduced from protocols for immunization with other vaccines. The exact amount of antigen-HCH2 polymer required can vary from subject to subject, depending on the species, age, weight and general condition of the subject, the particular fusion protein used, its mode of administration, and the like. Generally, dosage will approximate that which is typical for the administration of other vaccines, and may be in the range of about 10 ng/kg to 1 mg/kg.

Any known methods for the preparation of mixtures or emulsions of polypeptides disclosed herein and adjuvant can be used (see, e.g. Plotkin and Orenstein, eds, Vaccines, 4th Ed., 2004).

Immunizations against toxins and viral infection can be tested using in vitro assays and standard animal models. For example a mouse can be immunized with a viral antigen polypeptide expressed as a fusion protein with HCH2 polymers and delivered by the methods detailed herein. After the appropriate period of time to allow immunity to develop against the antigen, for example two weeks, a blood sample is tested to determine the level of antibodies, termed the antibody titer, using ELISA. In some instances the mouse is immunized and, after the appropriate period of time, challenged with the virus to determine if protective immunity against the virus has been achieved. Using these techniques the proper combination of antigen, adjuvant, and other vaccine components can be optimized to boost the immune response. Testing in humans can be contemplated after efficacy is demonstrated in animal models. Any known methods for immunization, including formulation of a vaccine composition and selection of doses, route of administration and the schedule of administration (e.g. primary and one or more booster doses) can be used (e.g. see Vaccines: From concept to clinic, Paoletti and McInnes, eds, CRC Press, 1999).

Generally accepted animal models can be used for testing of immunization against cancer using a tumor and cancer antigen polypeptides. For example, cancer cells (human or murine) can be introduced into a mouse to create a tumor, and one or more cancer associated antigens can be delivered by the methods described herein. The effect on the cancer cells (e.g., reduction of tumor size) can be assessed as a measure of the effectiveness of the immunization. Of course, immunization can include one or more adjuvants or cytokines to boost the immune response. The tests also can be performed in humans, where the end point is to test for the presence of enhanced levels of circulating cytotoxic T lymphocytes against cells bearing the antigen, to test for levels of circulating antibodies against the antigen, to test for the presence of cells expressing the antigen and so forth.

In some embodiments, the vaccine composition includes antigen presenting cells. The antigen presenting cell can be a dendritic cell (DC). DC may be cultivated ex vivo or derived in culture from peripheral blood progenitor cells (PBPC) and peripheral blood stem cells (PBSC). The dendritic cells may be prepared and used in therapeutic procedures according to any suitable protocol. Different protocols may be adopted to use with patients with different HLA types and different diseases. Incubation of cultured dendritic cells with HCH2 polymers of the invention is envisaged as one means of loading dendritic cells with antigen for subsequent transfer into hosts.

For any of the ex vivo methods of the invention, peripheral blood progenitor cells (PBPC) and peripheral blood stem cells (PBSC) are collected using apheresis procedures known. Briefly, PBPC and PBSC can be collected using conventional devices, for example, a Haemonetics® Model V50 apheresis device (Haemonetics, Braintree, Mass.). Four-hour collections can be performed typically no more than five times weekly until, for example, approximately $6.5 \times 10^8$ mononuclear cells (MNC)/kg patient are collected. The cells are suspended in standard media and then centrifuged to remove red blood cells and neutrophils. Cells located at the interface between the two phases (also known in the art as the buffy coat) are withdrawn and resuspended in HBSS. The suspended cells are predominantly mononuclear and a substantial portion of the cell mixture are early stem cells. The stem cells obtained in this manner can be frozen, then stored in the vapor phase of liquid nitrogen. Ten percent dimethylsulfoxide can be used as a cryoprotectant. After all collections from the donor have been made, the stem cells are thawed and pooled. Aliquots containing stem cells, growth medium, such as McCoy's 5A medium, 0.3% agar, and expansion factors (e.g. GM-CSF, IL-3, IL-4, flt3-ligand), are cultured and expanded at 37° C. in 5% $CO_2$ in fully humidified air for 14 days.

D. The Fc Receptors

There are three classes of Fc receptor (Gessner et al., 1998; Raghavan et al., 1996). FcγRI (CD64) binds monomeric IgG with high affinity whereas AIG and IC bind preferentially to FcγRII (CD32) and FcγRIII (CD 16), the low affinity receptors for Fc. FcγRII and FcγRIII are closely related in the structure of their ligand-binding domains. In humans three separate genes, FcγRIIA, FcγRIIB, and FcγRIIC, two of which give rise to alternatively spliced variants, code for FcγRII. FcγRIIa delivers activating signals whereas FcγRIIb delivers inhibitory signals. The functional basis for the divergent signals arises from signaling motifs located within the cytoplasmic tails of the receptors. An immunoreceptor tyrosine-based inhibitor motif (ITIM) located in the cytoplasmic tail of the FcγRIIb is involved in negative receptor signaling. The ITIM motif is a unique feature of the FcγRIIb receptor as it is not apparently present in any other Fcγ receptor class. In contrast, an activatory immunoreceptor tyrosine-based activation motif or ITAM is located in the cytoplasmic tail of FcγRIIa. ITAM motifs transduce activating signals. They are also found in the FcR γ-chains, which are identical to the γ-chains of the high affinity IgE receptor (FcεRI). While FcγRIIa and FcγRIIb are widely expressed on myeloid cells and some T-cell subsets they are notably absent from NK cells.

Human FcγRIII is also present in multiple isoforms derived from two distinct genes (FcγRIIIA and FcγRIIIB). FcγRIIIb is unique in its attachment to the cell membrane via a glycosylphosphatidyl anchor. FcγRIIIb expression is restricted to neutrophils while FcγRIIIa is expressed by macrophages, and NK cells. FcγRIIIa is also expressed by some γ T-cell subsets and certain monocytes. FcγRIIIa requires the presence of the FcR γ-chain or the CD3ζ-chain for cell surface expression and signal transduction. The FcR γ-chain and the CD3ζ-chain are dimeric and possess ITAM motifs. FcγRIIIa forms a multimeric complex with these subunits and signaling is transduced through them. Thus, there is considerable FcγR receptor heterogeneity and diverse expression profiles.

AIG and IC have been used to target FcγRIIIa on immune cells, but as noted earlier production of defined AIG and IC was seen to be problematic. Assembly of complexes by physical or chemical methods is difficult to control with precision resulting in heterogeneity within complexes of similar molecular weight in addition to variations between preparations and changes in composition upon storage. Molecular cloning has been used in the present invention to create molecules that can mimic or approximate AIG and IC function with respect to their interactions with FcγR and which allow for the inclusion and targeting of a second protein domain to cells expressing FcγR.

The binding sites for FcγRII and FcγRIII map to the hinge and proximal region of the CH2 domain of IgG, the same region originally identified for FcγRI (Duncan et al., 1988; Morgan et al., 1995; Lund et al., 1991). White et al. (2001) describe the cloning and expression of linear polymers of the hinge and CH2 (HCH2) fused to the Fc region of $IgG_1$ and demonstrate their biological activity. Legge et al. (2000) have recently shown that an aggregated PLP1 immunoadhesin, unlike the monomeric form, moderates disease severity in experimental autoimmune encephalomyelitis, the rodent model for multiple sclerosis. This change is due to the dual functionality of the aggregated Fc and PLP moieties within the complex.

In the later phase of a primary immune response or in chronic responses, large ICS form. These complexes signal through the low affinity IgG receptors that recognize ICS or IgG aggregates preferentially. The low affinity receptors are of two classes FcγRII (CD32) and FcγRIII (CD16). FcγRIIb provides an inhibitory signal for secretion of cytokines that augment immunoglobulin secretion including IgG secretion. FcRIIIa (found on NK cells, monocytes and γγδ T cells) preferentially recognizes IgG1. One thrust of this invention is directed towards activation of FcγRIIIa.

The ability of FcγR to bind IgG and transmit a signal into the cell depends upon the FcγRs alleles expressed, upon glycosylation, and how the receptor is associated with the signaling subunit. In addition, glycosylation patterns differ between cell types and this too can affect ligand binding to FcγRIIIa. FcγRIIIa on NK cells is glycosylated with high mannose oligosaccharides, whereas monocyte/macrophage FcγRIIIa is not. Perhaps this imparts lower receptor affinity to monocyte/macrophage FcγRIIIa relative to NK cell FcγRIIIa, adding yet another level of modification to receptor function (Galon et al., 1997; Edberg et al., 1997). Thus, FcγR function is regulated at several levels, which can have an impact on ligand binding and receptor signaling.

Recently, the inventors have initiated studies into the potential immunomodulatory role of immune complexes (IC) in human autoimmune syndromes. Central to these studies are the interactions between IC and FcR. The inventors have used molecular cloning to create molecules that can mimic or approximate IC function with respect to their interactions with FcR and which allow for the inclusion and targeting of a second protein domain to cells expressing FcR. The strategy pursued is to express multiple linear copies of the region of the IgG framework that binds FcR. Expressing only those determinants necessary for FcR engagement and presenting them in a particularly favorable configuration results in novel proteins that are considerably more potent than IC. Thus recombinant IC mimetic proteins described herein will provide both a valuable tool for the examination of IC deposition and in the therapeutic targeting of FcR in autoimmune disorders.

E. Antigen Presentation to Antigen Presenting Cells (APC)

In another embodiment of the invention, the polypeptides include linked antigens. In one embodiment, the polypeptides of the invention are used to target an antigen to the cell to enhance the process of internalization and presentation of the antigen by these cells, and ultimately to stimulate an immune response. In another embodiment, the polypeptides of the invention specifically bind the antigen directly or bind to epitopes attached to the antigen, e.g., a cloned Fab' fragment covalently attached to the polymer by genetic or chemical means which recognizes the antigen or epitopes attached to the antigen, and targets the bound antigen to antigen presenting cells (APC) for internalization, processing, and presentation. In another embodiment, the antigen is linked to the polymers of the invention and at the same time binds a surface receptor of an antigen-presenting cell. In another embodiment the antigen is covalently attached to the polymers of the invention by genetic or chemical means.

More broadly, the polypeptides of this invention can be linked to a cell surface marker. A cell surface marker is a protein, carbohydrate, glycolipid, etc. but most commonly comprises a protein localized to the plasma membrane of a cell having a portion exposed to the extracellular region (e.g. an integral membrane protein or a transmembrane glycoprotein), such that the extracellular portion can be specifically bound by an antibody or other ligand. The term cell surface marker also refers to a polynucleotide sequence encoding such a cell surface protein. Numerous cell surface proteins can be used as cell surface markers, such as, for example, a CD (cluster of differentiation) antigen present on cells of hematopoietic lineage (CD2, CD4, CD8, CD21), Gamma-glutamyltranspeptidase, an adhesion protein (ICAM-1, ICAM-2, ELAM-1, VCAM-1), a hormone, a growth factor, a cytokine receptor, ion channels, and the membrane-bound form of an immunoglobulin chain.

1. Polypeptides that Contain HCH2 Polymers for use in Vaccines.

Traditional vaccines consist of killed or attenuated pathogenic organisms or their products administered to develop an immune response. Drawbacks to the traditional approach include unwanted harmful immune responses, inoculation with potentially infectious pathogens, and poor immune responses. Typically these vaccines require co-administration of potent adjuvants to elicit effective antibody responses. Vaccines can be made more effective by delivering those antigenic determinants that are most likely to confer protective immunity. Early attempts to develop peptide based vaccines resulted in poor immune responses due in part to an inefficient presentation of antigen by APCs.

APCs capture, internalize and present antigen. In addition they provide important costimulatory signals to T-cells. T-cells, thus activated, are capable of stimulating the production of antibody-forming B cells. Monocytes, especially macrophages and dendritic cells, function as APC. Macrophages express all three classes of FcγR constitutively whereas dendritic cells express FcγRI and FcγRII.

Dendritic cells (DCs) are highly specialized and are potent APCs for T-cells. As a result of this capacity DCs are often referred to as 'professional APCs.' DCs present antigen efficiently on both MHC I and MHC II resulting in the initiation of CD8+ and CD4+ responses respectively. DCs can prime naive T-cells. Subsequent to activation by DCs, T-cells can interact with other APC. DCs have a proliferative immature stage followed by terminal differentiation into a non-proliferative mature stage. Immature DCs express FcγRI and FcγRII, are capable of internalizing and presenting antigen, and synthesize large amounts of MHC II. In contrast mature DCs no longer express FcγRs, become fully active APCs, activate T-cells, and secrete large amounts of IL-12 (which spurs differentiation of T-cells). DCs are a more potent APC than macrophages though much less numerous.

There has been great interest in the enhancement of antigen presentation by targeting antigen to FcγR expressed on APCs. Some peptide vaccines have antigenic determinants grafted into the variable region of IgG. These 'antigenized-antibodies' increased the half-life of antigen and facilitated uptake of antigen by APCs via the FcγRI receptor (Zaghouani et al., 1993; Zanetti et al., 1992). Use of antigenized-antibodies have been shown to be more effective at priming antigen specific T-cell responses than peptide alone. Antigenized-antibodies have several limiting features: Since they are directed towards FcγRI alone, they can be effectively competed against by monomeric serum IgG. Secondly, the design of the molecule limits the size of the antigenizing determinant to a small peptide fragment.

More recently antigen has been expressed as a fusion protein with or chemically conjugated to monoclonal antibodies and Fab fragments directed against FcγRI and FcγRII (Liu et al., 1996b; Guyre et al., 1997). Using tetanus toxoid epitopes conjugated to anti-FcγRI monoclonal antibody, one group reported that peptides directed to FcγRI were 100 to 1000 fold more efficient than peptide alone in T-cell stimulation (Liu et al., 1996a). However, use of anti-FcγRI Fab' required chemical cross-linking to achieve maximal responses to antigen, thus implicating the low affinity IgG receptors (Keler et al., 2000). Disadvantages of this approach include the promiscuous binding of antigen-linked monoclonal antibody to FcγRI expressed on non-APCs. Monoclonal antibodies trigger effector functions poorly. Fab' fragments have the additional disadvantage of a short half-life in the circulation.

Attachment of antigen to the HCH2 polymers in the inventive polypeptides described herein for the purpose of targeting APCs has distinct advantages over existing strategies. The inventive polypeptides present antigen to low affinity receptors (FcγRII and FcγRIII), thus bypassing competition from monomeric serum IgG for binding to FcγRI. Additionally there is no need for chemical cross-linking as is necessary when using anti-FcγRI Fab'. The inventive polypeptides imitate immune complexes. Antigen presented in the context of an immune complex may be a particularly appropriate substrate for APCs. Antigen-linked HCH2 polymers efficiently trigger effector functions that augment the immune response.

2. The Inventive Polypeptide in Tolerance Induction.

Immunologic tolerance can be characterized by the selective lack of an immune response, including lack of a pathogenic immune response to a specific antigen even while leaving other responses of the immune system intact. Induction and maintenance of T cell unresponsiveness to a specific antigen may be achieved by several mechanisms that can be broadly summarized as: 1) clonal deletion; 2) anergy; and 3) suppression. Clonal deletion is a process of negative selection whereby T cells with high affinity for self-antigens are deleted in the thymus. Deletion is achieved by programmed cell death (apoptosis). This process of negative selection in the thymus is known as 'central tolerance.' Anergy represents a state of immune inactivation characterized by abolished proliferative and cytokine responses. It is induced in cells that previously responded to a given antigen and results in an unresponsive state upon re-stimulation with antigen. Since this mechanism acts upon mature T cells that have exited the thymus and reside in the peripheral compartments, this form of tolerance is termed 'peripheral tolerance.' Anergy is induced by any of a number of molecular events and need not be permanent: it can be reversed by certain cytokines. Three common anergy-inducive mechanisms are T cell receptor (TCR) stimulation without co-stimulatory signals, sub-optimal TCR stimulation even in the presence of co-stimulation, and the autocrine inhibitory actions of IL-10. Suppression of T cell function is a third mechanism by which T cell tolerance can be achieved. Suppression ensues when regulatory T cells are induced to exert "non-specific" suppressive effects on antigen-specific T cells in their vicinity. This microenvironmental effect is also referred to as 'bystander suppression.'

B cell tolerance involves concepts and mechanisms similar but not identical to those encountered in T cell tolerance. In mature B cells tolerance can be induced through a block in Ig-receptor signaling which results in impaired expression of the B7 costimulatory molecules.

Induction of tolerance to either self- or foreign-antigens provides an important therapeutic approach to the treatment of allergies, autoimmune disease and host vs. graft disease (transplant rejection). In addition, the therapeutic potential of many foreign biologically active agents is limited by their immunogenicity. Tolerance induction represents one approach for the control of immune responses directed against biologically active foreign agents, thus improving their therapeutic potential. In some instances the antigen to be tolerized is presented orally, intradermally, or intravenously. The source of antigen can be in the form of a peptide, a protein, or nucleic acid which can express a peptide or protein. The antigen is then internalized by antigen presenting cells (APC) and presented on the surface of the cell, most typically as a MHC I-antigen complex or as a MHC II-antigen complex.

The inventive polypeptides, which comprise the HCH2 polymers, have several advantageous aspects for use as vehicles for tolerance induction. Antigen(s) linked to the HCH2 polymers by chemical or genetic means are targeted to Fc receptors expressed on APC such as macrophages, B cells, and dendritic cells (DC). Fc-receptor-mediated internalization results in processing and presentation of antigen at the cell surface—the key first step in tolerance induction.

Macrophages and DC express Fc receptors for both IgG and IgE. HCH2 polymers are expressible which bind both classes of Fc receptor simultaneously—coaggregation of different Fc receptor classes may have advantages over targeting a single class of receptor. Ligation of FcRs induces secretion of IL10 from certain immune cells and, as already noted, IL10 induces anergy in T cells. As is observed for immune complexes, binding of inventive polypeptides to FcRs may induce a pattern of cytokine secretion that deviates T cell immune responses from a THI type response to a TH2 type response. TH2 type T cells favor the establishment and maintenance of immune tolerance. Therefore, antigens linked to the HCH2 polymers can promote tolerance induction by both the efficient presentation of antigen to APC and the simultaneous induction of mechanisms that favor establishment of immune tolerance.

F. Use of the Inventive Polypeptides as In Vivo and In Vitro Immunological Agents a. Inventive Polypeptide Example—Modification of Recombinant Monoclonal Antibodies by the Introduction of an HCH2 Polymer It is an embodiment of the current invention that recombinant monoclonal antibodies (mAb) can be modified by the introduction of one or more HCH2 units into the Fc region to create an HCH2 polymer of appropriate length within a monoclonal antibody. Monoclonal antibodies modified in this manner will retain their target specificity while acquiring improved or more selective effector function. HCH2 polymers greatly enhance Fc—FcR receptor interactions. More specifically HCH2 polymers of the current invention have greatly improved binding to and enhanced activation of FcγRIIIa receptors over that seen with the Fc portion of mAb in current therapeutic use. As enhanced interaction of mAB with FcγRIIIa has been documented to have therapeutic benefit in the treatment of malignancies. The inventors envisage modifying existing mAb with the introduction of an HCH2 polymer into the Fc region of the mAb. Monoclonal antibodies with this modification will have enhanced interaction with FcγRIIIa receptors.

Functional IgG genes, those that direct expression of a mAb, are composed of heavy and light chain genes segments. Light chain (L) genes consist of three exons, containing the hydrophobic leader sequence, the variable regions and the L constant region ($C_L$). Separating the exons are the intervening sequences or introns. Similarly, the variable region of a functional Ig heavy chain (H) gene has a separate exon for each of the leader sequence, the variable region, and H chain constant region (CH1). The H gene also contains the Fc region that is composed of separate exons for the hinge, the CH2 region and CH3 regions. Once again the exons are separated by introns. The expression of mAb in mammalian cells typically involves cloning both the H and L gene segments from functional Ig genes into either a single expression vector or separate expression vectors (one for L, one for H genes) that posses the Ig promoter region. Once subcloned the expression vectors possessing the L and H genes are transfected into an appropriate cell line for expression. The use of gene segments insures the presence of intronic sequences, which contain enhancer and other elements that collectively allow for high levels of Ig expression in B cells and myeloma cells. Ig expression systems utilizing the Ig promoter and intronic genetic elements limit protein expression to cells of lymphoid derivation however.

More recently, Ig expression systems have been developed that use viral promoters and enhancer combinations, such as CMV. The use of viral promoter/enhancer combinations permits strong expression in both lymphoid and non-lymphoid cells lines such as CHO and COS (Norderhaug, et al., 1997). Inclusion of the intronic enhancer from the Ig H gene also directs high level expression in lymphoid cells. Additionally, H and L gene segments are no longer necessary for efficient expression and can be replaced by their corresponding cDNA's (McLean, et al., 2000).

The introduction of HCH2 polymers into mAb can be achieved by any of several approaches. In one method, using known molecular cloning techniques, H chain gene segments within expression vectors are modified by the insertion of the HCH2 polymer cloning cassette into the 5' end of the hinge exon. The modified hinge exon now consists of the HCH2 polymer fused in frame to the hinge sequences. The vector containing the modified H gene is introduced in conjunction with an L gene into an appropriate cell line for mAb expression. Another method is to replace the Fc gene segment with a cDNA segment comprising a splice acceptor signal, the HCH2 polymer fused to an Ig Fc cDNA and a polyA signal. The modified H gene is then transferred into an Ig expression vector capable of directing Ig expression without Ig gene intronic sequences. The vector containing the modified H gene is introduced in conjunction with an L gene into an appropriate cell line for expression.

The insertion of HCH2 polymers into mAb expressed from cloned cDNA within expression vectors can also be achieved using similar techniques. For instance, the cDNA encoding the Fc region can be removed from the H chain cDNA and replaced with a DNA segment encoding the HCH2 polymer fused to an Fc cDNA. Conversely, the cDNA encoding the H chain leader, variable and CH1 region can be excised and transferred to vectors containing the HCH2 polymer region genetically fused to an Fc cDNA. Alternatively, the HCH2 polymer cassette can be introduced into the H chain cDNA at the appropriate site. This site would sometimes be the junction between the CH1 region and the hinge. Subsequently, the modified H chain cDNA is then transferred into an Ig expression vector capable of directing Ig expression without Ig gene intronic sequences. The vector containing the modified H chain cDNA is introduced in conjunction with an L chain expression vector into an appropriate cell line for expression.

While interaction with FcγRIIIa receptors is important for the efficacy of several mAb in clinical use, the methods of modification described above are general. In other embodiments of the inventive polypeptides, HCH2 polymers can be introduced into mAb to enhance specificity for other individual FcR receptors, classes of FcR receptors, as blocking reagents for FcR receptors, or for binding to complement factors.

G. Autoimmune Diseases

Autoimmune diseases are processes in which the immune system mounts an attack against body tissue components. This attack may be mediated by anti-tissue component antibodies produced by B lymphocytes or by cell-mediated tissue destructive processes mediated by T cells, by NK cells, and by monocytes/macrophages. In some autoimmune diseases several tissue damaging mechanisms may operate either concurrently or sequentially. The inventive polypeptides of the current invention can be used in the treatment of autoimmune diseases. They can be used to alter immunity and to deliver therapeutic agents to a delivery site in a patient where the therapeutic agent is effective.

The number of autoimmune diseases is considerable and some persons may have more than one autoimmune disease. Similarly, signs and symptoms may cover a wide spectrum and severity may also vary widely between afflicted individuals and over time. The reasons why some persons develop autoimmunity while others do not are imperfectly understood but certain recurring themes can be signaled. In many autoimmune processes there is a genetically determined propensity to develop disease. Among the genes that have been linked to propensity to develop autoimmunity are those of the major histocompatibility complex. In addition, environmental factors are thought to play a role. During embryonic development many of those immune system cells that are capable of reacting against self-components are eliminated but some remain so that essentially everyone is at least theoretically capable of mounting an autoimmune response. This observation implies that under normal circumstances potentially auto-aggressive cells are held in check by physiologic restraint mechanisms and that a contributor to the pathogenesis of autoimmunity is a failure of normal restraint mechanisms.

Examples of commonly encountered autoimmune disorders include but are not limited to: systemic lupus erythematosus, rheumatoid arthritis, type 1 diabetes, Guillain-Barré syndrome, other immune mediated neuropathies including chronic inflammatory demyelinating polyneuropathy, multiple sclerosis and other immune-mediated central nervous system demyelinating diseases, rheumatoid arthritis, Crohn's disease, ulcerative colitis, myasthenia gravis, scleroderma/systemic sclerosis, and dermatomyositis/polymyositis to name some of the more commonly encountered entities. Additional autoimmune diseases include acute glomerulonephritis, nephrotic syndrome, and idiopathic IgA nephropathy among autoimmune processes that affect the kidneys.

Examples of autoimmune processes that affect the formed elements of the blood are autoimmune aplastic anemia, autoimmune hemolytic anemia, and idiopathic thrombocytopenic purpura.

Autoimmune diseases that affect the endocrine organs include Addison's disease, idiopathic hypoparathyroidism, Grave's disease, Hashimoto's thyroiditis, lymphocytic hypophysitis, autoimmune oophoritis, and immunologic infertility in the male.

The liver may also be the target of autoimmune processes. Examples include autoimmune hepatitis, hepatitis C virus-associated autoimmunity, immunoallergic reaction drug-induced hepatitis, primary biliary cirrhosis, and primary sclerosing cholangitis.

Autoimmune processes of the intestinal tract include pernicious anemia, autoimmune gastritis, celiac disease, Crohn's disease, and ulcerative colitis.

Cutaneous autoimmune diseases include dermatitis herpetiformis, epidermolysis bullosa acquisita, alopecia totalis, alopecia greata, vitiligo, linear IgA dermatosis, pemphigus, pemphigoid, psoriasis, herpes gestationis, and cutaneous lupus including neonatal lupus erythematosus.

Additional autoimmune diseases with rheumatological features include CREST syndrome, ankylosing spondylitis, Behçet's disease, juvenile rheumatoid arthritis, Sjögren's syndrome, and eosinophilia-myalgia syndrome.

Autoimmune diseases can affect the heart. Examples include myocarditis and idiopathic dilated cardiomyopathy, rheumatic fever, Chaga's disease and possibly some components of atherosclerosis.

There can be an autoimmune component to inflammatory diseases of the blood vessels. Examples include giant cell arteritis, Kawasaki's disease, Henoch-Schonlein purpura, polyarteritis nodosa, Goodpasture's syndrome, immune complex vasculitis, Wegener's granulomatosis, Churg-Strauss syndrome, Takayasu arteritis, necrotizing vasculitis, and anti-phospholipid antibody syndrome.

Autoimmune diseases of the central and peripheral nervous systems can occur as a remote effect of malignant tumors. Rarely these same entities occur in the absence of a tumor. Examples include the Lambert-Eaton syndrome, paraneoplastic myelopathy, paraneoplastic cerebellar degeneration, limbic encephalitis, opsoclonus myoclonus, stiff man syndrome, paraneoplastic sensory neuropathy, the POEMS syndrome, dorsal root ganglionitis, and acute panautonomic neuropathy.

Autoimmune diseases may affect the visual system. Examples include Mooren's ulcer, uveitis, and Vogt-Koyanagi-Harada syndrome.

Other autoimmune processes, or ones in which autoimmunity may contribute to disability, include interstitial cystitis, diabetes insipidus, relapsing polychondritis, urticaria, reflex sympathetic dystrophy, and cochleolabyrinthitis.

The list of autoimmune processes given above, while extensive, is not intended to be exhaustive. Rather it is intended to document that autoimmunity is a wide-ranging clinical phenomenon.

1. Multiple Sclerosis

This disease is characterized by destruction of CNS myelin and of the axons which myelin ensheathes. The illness can begin with focal attacks of tissue destruction in the white matter of the CNS which cause loss of neuronal function and as one attack follows another progressively accumulating disability. After a time most multiple sclerosis patients experience a decline in the frequency of their attacks but this decline is accompanied by a shift in the natural history of the illness to a slow but inexorable worsening of their neurological disabilities. The switch from a relapsing-remitting course to a progressive one ultimately occurs in better than 80% of multiple sclerosis victims.

Multiple sclerosis is an inflammatory disease. Lymphocytes and macrophages move from the blood into the CNS and attack and destroy myelin and ultimately the myelin forming cells known as oligodendrocytes. The process is one of autoimmunity but the precise target within the CNS against which the immune response is directed remains unknown. There is a genetically determined predisposition to develop multiple sclerosis but there is compelling evidence that environmental factors have a role as well, though the nature of the environmental factors in cause remains unknown.

There have been advances in the treatment of multiple sclerosis in recent years. Five agents are approved for the treatment of MS. These are interferon beta1a, interferon Beta1b, glatiramer acetate, natalizumab, and novantrone. All five modulate immune responses in a manner that favorably alters the hitherto bleak natural history of MS. Unfortunately all five are only modestly effective and each has side effects that are often troublesome. The present invention offers the prospect of a more efficient and effective therapy for MS.

Experimental autoimmune encephalomyelitis (EAE) is a widely used animal model for MS and serves as a useful model for the study of autoimmune diseases. EAE is a disease of the central nervous system and may be induced in susceptible animals by immunization with neuroantigens. EAE may also be adoptively transferred from one animal to the next by the serial transfer of T cells reactive against encephalitogenic determinants of myelin proteins or by the injection of T cell clones reactive against encephalitogenic determinants of myelin proteins. Myelin proteins that may be targets of the autoreactive response include proteolipid apoprotein (PLP), myelin basic protein (MBP), and myelin oligodendrocyte protein (MOG). Depending on the type and strain of animal used, the mode of induction, and the neuroantigen administered, the disease may be acute and monophasic in nature, or alternatively chronic, or relapsing-remitting.

Affected animals develop flaccid tails, paralysis of the hindlimbs, and incontinence. In severe disease, movement of the forelimbs may also become impaired and animals may become moribund. Histological analysis of the CNS reveals an inflammatory cell infiltrate during the acute stages of disease that may be accompanied by demyelination of the neurons during chronic phases of the disease. EAE is widely used for the study of autoimmune disease and serves as a model for testing potential efficacy of experimental drugs for the treatment of MS and for the treatment of autoimmune diseases in general.

The proteins of the current invention were tested for their effect on disease activity in a mouse model of EAE to gain insight into their potential use as therapeutics for the treatment of MS and other autoimmune diseases. Products of the current invention inhibited EAE in the SJL/J mouse. Administration of construct HSA1Fc and in particular of HSA1R4 decreased clinical disease activity during the early acute stages of disease and decreased the frequency of and severity of relapses at later time points as compared to saline-treated controls. Decreased inflammatory cell infiltrates were observed in the CNS of construct-treated animals compared to saline treated-controls.

H. Biological Functional Equivalents

As modifications or changes may be made in the structure of the polynucleotides and or proteins of the present invention, while obtaining molecules having similar or improved characteristics, such biologically functional equivalents are also encompassed within the present invention.

1. Modified Polynucleotides and Polypeptides

The biological functional equivalent may comprise a polynucleotide that has been engineered to contain distinct sequences while at the same time retaining the capacity to encode the "wild-type" or standard protein. This can be accomplished owing to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein.

In another example, a polynucleotide can be engineered to contain certain sequences that result in (and encode) a biological functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges on the protein's ability to carry out its designated function. It is thus contemplated by the inventors that various changes may be made in the sequence of genes and proteins disclosed herein, while still fulfilling the goals of the present invention.

In terms of functional equivalents, it is well understood by the skilled artisan that, inherent in the definition of a "biologically functional equivalent" protein or polynucleotide, is the concept that there is a limit to the number of changes that may be made within a defined portion of the molecule while retaining a molecule with an acceptable level of equivalent biological activity, such as binding to FcγRs. Biologically functional equivalents are thus defined herein as those proteins (and polynucleotides) in which selected amino acids (or codons) may be substituted.

In general, the shorter the length of the molecule, the fewer the changes that can be made within the molecule while retaining function. Longer domains may have an intermediate number of changes. The full-length protein will have the most tolerance for a larger number of changes. However, it must be appreciated that certain molecules or domains that are highly dependent upon their structure may tolerate little or no modification.

Amino acid substitutions are generally based on the relative similarity of the amino acid side-chain substituents, for example, their hydrophobicity, hydrophilicity, charge, size, or the like. An analysis of the size, shape or type of the amino acid side-chain substituents reveals that arginine, lysine or histidine are all positively charged residues; that alanine, glycine or serine are all of similar size; or that phenylalanine, tryptophan or tyrosine all have a generally similar shape. Therefore, based upon these considerations, arginine, lysine or histidine; alanine, glycine or serine; or phenylalanine, tryptophan or tyrosine; are defined herein as biologically functional equivalents.

To effect more quantitative changes, the hydropathic index of amino acids may be considered. Each amino acid has been assigned a hydropathic index on the basis of their hydrophobicity or charge characteristics, these are: isoleucine (+4.5); valine (+4.2); Leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); or arginine (−4.5).

Hydropathic amino acid index can be used to confer interactive biological function on a protein (Kyte & Doolittle, 1982). In some instances, certain amino acids may be substituted for other amino acids having a similar hydropathic index or score or still retain a similar biological activity. In making changes based upon the hydropathic index, the substitution of amino acids with hydropathic indices can be within ±2 or within ±1, or within ±0.5.

The substitution of like amino acids can be made effectively on the basis of hydrophilicity, particularly where the biological functional equivalent protein or peptide thereby created is intended for use in immunological embodiments, as in certain embodiments of the present invention. U.S. Pat. No. 4,554,101 states that the greatest local average hydrophilicity of a protein, as governed by the hydrophilicity of its adjacent amino acids, correlates with its immunogenicity or antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, the substitution of amino acids with hydrophilicity values can be within ±2, or within ±1, or within ±0.5.

The term "substantially similar" means a variant amino acid sequence that is at least 80% identical to a native amino acid sequence, or at least 90% identical. The percent identity may be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). Some default parameters for the GAP program can include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353 358, 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are known. Naturally occurring variants are also encompassed by the invention. Examples of such variants are proteins that result from alternate mRNA splicing events or from proteolytic cleavage of the native protein, wherein the native biological property is retained.

2. Codons

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented below for use in such embodiments, as well as for other uses, such as in the design of probes and primers and the like.

Tables 1 and 2. Amino Acid Designations and Codon Table

TABLE 1

Amino Acid Designations

| | | |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

TABLE 2

Codons for Amino Acids

| |
|---|
| GCA GCC GCG GCU |
| UGC UGU |
| GAC GAU |
| GAA GAG |
| UUC UUU |
| GGA GGC GGG GGU |
| CAC CAU |
| AUA AUC AUU |
| AAA AAG |
| UUA UUG CUA CUC CUG CUU |
| AUG |
| AAC AAU |
| CCA CCC CCG CCU |
| CAA CAG |
| AGA AGG CGA CGC CGG CGU |
| AGC AGU UCA UCC UCG UCU |
| ACA ACC ACG ACU |
| GUA GUC GUG GUU |
| UGG |
| UAC UAU |

The term "functionally equivalent codon" is used herein to refer to codons that encode the same amino acid, such as the six codons for arginine or serine, and also refers to codons that encode biologically equivalent amino acids (see Codon Table, above).

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

3. Altered Amino Acids

The present invention, in many aspects, relies on the synthesis of peptides and polypeptides in cyto, via transcription and translation of appropriate polynucleotides. These peptides and polypeptides will include the twenty "natural" amino acids, and post-translational modifications thereof. However, in vitro peptide synthesis permits the use of modified or unusual amino acids. A table of exemplary, but not limiting, modified or unusual amino acids is provided herein below.

TABLE 3

Modified or Unusual Amino Acids

| Abbr. | Amino Acid | Abbr. | Amino Acid |
|---|---|---|---|
| Aad | 2-Aminoadipic acid | EtAsn | N-Ethylasparagine |
| BAad | 3-Aminoadipic acid | Hyl | Hydroxylysine |
| BAla | beta-alanine, beta-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| BAib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

4. Mimetics

In addition to the biological functional equivalents discussed above, the present inventors also contemplate that structurally similar compounds may be formulated to mimic the key portions of peptide or polypeptides of the present invention. Such compounds, which may be termed peptidomimetics, may be used in the same manner as the peptides of the invention and, hence, also are functional equivalents.

Certain mimetics that mimic elements of protein secondary and tertiary structure are described in Johnson et al. (1993). The underlying rationale behind the use of peptide mimetics is that the peptide backbone of proteins exists chiefly to orient amino acid side chains in such a way as to facilitate molecular interactions, such as those of antibody or antigen. A peptide mimetic is thus designed to permit molecular interactions similar to the natural molecule.

Some successful applications of the peptide mimetic concept have focused on mimetics of β-turns within proteins, which are known to be highly antigenic. Likely β-turn structure within a polypeptide can be predicted by computer-based algorithms. Once the component amino acids of the turn are determined, mimetics can be constructed to achieve a similar spatial orientation of the essential elements of the amino acid side chains.

Other approaches have focused on the use of small, multi-disulfide-containing proteins as attractive structural templates for producing biologically active conformations that mimic the binding sites of large proteins (Vita et al., 1998). A structural motif that appears to be evolutionarily conserved in certain toxins is small (30-40 amino acids), stable, and highly permissive for mutation. This motif is composed of a beta sheet and an alpha helix bridged in the interior core by three disulfides.

Beta II turns have been mimicked successfully using cyclic L-pentapeptides and those with D-amino acids. (Weisshoff et al., 1999). Also, Johannesson et al. (1999) report on bicyclic tripeptides with reverse turn-inducing properties.

Methods for generating specific structures have been disclosed in the art. For example, alpha-helix mimetics are disclosed in U.S. Pat. Nos. 5,446,128; 5,710,245; 5,840,833; and 5,859,184. Theses structures render the peptide or protein more thermally stable, also increase resistance to proteolytic degradation. Six, seven, eleven, twelve, thirteen and fourteen membered ring structures are disclosed.

Methods for generating conformationally restricted beta turns and beta bulges are described, for example, in U.S. Pat. Nos. 5,440,013; 5,618,914; and 5,670,155. Beta-turns permit changed side substituents without having changes in corresponding backbone conformation, and have appropriate termini for incorporation into peptides by standard synthesis procedures. Other types of mimetic turns include reverse and gamma turns. Reverse turn mimetics are disclosed in U.S. Pat. Nos. 5,475,085 and 5,929,237, and gamma turn mimetics are described in U.S. Pat. Nos. 5,672,681 and 5,674,976.

I. Proteinaceous Compositions

In certain embodiments, the present invention concerns novel compositions comprising at least one proteinaceous molecule, such as a polypeptide with multiple HCH2 regions. As used herein, a "proteinaceous molecule", "proteinaceous composition", "proteinaceous compound", "proteinaceous chain" or "proteinaceous material" generally refers to, but is not limited to, a protein of greater than about 200 amino acids or the full length endogenous sequence translated from a gene; a polypeptide of greater than about 100 amino acids; or a peptide of from about 3 to about 100 amino acids. All the "proteinaceous" terms described above may be used interchangeably herein.

In certain embodiments the size of at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino molecule residues, and any range derivable therein.

As used herein, an "amino molecule" refers to any amino acid, amino acid derivative, or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown in Table 3.

In certain embodiments the proteinaceous composition comprises at least one protein, polypeptide or peptide. In further embodiments the proteinaceous composition comprises a biocompatible protein, polypeptide or peptide. As used herein, the term "biocompatible" refers to a substance that produces no significant untoward effects when applied to, or administered to, a given organism according to the methods and amounts described herein. Organisms include, but are not limited to, a bovine, a reptilian, an amphibian, a piscine, a rodent, an avian, a canine, a feline, a fungus, a plant, an archebacteria, or a prokaryotic organism, with a selected animal or human subject being sometimes preferred. Such untoward or undesirable effects are those such as significant toxicity or adverse immunological reactions. In some embodiments, biocompatible protein, polypeptide or peptide containing compositions will generally be mammalian proteins or peptides, or synthetic proteins or peptides, each essentially free from toxins, pathogens and harmful immunogens.

Proteinaceous compositions may be made by any technique known, including the expression of proteins, polypeptides or peptides through standard molecular biological techniques, the isolation of proteinaceous compounds from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified or expressed using the techniques disclosed herein or otherwise known. Alternatively, various commercial preparations of proteins, polypeptides and peptides are known.

In certain embodiments a proteinaceous compound may be purified. Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, that may be known for the specific or desired protein, polypeptide or peptide.

In certain embodiments, the proteinaceous composition may comprise at least one antibody. As used herein, the term "antibody" is intended to refer broadly to any immunologic binding agent such as IgG, IgM, IgA, IgD, and IgE. Generally, IgG or IgM may be preferred because they are the most common antibodies in the physiological situation and because they are most easily made in a laboratory setting.

Polypeptide regions of proteinaceous compounds may be linked via a linker group. A linker group is able to join the compound of interest via a biologically-releasable bond, such as a selectively-cleavable linker or amino acid sequence.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known. Means for preparing and characterizing antibodies are also known (See, e.g., Antibodies: A Laboratory Manual, Cold Spring Harbor Laboratory, 1988).

It is contemplated that virtually any protein, polypeptide, or peptide containing component may be used in the compositions and methods disclosed herein. However, the proteinaceous material may be biocompatible. Proteins and peptides suitable for use in this invention may be autologous proteins or peptides, although the invention is clearly not limited to the use of such autologous proteins. As used herein, the term "autologous protein, polypeptide or peptide" refers to a protein, polypeptide or peptide that is derived from or obtained from an organism. Organisms that may be used include, but are not limited to, a bovine, a reptilian, an amphibian, a piscine, a rodent, an avian, a canine, a feline, a fungus, a plant, or a prokaryotic organism, with a selected animal or human subject being sometimes being preferred. The "autologous protein, polypeptide or peptide" may then be used as a component of a composition intended for application to the selected animal or human subject. It can be biocompatible (i.e. from mammalian origin for mammals, from human origin for humans, from canine origin for canines, etc.; it is autologous; it is non-allergenic, or it is non-immunogenic).

J. Mechanisms of Action and Applications

Autoimmune disease often involves both T-cell and B-cell mediated components that may act dependently or independently of one another, simultaneously or sequentially, resulting in a host-damaging disease often characterized by tissue or cell compromise and a loss of one or more bodily functions. Fc receptors and proteins of the complement cascade are often intimately associated with the generation of the autoimmune response, the regulation of the ongoing immune response, and the effector phase of the immune response (i.e. those mechanisms that lead to tissue or cell destruction or damage). The inventive polypeptides, through their ability to bind Fc receptors or complement, may influence disease outcome by their impact upon one or more of these areas.

The inventive polypeptides may favorably alter disease activity by multiple pathways depending on the fusion protein design and type of disease treated. Inventive polypeptides may be designed to contain; multiple units of HCH2 regions, or portions thereof, able to bind Fc receptors, multiple units of HCH2 regions able to bind complement components, or both. It is contemplated that the inventive polypeptide design can be modified to maximize potential benefits achieved from its use in treating a specific disease and its composition may vary from one disease to the next. For example, for the treatment of some diseases it may be preferable to retain the Fc receptor binding ability of the fusion proteins but exclude or diminish binding of components of the complement cascade. The obverse may be preferred for the treatment of other diseases.

The effect of the inventive polypeptides on disease outcome will depend not only on whether they contain multiple units able to bind Fc receptors, multiple units able to bind complement components, or both, but also on other protein domains that may be coexpressed in the inventive polypeptides to give them an additional function, binding capability, or other added feature. An additional modification to the inventive polypeptides includes the binding of additional proteins, protein domains, or peptides to the inventive polypeptides that give them an additional function, binding capacity, or other added feature. The flexibility in the fusion protein design enables the inventors to, depending on disease type, modify the inventive polypeptides to maximize their therapeutic potential. It is an embodiment of the current invention that in addition to the treatment of autoimmunity, modifications of the inventive polypeptides as described above are applicable to their use in the treatment of neoplasms, the treatment of infections by viruses or other pathogens, the treatment of warts, and the purposeful induction of an immune response directed against a particular antigen or antigens, as for example in a vaccine.

Inventive polypeptides able to bind Fc receptors may influence disease outcome through multiple mechanisms including but not limited to blocking Fc receptor accessibility to endogenously produced Ig and immune complexes. Such blockade would be expected to limit self-antigen presentation by antigen presenting cells and to, as a consequence, diminish autoimmune responses. Blockade of Fc receptors may also limit or diminish tissue and cell destruction. Tissue and cell destruction in autoimmune disease can be mediated by Fc receptor-expressing effector cells (monocytes, neutrophils, macrophages, microglia, NK cells, as well as other cell types) that bind self-antigen reactive Ig bound to tissue or cells. For example, in ATP, the inventive polypeptides could limit platelet destruction and clearance by the body by decreasing their uptake by Kupffer cells in the liver and spleen via Fc receptor-mediated mechanisms. Similarly inventive polypeptides might limit demyelination in the CNS in multiple sclerosis or acetylcholine receptor destruction of motor neural endplates in myasthenia gravis by decreasing macrophage accessibility to Ig bound to self Ag in target tissues. The inventive polypeptides may favorably alter numerous autoimmune diseases via similar mechanisms.

The inventive polypeptides may modify autoimmune disease by activating cells through Fc receptors and thereby altering the secretion of immunomodulators, the expression of specific cell surface markers, or the type or magnitude of specific cell functions. Modulation of protein secretion might include the decreased or increased production of interleukins including but not limited to IL-2, IL-4, IL-10, IL-12, IL-18; cytokines including but not limited to TGFβ, TNFα, TNFβ; interferons γ, β, and α; growth factors, and products of the arachidonate cascade. Cellular functions that may be altered include cellular cytotoxicity, cell division, and activation state.

The inventive polypeptides may also be used to suppress or amplify immunity to a specific antigen. Autoimmune disease may be treated by inducing tolerance to a specific antigen or by deviating the autoimmune response to a specific antigen from a harmful pathogenic one to a less harmful type. For example, in multiple sclerosis the elaboration of type 1 cytokines (IL-12, IL-2) in response to autoantigen is generally thought to be deleterious to the host while induction of a type 2 response (IL-4, IL-10) is thought to be protective. The purposeful deviation of the immune response from a Th1 type to a Th2 type would likely be beneficial in the treatment of multiple sclerosis. In contrast, a Th2 type response is thought to be harmful in other autoimmune diseases such as lupus erythematosus, and consequently the purposeful deviation of the response to autoantigen in this disease from a Th2 type response to a Th1 type response would likely be beneficial. Thus, modification of the inventive polypeptides would vary depending on the disease type and the mechanisms involved.

It is an embodiment of the current invention to coexpress one or more protein domains of a specific antigen or bind one or more specific antigens or antigenic determinants to the inventive polypeptides that would induce a protective immune response, deviate a harmful immune response to a less harmful one, or induce a state of nonresponsiveness to antigen (Lasalle et al., 1994). For example, the inventors contemplate, in the treatment of multiple sclerosis, to coexpress a neuroantigen peptide in the fusion protein that induces a protective Th2 type response or an unresponsive state. A nonlimiting list of potential neuroantigens that might be used for the treatment of multiple sclerosis include proteolipid protein, myelin basic protein and myelin oligodendrocyte glycoprotein. Similarly, a T cell receptor or Ig domain may be expressed in the fusion protein that would induce a protective anti-T cell receptor or anti-idiotype response. The inventors contemplate that varying the protein coexpressed based upon disease type should allow the inventive polypeptides to be used for the treatment of numerous autoimmune diseases.

As mentioned earlier, the adaptive immune system is often referred to as having two components, cellular immunity (or Th1 type response) and humoral immunity (or Th2 type response). Response to an antigen evokes one or both of these components. Immunomodulators such as lymphokines and monokines that promote one component often inhibit the other. Thus a strong cellular response will often occur in the presence of a blunted humoral response and vice versa. Factors important to the development of one or the other response include the presence or absence of cytokines, costimulatory factors, as well as other factors that are known to those familiar in the art (Lasalle et al., 1994). For example the presence of IL-4 has been shown to enhance a Th2 type response while the presence of interferon gamma induces a Th1 type response (Swain et al., 1988). In the treatment of autoimmune disease, neoplasms, or viral infections, or in the induction of immunity to pathogens by vaccine based therapies, selective modulation of one or both of these components may be used. The coadministration of cytokines, steroids, or other immunomodulators may be used in the treatment of varying diseases or when attempting to induce immunity to an antigen or antigens based upon the type of response desired.

1. Neoplastic Cell Targets

Many so-called "tumor antigens" have been described, any one of which could be employed as a target in connection with the combined aspects of the present invention. A large number of exemplary solid tumor-associated antigens are listed herein below. The preparation and use of antibodies against such antigens is known, and exemplary antibodies include from gynecological tumor sites: OC 125; OC 133; OMI; Mo v1; Mo v2; 3C2; 4C7; $ID_3$; DU-PAN-2; F 36/22; $4F_7/7A_{10}$; OV-TL3; B72.3; $DF_3$; $2C_8/2F_7$; MF 116; Mov18; CEA 11-H5; CA 19-9 (1116NS19-9); H17-E2; 791T/36; $NDOG_2$; H317; 4D5, 3H4, 7C2, 6E9, 2C4, 7F3, 2H11, 3E8, 5B8, 7D3, SB8; HMFG2; 3.14.A3; from breast tumor sites: DF3; NCRC-11; 3C6F9; MBE6; CLNH5; MAC 40/43; EMA; HMFG1 HFMG2; 3.15.C3; M3, M8, M24; M18; 67-D-11; D547Sp, D75P3, H222; Anti-EGF; LR-3; TA1; H59; 10-3D-2; HmAB1,2; MBR 1,2,3; 24•17•1; 24-17•2 (3E1•2); F36/22.M7/105; C11, G3, H7; B6•2; B1•1; Cam 17•1; SM3; SM4; C-Mul (566); 4D5 3H4, 7C2, 6E9, 2C4, 7F3, 2H11, 3E8, 5B8, 7D3, 5B8; OC 125; MO v2; DU-PAN-2; $4F_7/7A_{10}$; $DF_3$; B72•3; ccccCEA 11; H17-E2; 3•14•A3; FO23C5; from colorectal tumor sites: B72•3; (17-1A) 1083-17-1A; CO17-1A; ZCE-025; AB2; HT-29-15; 250-30.6; 44X14; A7; GA73•3; 791T/36; 28A32; 28.19.8; X MMCO-791; DU-PAN-2; $ID_3$; CEA 11-H5; $2C_8/2F_7$; CA-19-9 (1116NS19-9); PR5C5; PR4D2; PR4D1; from melanoma sites 4•1; 8•2 $M_{17}$; 96•5; 118•1, 133•2, (113•2); $L_1$, $L_{10}$, $R_{10}(R_{19})$; $I_{12}$; $K_5$; 6•1; R24; 5•1; 225.28S; 465.12S; 9•2•27; F11; 376.96S; 465.12S; 15•75; 15•95; Mel-14; Mel-12; Me3-TB7; 225.28SD; 763.24TS; 705F6; 436910; M148; from gastrointestinal tumors: ID3; DU-PAN-2; OV-TL3; B72•3; CEA 11-H5; 3•14•A3; C COLI; CA-19-9 (1116NS19-9) and CA50; OC125; from lung tumors: 4D5 3H4, 7C2, 6E9, 2C4, 7F3, 2H11, 3E8, 5B8, 7D3, SB8; MO v2; B72•3; DU-PAN-2; CEA 11-H5; MUC8-22; MUC2-63; MUC2-39; MUC7-39; and from miscellaneous tumors: PAb 240; PAb 246; PAb 1801; ERIC•1; M148; FMH25; 6•1; CA1; 3F8; $4F_7/7A_{10}$; $2C_8/2F_7$; CEA 11-H5.

Another means of defining a targetable tumor is in terms of the characteristics of a tumor cell itself, rather than describing the biochemical properties of an antigen expressed by the cell. Accordingly, the ATCC catalogue exemplifies human tumor cell lines that are publicly available (from ATCC Catalogue). Exemplary cell lines include J82; RT4; ScaBER; T24; TCCSUP; 5637; SK-N-MC; SK-N-SH; SW 1088; SW 1783; U-87 MG; U-118 MG; U-138 MG; U-373 MG; Y79; BT-20; BT-474; MCF7; MDA-MB-134-VI; MDA-MD-157; MDA-MB-175-VII; MDA-MB-361; SK-BR-3; C-33 A; HT-3; ME-180; MS751; SiHa; JEG-3; Caco-2; HT-29; SK-CO-1; HuTu 80; A-253; FaDu; A-498; A-704; Caki-1; Caki-2; SK-NEP-1; SW 839; SK-HEP-1; A-427; Calu-1; Calu-3; Calu-6; SK-LU-1; SK-MES-1; SW 900; EB1; EB2; P3HR-1; HT-144; Malme-3M; RPMI-7951; SK-MEL-1; SK-MEL-2; SK-MEL-3; SK-MEL-5; SK-MEL-24; SK-MEL-28; SK-MEL-31; Caov-3; Caov-4; SK-OV-3; SW 626; Capan-1; Capan-2; DU 145; A-204; Saos-2; SK-ES-1; SK-LMS-1; SW 684; SW 872; SW 982; SW 1353; U-20S; Malme-3; KATO III; Cate-1B; Tera-1; Tera-2; SW579; AN3 CA; HEC-1-A; HEC-1-B; SK-UT-1; SK-UT-1B; SW 954; SW 962; NCI-H69; NCI-H128; BT-483; BT-549; DU4475; HBL-100; Hs 578Bst; Hs 578T; MDA-MB-330; MDA-MB-415; MDA-MB-435S; MDA-MB-436; MDA-MB-453; MDA-MB-468; T-47D; Hs 766T; Hs 746T; Hs 695T; Hs 683; Hs 294T; Hs 602; JAR; Hs 445; Hs 700T; H4; Hs 696; Hs 913T; Hs 729; FHs 738Lu; FHs 173We; FHs 738B1; NIH:0VCAR-3; Hs 67; RD-ES; ChaGo K-1; WERI-Rb-1; NCI-H446; NCI-H209; NCI-H146; NCI-H441; NCI-H82; H9; NCI-H460; NCI-H596; NCI-H676B; NCI-H345; NCI-H820; NCI-H520; NCI-H661; NCI-H510A; D283 Med; Daoy; D341 Med; AML-193 and MV4-11.

One may consult the ATCC Catalogue of any subsequent year to identify other appropriate cell lines. Also, if a particular cell type is desired, the means for obtaining such cells, or their instantly available source, are known. An analysis of the scientific literature will thus readily reveal an appropriate choice of cell for any tumor cell type desired to be targeted.

Recent technological advances allow rapid and efficient comparisons of gene expression in neoplastic tissue to that of normal tissue. These technological advances include but are not limited to differential gene analysis using gene chip arrays and protein arrays. Using these technologies one is able to compare mRNA species and proteins expressed in neoplastic tissue to that found in normal tissue. Those mRNA species or proteins that are differentially expressed in neoplastic tissue compared to normal tissue may be readily discerned. Proteins found to be preferentially expressed in neoplastic tissue or in neoplastic cells using these screening technologies serve as likely candidates for the further development of cancer or tumor specific therapies. It is an embodiment of the current invention that tumor associated proteins or tumor specific proteins discovered using these technologies may be employed as targets in connection with the combined aspects of the present invention.

K. Combined Treatment

Combination of the inventive polypeptides with other therapeutic agents is contemplated for use in the clinical treatment of various diseases that involve altering immunity, inflammation or neoplasms.

Naturally, before wide-spread use, animal studies and clinical trials will be conducted. The various elements of conducting a clinical trial, including patient treatment and monitoring, are known, especially in light of the present disclosure.

The present invention contemplates that the inventive polypeptides may be used in combination with other therapies. Therapies for autoimmune diseases include but are not limited to interferon-β, interferon-α, i.v. immunoglobulins, monoclonal antibodies such as h5G1.1-mAb, polyclonal antibodies such as anti-RhoD (WinRho SDF), retinoic acid and other immunomodulatory agents such as glatiramer acetate.

Therapies for diseases that involve inflammation include, but are not limited to non-steroidal inflammatory drugs (NSAIDs) such as cyclo-oxygenase 2 (COX-2) inhibitors.

The present invention contemplates that the inventive polypeptides may be used as an adjuvant in combination with vaccines. Vaccines include, for example, mAb 105AD7 anti-idiotype vaccine, mAb 11D10 anti-idiotype vaccine, mAb 3H1 anti-idiotype vaccine, GM2, GM2-KLH, and MUC-1 antigen among many others.

Cancer therapies include a variety of combination therapies that are contemplated with the inventive polypeptides including immunological, chemical and radiation based treatments. Combination immunotherapies include, for example, interleukin-2, monoclonal or bispecific antibodies such as Rituximab, Herceptin (Trastuzumab), mAb Lym-1, mAb ml70, mAb BC8, mAb Anti-B1 (tositumomab), Campath-1H, anti-CEA mAb MN-14, mAb HuG1-M195, mAb HuM291, mAb 3F8, mAb C225 (cetuximab), anti-Tac mAb (daclizumab), and mAb hLL2 (epratuzumab).

Combination immunotherapies also include monoclonal antibodies (mAb) linked to toxins or other agents. Examples include mAb gemtuzumab ozogamicin (mylotarg), mAb Mono-dgA-RFB4, mAb ibritumomab tiuxetan (IDEC-Y2B8), and Anti-Tac(Fv)-PE38. Combination chemotherapies include, for example, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate or any analog or derivative variant thereof.

For precancerous conditions such as benign prostatic hyperplasia, a second therapeutic agent selected from an α-1 adrenergic receptor blocker such as terazosin, doxazosin, prazosin, bunazosin, indoramin, tamsulosin, pracicin or alfuzosin; a 5-α-reductase enzyme blocker such as finasteride or an azasteroid derivative; a combination of an α-1 adrenergic receptor blocker, and a 5-α-reductase enzyme blocker, a potassium channel opener such as minoxidil, and a retinoic acid derivative.

Various combinations may be employed, for instance where the inventive polypeptide is "A" and the radio-, chemotherapeutic or other therapeutic agent is "B":

A/B/A B/A/B B/B/A A/A/B A/B/B B/A/A A/B/B/B

B/A/B/B B/B/A/B B/B/A/B A/A/B/B A/B/A/B A/B/B/A

B/B/A/A B/A/B/A B/A/A/B A/A/B/B A/A/A/A A/B/A/A

A/A/B/A

The terms "contacted" and "exposed," when applied to a cell, are used herein to describe the process by which a therapeutic composition and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapy including inventive polypeptides may precede or follow the other agent treatment by intervals ranging from minutes to weeks. In embodiments where the other agent and inventive polypeptide are applied separately to the cell, one would generally ensure that a significant period of time did not expire between the time of each delivery, such that the agent and the fusion protein would still be able to exert an advantageously combined effect on the cell. In such instances, it is contemplated that one would contact the cell with both modalities within about 12-24 h of each other or within about 6-12 h of each other, with a delay time of only about 12 h being also possible. In some situations, it may be desirable to extend the time period for treatment significantly, however, where several days (2, 3, 4, 5, 6 or 7) to several weeks (1, 2, 3, 4, 5, 6, 7 or 8) elapse between the respective administrations.

L. Pharmaceutical Compositions

Pharmaceutical compositions of the present invention comprise an effective amount of one or more inventive polypeptides, therapeutic agents or additional agent dissolved or dispersed in a pharmaceutically acceptable carrier. Aqueous compositions of the present invention comprise an effective amount of the inventive polypeptides, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof (see, for example, Remington's Pharmaceutical Sciences, 18th Ed. Mack Printing Company, 1990, pp. 1289-1329). The use of such media and agents for pharmaceutical active substances is known. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologic Standards.

The biological material should be dialyzed to remove undesired small molecular weight molecules or lyophilized for more ready formulation into a desired vehicle, where appropriate. The active compounds will then generally be formulated for parenteral administration, e.g., formulated for injection via the intravenous, intramuscular, sub-cutaneous, intranasal, intralesional, or even intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inventive polypeptides can be formulated into a composition in a free base, in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, isotonic agents, for example, sugars or sodium chloride can be included. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

In certain embodiments, the use of liposomes or nanoparticles is contemplated for the formulation and administration of the fusion proteins or analogs thereof. The formation and use of liposomes is generally known and is also described below.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

The therapeutic agent may comprise different types of carriers depending on whether it is to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, by inhalation (e.g. aerosol inhalation), by injection, by infusion, by continuous infusion, localized perfusion bathing target cells directly, via a catheter, via a lavage, in cremes, in lipid compositions (e.g., liposomes), or by other methods or any combination of the foregoing (see, for example, Remington's Pharmaceutical Sciences, 18th Ed. Mack Printing Company, 1990).

The actual dosage amount of a composition of the present invention administered to an animal patient can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In some cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in some embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the inventive polypeptides are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Some carriers for oral administration comprise inert diluents, assimilable edible carriers or combinations thereof. In other aspects of the invention, the oral composition may be prepared as a syrup or elixir. A syrup or elixir, may comprise, for example, at least one active agent, a sweetening agent, a preservative, a flavoring agent, a dye, a preservative, or combinations thereof.

In certain embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, or about 1% to about 2%.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

The invention also provides for the use of adjuvants as components in an immunogenic composition compatible with the purified proteins to boost the immune response resulting from vaccination. One or more adjuvants can be selected from the group comprising saponins (e.g, GP-0100), or derivatives thereof, emulsions alone or in combination with carbohydrates or saponins, and aluminum-based adjuvants (collectively, "alum" or "alum-based adjuvants") such as aluminum hydroxide, aluminum phosphate, or a mixture thereof. Aluminum hydroxide (commercially available as "Alhydrogel") was used as alum in the Examples. A saponin is any plant glycoside with soapy action that can be digested to yield a sugar and a sapogenin aglycone. Sapogenin is the nonsugar portion of a saponin. It is usually obtained by hydrolysis, and it has either a complex terpenoid or a steroid structure that forms a practicable starting point in the synthesis of steroid hormones. The saponins of the invention can be any saponin as described above or saponin-like derivative with hydrophobic regions, especially the strongly polar saponins, primarily the polar triterpensaponins such as the polar acidic bisdesmosides, e.g. saponin extract from Quillsjabark Araloside A, Chikosetsusaponin IV, *Calendula*-Glycoside C, chikosetsusaponin V, *Achyranthes*-Saponin B, *Calendula*-Glycoside A, Araloside B, Araloside C, Putranjia-Saponin III, Bersamasaponiside, Putrajia-Saponin IV, Trichoside A, Trichoside B, Saponaside A, Trichoside C, Gypsoside, Nutanoside, Dianthoside C, Saponaside D, aescine from *Aesculus hippocastanum* or sapoalbin from *Gyposophilla struthium*, saponin extract *Quillaja saponaria* Molina and Quil A. In addition, saponin may include glycosylated triterpenoid saponins derived from Quillaja *Saponaria* Molina of Beta Amytin type with 8-11 carbohydrate moieties as described in U.S. Pat. No. 5,679,354. Saponins as defined herein include saponins that may be combined with other materials, such as in an immune stimulating complex ("IS-COM")-like structure as described in U.S. Pat. No. 5,679, 354. Saponins also include saponin-like molecules derived from any of the above structures, such as GPI-0100, such as described in U.S. Pat. No. 6,262,029. The saponins of the invention can be amphiphilic natural products derived from the bark of the tree, *Quillaja saponaria*. They can consist of mixtures of triterpene glycosides with an average molecular weight (Mw) of 2000. In another embodiment of the invention a purified fraction of this mixture is used.

M. Kits

Any of the compositions described herein may be comprised in a kit. In a non-limiting example, an inventive polypeptide, a nucleic acid coding for an inventive polypeptide or additional agent, may be comprised in a kit. The kits will thus comprise, in suitable container means, an inventive polypeptide, a nucleic acid coding for an inventive polypeptide or an additional agent of the present invention. The inventors envisage other components that may be included in a kit. These include but are not limited to immunodetection agents such as peroxidase and alkaline phosphatase linked monoclonal and polyclonal antibodies, immunoprecipitation reagents such as protein A- or protein G-linked beads, immune cell purification reagents such as magnetic beads, cloning reagents for the purpose of manipulating an expression vector, protein expression reagents including prokaryotic and eukaryotic cell lines for the purpose of protein expression.

The kits may comprise a suitably aliquoted inventive polypeptide or additional agent compositions of the present invention, whether labeled or unlabeled, as may be used to prepare a standard curve for a detection assay. The components of the kits may be packaged either in aqueous media or in lyophilized form. The container means of the kits will generally include at least one vial, test tube, flask, bottle, syringe or other container means, into which a component may be placed, or suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the inventive polypeptide, lipid, additional agent, and any other reagent containers in close confinement for commercial sale. Such containers may include injection or blow-molded plastic containers into which the desired vials are retained.

Therapeutic kits of the present invention comprise an inventive polypeptide, other polypeptide, peptide, inhibitor, gene, vector or other effectors. Such kits will generally contain, in suitable container means, a pharmaceutically acceptable formulation of an inventive polypeptide in a pharmaceutically acceptable formulation. The kit may have a single container means, or it may have distinct container means for each compound.

When the components of the kit are provided in one or more liquid solutions, the liquid solution is an aqueous solution, with a sterile aqueous solution being sometimes preferred. The inventive polypeptide composition may also be formulated into a syringeable composition, in which case, the container means may itself be a syringe, pipette, or other such like apparatus, from which the formulation may be applied to an infected area of the body, injected into an animal, or even applied to or mixed with the other components of the kit.

However, the components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the immunoglobulin fusion protein formulation is placed, preferably, suitably allocated. The kits may also comprise a second container means for containing a sterile, pharmaceutically acceptable buffer or other diluent.

The kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, an instrument for assisting with the injection/administration or placement of the ultimate inventive polypeptide within the body of an animal. Such an instrument may be a syringe, pipette, forceps, or any such medically approved delivery vehicle.

As used herein the specification, "a" or "an" may mean one or more. As used herein in the claim(s), when used in conjunction with the word "comprising", the words "a" or "an" may mean one or more than one. As used herein "another" may mean at least a second or more. As used herein, "or" takes on its usual meaning in that it also includes the conjunctive sense of and.

Some of the abbreviations used in this application can be found in Table 4.

TABLE 4

| | |
|---|---|
| AIG | Aggregated Igg |
| IC | Immune Complex |
| FcγR | Fc Gamma Receptor |
| SLE | Systemic Lupus Erythematosus |
| MS | Multiple Sclerosis |
| CDCC | Complement-Dependent Cellular Cytotoxicity |
| ADCC | Antibody-Dependent Cell-Mediated Cytotoxicity |
| CDC | Complement-Dependent Cytotoxicity |
| EAE | Experimental Autoimmune Encephalomyelitis |
| NK cells | Natural Killer Cells |
| PBMC | Peripheral Blood Mononuclear Cells |

N. Examples

The following examples are included to demonstrate some embodiments of the invention. It will be appreciated that many changes can be made in the specific embodiments that are disclosed and still obtain a like or similar result without departing from the spirit and scope of the invention.

Examples 1, 2, and 3 describe the cloning and construction of the Fc framework region and HCH2 polymer region of the ligands described in this application. This sequence in the mature polypeptide referred to as R4 is 742 amino acids long and is SEQ ID NO: 13.

EXAMPLE 1

Cloning of the cDNA for the Fc region of Human IgG1

The Fc region of human IgG$_1$ corresponds to the constant region domains that include the hinge region and CH2 and CH3 domains, (H—CH2-CH3). The cDNA for the Fc region was isolated to serve as template for HCH2 polymer construction. In addition the HCH2 polymers wer expressed as fusion to the Fc region. While the Fc region was derived from human IgG1 cDNA one could equally use the H—CH2-CH3 domains from human IgG3 for this same purpose. To obtain the H—CH2-CH3 sequence for human IgG1, total RNA was isolated from the cell line ARH-77 (ATCC #: CRL-162) using the method of Chomczynski and Sacchi (Chomczynski, 1986). cDNA was produced from the total RNA using reverse transcription. First strand cDNA synthesis was primed with 100 pmol random hexamers using 200 U SuperScript II reverse transcriptase (Invitrogen) and 5 µg of total RNA in a 20 µL reaction mixture that was 500 µM in dNTPs (Pharmacia), 1 U RNasin/µL (Promega), 10 µM in DTT, and 1× in first strand buffer. Reaction proceeded at 42° C. for 50 min.

The fragment containing the H—CH2-CH3 region (corresponding to amino acid residues 226-457) was subcloned using RT-PCR, the primer, FRM-5p-H3, which introduced a HindIII site immediately 5' of the hinge region and a second primer, FRM-3p-Sal, which introduced a SalI site immediately 3' of the stop codon (Table 5). PCR reactions were carried out in a volume of 50 µL and consisted of 1×PCR buffer (10 mM Tris pH 8.3 and 50 mM KCL), 1.5 mM MgCl$_2$, 150 µM of dNTPs, 15 pmol each of forward and reverse primers, 5 µL of reverse transcription products and 1.25 U TAQ polymerase. Cycling parameters consisted of 30s denaturation at 94° C., 1 min annealing at 60° C. and 1 min extension at 72° C. and reactions proceeded for 30 cycles. The contents of 4 identical PCR reactions were pooled and extracted once with 1:1:0.05 mixture of phenol:CHCl$_3$: isoamyl alcohol (PCIA) and subsequently extracted 1× with CHCl$_3$. DNA was recovered by precipitation with sodium acetate, pH5.4, and ethanol. DNA pellets were washed 1× with 75% ethanol, and air dried. Amplified cDNAs were dually digested for two hours in a 120 µL digestion buffer containing 150 U of HindIII and 150 U SalI. The digest was extracted 1× with PCIA and 1× with CHCl$_3$ and DNA was recovered by ethanol precipitation. DNA pellets were washed 1× with 75% ethanol, air dried and resuspended in 15 µL of TE buffer (10 mM Tris, 1 mM EDTA, pH 8.0). The HindIII and SalI digested PCR products were ligated into like-digested pBSKS+vector (Stratagene).

The ligation reaction contained 50-100 ng of vector, 20-400 ng of insert, 2 µL of 10× reaction buffer (660 mM Tris-HCl, pH &0.5, 50 mM MgCl$_2$, 50 mM DTT, 10 mM ATP), 1 µL of 5 mM ATP, and 5 U T4 DNA ligase in a final volume of 20 µL. The ligation reaction proceeded overnight at 16° C. 10 µL of ligation product was used to transform DH5α cells (subcloning-efficiency, Invitrogen). Transformed bacteria were plated onto LB-Amp plates. 10 colonies from each transformation were grown up over-night in LB-Amp medium and mini-prep DNA was isolated and analyzed by HindIII and SalI digestion.

Plasmid preparation: To produce larger quantities of plasmid, single colonies were used to inoculate 75 mL of LB medium supplemented with the appropriate antibiotic and the cultures were grown over-night. Plasmid DNA was isolated from bacteria using the Qiagen plasmid midi purification kit following the manufacturers protocol (Qiagen). Plasmid DNA was resuspended in TE buffer and UV absorbance at 260/280 nm is used to determine concentration and purity. Plasmid concentration and purity was confirmed by electrophoresis on agarose gels and visualization of DNA by ethidium bromide staining. Two positive clones were analyzed by DNA sequencing to verify sequence integrity. The resulting clone pFRM-HS was used for further expression construct assembly as describe in the following examples. Primers for this and subsequent steps involving IgG1 cloning were designed using sequence data from the human IgG1 constant region gene as a guide (accession # Z17370).

TABLE 5

Sequence of Primers used for human IgG1 HCH2 polymer PCR Amplification

| Name | Sequence |
|---|---|
| FRM-5P-H3 | GgccgctaAAGCTTGAGCCCAAATCTTGTGACAAAACTC (SEQ ID NO:1) |
| FRM-3P-Sal | GgccgctaGTCGACTCATTTACCCGGAGACAGGGAGAG (SEQ ID NO:2) |
| Hinge1 | CccgtaGAATTCGAGCCCAAATCTTCTGACAAAACTCAC ACATCCCCACCGTCCCCA (SEQ ID NO:3) |

TABLE 5-continued

Sequence of Primers used for human IgG1 HCH2 polymer PCR Amplification

| Name | Sequence |
|---|---|
| CH2NH3 | GgccgcatAAGCTTggagccTCGCGATTTGGCTTTGGAG ATGGTTTTCTC (SEQ ID NO:4) |
| SMA-DELH | GgccgcatCCCGGGGAGCCCAAATCTTCTGACAAAACT (SEQ ID NO:5) |
| CH2H3 | GgccgcatAAGCTTTTTGGCTTTGGAGATGGTTTTCTC (SEQ ID NO: 6) |

The small letters indicate bases used as clamps or spacers. Bold face letters denote the location of restriction sites.

EXAMPLE 2

Hinge Mutagenesis and CH2 Subcloning

This example describes the isolation and construction of a cDNA coding for the hinge and CH2 region (HCH2) used for the construction of the HCH2 polymer. The region of Fc that binds to FcγRI, FcγRII, and FcγRIII is found within the HCH2 region. The HCH2 region (corresponding to amino acid residues 226-350 of IgG1) was isolated as a separate monomer unit using PCR. The hinge region within the HCH2 monomer unit was modified using PCR mutagenesis to change the three cysteines that form inter-chain disulfide bridges between Fc units to serines. Since the mature polypeptide will contain from 2 to 6 HCH2 units in each polypeptide chain, we mutated the three cysteines in each hinge region (H) so that aberrant disulfide bonds do not form during the translation of the mRNA to a polypeptide. The polymer was constructed using three differing constructs, referred to as ENH, SNH, and SH3. These units differ one from another only at their 5' or 3' ends in that they have different flanking restriction sites as detailed below. These units allow for the construction of the HCH2 polymers as detailed in Example 3.

The first unit produced, composed of 5' EcoRI-ΔHCH2-NruI-HindIII 3', is termed "ENH" to denote the sequence of restriction sites and the 'delta' is included in front of the hinge, H, to denote that the hinge region was mutagenised. The ENH construct served as the starting unit for polymer construction. This was accomplished by amplifying the HCH2 region (corresponding to amino acid residues 226-350 of IgG1) using a 5' primer, Hingel (Table 5) which introduced single nucleotide changes in each of the three hinge cysteine codons resulting in their alteration to serine residues. The 5' primer also introduced an EcoRI site immediately 5' of the hinge region. The 3' primer, CH2NH3 (Table 5), directed the amplification of the CH2 domain and introduced an in-frame 3' NruI site separated by a 6 nucleotide spacer from a HindIII site. Clone pFRM-HS was the template for the PCR reactions. PCR reactions conditions were identical to those described in Example 1. PCR reactions were pooled, extracted with phenol:Chloroform to remove the Taq polymerase and the amplified DNA was recovered with sodium acetate precipitation as described for Example 1. Amplified cDNA was dually digested for two hours in a 120 µL digestion buffer containing 150 U of EcoRI and 150 U HindIII. The digest was extracted and DNA was recovered by ethanol precipitation as described for Example 1. The EcoRI and HindIII digested PCR products were ligated into like-digested pBSKS+vector (Stratagene). Ligation reaction conditions were the same as described for Example 1. 10 µL of ligation product was used to transform DH5α cells (subcloning-efficiency, Invitrogen). Transformed bacteria were plated onto LB-Amp plates. 10 colonies from each transformation were grown up over-night in LB-Amp medium and mini-prep DNA was isolated and analyzed by EcoRI and HindIII digestion.

Two clones identified as positive by restriction analysis were used to inoculate 75 mL cultures to produce larger quantities of plasmid using Qiagen midi columns as described for Example 1. The clones were analyzed by DNA sequencing to verify sequence integrity. Clone pENH18 was used in subsequent cloning steps.

Two additional constructs, an extension unit designated pSNH, and a capping unit designated pSH3, were generated. These varied from pENH$_{18}$ only in their flanking restriction sites. pSNH has 5' SmaI-HCH2-NruI-HindIII 3' and was amplified using pENH18 as template and primers that introduced the flanking restriction sites (Table 5). The second construct, pSH3, contains 5' SmaI-HCH2-HindIII 3' and was amplified from pENH18 template using a 5' primer, SMA-DELH, and a 3' primer, CH2H3 (Table 5), which introduced a single HindIII site that flanks the 3' end of the CH2 domain. In both instances, the techniques and conditions for the PCR reactions, restriction digest, ligation and plasmid preparation are identical to those described for Example 1. For polymer construction, both pSNH and pSH3 plasmids were digested with SmaI and HindIII. The digestion released the 5' SmaI-HCH2-NruI-HindIII 3' and 5' SmaI-HCH2-HindIII 3' inserts from the vector. The restriction digests were extracted once with 1:1:0.05 mixture of phenol:CHCl$_3$:isoamyl alcohol (PCIA) and subsequently extracted 1× with CHCl$_3$. DNA was recovered by precipitation with sodium acetate, pH5.4, and ethanol. DNA pellets were washed 1× with 75% ethanol, and air dried. The pelleted digests were resuspended in 20 µL of TE, mixed with 6× loading dye (0.025% xylene cyanol, 0.025% bromphenol blue, and 50% sucrose in Tris-EDTA buffer) and loaded onto 1% low-melt agarose gels in TAE running buffer. The inserts were visualized on a UV gel box, and the inserts were excised from the gel and transferred to microfuge tubes. The DNA inserts were purified from the gel using the QIAEX II Gel Extraction kit (Qiagen) following manufacturers instructions. The inserts were eluted in 50 µL of TE and stored for use in polymer construction (Example 3).

EXAMPLE 3

Polymer Construction

Figure 1:
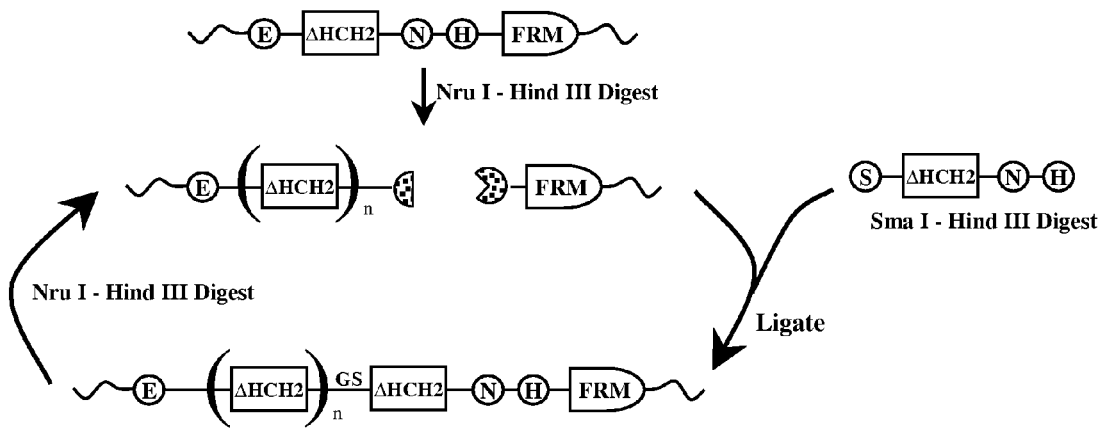
FIG. 1. Design Rationale. Schematic depicts the design rationale utilized in the construction of the HCH2 polymer, a feature of which is the iterative regeneration of cloning sites in the extension step. The ΔHCH2 shown in the schematic represents an HCH2 monomer in which the hinge cysteines have been changed to serines.

Polymers composed of HCH2 units were built using the scheme presented in FIG. 1. The HCH2 polymers were constructed by the sequential addition of a single starting unit (ENH), multiple extension units (SNH), and ended by addition of a single capping unit (SH3).

Clone pENH18 was digested with NruI and HindIII resulting in a 5' blunt end and a 3' sticky end. Next a 5' SmaI-HCH2-NruI-HindIII 3' insert, isolated as described in Example 2, was ligated into the linearized vector resulting in the in-frame insertion of a HCH2 repeat unit at the 3' end of the pENH18 starting unit. The insertion also regenerated the original sequence of restriction sites (NruI—spacer-Hin dIII) that were used in the next round of extension. Conditions for the ligation reaction were identical to those described for Example 1. The ligation mixture is transformed into DH5α cells. Transformed bacteria were plated onto LB-Amp plates and 10 colonies from the transformation were grown up over-night in LB-Amp medium and min-prep DNA was isolated and analyzed by EcoRI and HindIII digestion to confirm the insertion. Two colonies were expanded into 75 mL of LB-Amp broth and grown overnight. Plasmid DNA was isolated using the Qiagen midi columns as described in Example 1. Sequence integrity was confirmed with DNA sequencing. The extension process continued with NruI and HindIII digestion of the nascent polymer vector followed by ligation with the next SNH insert as described above. This cycle of digestion, ligation, transformation, and plasmid isolation was repeated twice more to generate the HCH2 polymer sequence for R4. In the final round of polymer construction a 'capping' unit (SH3 insert) is ligated into the polymer instead of the SNH insert. This resulted in the loss of the internal cloning site but importantly it results in an identical junction between all the inserted HCH2 units of the polymer. The result was the stepwise insertion of HCH2 units into the framework expression vector. Directionality of HCH2 insertion was maintained by the use of non-compatible flanking restriction sites but HCH2 insertion was confirmed with DNA sequencing at each step.

Figure 2:
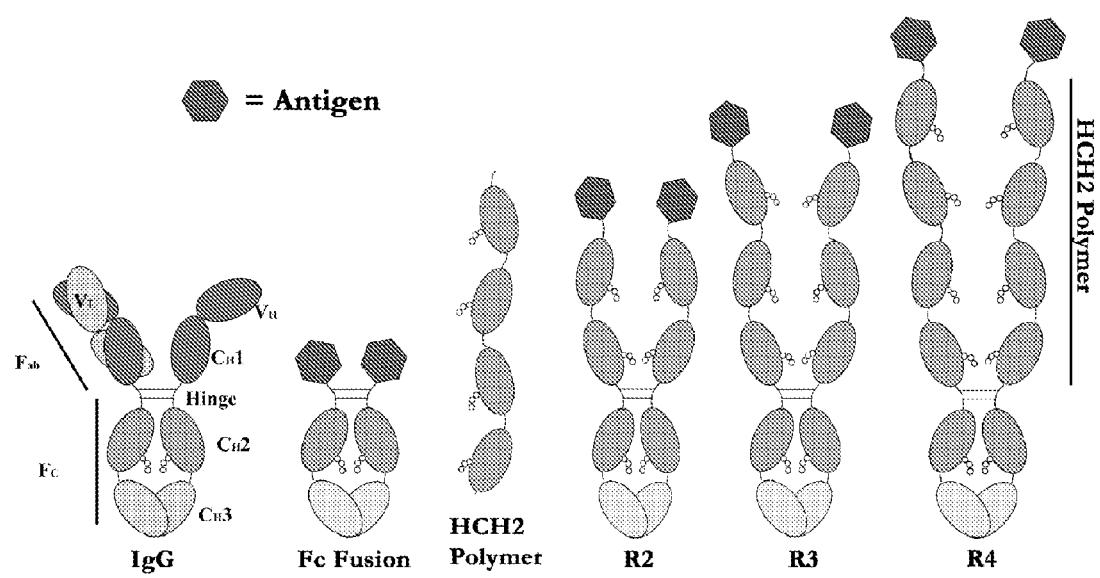
FIG. 2. Schematic illustrating the structures of IgG, Fc fusion protein, HCH2 polymers, R2, R3, and R4. Drawing on the left represents $IgG_1$ polypeptide. The element labeled Fc represents the $IgG_1$ framework composed of the hinge, CH2 and CH3 domains of human $IgG_1$ with one light chain missing to reveal heavy chain structure. The small chain extending from the CH2 region represents N-linked carbohydrate at Asn297. The second drawing depicts an Fc fusion protein wherein an antigen portion (represented as a hexagon in the drawing and labeled as antigen) has been fused to the Fc region. The third drawing shows an HCH2 polymer. The darkened ovals represent 4 repeated hinge region and CH2 domain units. To prevent inter-chain disulfide bond formation between repeat units, hinge region cysteines were mutated to serines. The mutations leave intact those hinge residues known to interact with FcγRs. The final three drawings show HCH2 polymers with 2, 3, and 4 HCH2 monomers per polymer integrated into Fc fusion protein structure.

The junction between the HCH2 units was composed of the fusion of the 5' NruI half-site to the 3' SmaI half-site, resulting in an in-frame Gly-Ser spacer between the protein domains. Choice of restriction sites determines the amino acid composition of the spacer. Guiding the choice of restriction sites was the desire to introduce spacers between the HCH2 units that were composed of small, hydrophilic amino acids such as glycine and serine. The completed polymer constructs were liberated from the pBSKS+cloning vector by digestion with EcoRI and HindIII and the inserts were purified from low-melt agarose gels as described in Example 2. The polymer inserts were ligated into EcoRI and Hind III digested pFRM-HS resulting in the in-frame joining of the HCH2 polymers to the IgG$_1$ framework region (FIG. 2.).

Examples 1, 2, and 3, provide a step by step process that one can use to produce a set of constructs that contain the framework region of human IgG1 with 2, 3 or 4 HCH2 units. The steps given here use specific sequences from human IgG1. However, this procedure can be readily modified to create polypeptides that contain up to 6 HCH2 repeat units by increasing the number of cycles of SNH insertion used to create the linear polymers.

EXAMPLE 4

Cloning and Expression of an Antigen in Mice, Human Serum Albumin (HSA) Domain I, Fused to the HCH2 Polymer, R4

This example describes the preparation of fusion proteins formed between the antigen, HSA1, and the polypeptide, R4, for its use in vaccines.

Background. HSA1 was selected as an antigen since it is poorly antigenic in the mouse. For this reason, we chose to use it to show the utility of using the R4 polypeptide to increase immune responses to a weak antigen in a vaccine formulation. Although HSA1 is used as the antigen in this specific example, these same steps can be used to link other polypeptide antigens to the R4 polypeptide for use in vaccines. HSA1, which spans residues 1-197 of the mature HSA polypeptide (Minghetti et al., 1986), is 67% identical and 82% similar to its murine homolog. HSA1, although weakly antigenic for mice, contains both T and B cell epitopes, and accordingly, provides a useful study of techniques to facilitate T cell-dependent Ab responses against weak Ags (Kenney et al., 1989; Marusic-Galesic et al., 1991; Marusic-Galesic et al., 1992). HSA can be converted into a stronger Ag when presented to APCs in an IC, and is widely employed as a carrier for haptens (Marusic-Galesic et al., 1991; Marusic-Galesic et al., 1992). HSA1 was expressed in a construct with R4 (HSA1R4). HSA1 was also expressed as an Fc fusion protein (HSA1Fc), or with a 6× Histidine tag (HSA1) to be used as comparators in these examples. HSA1Fc is an IgG fusion protein where HSA1 has been fused to the framework region of IgG as described in Example 1. The experiments described below also serve to demonstrate the general utility of the expression system Method. HSA1, HSA1Fc, and HSA1R4 cloning. Total RNA was isolated from cell line Hep G2 (ATCC HB-8065) using the method of Chomczynski and Sacchi (1987). First strand cDNA synthesis was primed with 100 pmol random hexamers using 200 U SuperScript II reverse transcriptase (Invitrogen, Carlsbad, Calif.) and 5 µg of total RNA in a 20 µL reaction mixture that was 500 µM in dNTPs (Pharmacia, Piscataway, N.J.), 1 U RNasin/µL (Promega Corp., Madison, Wis.), 10 µM in DTT, and 1× in first strand buffer. Reaction proceeded at 42° C. for 50 min. Domain 1 of mature HSA (HSA1) was amplified from Hep G2 cDNA using PCR, the forward primer Dom1-F (5'-GGC-CGCATCTCGAGATGAAGTGGGTAACCTTTATTTCC-3'; SEQ ID NO:11), and the reverse primer Dom1-R (5'-CCGCATGAATTCTCTCTGTTTGGCAGACGAAGCCTT-3'; SEQ ID NO:12). The leader sequence and the first 197 amino acid residues of mature HSA (i.e., HSA1) (Minghetti et al., 1986) were amplified, and flanking 5' Xho 1 and 3' Eco RI sites were introduced. The PCR product was digested with Xho I and Eco RI and ligated into like-digested pBSKS+ cloning vector (Stratagene, La Jolla, Calif.) to produce clone pHSA-BS.

The HSA1 fragment was subcloned into the (White et al., 2001) Fc and HCH2 polymer expression vectors described in Examples 1 and 3 to yield pHSA1Fc, pHsa1R2, pHSA1R3 and pHSA1R4 respectively. To express HSA1 with a 6×HIS-tag, a short linker that introduces a His tag and a 3' stop codon was ligated into the Eco RI and Sal I sites of pHSA-BS. Fusion protein cDNAs were transferred into the baculovirus expression vector, pFastBacl (Invitrogen), by digestion with Bam HI and Sal I and subsequent ligation of the isolated cDNA fragments into the same sites on pFastBacl to produce pHSA1-FB, pHSA1Fc-FB and pHSA1R4FB. The pFastBacl vector places fusion protein constructs under the control of a strong baculovirus-specific promoter for expression in insect cells. The vector is also used to generate virus that express the recombinant proteins. The pFastBacl expression constructs were transformed into DH10Bac competent cells (Invitrogen) following manufacturer's instructions and correctly recombined virus was identified using PCR.

EXAMPLE 5

Baculovirus Mediated Protein Expression and Purification

Cell line SF9 (ATCC CRL-1171) was maintained in ExCell 420 serum free medium (JRH Biosciences, Lenexa, Kans.) supplemented with 100 u/ml penicillin and 100 µg/ml streptomycin. For bacmid transfection, 1×10$^6$ cells were plated into each well of a 6 well cluster and allowed to grow overnight. Transfection medium was replaced with 2 ml fresh ExCell 420 without antibiotics. Two hours later, Bacmid DNA (6 µg) was transfected into SF9 cells using Cellfectin reagent (Invitrogen). After 9 hours, the medium was replaced with fresh medium containing antibiotics. Forty-eight hours later, medium containing virus was harvested and used in a second round of viral amplification.

For protein expression, 100 ml of medium supplemented with 1% Pluronic F-68 (Invitrogen) in shaker flasks was seeded with $4\times10^5$ SF9 cells/ml and shaken at 110 RPM at 27° C. for 24 hours at which time virus was introduced. Conditioned medium was harvested 72 hours later, and the protease inhibitor PMSF (Research Organics, Cleveland, Ohio) plus pepstatin A (Peptides International, Louisville, Ky.) were added to a final concentration of 1 mM and 1 µM respectively. HSA1Fc and HSA1R4 were purified using protein G-Sepharose (Pharmacia) as described previously (White et al., 2001).

The 6×His tagged HSA1 protein was purified using a $Ni^{2+}$ immobilized resin (Ni-NTA, Qaigen, Valencia, Calif.). Prior to application to the column, interfering ions and peptides were removed by dialyzing the conditioned medium (12,000-14,000 MWCO Spectrapor tubing) against 20 mM Tris, pH 7.9 and 0.5 M NaCl (TN) with 5 mM imadazole for 36 h (1 buffer change). Dialyzed conditioned medium was loaded onto a 2.5 mL bed column at a rate of 1 ml/min. The column was washed with buffer TN with 30 mM imadazole, and HSA1 was eluted from the column with 0.5 M imidazole in buffer TN. Eluted proteins were dialyzed extensively against endotoxin free PBS pH 7.0, tested for endotoxin content using the Kinetic-QCL *limulus amebocyte* assay (BioWhittaker, Walkersville, Md.), aliquoted, and stored at −70° C. for future use.

mammalian expression vector (Invitrogen). The pcDNA3.0 vector uses the strong CMV viral promoter to drive gene expression in a wide variety of mammalian cells. The vector also expressed the geneticin/G418 resistance gene permitting the selection of stably expressing cell lines. The HSA1R4 coding regions were liberated from pFastBac vector by digestion with Bam HI and Sal I and the excised DNA fragment was purified from agarose gels using techniques described in Example 2. The fragment was ligated into Bam HI and Xho I digested pcDNA3.0 expression vector. The ligation conditions were identical to those described in Example 1. The HSA1R4-pcDNA3.0 expression construct was transfected into HEK293 cells using lipofectamine (Invitrogen). Two days post-transfection, cells were subjected to selection with culture medium supplemented with 500 ug/mL of geneticin (G418). Cells were passaged for 1 month in G418 selection medium at which time they were seeded into 100 mLs of growth medium in 500 mL Erlenmeyer flasks and grown with gentle shaking (100 rpm) for two weeks. Conditioned medium was harvested after two weeks and HSA1R4 was isolated from the conditioned medium using protein G affinity chromatography as described in Example 4.

Results: HSA1R4 is well expressed in HEK293 cells. The expressed protein has comparable polyacrylamide gel migration as HSA1R4 produced in SF9 insect cells.

TABLE 6

Sequence of Primers used for mouse IgG2a HCH2 polymer PCR Amplification

| Name | Sequence (5' to 3') |
| --- | --- |
| MU_Hinge_F (SEQ ID NO: 15) | CCGCTAGAATTCGAGCCCAGAGGGCCCACAATCAAGCCCTCTCCTCCATCCAAATCCCCA |
| MU_CH2NH3 (SEQ ID NO: 16) | GGCCGCATAAGCTTGGAGCCTCGCGATTTGGGTTTTGAGATGGTTCTCTC |
| MU_XS_DELH (SEQ ID NO: 17) | CCGCATTCTAGACCCGGGGAGCCCAGAGGGCCCACAATCAAG |
| MU_CH2H3 (SEQ ID NO: 18) | GGCCGCATAAGCTTTTTGGGTTTTGAGATGGTTCTCTC |
| Mu_FRM5P-H3 (SEQ ID NO: 19) | GGCCGCTAAAGCTTGAGCCCAGAGGGCCCACAATCAAG |
| Mu_FRM3P-S (SEQ ID NO: 20) | GGCCGCTAGTCGACTCATTTACCCGGAGTCCGGGAGAAG |

The underlined letters indicate bases used as clamps or spacers. Bold face letters denote the location of restriction sites.

Results: The expressed polymers are stable, secreted, and soluble and are readily concentrated to useful levels. The proteins are glycosylated, as documented by the difference in predicted and observed molecular weights. Yields correlate inversely with protein size and fall in the range of 0.8 to 2.0 µg/mL of conditioned medium.

EXAMPLE 6

Expression of HSA1R4 in Human Embryonic Kidney (HEK) 293 Cells

To express HSA1R4 in HEK293 cells, the coding region was transferred from the pFastBac vector into the pcDNA3.0

EXAMPLE 7

Murine HCH2 Polymers Derived from Mouse IgG2a Sequences

For studies in mice, HCH2 polymers were produced that are composed of murine IgG2a sequences. Murine IgG2a is syntenic with human IgG1.

Murine HCH2 fragment subcloning and hinge mutagenesis: Examples 1, 2 and 3 describe the procedure for assembling linear HCH2 polymers from small cDNA fragments containing the HCH2 region. The techniques and reaction conditions used were the same as those described in Examples 1, 2, and 3. This procedure was applied to produce HCH2 polymers from mouse IgG2A HCH2 cDNA. To obtain the template sequence for mouse IgG2a, total RNA was isolated from the murine cell line F50-8A5.5 and the fragment containing the H—CH2-CH3 region was subcloned using RT-PCR, the primer, Mu_FRM5p-H3, which introduced a HindIII site immediately 5' of the hinge region and a second primer, Mu_FRM3p-S, which introduced a SalI site immediately 3' of the stop codon (Table 6). The resulting clone Mu_FRM-HS was characterized by DNA sequencing and used as a sequence template for further rounds of PCR. Prior to murine HCH2 polymer construction, PCR mutagenesis was used to change the three cysteines that form inter-chain disulfide bridges between Fc units to serines. As detailed in Example 2, the hinge cysteines were mutated to serines, the HCH2 region amplified and a 5' flanking EcoRI site and 3' flanking NruI and HindIII site were introduced using primers Mu_Hinge-F, Mu_CH2NH3 in a PCR amplification wherein the IgG2A framework clone, Mu_FRM-HS, served as template. The HCH2-ENH region was subcloned and served as template for the production of two additional HCH2 region fragments that differ from HCH2_ENH only by 5'- or 3'-flanking restriction sites: Fragment HCH2-SNH, which differs from HCH2-ENH only by the presence of a 5' flanking Sma I site was produced using primers Mu_XS_DELH and Mu_CH2NH3 (Table 6) in a PCR amplification wherein HCH2-ENH served as template. Fragment HCH2-SH differs from HCH2-SNH only by the removal of the NruI site from the 3' flanking sequences, leaving Hind III site intact. HCH2-SH was produced using primers Mu_XS_DELH and Mu_CH2H3 in a PCR amplification wherein HCH2-SNH served as template. Three HCH2 region fragments result; HCH2-ENH, HCH2-SNH, and HCH2-SH. All possess mutations that alter hinge region cysteines to serines.

Murine HCH2 polymer construction: Polymers composed of murine HCH2 units were built using the scheme presented in FIG. 1. As a first step, clone HCH2-ENH was opened at the 3' flanking Nru I sites and Hind III sites using restriction endonucleases. Clone HCH2-SNH was digested with Sma I and Hind III and the insert thus liberated was gel purified and ligated into compatible sites in the HCH2-ENH clone. The result of the ligation was the tandem addition of one HCH2 fragment to another. The insertion also regenerated the original sequence of restriction sites (NruI—spacer-HindIII) which were used in the next round of extension. Repeating this process of digestion and ligation adds HCH2 units in a stepwise manner. In the last round of polymer construction an insert derived from Sma I and Hind III digestion of HCH2-SH was used resulting in an HCH2 polymer with a flanking 3' Hind III site. The completed murine R4 polymer was digested with EcoRI and HindIII to release the polymer inserts from the cloning vector and ligated into like-digested Mu_FRM-HS resulting in the in-frame joining of the HCH2 polymers to the murine IgG2a framework region. HCH2 polymer and framework region were liberated by digestion with Eco RI and Sal I and ligated into like digested pFactBac expression vector (FIG. 2).

Figure 4:
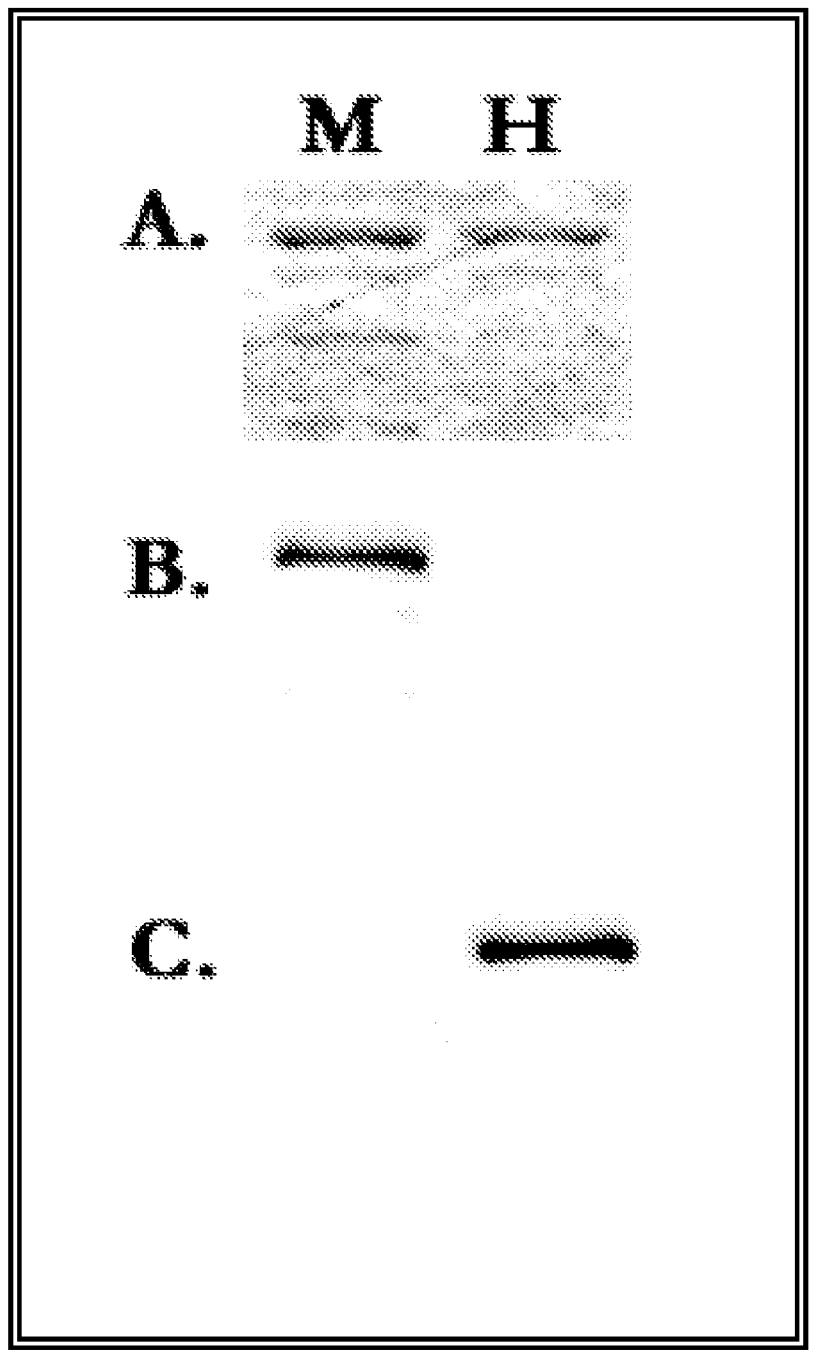
FIG. 4. Western blot Analysis. HSA1R4 and MSA1mR4 (75 ng) were electrophoresed on 7% SDS-polyacrylamide gels (SDS-PAGE). Gels were either stained with Coomassie Blue to reveal total protein (Panel A) or transferred to nitrocellulose membranes for Western Blot analysis (Panels B and C). Panel A. MSA1mR4 (Lane M) and HSA1R4 (Lane H) were resolved on SDS-PAGE gels and stained to reveal total protein. As expected, the panel shows that MSA1mR4 and HSA1R4 have similar molecular weights. Panel B. MSA1mR4 and HSA1R4 were run on SDS-PAGE gels and transferred to a nitrocellulose membrane. The membrane was probed with goat anti-mouse IgG2a-HRPO (Caltag) to reveal the presence of proteins with mouse IgG2A sequences. Only MSA1mR4 bound the antibody indicating that MSA1mR4 and HSA1R4 are antigenically distinct. Panel C. The membrane from Panel B. was stripped of detecting antibody and reprobed with goat anti-human Fc-HRPO (Bethyl Labs) to reveal human Fc sequences. Only HSA1R4 bound the detecting antibody again indicating that HSA1R4 and MSA1mR4 are distinct.

Domain I of murine serum albumin (MSA1): Total RNA was isolated from mouse liver using the method of Chomczynski and Sacchi (1987). First strand cDNA synthesis was primed with 100 µmol random hexamers using 200 U SuperScript II reverse transcriptase (Invitrogen, Carlsbad, Calif.) and 5 µg of total RNA in a 20 µL reaction mixture that was 500 µM in dNTPs (Pharmacia, Piscataway, N.J.), 1 U RNasin/µL (Promega Corp., Madison, Wis.), 10 µM in DTT, and 1× in first strand buffer. Reaction proceeded at 42° C. for 50 min. MSA1 was amplified from murine liver cDNA using PCR, the forward primer MSA_DomI_F (SEQ ID NO: 21) (5' GGCCGCATGGATCCAAAATGAAGTGGG-TAACCTTTCTC 3'), and the reverse primer MSA_DomI_R (SEQ ID NO: 22) (5' CCGCATGAATTCTCTCTGACGGA-CAGATGAGACC 3'). The resulting cDNA spans the first 221 amino acid residues, including the leader sequence, of mouse serum albumin (i.e., MSA1) and flanking 5' Bam HI and 3' Eco RI sites were introduced. The amplified cDNA was digested with Bam HI and Eco RI and ligated into like-digested pFastBac expression vector into which the mR4 polymer and associated framework region had already been transferred. The resulting expression construct directs expression of an amino-terminal MSA1 fused to a polymer of 4 HCH2 regions in tandem followed by an IgG2a framework region on the carboxyl end (MSA1mR4). MSA1mR4 was expressed in SF9 cells and purified as described in Example 5 (FIG. 4).

TABLE 7

Number of HCH2 units, potential N-linked glycosylation sites, predicted molecular weights, and contribution of N-linked glycosylation to apparent molecular weight of HSA1-HCH2 polymers fused to the IgG1 - Fc framework.

| Construct | Number of CH2 units inserted | Number of HCH2 units in single chain | Number of HCH2 units in mature polypeptide | N-Linked glycosylation sites | Predicted MW (KD) | Apparent MW (KD) |
|---|---|---|---|---|---|---|
| HSA1Fc | 0 | 1 | 2 | 2 | 48.8 | 52.5 |
| HSA1R2 | 2 | 3 | 6 | 4 | 77.5 | 86.0 |
| HSA1R3 | 3 | 4 | 8 | 5 | 91.6 | 117.2 |
| HSA1R4 | 4 | 5 | 10 | 6 | 105.7 | 140.5 |

EXAMPLE 8

Structural Integrity

To examine the structural integrity and antigenic content, the recombinant proteins were resolved on SDS-PAGE gels and analyzed by Western blot. Proteins were electrophoresed on 7% SDS-PAGE gels (Laemmli et al., 1970) and transferred to nitrocellulose membranes (MSI). Membranes were blocked overnight in 5% non-fat milk in Tris-buffered saline, pH 7.4 (TBS). For analysis of Fc domains, a total of 50 ng of recombinant protein or 0.5 µg of control proteins (human IgG and BSA) were loaded onto the gels. The membrane was incubated for two hours with horse radish peroxidase (HRP)-labeled goat anti-human Fc polyclonal antibody (Caltag) used at 1:10000 dilution in a binding buffer consisting of 0.1% non-fat milk and 0.1% normal goat serum in TBS. The blot was washed with TBS-tween and detection performed using the ECL-plus chemoluminescent reagent following manufacturers instructions (Amersham). For direct visualization of proteins, gels were stained with Coomassie brilliant blue.

Figure 3:
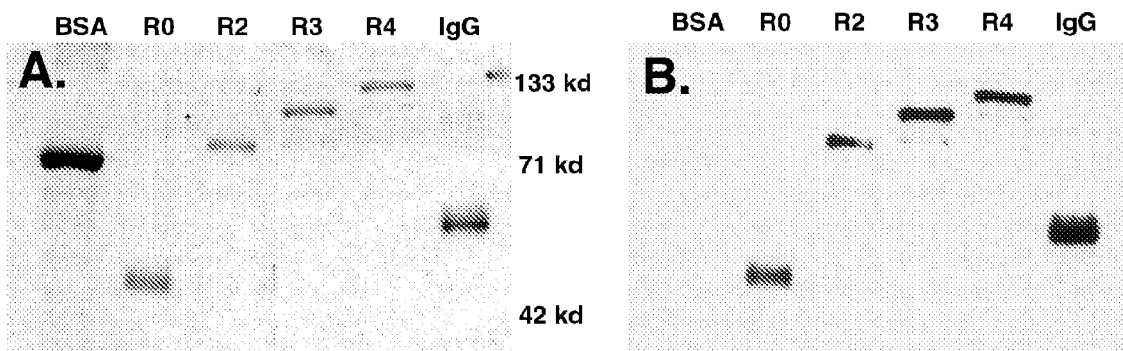
FIGS. 3A, and 3B. Western Blot analyses of Fc, R2, R3 and R4.

Results: As shown in FIG. 3A the HCH2 polymers are expressed, stable, and secreted. The observed molecular weight is larger than predicted for the peptide backbone alone, which indicates that the proteins are glycosylated (see Table 7). A Western blot probed with antibodies directed against human Fc revealed binding to the HCH2 polymers in a fashion similar to the IgG control (FIG. 3B).

EXAMPLE 9

HCH2 Polymers can be Expressed to Minimize Interaction with Complement Factor C1q Insect cells are known to express proteins that can have altered carbohydrate moieties. These alterations may weaken binding of complement factor C1q to these proteins. For this reason the binding of C1q to HCH2 polymers expressed in insect cell line SF9 was investigated. An assay examining the binding of C1q to human IgG or to HCH2 polymers expressed in insect cells was undertaken. Various concentrations of human C1q were allowed to bind to monomeric human IgG, to HSA1Fc, or to HSA1R4 previously immobilized onto wells of a 96 well ELISA plate. The extent of C1q binding was detected using a goat anti-human C1q polyclonal antibody.

C1q Binding Assay. Binding of human C1q to monomeric human IgG, HSA1Fc, and HSA1R4 was determined using modifications of a previously described ELISA protocol (Hinton et al., 2006). Ligands (2-10 ug/ml) were diluted in PBS and coated onto Costar high-binding ELISA assay plates overnight at 4° C. Plates were washed with 0.05% Tween-20 in PBS (PBS-T) and overlain with 4 µg/ml of C1q (Calbiochem) prepared in PBS-T with 0.1% gelatin (PTG) for four hours at room temperature. Plates were washed with PBS-T and incubated for 1 hour with goat anti-human C1q (Calbiochem, La Jolla, Calif.) diluted 1:1000 in PTG. Plates were washed with PBS-T and incubated for 1 hour with rabbit anti-goat IgG conjugated to horse radish peroxidase diluted 1:10,000 in PTG. The rabbit anti-goat IgG detecting antibody was preincubated with 2.5 ng/mL of human IgG to eliminate residual cross-reactivity to human Igs. Finally, plates were washed with PBS-T and developed with 0.5 mg/mL o-phenylenediamine (Sigma) peroxidase substrate. Absorbance was measured at 450 nm using a ThermoMax plate reader (Molecular Devices).

Figure 5:
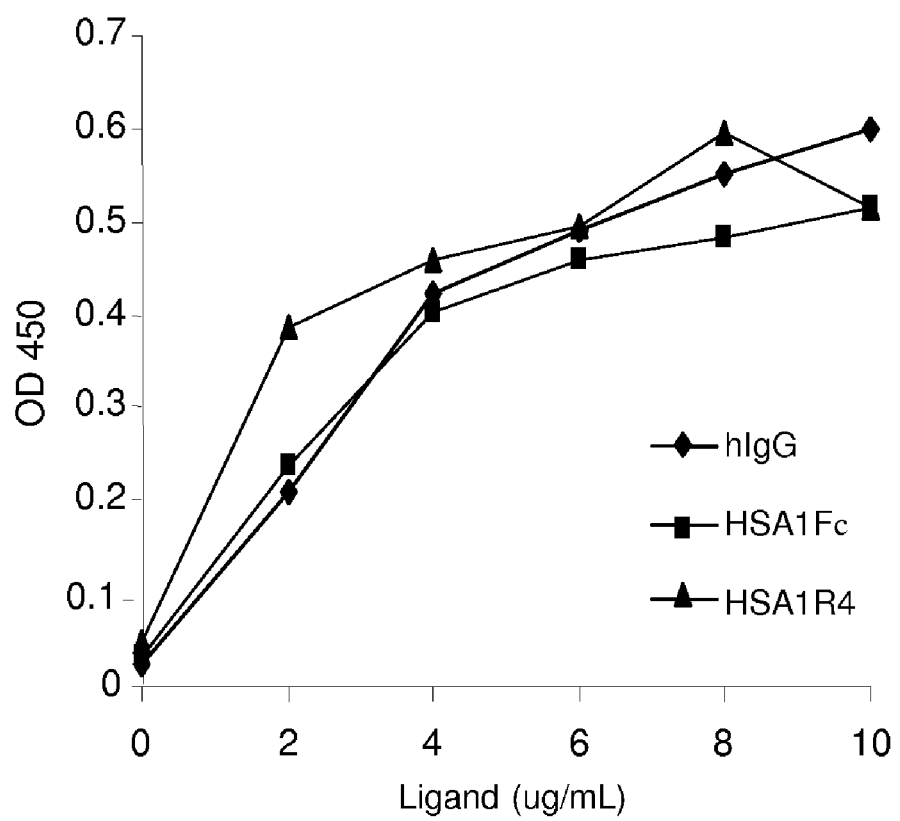
FIG. 5. Binding of C1q to HSA1R4 measured by ELISA. HSA1R4, HSA1Fc, and monomeric human IgG (Sigma Corp.) were immobilized onto ELISA plates at 2 to 10 μg/ml. C1q was added to ELISA plates at 4 μg/ml. Bound C1q was detected using HRP conjugated goat anti-C1q IgG followed by OPD addition. Data are expressed as O.D. Approximately equal amounts of C1q bind HSA1R4, HSA1Fc, and monomeric IgG at all concentrations of ligand tested. Data shown are representative of three separate experiments.

The results, shown graphically in FIG. 5, demonstrate that HCH2 polymers isolated from an insect cell expression system engage C1q more weakly than native IgG.

EXAMPLE 10

Fc Receptor Binding Assay

The receptor binding assay measures the binding of HCH2 polymers, Fc fusion proteins or IgG to recombinant ligand-binding domains of FcγRI, FcγRIIa, FcγRIIb, FcγRIIIa-158F and FcγRIIIa-158V. FcγRI has high affinity for the Fc region of IgG and binds avidly to HCH2 polymers, Fc fusion proteins, or monomeric IgG. The low affinity Fc receptors, FcγRIIa, FcγRIIb, FcγRIIIa-158F and FcγRIIIa-158V bind the Fc regions of IgG with low affinity.

Recombinant Fc receptor ligand binding domains: PCR was used to amplify ligand binding domains (LBD) and to add the 6xHis Tag for easy purification. The templates for PCR were the full-length cDNAs IMAGE clones for each receptor that were acquired from OpenBiosystems. The PCR products were digested with Hind III and Eco RI and ligated into like digested expression plasmid vector pcDNA3.1 (Invitrogen). Fc receptor expression vectors were transfected into HEK293 cells using lipofectamine (Invitrogen) mediated transfection. The histidine tagged Fc receptors were purified by immobilized metal affinity chromatography using a Ni2+ immobilized resin (Ni-Sepharose 6 Fast Flow, GE Biosciences). His tagged Fc receptors were extensively dialyzed against endotoxin fee PBS pH 7.0.

Fc Receptor binding assay: The recombinant FcγRI, FcγRIIa, FcγRIIb, FcγRIIIa-158F and FcγRIIIa-158V receptors were coated onto 96-well ELISA plates at 4 µg/mL in DPBS, pH 7.6. FcγRI was coated onto plates at 2 µg/mL. Receptors were incubated overnight at 4° C. Wells were washed once with DPBS+0.5% Tween-20 (PBST) and blocked by the addition of 200 µL of 1% Sanalac (Conagra, Irvine, Calif.) in DPBS to prevent non-specific binding. Blocking proceeded over night at 4° C. Plates were washed 4× with PBST to remove non-adherent receptors and blocking buffer. Human IgG, HSA1Fc, or HSA1R4 were diluted in 1% Sanalac in DPBS at the indicated concentrations and 0.1 mL was added to duplicate wells and incubated for 3 hours to allow receptor binding to occur. The plates were washed 4× with PBST to remove unbound ligands. Ligands were detected by the addition of Protein-G conjugated to horseradish peroxidase (HRPO). Protein-G binds the CH3-CH2 interface on IgG and thus binds to a single site on each ligand. Detection was achieved by incubating with the OPD substrate at 1 mg/mL (o-phenylenediamine, Sigma P-1526) in citrate buffer, pH 5.4. Data was acquired on the ThermoMax plate reader using the dual wavelength endpoint (450 nm-650 nm) method and expressed as OD 450 after correction for blank absorbance.

Figure 6:
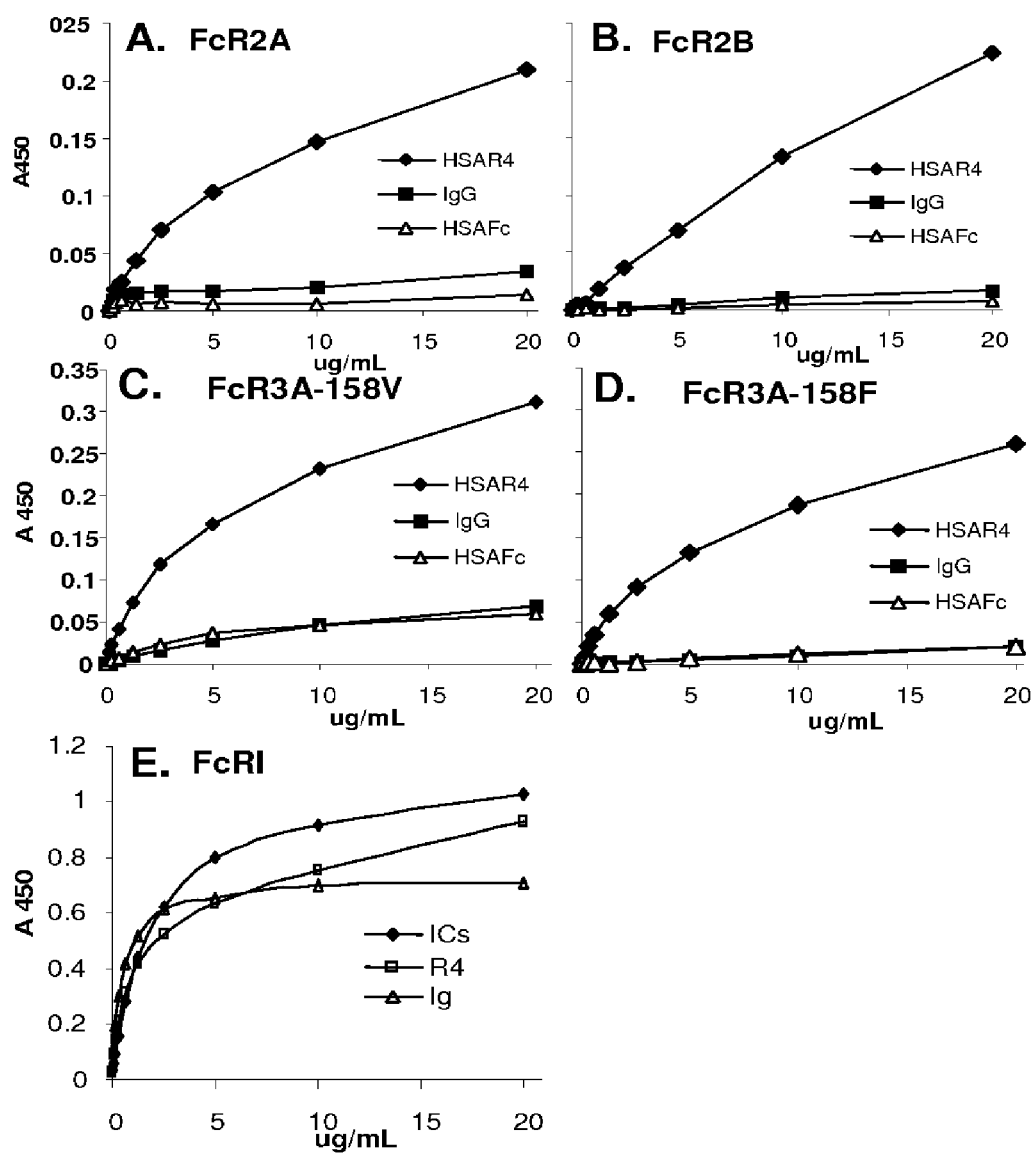
FIG. 6. R4 ligand binds far more efficiently to FcγR than monomeric Ig or Ig fusion proteins. Panels A-E display binding results for five different Fc receptors. Low-affinity FcγR were coated onto 96 well plates at 4 μg/mL, FcγRI was at 2 μg/mL. Plates were washed, blocked, and overlain with the FcγR ligands at the indicated concentrations. Plates were washed and bound ligand was detect using HRPO-Protein G which binds all ligands at a single site. Results shown are from a representative assay of four performed.

Results and Discussion: HCH2 polymers bind better to all of the human low-affinity FcγRs tested, at all concentrations tested, than native human IgG, or the Fc fusion protein control protein (FIG. 6). It should be noted that the highest concentration tested, 20 ug/mL, represents the amount of circulating immune complexes present in normal human blood. Thus the concentration range used in this study parallels physiologically relevant concentrations of FcγR ligands.

HCH2 polymers bind avidly to low affinity Fc receptors. This property distinguishes HCH2 polymers from Fc fusion proteins or IgG that do not have significant binding to the low-affinity Fc receptors. Fc fusion proteins alone or IgG alone do not bind to the low affinity Fc receptors. In order for them to bind they must first be modified by incorporation into an immune complex. HCH2 polymers alone are sufficient to bind low affinity Fc receptors. The ability of HCH2 polymers to bind directly to low affinity Fc receptors distinguishes HCH2 polymers from Fc fusion proteins or IgG.

EXAMPLE 11

Fc-HCH2 Interactions Assessed Using FACS

This example shows that the HCH2 polymers bind to more than one FcγR type expressed on the surface of living cells and that they bind to the ligand binding site of the receptors.

Method. Binding of HSA1R4 to FcγRs was determined by flow cytometry using the human monocytic cell line, U937. U937 cells constitutively express FcγRI and FcγRII (Liao et al., 1992). U937 cells (ATCC#: CRL-1593.2, Rockville, Md.) were maintained in RPMI 1640 supplemented with 10% FBS and 2 mM L-Glutamax. Cells were suspended in wash buffer (1% OVA in DPBS) at $1 \times 10^7$ cells/ml. To detect binding, 5 µg of HSA1R4 was added to a 0.05 ml suspension of cells. The cells were incubated at 4° C. for 20 min, washed, and resuspended in 0.05 ml of wash buffer containing affinity purified anti-HSA FITC conjugated goat IgG (1:100 dilution, Bethyl Labs, Montgomery, Tex.). To show specificity of binding, U937 cells were preincubated at 4° C. for 20 min with 5 µg of monoclonal antibodies to FcγRI (CD64; clone 10.1; BD Biosciences) and to FcγRII (CD32; clone FLI8.26; BD Biosciences) to block the ability of HSA1R4 to bind to FcγRs. Cells were analyzed using a FACScan II (BD Biosciences, San Jose, Calif.).

Figure 7:
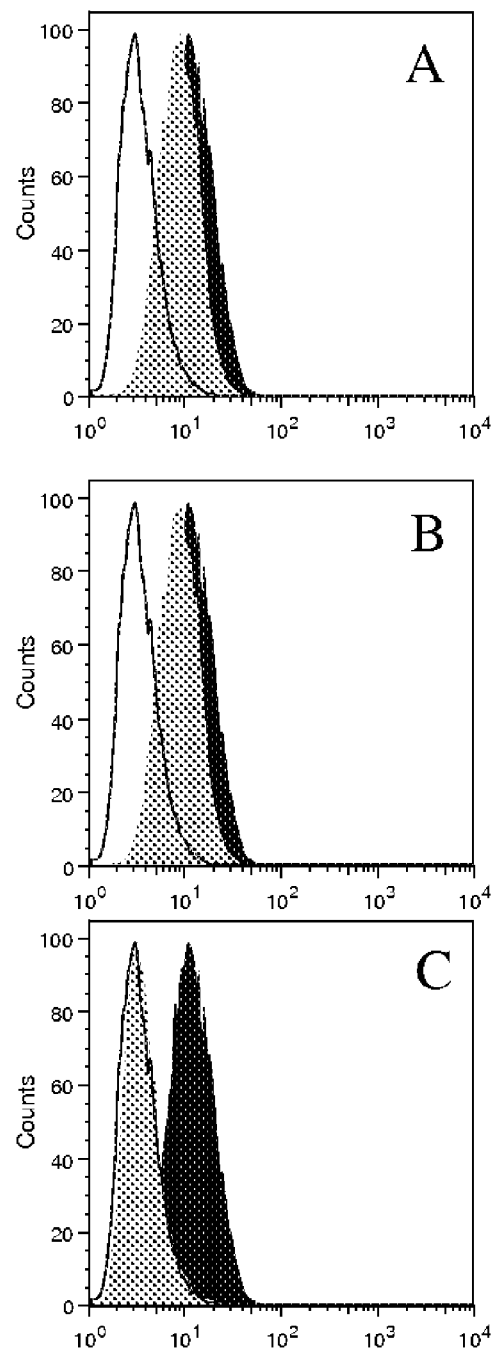
FIG. 7A, 7B, 7C. HSA1R4 binds to FcγRs expressed on the surface of living cells. Flow cytometric analysis of HSA1R4 binding detected with FITC anti-HSA goat Ig is shown in black; background fluorescence of cells stained with HSA1R4 and FITC goat Ig in white.

Results and Discussion. Increased fluorescence is uniformly observed when U937 cells are incubated with HSA1R4 followed by FITC conjugated goat anti-HSA polyclonal IgG to detect surface bound HSA1R4 (FIG. 7A). To detect binding to specific FcγRs, U937 cells were pre-incubated with blocking monoclonal antibodies (mAbs) to FcγRI, to FcγRII, or to both. Decreased fluorescence is observed following pre-incubation with either mAb while pre-incubation with both reduces fluorescence to background levels (FIG. 7A, 7B, 7C). Thus, HSA1R4 appears to bind exclusively to FcγRI and FcγRII receptors on U937 cells. These data show that the HCH2 polymers bind to both FcγRI and FcγRII on the surface of U937 cells. In addition, the data indicate that the HCH2 polymers bind to the ligand binding site on both FcγRI and FcγRII.

EXAMPLE 12

Assessment of HCH2 Polymer—FcγRIII Interactions

To assess potential HCH2 polymer—FcγRIII interactions, the HCH2-polymers, HSA1R2, HSA1R3, and HSA1R4 were assayed for their ability to activate NK cells within PBMC isolates and compared to responses achieved using the Ig-fusion protein, HSA1Fc. NK cells express both the low affinity IL-2 receptor, and FcγRIII (CD16) (Nagler et al., 1990). When primed with high levels of IL-2 (1 ng/mL), NK cells mount a proliferative response to CD16 ligation. This triggered response was used as a test of the fitness of the recombinant molecules to engage FcγR.

Methods

PBMC Purification and Proliferative Assays.

Peripheral blood mononuclear cells (PBMC) from four healthy donors were isolated from heparinized blood on a Ficoll-Paque gradient (Pharmacia Biotech Inc) and suspended in AIM V defined serum free medium (Gibco BRL). Recombinant protein stocks were initially prepared in RPMI 1640 (concentration 1 mg/ml). Recombinant protein stocks were diluted in AIM V medium (Fisher Scientific) to achieve the desired final concentrations as indicated in the drawings. PBMC were plated at a final concentration of $2\times10^6$ cells/ml in 96 well flat bottom plates (0.200 ml/well final volume). Cells were incubated for 72 hours in a humidified incubator at 37° C. in 5% atmospheric $CO_2$. During the last 5 hours of culture, wells were pulsed with 1 µCi of [methyl-3H] thymidine (Amersham Corp). Cells were harvested using a PhD cell harvester (Cambridge Technologies). Radioactivity was determined using a Beckman Scintillation Counter LS 5000TD (Beckman Instruments).

Figure 8:
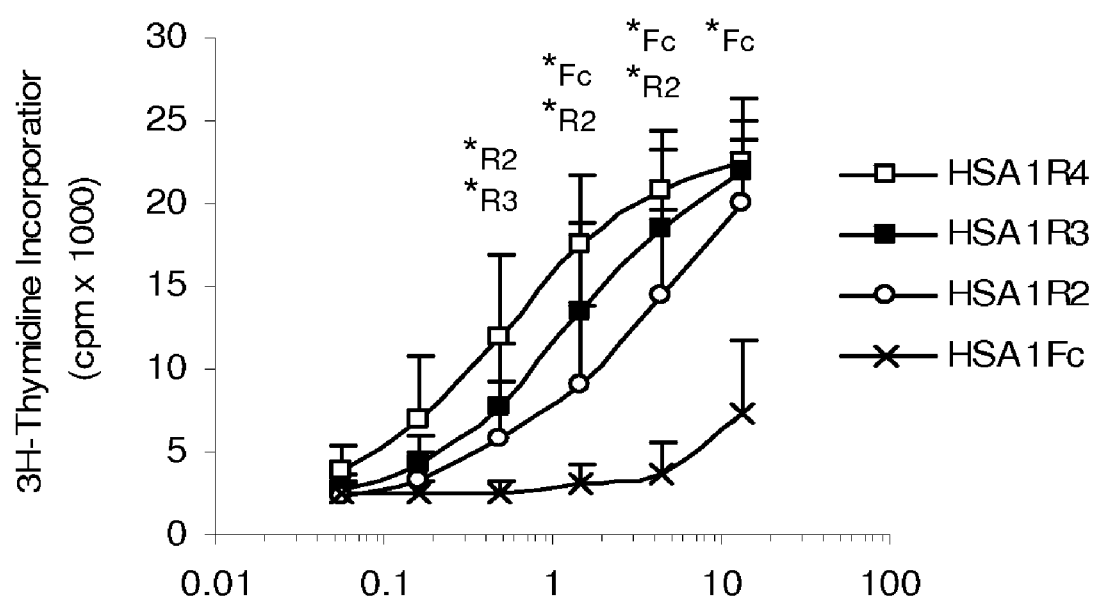
FIG. 8. HSA1R4 induces greater proliferative responses in PBMC than does HSA1R3, HSA1R2, or HSA1Fc. PBMC activation with HCH2 polymer proteins correlates directly with the number of HCH2 region repeats indicating a high level of sensitivity of Fcγ receptors to HCH2 number in the HCH2 polymer proteins. $2 \times 10^5$ freshly isolated PBMC were plated into 96 well plates in the presence of medium alone, or with IL-2 (1 ng/mL) and varying concentrations of HSA1R4, HSA1R3, HSA1R2, or HSA1Fc for 72 hr. During the last 5 hr the cells were pulsed with 1 μCi of [methyl-3H] thymidine. The graph compares the proliferative response of PBMC to varying dilutions of each HCH2 polymer protein used. CPM is shown on the y-axis and micrograms/ml of HCH2 polymer protein used is shown on the x-axis. The dose response curves show that as the number of HCH2 repeats increases in each ligand so does the efficiency with which it induces PBMC proliferation. HSA1R4 induces significantly greater proliferation by PBMC than does HSA1R3, HSA1R2, and HSA1Fc at the concentrations indicated on the figure. *Fc=$p<0.05$ for HSA1Fc vs HSA1R4; *R2=$p<0.05$ for HSA1R2 vs HSA1R4; *R3=$p<0.05$ for HSA1R3 vs HSA1R4, students' paired TTest. cpm of PBMC in medium=787±447; with IL-2=1957±1117; with HSA1Fc (20 μg/ml) 778±132; with HSA1R2 (20 μg/ml)=898+229; with HSA1R3 (20 μg/ml)=964±250; with HSA1R4 (20 μg/ml)= 1131±270. Data represent the average from four individuals±SEM.

Results. The HCH2 polymer constructs, expressing domain one of human serum albumin were tested for their ability to induce proliferative responses in PBMC. Use of these ligands allows us to determine the impact of decreasing HCH2 repeat number on FcγRIII triggered cell activation. PBMC were incubated with decreasing concentrations of HSA1R4, HSA1R3, and HSA1R2, in the presence of IL-2 and proliferative responses were measured as above. PBMC were also incubated with decreasing doses of HSA1Fc plus IL-2 to allow comparison with the HCH2 polymers. As shown in FIG. 8, PBMC proliferative responses triggered by the HCH2 polymers correlated with the number of HCH2 repeats present within the ligand. As the number of HCH2 units increased within each polymer so did its ability to induce proliferation by PBMC. HSA1R4 was the most effective ligand for inducing proliferative responses of PBMC; greater proliferative responses were observed in PBMC in response to all doses of HSA1R4 tested than in response to HSA1R3, HSA1R2 or HSA1Fc (FIG. 8).

EXAMPLE 13

Method of Using R4 in a Vaccine Formulation to Increase Antibody Titers to HSA1

The purpose of this example is to demonstrate the feasibility of using R4 as an antigen delivery vehicle to increase antigen specific antibody responses. In this example we have used domain one of human serum albumin (HSA1) as an antigen fused to the amino terminus of R4 to generate the polypeptide we term, HSA1R4. In Example 4 we showed how the construct, HSA1R4, was produced. In Example 5 we showed how HSA1R4 could be expressed and purified. We have used the HSA1R4 polypeptide to immunize mice and compared the responses achieved to those obtained using the antigen alone, HSA1.

Though we have used HSA1 in this example there are numerous other antigenic epitopes that could be expressed at the amino terminus of R4 to generate a hybrid molecule. The polypeptide containing the antigenic epitope(s) could be linked to the amino terminus of R4, as is shown in this example where HSA1 is used as an antigen, or alternatively the antigenic epitopes could be linked to the carboxyl end of R4. Numerous antigens of choice may be used as detailed in this patent application. In some instances, the polypeptide sequence would be less than 500 amino acids long and soluble in aqueous solutions.

Methods

Mice. SJL/J mice and C57BL6 mice, 5 to 6 wk old, from Jackson Laboratories (Bar Harbor, Me.) or from Taconic (Germantown, N.Y.), were maintained in a Barrier facility and acclimated for one to two wks before study. Animal care and experiments were performed according to NIH guidelines, as approved by the animal use committee of the University of Chicago.

Immunization. HSA1, HSA1Fc, or HSA1R4, dissolved in 0.15 ml saline, was injected into a tail vein. For s.c. injections, HSA1, HSA1Fc, HSA1R4, or ovalbumin (OVA; Sigma Corp., St. Louis, Mo.) were suspended in Ribi adjuvant (Sigma Corp.) according to manufacturer's instructions. Ribi adjuvant contains MPL and synthetic TDM incorporated into a mix of squalene and Tween-80, and serves as an immunostimulant with little toxicity. Proteins were dissolved in 2 ml of saline at 0.25 mg/ml, transferred into vials containing 0.5 mg of MPL and 0.5 mg of TDM and vortexed for 4 min to create an oil-in-water emulsion. Mice were immunized subcutaneously at two sites, one on each flank. A total volume of 0.1 ml containing from 0.125 µg to 25 µg of protein was injected at each site. Mice were bled retro-orbitally.

ELISA. ELISA plates (Corning Inc., Corning, N.Y.) were overlain with 0.1 ml/well of carbonate buffer (0.1M, pH 8.4) containing 5 µg of HSA or OVA and incubated at room temperature for 5 hours. Wells were treated by the addition of 0.1 ml/well of 0.25% Sanalac in DPBS to prevent non-specific binding (Conagra, Irvine, Calif.). After 2 hours at room temperature, wells were washed with 0.5% Tween-20 in DPBS (wash buffer) and 1:200, 1:250, 1:500, 1:2,500, 1:12,500, 1:62,500, 1:125,000, 1:250,000, 1:500,000, 1:1,000,000, and 1:2,000,000 dilutions of serum samples in 0.25% Sanalac were added to duplicate wells. Sera from naïve mice were diluted 1:200 and added to duplicate wells to provide background O.D. values. Plates were left overnight at 4° C., then washed, and overlain with a cocktail of biotinylated rat mAbs (each at 0.5 µg/ml) specific for murine Ig (mAbs clones: anti-$IgG_1$ A85-1; anti-$IgG_{2b}$ R12-3; anti-$IgG_3$ R40-82; all from Invitrogen: and anti-$IgG_{2c}$ 5.7 from BD Biosciences). $IgG_2$, was measured since SJL and C57BL6 mice express $IgG_{2c}$ rather than $IgG_{2a}$ (Martin et al., 1998). To quantitate levels of HSA1-reactive $IgG_1$ or $IgG_{2c}$, wells were overlain with biotinylated Abs specific for those isotypes. Following incubation with biotinylated Abs, wells were washed, and overlain with 0.1 ml of affinity purified peroxidase-conjugated goat anti-biotin Ab (1:500 dilution:Zymed, South San Francisco, Calif.) for 45 min. Wells were washed, and 0.2 ml of ortho-phenylenediamine (1 mg/ml) and $H_2O_2$ (1 µl/ml) in citrate buffer (0.1 M, pH 4.5) was added to each well. Absorbance was measured 15 min later using a ThermoMax Microplate Reader (Molecular Devices Corp., Sunnyvale, Calif.). Serum dilutions were considered positive when their O.D. values exceeded twice the mean O.D. values obtained from wells containing non-immune sera. As a control, absorbance values were measured from wells not coated with HSA or OVA but overlain with immune sera. Absorbance values of control wells always approximated those found in blanks.

Statistics. Ab titers were compared using Student's unpaired T test.

Results and Discussion

Figure 9:
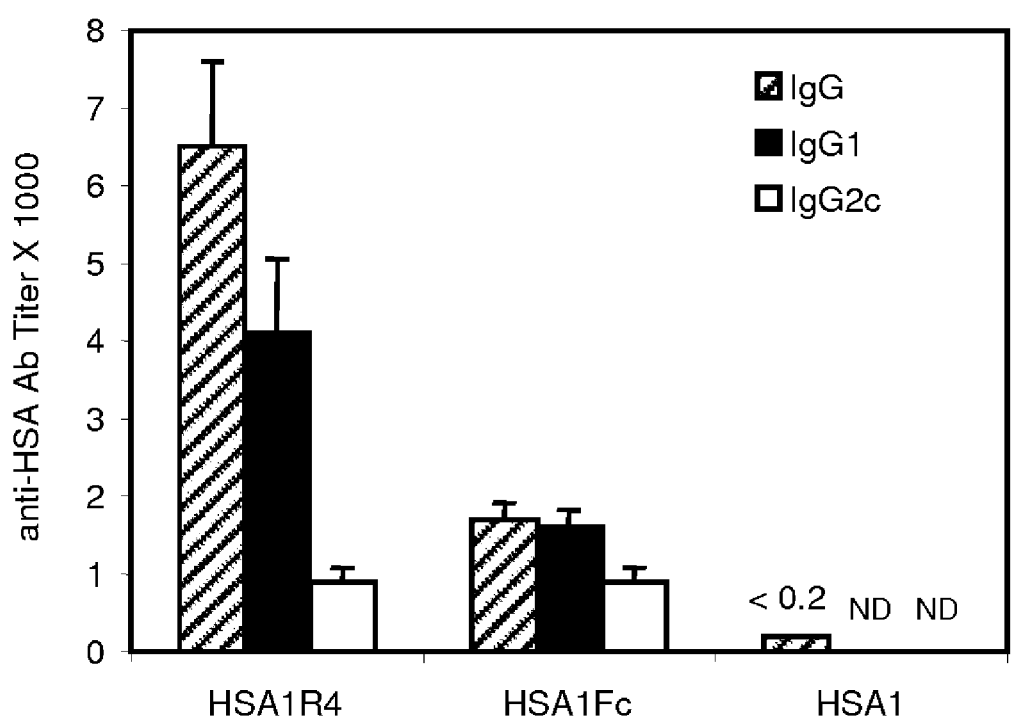
FIG. 9. I.V. injection of HSA1R4 increases HSA1-specific IgG antibody responses in SJL mice. HSA1R4 increases HSA1-specific IgG antibody responses in SJL mice following i.v. injection of 50 μg of HSA1R4, HSA1Fc, or HSA1. Titers of HSA-reactive IgG at two wk post-immunization (four mice per group) are shown as a mean ±SEM. Also shown are $IgG_1$ and $IgG_2$, titers of the same sera. HSA-specific antibody titers are significantly higher in mice receiving HSA1R4 than in mice receiving HSA1 ($p<0.001$) or HSA1Fc ($p<0.05$). ND=not done.
Figure 10:
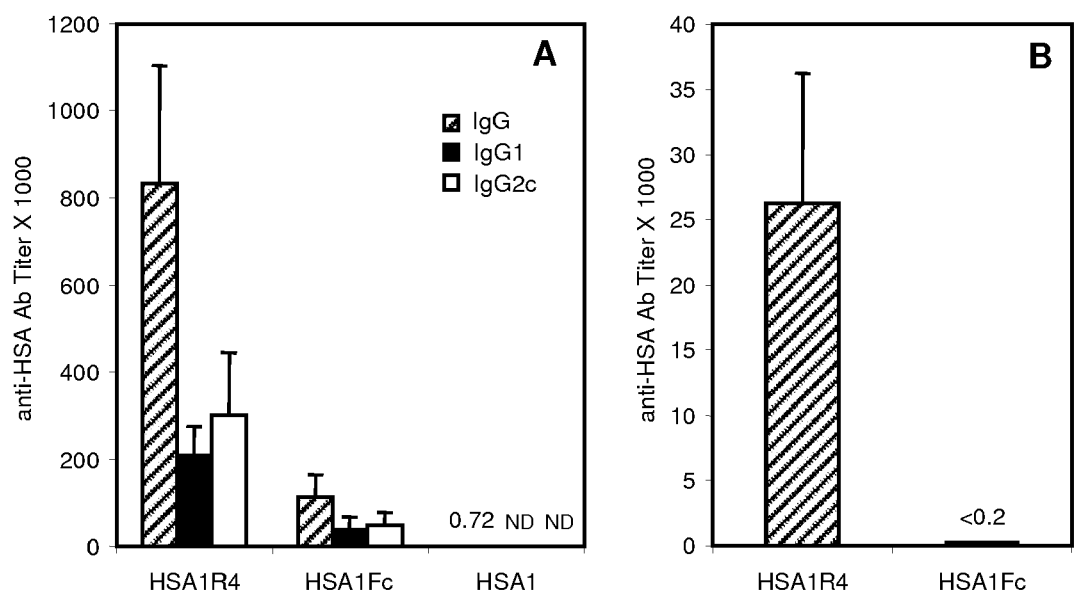
FIG. 10A, 10B. HSA1R4 in Ribi adjuvant enhances antigen specific antibody responses in SJL mice.

In this example we tested HSA1R4 in the high responder mouse strain SJL and in the low responder mouse strain C57BL6. SJL mice respond to vaccination with high antibody titers to antigen while C57BL6 mice respond to vaccination with lower antibody titers. SJL mice were injected intravenously with 50 µg of HSA1, HSA1Fc, or HSA1R4, and serum was obtained 14 days later, and Ab responses were assayed by ELISA. Anti-HSA Ab titers were not detected in mice given HSA1 alone at the minimum 1:200 serum dilution used as a cutoff (FIG. 9). Mice given HSA1R4 or HSA1Fc developed substantial Ab responses to HSA (FIG. 9). HSA specific titers were fourfold higher in mice injected with HSA1R4 than in mice injected with HSA1Fc ($p<0.05$). Equal mass weights of the proteins were injected so that the amount of HSA1 in HSA1Fc was 2.5 times that in HSA1R4 (FIG. 9). Anti-HSA IgG1 and $IgG_2$, were increased in response to both immunizations indicating activation of both Th1 and Th2 type T cells (FIG. 10). These data show that SJL mice injected with HSA1 covalently linked to R4 generate greater antibody responses to HSA1 than in mice injected with HSA1 alone or to HSA1Fc. When Ag/Ab complexes are injected intravenously in mice, greater Ab responses are observed than with Ag alone (Wernersson et al., 1999; Wernersson et al., 2000; Getahun et al., 2004).

Vaccines are typically injected subcutaneously. Accordingly, the efficacy of HSA1R4 as an Ag delivery agent was assessed. HSA1R4 was emulsified in Ribi adjuvant. Ribi adjuvant contains monophosphoryl lipid A (MPL) which signals through Toll-like receptor 4 (TLR4) to activate APC maturation and to increase co-stimulatory molecule expression (Ismaili et al., 2002; Martin et al., 2003). Mice were immunized with HSA1 alone, HSA1Fc, or HSA1R4 (50 µg/mouse), and anti-HSA Ab titers determined in sera obtained 14 days later. In mice immunized with HSA1 alone, anti-HSA Ab titers were only detectable in sera from 2 of 5 mice at the 1:200 cutoff threshold employed (FIG. 10A, 10B). Ab titers of mice given HSA1R4 averaged 1100 times those of mice given HSA1 ($p<0.001$), and were seven-fold those of mice given HSA1Fc ($p=0.01$). Isotype analysis revealed that both IgG1 and $IgG_2$, Ab titers rose following immunization with HSA1R4.

A 200 fold lower dosage of immunogens (250 ng) was next tested, again in Ribi adjuvant, with Ab measured in sera obtained 14 days post-immunization. Mice given HSA1R4 developed 130 times as much HSA1 specific Ab as mice immunized with HSA1Fc ($p<0.001$; FIG. 10B).

Figure 11:
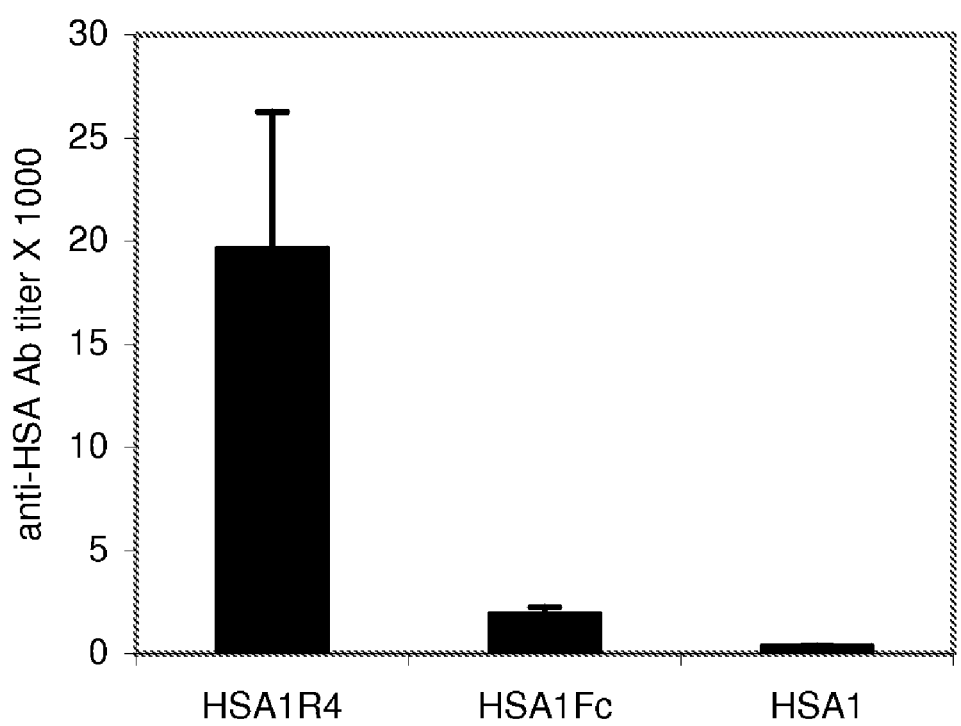
FIG. 11. HSA1R4 increases HSA1-specific Ab responses in C57BL/6 mice. Mice were immunized with 50 μg of HSA1R4, HSA1Fc, and HSA1 subcutaneously in Ribi adjuvant. Sera were obtained two weeks later (7 mice per group). Titers of HSA-reactive IgG are shown as mean ±SEM. HSA-specific Ab titers are 10 fold higher in mice given HSA1R4 than in mice given HSA1Fc ($p<0.05$) and 50 fold higher than in mice given HSA1 ($p<0.005$).

Since SJL mice can produce abnormally high levels of IgG (Jiang et al., 2000), we next determined responses in C57BL6 mice that have lower antibody responses to vaccination. C57BL6 mice were immunized with HSA1R4, HSA1Fc, and HSA1 all in Ribi adjuvant. Sera were collected 14 days later and assayed for HSA-specific Ab titers. C57BL6 mice developed Ab titers that were substantially lower than those observed in SJL mice. Nonetheless, anti-HSA Ab titers in C57BL6 mice receiving HSA1R4 were 10 fold those receiving HSA1Fc ($p<0.05$) and 50 fold higher than those receiving HSA1 ($p<0.005$) (FIG. 11).

EXAMPLE 14

Method of Using R4 in a Vaccine Formulation to Increase T Cell Responses to HSA1

This example shows that in mice immunized with an antigen linked to R4, the primary T cell response to that antigen is augmented. In this example the antigen is HSA1, and the mice are immunized with HSA1R4 in Ribi adjuvant and also with HSA1Fc in Ribi adjuvant as a comparator.

Method

Mice. SJL/J mice were purchased and maintained as in Example 13.

Immunization. Mice were immunized with HSA1Fc and HSA1R4 as in Example 14. To generate HSA1-reactive T cells for in vitro use, mice were injected with 0.1 ml of an emulsion consisting of 0.05 ml saline containing 100 µg of HSA (Sigma) and 0.05 ml of CFA distributed intradermally with 0.025 ml given in each flank and over each scapula.

Proliferative Responses. LNs and spleens were harvested from mice immunized 14 days earlier with: 1) HSA in CFA or with; 2) HSA1R4 or HSA1Fc in Ribi adjuvant. LN and spleen fragments were placed in saline, and disrupted mechanically using a tissue homogenizer to obtain a single cell suspension. RBCs were removed by centrifugation on ficoll-hypaque gradients. Buffy layers were harvested from the gradients, cells were washed with HBSS, and resuspended in HL-1 Ventrex medium (Fisher Scientific, Pittsburgh, Pa.) supplemented with 2 mM L-Glutamax, 50 µm 2-mercaptoethanol, 1×MEM amino acids, and 10 µg/ml gentamicin (Invitrogen). Cells were plated in 96 well flat bottom plates at $6 \times 10^5$ splenocytes/well or $4 \times 10^5$ LN-derived cells/well and HSA1Fc or HSA1R4 added as indicated in the results section. As a source of APCs, splenocytes from native mice, processed as described above, were incubated at 37° C. in RPMI containing 75 µg/ml of mitomycin C (Sigma) for 20 min, washed five times in saline, and added ($3 \times 10^5$ cells/well) to wells containing LN-derived cells. Cells were incubated at 37° C. for 72 h and pulsed for an additional 8 h with 1 µCi/well of 3H-Thymidine. Cells were harvested using a Cambridge Phd cell harvester and radioactivity determined by liquid scintillography.

Statistics. Proliferative responses of HSA-reactive LN cells, were compared using Student's unpaired T test. Proliferative responses of splenocytes were compared using Chi-square analysis of values above or below a SI of 3.

Figure 12:
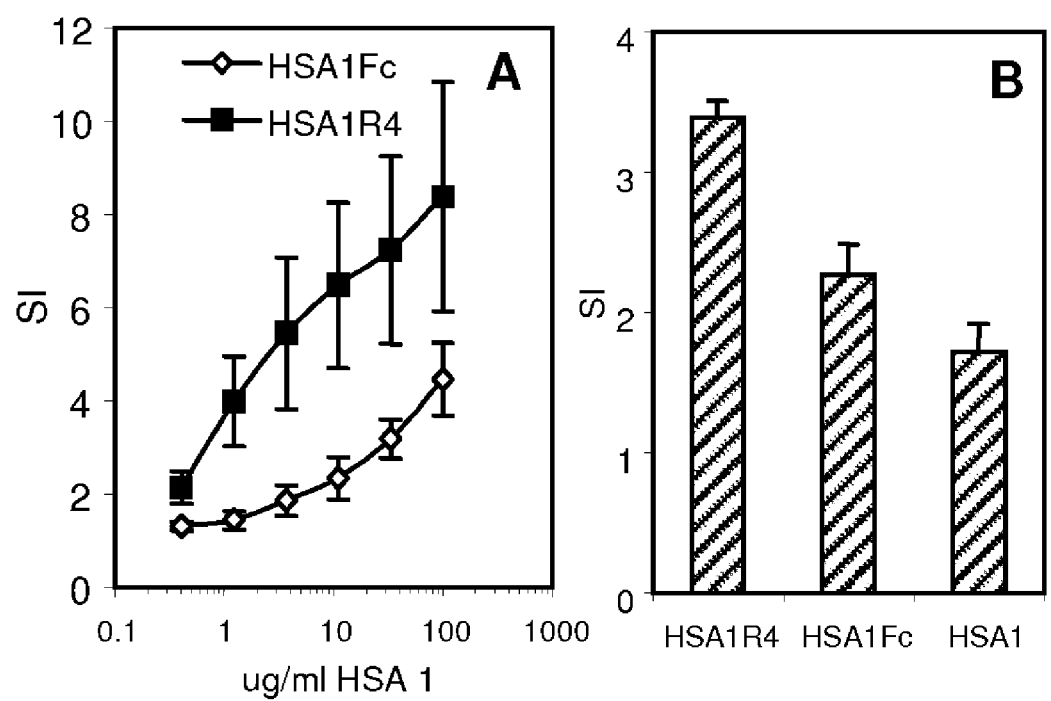
FIG. 12A, 12B.

Results and Discussion. These data show that HSA1R4 is a potent Ag delivery vehicle for induction of T cell responses. Mice were immunized with 50 ug of HSA1R4 or HSA1Fc in Ribi adjuvant. HSA1-specific splenic T cell proliferative responses were measured 14 days later. Taking a stimulation index (SI) of 3 as indicative of response, T cells from mice given HSA1R4 responded to a 20 fold lower concentration of HSA1 than T cells from mice given HSA1Fc (FIG. 12A). T cells from mice given HSA1R4 responded better to all 6 concentrations of HSA1 tested than T cells from mice given HSA1Fc (p<0.004) (FIG. 12A). The potency of HSA1R4 may be understated in our assay as mice given HSA1Fc received 2.5 times as much HSA1 as those given HSA1R4.

HSA1R4 presents Ag to T cells more efficiently than HSA1Fc (FIG. 12B). Targeting of Ag to FcγRs increases Ag uptake by APCs, Ag processing by them, and Ag presentation to T cells (Zaghouani et al., 1993; Brumeanu et al., 1993). Accordingly, studies were conducted to determine whether HSA1R4 could increase Ag presentation to T cells. Cells isolated from draining LNs of mice immunized with HSA in CFA 14 days earlier were used as a source of HSA-reactive T cells. Mitomycin C treated splenocytes from naïve mice served as a source of APCs. HSA-reactive T cells respond more briskly to HSA1R4 than to HSA1Fc (p<0.008) or to HSA1 (p<0.001) at molar equivalents ($1.6 \times 10^{-9}$ M) (FIG. 12B).

These results demonstrate that robust Ab responses to HSA1, a weakly antigenic peptide, can be obtained by coupling it to the HCH2 polymer R4. HSA1R4 has 10 potential FcγR binding regions and 2 copies of HSA1. ICs in Ab excess, known facilitators of Ab responses to weak Ags, bind to FcγRs expressed by APCs (Marusic-Galesci et al., 1991; Marusic-Galesci et al., 1992). Binding of ICs to FcγRs triggers IC internalization so that more Ag enters the APC than when Ag alone is given. Augmented Ag processing, and increased presentation of processed Ag to T cells, ensue. In HSA1R4, these properties of ICs have been integrated into a single defined molecule. Additionally, placement of Ag at the amino terminus of the HSA1R4 molecule renders the Ag fully accessible to processing enzymes. Thus, any antigenic peptide, of any size, or more than one when the goal is to develop a polyvalent vaccine, can be linked to R4 for Ag delivery.

EXAMPLE 15

Design and Construction of HCH2 Polymers for Delivery of Botulinum Neurotoxin Subtype A Antigens (BoNT/A)

BoNT/A activities map to discrete regions within the polypeptide chains: Endoprotease activity resides within the light chain. The heavy chain is responsible for receptor binding and translocation. The heavy chain can be further subdivided both functionally and proteolytically into an amino-terminal fragment ($H_N$), involved in ion-channel formation and light chain translocation, and a carboxyl-terminal fragment ($H_C$) involved in receptor binding The $H_C$ fragment is composed of two ~200 amino acid sub-domains that are structurally distinct. The amino-terminal portion, $H_CN$ (residues 871 to 1078 of the holotoxin) forms a lectin-like sub-domain. The carboxyl-terminal portion, $H_CC$ (residues 1090 to 1296 of the holotoxin) adopts a β-trefoil structure. The respective roles of $H_CN$ and $H_CC$ in receptor recognition and binding to neurons are not fully understood (FIG. 13).

Expression of Hc antigens in heterologous systems has previously proven problematic due to the codon bias in the *C. Botulinum* gene. To circumvent this limitation a synthetic gene approach was pursued. Designing the gene segments de novo permitted the introduction of restriction sites to facilitate the subcloning of the Hc fragments into expression vectors. The strategy was to synthesize the $H_CN$ and $H_CC$ gene segments separately and to combine segments to produce the Hc gene segment. The *C. Botulinum* Hc codon usage was optimized for expression in the *spodoptera frugiperda* (SF) cell lines using the UPGENE codon optimization algorithm (<<http://www.vectorcore.pitt.edu/upgene/upgene.html>>). The codon usage data set was derived from highly expressed genes in SF cells (<<http://www.kazusa.or.jp/codon/>>). The optimization scheme resulted in the resolution of two types of codon bias: First was to reduce or eliminate the use of rare codons, as seen for example in the almost exclusive use of the TTA codon (LEU) in *C. Botulinum*. The second was the balanced use of codons when multiple codons were available, as exemplified by the AAT codon (ASN).

The HcN and HcC gene segments were either subcloned individually or combined At internal restriction sites to produce the Hc gene. The three gene segments (SEQ ID NO: 24 for Hc; SEQ ID NO: 26 for HcN; SEQ ID NO: 28 for HcC) were subcloned into the pFastBac expression vector. The leader sequence from human IgG1 was cloned upstream and in-frame to the synthetic genes to direct their secretion from the cell into the medium. The HcN, HcC, and Hc genes were followed in frame either by a short sequence coding for a 6× histidine tag or by the R4 ligand coding sequences. The R4 ligands are based on human IgG1 sequences as described in Example 3. We have also developed identical ligands, mR4, based on murine IgG2a sequences (Example 7) for use in mice. The murine Ig2a sequences are syntenic to human IgG1. Accordingly we subcloned the Hc gene segments in-frame with the mR4 sequences.

Recombinant virus was derived and used to infect SF9 cells as we have described in Example 5 and Jensen et al., 2007). Conditioned media containing the 6×His tagged recombinant antigens, $H_CNHis$, $H_CCHis$, and HcHis control antigens were purified in a single step by passage of the conditioned medium over a Nickel affinity column. The Hc antigens fused to the R4 ligand, $H_CNR4$, $H_CCR4$, and HcR4, were purified in a single step from conditioned medium by affinity chromatography using protein-G Sepharose columns. Table 8 lists the number of amino acids in each of the recombinant Hc antigens as well as their apparent molecular weights as estimated from SDS-PAGE. Sizes and weights for $H_CNR4$, $H_CCR4$, and HcR4 reflect the dimerization that is a feature of the R4 ligands. Also listed in Table 8 are the antigen percentages in each of the HcR4 ligands. Antigen percentage is used to calculate the antigen load for vaccination, for example an immunization with 5 ug of HcR4 represents a load of 1.65 ug of Hc antigen.

TABLE 8

| Hc Antigens | | | |
|---|---|---|---|
| ID | AA | Daltons | wt % Ag |
| HcN (SEQ ID NO: 25) | 238 | 28260 (predicted) | 100% |
| HcC (SEQ ID NO: 27) | 231 | 26781 (predicted) | 100% |
| Hc (SEQ ID NO: 23) | 440 | 55976 | 100% |

TABLE 8-continued

| | Hc Antigens | | |
|---|---|---|---|
| ID | AA | Daltons | wt % Ag |
| HcNR4 | 1970 | 271542 | 20% |
| HcCR4 | 1956 | 283766 | 20% |
| HcR4 | 2374 | 313810 | 33% |

EXAMPLE 16

Figure 14:
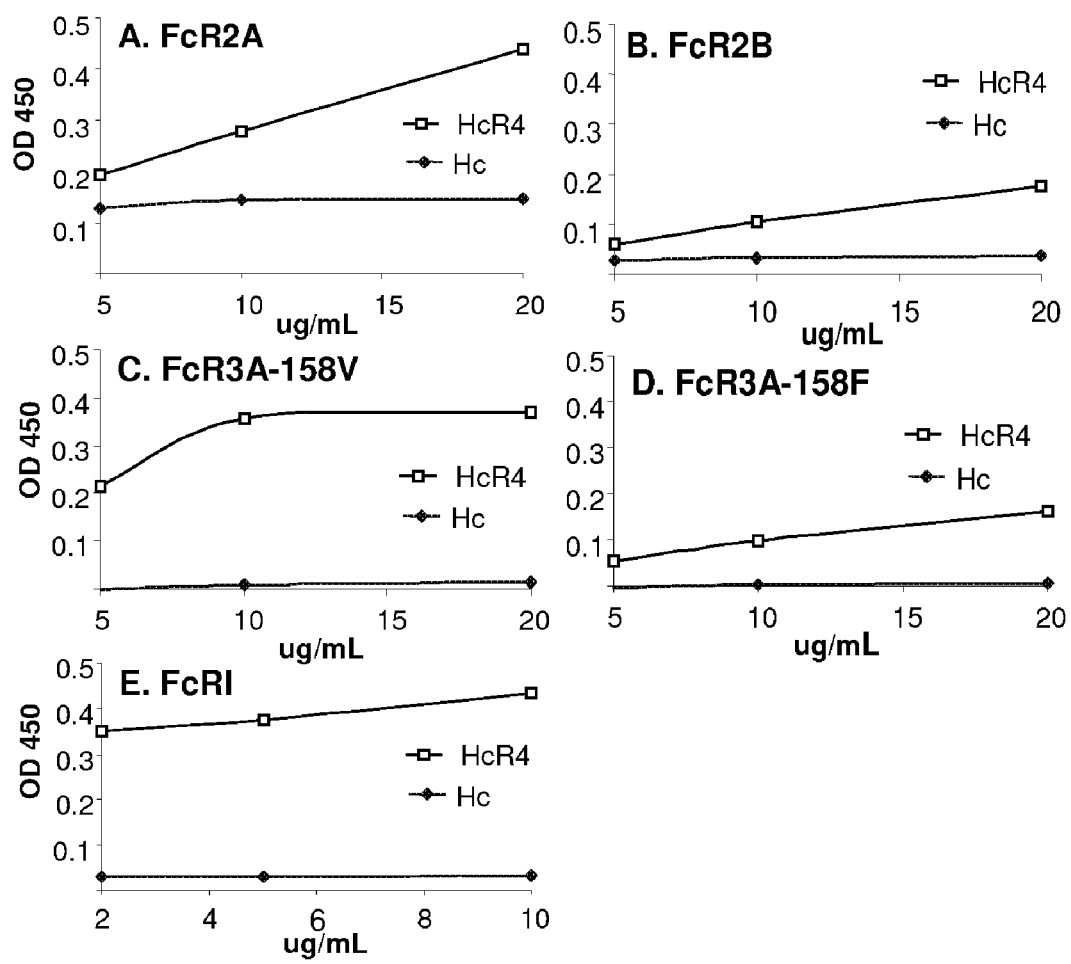
FIG. 14. HcR4 antigens bind efficiently to FcγR. Panels A-E display binding results for five different Fc receptors. The binding of the HcR4 ligand to FcγR was determined using the receptor binding assay described in Example 6.

HCH2 Polymers that Deliver Botulinum neurotoxin Subtype A (BoNT/A) Antigens Bind to Fc Receptors Avidly In this study we determined if HcR4 ligand can target Hc antigens to FcγR. We used the receptor binding assay introduced in Example 10. HcR4 was incubated with the immobilized receptors, plates were washed and residual ligand binding was determined. Hc antigen served as a control in these studies. Results: HcR4 binds exceptionally well to both low-affinity and high-affinity FcγRs (FIG. 14). Hc antigens alone fail to engage the Fc receptors. Antigens delivered as HCH2 polymers engage Fc receptors directly and do not need to be incorporated into immune complexes.

HCH2 polymers that deliver Hc region from Botulinum neurotoxin subtype A worked as well as HCH2 polymers that delivered domain I of human serum albumin. Thus it is the HCH2 polymer that confers enhanced binding to the low affinity Fc receptors. HCH2 polymers also avidly bind FcγRI, the high affinity receptor for the Fc region of IgG

EXAMPLE 17

HcR4 Efficiently Targets HC Antigen to APCs Resulting in Heightened Antigen Specific B Cell Responses In Vivo The goal of this study was to determine if the Hc, HcR4, and HcmR4 antigens could direct antigen-specific responses. The SJL strain has been identified as a high responder to Hc immunizations whereas the C57BL/6 strain is a poor/non-responder to Hc antigens. Thus we examined responses in the SJL mice to single dose SC immunizations with Hc and HcR4 at the 0.5 μg and 1 μg doses. The immunization protocol was identical to that described in Example 14 above; antigens were administered as an emulsion in Ribi adjuvant. Mice were immunized in their flanks and bled 14 days later. To detect antigen specific responses we developed an ELISA employing recombinant Hc as capture antigen. Hc-based ELISA has been validated as being predictive for the presence of neutralizing antibodies and correlates with an in vivo lethal challenge toxin model. Rabbit anti-sera produced against native BoNT/A binds avidly to the immobilized recombinant Hc and serves as a positive control.

Results for SJL: Immunization with 0.5 ug HcmR4 produced robust antigen-specific responses by day 14. In contrast, immunization with Hc alone resulted in poor antigen-specific responses at 14 days. To further characterize the antibody responses, antigen specific antibody titers were determined using the ELISA described above. Immunization with a single 0.5 μg of HcR4, or its murine analog, HcmR4 results in large Hc-specific antibody titers whereas immunization with a similar dose of Hc results in poor antibody titers (FIG. 15A.). Similar trends are observed at the 1 ug dose (FIG. 15B.).

Results for C57BL/6: The C57BL/6 strain is a poor/non-responder to Hc antigens. To determine the responses of the C57BL/6 strain to Hc and HcR4, mice received single dose SC immunizations of either 5 μg or 10 μg of HcR4 and Hc. Responses were determined 14 days later. C57BL/6 mice responded poorly to immunization with 5 μg of Hc with only a single mouse of ten immunized having shown responses whereas 6 of 10 mice immunized with 5 μg HcR4 had meaningful responses (FIG. 16). The superior results with HcR4 were achieved using 5 μg of HcR4 that delivers a dose of 1.67 μg of Hc antigen (See Table 8). A similar trend was observed when the immunization dose is increased to 10 ug.

Conclusions: Immunization with either HcR4 or HcmR4 results in larger anti-Hc antibody titers than can be achieved by immunization with Hc alone. The data indicate that the murine ligand, HcmR4, induces higher Hc-specific antibody responses in mice than its human R4 counterpart. These results might be expected as the murine ligand is likely better at engaging murine Fc receptors than the human ligand. Nevertheless, the results validate the use of the human ligand, HcR4, as an immunogen to achieve large and rapid responses to Hc in mice. It is also likely that the human HcR4 will work even better in humans than seen here with mice, just as the murine ligand, HcmR4, results in higher antibody titers in mice. The use of equal mass dosing in these experiments actually understates the efficacy of HcR4 and HcmR4 in comparison to Hc as 1 μg of HcR4 (or HcmR4) delivers an Hc antigen load of 0.33 μg (Table 8). Taken together these results indicate that Hc delivered as a R4 ligand directs better antigen-specific responses especially at lower antigen doses.

EXAMPLE 18

The HCH2 Polymers are Potent Antigen Delivery Vehicles for the Induction of Botulinum neurotoxin Subtype A (BoNT/A) Hc-Specific T Cell Responses In this study we establish that BoNT/A antigens delivered using polypeptides that include HCH2 polymers are better at inducing antigen-specific T cell responses than antigen alone.

Methods: To establish that use of HcR4 and HcmR4 leads to more efficient presentation of Hc antigens on APCs, we used the in vitro T cell assay introduced in Example 15. Mice were immunized with recombinant Hc and 14 days later T cells were isolated from draining lymph nodes as a source of Hc-reactive T cells. APCs were loaded with equal concentrations of Hc, HcR4 and HcmR4 ligands in the presence of Hc-reactive T cells to serve as a read out for the assay.

Results: Hc-reactive T cells respond more strongly to Hc antigens when APCs are primed with $3.6 \times 10^{-8}$ M of HcR4 than when APCs are primed with $3.6 \times 10^{-8}$ M of Hc alone (FIG. 17A). Similar trends are observed at low dose ($1.2 \times 10^{-8}$ M) (FIG. 17B). The data in FIG. 17B support a trend seen in antibody titer data indicating that HcmR4 performs better in mice than HcR4, due to a more favorable interaction between the murine ligand and murine Fcγ receptors.

EXAMPLE 19

R4 Administered Nasally Induces Robust Antibody Responses to Antigen

Mucosal administration of HcR4 ligands results in large and rapid Botulinum neurotoxin subtype A (BoNT/A) Hc-specific antibody responses: the second route for delivery of antigens using HCH2 polymers for the induction of immune responses to delivered antigens.

In this study we sought to determine if HCH2 polymers can deliver antigen when administered mucosally. Induction of mucosal immune responses has the advantage of inducing both serum IgG and IgA as well as increased protection at the mucosal surfaces due primarily to locally expressed antigen-specific IgA. Mucosal immunity might prove to be critical in those circumstances where there is a potential for exposure to aerosolized BoNT/A, such as in a biothreat scenario. Mucosal vaccination has the additional advantage of needle-free administration. The R4 ligands may target APCs in the mucosal epithelium by several routes; FcγR-bearing DCs can directly sample mucosal ICs through mucosal epithelial barriers or in collaboration with M cells within the nasal-associated lymphoid tissues. A second mechanism may involve the transport of the R4 polymer across the mucosal epithelia by FcRn. The FcRn binding site encompasses parts of both the CH2 and CH3 domains of IgG1. These sequences are present in the Fc region at the carboxyl end of the R4 polypeptide but absent from the HCH2 polymer. Antigen transcytosed by vesicular transport or FcRn could then be captured by macrophages and DCs and transported to draining lymph nodes. Hc itself binds to epithelial cells and is transcytosed by them. The Hc contained in HcR4 could contribute to transcytosis. Mucosal administration of Hc results in systemic IgG and IgA titers as well as induction of antigen specific mucosal IgA responses. As is the case for Hc administered in adjuvant SC, immune responses to mucosally administered Hc are modest.

Methods: To determine if linking Hc to the R4 ligand can improve mucosal immune response, HcR4 was instilled nasally into SJL mice at a dose of 25 μg/nostril on days 0, 7, and 14. Serum was obtained on days 21 and 28 and assessed for Hc specific IgG titers.

Results: Intranasal (IN) administration of HcR4 resulted in large and rapid induction of systemic antigen specific antibody titers (FIG. 18). The magnitude of the response is 20~30 fold larger, achieved with fewer IN immunizations and two weeks earlier than in a published reports employing Hc alone. The rapidity and magnitude of the response suggest a synergism between the FcγR targeting capacity of the R4 ligand and the intrinsic binding capacity of the Hc domain.

EXAMPLE 20

Cloning and Expression of Fatty Acid Binding Protein 7 Fused to the HCH2 Polymer R4

Fatty acid binding proteins (FABPs) are a family of small generally cytosolic proteins with high affinity for long chain fatty acids and their CoA derivatives. Fatty acid binding proteins are involved in the uptake and transport of fatty acids and as such impact fatty acid metabolism and lipid biosynthesis. FABPs are also involved in the modulation of other cellular functions including gene expression, differentiation and signal transduction.

The brain form of fatty acid binding protein, FABP7, is mainly expressed early in the development of the CNS but sparsely in the adult brain. FABP7 is expressed in a subset of adult glial tumors or gliomas, FABP7 expression enhances glioma cell migration and may therefore contribute to tumor spreading. In addition to cancers of the brain, FABP7 is frequently over expressed in melanoma where it also contributes to extracellular matrix invasion. FABP7 has characteristics favorable for targeted immunotherapy: it is expressed in the cancer cells but not in normal adult tissue and its expression in the cancer cells contributes to the malignant properties of the cancer.

As a first step in the evaluation of an FABP7 therapeutic vaccine, FABP7 was expressed as a fusion to the R4 HCH2 polymer. We have expressed murine FABP7 fused to the murine IgG2a R4, mR4, for use in mouse cancer models. We have expressed human FABP7 fused to human IgG1 based R4 for evaluation in humans.

Murine FABP7: The full-length cDNA for murine FABP7 is present in IMAGE clone 5700428, Genbank Accession # BC057090, and was used as template for PCR reactions. The coding sequences were amplified from the full-length cDNA using PCR and the oligonucleotides primers Mu_FABP7-F1,

```
                                        (SEQ ID NO: 36)
(5' GGCCGCATCTCGAGGTAGATGCTTTCTGCGCAACCTG 3'),
and Mu_FABP7-R1,
                                        (SEQ ID NO: 37)
(5' GGCCGCATGAATTCTGCCTTTTCATAACAGCGAACAGC 3').
```

The primers direct amplification of the coding region of murine FABP7 absent the initiation ATG and stop codon and introduce a 5' flanking Xho I site and a 3' flanking Eco RI site. The PCR products were digested with Eco RI and Xho I and ligated into like digested mR4 pFastBac expression vector.

Human FABP7: The full-length cDNA for human FABP7 is present in IMAGE clone IMAGE:4707233, Genbank Accession # BC012299, and was used as template for PCR reactions. The coding sequences were amplified from the full-length cDNA using PCR and the oligonucleotides primers Hu_FABP7-F1,

```
                                        (SEQ ID NO: 31)
(5' GGCCGCATCTCGAGGTGGAGGCTTTCTGTGCTACCTGG 3'),
and Hu_FABP7-R1,
                                        (SEQ ID NO: 32)
(5' GGCCGCATGAATTCTGCCTTCTCATAGTGGCGAACAGC 3').
```

The primers direct amplification of the coding region of human FABP7 absent the initiation ATG or the stop codon and introduce a 5' flanking Xho I site and a 3' flanking Eco RI site. The PCR products were digested with Eco RI and Xho I and ligated into like digested human IgG1 R4 pFastBac expression vector.

The recombinant FABP7-R4 fusion proteins were directed into the secretory pathway by proceeding the FABP7 coding region with the leader sequence from human IgG1 (MEFGLSWVFLVAILKGVQC) (SEQ ID NO: 45). When the IgG1 leader sequence precedes the FABP7-R4 coding region, it directs secretion of the expressed proteins from the cell into the medium. The recombinant proteins are purified from the conditioned medium.

EXAMPLE 21

Cloning and Expression of PLP and MBP Peptides Either Single or in Tandem Fused to the HCH2 Polymer R4

Proteolipid protein (PLP) and myelin basic protein (MBP) are components of the myelin sheath that surrounds the axons of nerve cells. PLP and MBP are targets for autoimmune reactions in multiple sclerosis in humans and in experimental autoimmune encephalomyelitis (EAE), the mouse model of the disease. Specific peptide antigens have been identified within PLP and MBP that are encephalitogenic T cell epitopes capable of inducing EAE in mice.

The PLP and MBP peptides were expressed as fusions to the human IgG1 R4 HCH2 polymers either as single peptides or in tandem. The PLP peptide, HSLGKWLGHPDKF (SEQ ID NO: 49), spans 13 amino acids. The cysteine present in the wild-type sequence was changed to serine to prevent unwanted disulphide bond formation. Complementary oligonucleotides coding for the peptide and that introduce a flanking 5' Xho I half-site and a flanking 3' EcoR I half-site were prepared. Most restriction enzymes, (e.g., Eco RI and Xho I) result in recessed 3' ends (5' overhangs) but blunt end restriction sites result in evenly matched ends (e.g., Sma I) and some restriction enzymes result in recessed 5' ends (e.g., Sac I and Kpn I). By designing complementary oligonucleotides with appropriate 5' or three 3' overhangs, the hybridized double-stranded oligonucleotides can be ligated directly into restriction digested expression vectors. Accordingly, the complementary oligonucleotides coding for the peptide were treated with poly-nucleotide kinase (New England Biolabs) to phosphorylate the oligonucleotides. Oligonucleotides were purified and hybridized to form double stranded DNA from the complementary oligonucleotides. The phosphorylated, hybridized oligonucleotides were ligated directly into the R4 pFastBac expression vector that had been previously prepared by digestion with Eco RI and Xho I. The MBP peptide, VHFFKNIVTPRTP (SEQ ID NO: 40), spans 13 amino acids and was introduced into the R4 pFastBac expression vector using a strategy identical to that pursued for the PLP peptide.

PLP-PLP peptides expressed in tandem: two copies of the PLP peptide were expressed separated by a 2 amino acid linker (HSLGKWLGHPDKFGTHSLGKWLGHPDKF) (SEQ ID NO: 43). To express two PLP peptides in tandem, complementary oligonucleotides were synthesized as described above that code for a single peptide but also introduce a Kpn I site proximal to the Eco RI half-site. Kpn I was chosen as it codes for gly-thr (GT) when expressed in frame. The oligonucleotides were phosphorylated, hybridized and ligated into the R4 pFastBac expression vector. The result was the introduction of as single PLP peptide with an in frame 3' unique Kpn I site between the peptide sequences and the Eco RI site. The resultant expression construct was termed PLPR4-KE to denote the addition of the internal Kpn I site in frame with the Eco RI site. To introduce the second peptide sequence, complementary oligonucleotides were once again synthesized that coded for the peptide but that introduce a flanking 5' Kpn I half-site and a flanking 3' EcoR I half-site. These oligonucleotides were phosphorylated, hybridized to make them into double-stranded DNA and ligated into the PLPR4-KE construct that had been digested with Kpn I and Eco RI. This resulted in the PLP-PLPR4 pFastBac expression vector.

Combined PLP-MBP peptides expressed in tandem: A similar strategy was pursued to make the PLP-MBP tandem peptides (HSLGKWLGHPDKFGTVHFFKNIVTPRTP) (SEQ ID NO: 52). Complementary oligonucleotides were synthesized that coded for the MBP peptide but that introduce a flanking 5' Kpn I half-site and a flanking 3' EcoR I half-site. These oligonucleotides were phosphorylated, hybridized to make them into double-stranded DNA and ligated into the PLPR4-KE construct that had been digested with Kpn I and Eco RI. This resulted in the production of PLP-MBPR4 pFastBac expression construct.

The recombinant PLPR4, MBPR4, PLP-PLPR4 and PLP-MBPR4 fusion proteins Were directed into the secretory pathway by preceding the peptide coding regions with the leader sequence from human IgG1 (MEFGLSWVFLVAILKGVQCLE) (SEQ ID NO: 45). When the IgG1 leader sequence precedes the coding regions, it directs secretion of the expressed proteins from the cell into the medium. The recombinant proteins are purified from the conditioned medium.

TABLE 9

SUMMARY OF SEQUENCES

| Sequence with SEQ ID NO. | Comments or Notes |
| --- | --- |
| GgccgctaAAGCTTGAGCCCAAATCTTGTGACAAAACTC (SEQ ID NO: 1) | Seq ID 1. Forward primer for human IgG1 Fc region amplification. FRM-5P-H3 |
| GgccgctaGTCGACTCATTTACCCGGAGACAGGGAGAG (SEQ ID NO: 2) | Seq ID 2. Reverse primer for human IgG1 Fc Region amplification. FRM-3P-Sal |
| CccgtaGAATTCGAGCCCAAATCTTCTGACAAAACTCACACATCCCCACCGTCCCCA (SEQ ID NO:3) | Seq ID 3. Forward primer for human IgG1 hinge mutagenesis Hinge 1 |
| GgccgcatAAGCTTggagccTCGCGATTTGGCTTTGGAGATGGTTTTCTC (SEQ ID NO:4) | Seq ID 4 reverse primer for amplification of Human IgG1 HCH2 unit with 3' Nru I and Hind III CH2NH3 |
| GgccgcatCCCGGGGAGCCCAAATCTTCTGACAAAACT (SEQ ID NO:5) | Seq ID 5 forward primer for mutated IgG1 hinge, introduces Sma I site SMA-DELH |
| GgccgcatAAGCTTTTTGGCTTTGGAGATGGTTTTCTC (SEQ ID NO:6) | Seq ID 6 reverse primer for amplification of Human IgG1 HCH2 unit with 3' Hind III CH2H3 |

TABLE 9-continued

SUMMARY OF SEQUENCES

| Sequence with SEQ ID NO. | Comments or Notes |
|---|---|
| GgccgctaCTCGAGATGGCCTTACCAGTGACCGCCTTG<br>(SEQ ID NO: 7) | Seq ID 7 Forward primer for CD8 alpha extracellular domain CD8-5PXho |
| GgccgctaGAATTCCGTCGTGGTGGGCTTCGCTGGCAG<br>(SEQ ID NO: 8) | Seq ID 8 Reverse primer for CD8 alpha extracellular domain CD8-3P119Eco |
| ELLGGPS<br>(SEQ ID NO: 9) | Seq ID 9 Amino acid residues 233 to 239 of human IgG1 heavy chain (Eu numbering). |
| 216 EPKSCDKTHT CPPCPAPELL GGPSVFLFPP KPKDTLMISR TPEVTCVVVD VSHEDPEVKF<br>276 NWYVDGVEVH NAKTKPREEQ YNSTYRVVSV LTVLHQDWLN GKEYKCKVSN KALPAPIEKT<br>336 ISKAK<br>(SEQ ID NO: 10) | Seq ID 10 HCH2 region from Human IgG1 with original cysteines<br>Amino acid residues 216 to 340 of human IgG1 heavy chain (Eu numbering). |
| GGCCGCATCTCGAGATGAAGTGGGTAACCTTTATTTCC<br>(SEQ ID NO:11) | Seq ID 11-Forward primer for HSA1 domain. PCR primer Dom1-F |
| CCGCATGAATTCTCTCTGTTTGGCAGACGAAGCCTT<br>(SEQ ID NO:12) | Seq ID 12-Reverse primer for HSA1 domain. PCR Primer Dom1-R |
| 1 EFEPKSSDKT HTSPPSPAPE LLGGPSVFLF PPKPKDTLMI SRTPEVTCVV<br>51 VDVSHEDPEV KFNWYVDGVE VHNAKTKPRE EQYNSTYRVV SVLTVLHQDW<br>101 LNGKEYKCKV SNKALPAPIE KTISKAKSGE PKSSDKTHTS PPSPAPELLG<br>151 GPSVFLFPPK PKDTLMISRT PEVTCVVVDV SHEDPEVKFN WYVDGVEVHN<br>201 AKTKPREEQY NSTYRVVSVL TVLHQDWLNG KEYKCKVSN ALPAPIEKTI<br>251 SKAKSGEPKS SDKTHTSPPS PAPELLGGPS VFLFPPKPKD TLMISRTPEV<br>301 TCVVVDVSHE DPEVKFNWYV DGVEVHNAKT KPREEQYNST YRVVSVLTVL<br>351 HQDWLNGKEY KCKVSNKALP APIEKTISKA KSGEPKSSDK THTSPPSPAP<br>401 ELLGGPSVFL FPPKPKDTLM ISRTPEVTCV VVDVSHEDPE VKFNWYVDGV<br>451 EVHNAKTKPR EEQYNSTYRV SVLTVLHQD WLNGKEYKCK VSNKALPAPI<br>501 EKTISKAKKL EPKSCDKTHT CPPCPAPELL GGPSVFLFPP KPKDTLMISR<br>551 TPEVTCVVVD VSHEDPEVKF NWYVDGVEVH NAKTKPREEQ YNSTYRVVSV<br>601 LTVLHQDWLN GKEYKCKVSN KALPAPIEKT ISKAKGQPRE PQVYTLPPSR<br>651 EEMTKNQVSL TCLVKGFYPS DIAVEWESNG QPENNYKTTP PVLDSDGSFF<br>701 LYSKLTVDKS RWQQGNVFSC SVMHEALHNH YTQKSLSLSP GK<br>(SEQ ID NO: 13) | Seq ID 13 Polypeptide sequence of human IgG1 R4-Fc polymer<br>Amino acid sequence of IgG1 HCH2 Polymer R4: a linear HCH2-polymer consisting of four HCH2 units (residues 3 to 508), similar to human IgG1 sequences. The polymer itself is genetically fused to residues 216 to 340 of the human IgG1 framework region (residues 511 to 733 in polypeptide below).<br>Notes on polypeptide Sequence:<br>IgG1 HCH2 Polymer R4: residues 3-508<br>IgG1 Framework region: residues 511-733 |
| 1 EFELKTPLGD TTHTSPRSPE PKSSDTPPPS PRSPEPKSSD TPPPSPRSPE<br>51 PKSSDTPPPS PRSPAPELLG GPSVFLFPPK PKDTLMISRT PEVTCVVVDV<br>101 SHEDPEVQFK WYVDGVEVHN AKTKPREEQY NSTFRVVSVL TVLHQDWLNG<br>151 KEYKCKVSNK ALPAPIEKTI SKTKSGELKT PLGDTTHTSP RSPEPKSSDT<br>201 PPPSPRSPEP KSSDTPPPSP RSPEPKSSDT PPPSPRSPAP ELLGGPSVFL<br>251 FPPKPKDTLM ISRTPEVTCV VVDVSHEDPE VQFKWYVDGV EVHNAKTKPR<br>301 EEQYNSTFRV VSVLTVLHQD WLNGKEYKCK VSNKALPAPI EKTISKTKSG<br>351 ELKTPLGDTT HTSPRSPEPK SSDTPPPSPR SPEPKSSDTP PPSPRSPEPK<br>401 SSDTPPPSPR SPAPELLGGP SVFLFPPKPK DTLMISRTPE VTCVVVDVSH<br>451 EDPEVQFKWY VDGVEVHNAK TKPREEQYNS TFRVVSVLTV LHQDWLNGKE<br>501 YKCKVSNKAL PAPIEKTISK TKSGELKTPL GDTTHTSPRS PEPKSSDTPP<br>551 PSPRSPEPKS SDTPPPSPRS PEPKSSDTPP PSPRSPAPEL LGGPSVFLFP<br>601 PKPKDTLMIS RTPEVTCVVV DVSHEDPEVQ FKWYVDGVEV HNAKTKPREE<br>651 QYNSTFRVVS VLTVLHQDWL NGKEYKCKVS NKALPAPIEK TISKTKKLEL<br>701 KTPLGDTTHT CPRCPEPKSC DTPPPCPRCP EPKSCDTPPP CPRCPEPKSC<br>751 DTPPPCPRCP APELLGGPSV FLFPPKPKDT LMISRTPEVT CVVVDVSHED<br>801 PEVQFKWYVD GVEVHNAKTK PREEQYNSTF RVVSVLTVLH QDWLNGKEYK<br>851 CKVSNKALPA PIEKTISKTK GQPREPQVYT LPPSREEMTK NQVSLTCLVK<br>901 GFYPSDIAVE WESSGQPENN YNTTPPMLDS DGSFFLYSKL TVDKSRWQQG<br>951 NIFSCSVMHE ALHNRFTQKS LSLSPGK<br>(SEQ ID NO: 14) | Seq ID 14 Polypeptide sequence of Human IgG3 R4-Fc polymer<br>Primers used to amplify fragment from murine IgG2a for construction of murine mR4 (similar to the human HSR4)<br>These four primers mutate the hinge and amplify the HCH2 region: |
| CCGCTAGAATTCGAGCCCAGAGGGCCCACAATCAAGCCCTCTCCTCCATCCAAATCCCCA<br>(SEQ ID NO: 15) | MU_Hinge_F |
| GGCCGCATAAGCTTGGAGCCTCGCGATTTGGGTTTTGAGATGGTTCTCTC<br>(SEQ ID NO: 16) | MU_CH2NH3 |
| CCGCATTCTAGACCCGGGGAGCCCAGAGGGCCCACAATCAAG<br>(SEQ ID NO: 17) | MU_XS_DELH |

TABLE 9-continued

SUMMARY OF SEQUENCES

| Sequence with SEQ ID NO. | Comments or Notes |
|---|---|
| GGCCGCATAAGCTTTTTGGGTTTTGAGATGGTTCTCTC<br>(SEQ ID NO: 18) | MU_CH2H3 |
| GGCCGCTAAAGCTTGAGCCCAGAGGGCCCACAATCAAG<br>(SEQ ID NO: 19) | This PCR primer amplifies the murine IgG2a Fc region:<br>Mu_FRM5P-H3 |
| GGCCGCTAGTCGACTCATTTACCCGGAGTCCGGGAGAAG<br>(SEQ ID NO: 20) | This PCR primer amplifies the murine IgG2a Fc region:<br>Mu_FRM3P-S |
| GGCCGCATGGATCCAAAATGAAGTGGGTAACCTTTCTC<br>(SEQ ID NO: 21) | This primer is used to amplify domain I of murine serum albumin (mouse form of HSA1):<br>MSA_DomI_F |
| CCGCATGAATTCTCTCTGACGGACAGATGAGACC<br>(SEQ ID NO: 22) | This primer is used to amplify domain I of murine serum albumin (mouse form of HSA1):MSA_DomI_R |

```
  1 VDNQRLLSTF TEYIKNIINT SILNLRYESN HLIDLSRYAS KINIGSKVNF
 51 DPIDKNQIQL FNLESSKIEV ILKNAIVYNS MYENFSTSFW IRIPKYFNSI
101 SLNNEYTIIN CMENNSGWKV SLNYGEIIWT LQDTQEIKQR VVFKYSQMIN
151 ISDYINRWIF VTITNNRLNN SKIYINGRLI DQKPISNLGN IHASNNIMFK
201 LDGCRDTHRY IWIKYFNLFD KELNEKEIKD LYDNQSNSGI LKDFWGDYLQ
251 YDKPYYMLNL YDPNKYVDVN NVGIRGYMYL KGPRGSVMTT NIYLNSSLYR
301 GTKFIIKKYA SGNKDNIVRN NDRVYINVVV KNKEYRLATN ASQAGVEKIL
351 SALEIPDVGN LSQVVVMKSK NDQGITNKCK MNLQDNNGND IGFIGFHQFN
401 NIAKLVASNW YNRQIERSSR TLGCSWEFIP VDDGWGERPL
(SEQ ID NO: 23)
```
Botulinum Neurotoxin Hc sequences:<br>Hc region peptide, 440 amino acids:

```
   1 CTCGAGGTTG ATAATCAGCG TCTCCTGAGT ACATTTACAG AGTACATCAA GAACATCATC
  61 AATACTTCCA TCCTGAACCT GCGCTACGAG TCAAATCACC TCATCGATCT GTCCAGGTAC
 121 GCTTCCAAGA TCAACATCGG CAGCAAGGTG AACTTCGACC CCATCGATAA AAATCAGATA
 181 CAACTGTTCA ATTTGGAAAG CAGCAAAATC GAGGTGATCC TGAAAAACGC AATCGTGTAT
 241 AATTCAATGT ATGAGAATTT TTCCACCTCT TTCTGGATAA GAATCCCAAA GTACTTTAAC
 301 TCTATCTCCC TGAACAACGA ATACACCATT ATCAATTGCA TGGAGAATAA CAGTGGTTGG
 361 AAAGTCTCCC TCAACTACGG CGAGATCATT TGGACGCTGC AAGACACCCA GGAGATTAAG
 421 CAGCGTGTCG TGTTCAAGTA CAGCCAGATG ATTAACATCT CAGACTACAT AAACAGGTGG
 481 ATATTTGTAA CAATCACCAA TAACCGTCTC AATAACTCTA AGATTTACAT TAACGGTCGC
 541 CTTATCGACC AGAAGCCCAT TTCCAACTTG GGTAACATTC ATGCCAGCAA CAATATTATG
 601 TTCAAGCTCG ATGGCTGCAG GGACACTCAC CGCTACATAT GGATCAAGTA CTTCAACCTG
 661 TTCGACAAGG AACTGAACGA AAAAGAGATC AAGGATCTGT ACGACAACCA GTCAAACTCC
 721 GGCATTCTCA AAGACTTTTG GGGAGATTAC CTGCAGTATG ACAAGCCATA CTACATGCTC
 781 AACCTGTATG ACCCTAATAA GTACGTTGAC GTGAACAACG TTGGCATTCG CGGTTACATG
 841 TACCTGAAGG GCCCTCGCGG TAGCGTCATG ACAACTAACA TCTACCTGAA TAGCTCACTG
 901 TACAGGGGTA CCAAGTTCAT TATTAAGAAA TACGCATCTG GCAACAAGGA TAATATAGTG
 961 AGGAATAACG ACCGTGTGTA CATCAACGTC GTGGTGAAAA ACAAGGAATA CCGTCTTGCG
1021 ACCAACGCTT CTCAAGCCGG AGTAGAGAAA ATCTTGAGTG CACTTGAGAT TCCAGACGTC
1081 GGTAACTTGT CCCAGGTGGT AGTGATGAAA TCCAAGAATG ACCAGGGTAT CACTAACAAG
1141 TGCAAGATGA ATCTGCAAGA CAACAACGGA AACGACATCG GTTTTATCGG TTTCCACCAA
1201 TTCAACAATA TTGCTAAGCT CGTCGCCAGC AATTGGTATA ACCGCCAGAT CGAACGTTCT
1261 TCCAGAACCC TCGGTTGTAG CTGGGAGTTC ATCCCCGTGG ACGATGGCTG GGGAGAGCGC
1321 CCCTTGGAAT TC
(SEQ ID NO: 24)
```
Hc region cDNA: sequences in bold denote restriction sites Xho I, Nde I and Eco RI respectively.

```
  1 VDNQRLLSTF TEYIKNIINT SILNLRYESN HLIDLSRYAS KINIGSKVNF
 51 DPIDKNQIQL FNLESSKIEV ILKNAIVYNS MYENFSTSFW IRIPKYFNSI
101 SLNNEYTIIN CMENNSGWKV SLNYGEIIWT LQDTQEIKQR VVFKYSQMIN
151 ISDYINRWIF VTITNNRLNN SKIYINGRLI DQKPISNLGN IHASNNIMFK
201 LDGCRDTHRY IWIKYFNLFD KELNEKEIKD LYDNQSNS
(SEQ ID NO: 25)
```
BoNT/A HcN peptide sequence: 238 amino acids

```
   1 CTCGAGGTTG ATAATCAGCG TCTCCTGAGT ACATTTACAG AGTACATCAA GAACATCATC
  61 AATACTTCCA TCCTGAACCT GCGCTACGAG TCAAATCACC TCATCGATCT GTCCAGGTAC
 121 GCTTCCAAGA TCAACATCGG CAGCAAGGTG AACTTCGACC CCATCGATAA AAATCAGATA
 181 CAACTGTTCA ATTTGGAAAG CAGCAAAATC GAGGTGATCC TGAAAAACGC AATCGTGTAT
 241 AATTCAATGT ATGAGAATTT TTCCACCTCT TTCTGGATAA GAATCCCAAA GTACTTTAAC
 301 TCTATCTCCC TGAACAACGA ATACACCATT ATCAATTGCA TGGAGAATAA CAGTGGTTGG
 361 AAAGTCTCCC TCAACTACGG CGAGATCATT TGGACGCTGC AAGACACCCA GGAGATTAAG
 421 CAGCGTGTCG TGTTCAAGTA CAGCCAGATG ATTAACATCT CAGACTACAT AAACAGGTGG
 481 ATATTTGTAA CAATCACCAA TAACCGTCTC AATAACTCTA AGATTTACAT TAACGGTCGC
 541 CTTATCGACC AGAAGCCCAT TTCCAACTTG GGTAACATTC ATGCCAGCAA CAATATTATG
 601 TTCAAGCTCG ATGGCTGCAG GGACACTCAC CGCTACATAT GGATTAAGTA CTTCAACCTG
```
HcN cDNA sequences. Bolded sequences represent flanking restriction sites introduced for cloning purposes.

TABLE 9-continued

SUMMARY OF SEQUENCES

| Sequence with SEQ ID NO. | Comments or Notes |
|---|---|
| 661 TTCGATAAGG AGCTGAACGA GAAGGAAATC AAAGACTTGT ATGACAACCA GAGCAACTCT<br>721 GAATTC<br>(SEQ ID NO: 26) | |
| 1 YIWIKYFNLF DKELNEKEIK DLYDNQSNSG ILKDFWGDYL QYDKPYYMLN<br>51 LYDPNKYVDV NNVGIRGYMY LKGPRGSVMT TNIYLNSSLY RGTKFIIKKY<br>101 ASGNKDNIVR NNDRVYINVV VKNKEYRLAT NASQAGVEKI LSALEIPDVG<br>151 NLSQVVVMKS KNDQGITNKC KMNLQDNNGN DIGFIGFHQF NNIAKLVASN<br>201 WYNRQIERSS RTLGCSWEFI PVDDGWGERP L<br>(SEQ ID NO: 27) | BoNT/A HcC peptide sequences:<br>231 Amino acids |
| 1 CTCGAGTACA TATGGATCAA GTACTTCAAC CTGTTCGACA AGGAACTGAA CGAAAAAGAG<br>61 ATCAAGGATC TGTACGACAA CCAGTCAAAC TCCGGCATTC TCAAAGACTT TTGGGGAGAT<br>121 TACCTGCAGT ATGACAAGCC ATACTACATG CTCAACCTGT ATGACCCTAA TAAGTACGTT<br>181 GACGTGAACA ACGTTGGCAT TCGCGGTTAC ATGTACCTGA AGGGCCCTCG CGGTAGCGTC<br>241 ATGACAACTA ACATCTACCT GAATAGCTCA CTGTACAGGG GTACCAAGTT CATTATTAAG<br>301 AAATACGCAT CTGGCAACAA GGATAATATA GTGAGGAATA ACGACCGTGT GTACATCAAC<br>361 GTCGTGGTGA AAAACAAGGA ATACCGTCTT GCCACCAACG CTTCTCAAGC CGGAGTAGAG<br>421 AAAATCTTGA GTGCACTTGA GATTCCAGAC GTCGGTAACT TGTCCCAGGT GGTAGTGATG<br>481 AAATCCAAGA ATGACCAGGG TATCACTAAC AAGTGCAAGA TGAATCTGCA AGACAACAAC<br>541 GGAAACGACA TCGGTTTTAT CGGTTTCCAC CAATTCAACA ATATTGCTAA GCTCGTCGCC<br>601 AGCAATTGGT ATAACCGCCA GATCGAACGT TCTTCCAGAA CCCTCGGTTG TAGCTGGGAG<br>661 TTCATCCCCG TGGACGATGG CTGGGGAGAG CGCCCCTTGG AATTC<br>(SEQ ID NO: 28) | HcC cDNA sequences. Bolded sequences represent flanking restriction sites introduced for cloning purposes. |
| 1 MVEAFCATWK LTNSQNFDEY MKALGVGFAT RQVGNVTKPT VIISQEGDKV<br>51 VIRTLSTFKN TEISFQLGEE FDETTADDRN CKSVVSLDGD KLVHIQKWDG<br>101 KETNFVREIK DGKMVMTLTF GDVVAVRHYE KA<br>(SEQ ID NO: 29) | Human FABP7 sequences were derived from an IMAGE clone: *Homo sapiens* fatty acid binding protein 7, brain, mRNA (cDNA clone MGC:21253 IMAGE:4707233) Accession #: BC012299<br>Human FABP7 (Fatty acid binding protein 7) polypeptide: 132 amino acids |
| 1 ATGGTGGAGG CTTTCTGTGC TACCTGGAAG CTGACCAACA GTCAGAACTT TGATGAGTAC<br>61 ATGAAGGCTC TAGGCGTGGG CTTTGCCACT AGGCAGGTGG GAAATGTGAC CAAACCAACG<br>121 GTAATTATCA GTCAAGAAGG AGACAAAGTG GTCATCAGGA CTCTCAGCAC ATTCAAGAAC<br>181 ACGGAGATTA GTTTCCAGCT GGGAGAAGAG TTTGATGAAA CCACTGCAGA TGATAGAAAC<br>241 TGTAAGTCTG TTGTTAGCCT GGATGGAGAC AAACTTGTTC ACATACAGAA ATGGGATGGC<br>301 AAAGAAACAA ATTTTGTAAG AGAAATTAAG GATGGCAAAA TGGTTATGAC CCTTACTTTT<br>361 GGTGATGTGG TTGCTGTTCG CCACTATGAG AAGGCATAA<br>(SEQ ID NO: 30) | Human FABP7 (Fatty acid binding protein 7) cDNA (coding sequence only): |
| GGCCGCATCTCGAGGTGGAGGCTTTCTGTGCTACCTGG<br>(SEQ ID NO: 31) | Human FABP7 PCR primers: Underlines sequences are clamps, bolded are added restriction sites we introduce to facilitate cloning.<br>This is used to amplify the FABP7 coding region for expression as an R4 fusion protein Hu_FABP7-F1, Length = 38 |
| GGCCGCATGAATTCTGCCTTCTCATAGTGGCGAACAGC<br>(SEQ ID NO: 32) | This is used to amplify the FABP7 coding region for expression as an R4 fusion protein Hu_FABP7-R1, Length = 38 |
| CCGCATAAGCTTTCAATGGTGATGGTGATGATGTGCCTTCTCATAGTGGCGAACAGC<br>(SEQ ID NO: 33) | The primer below introduces a 6xHis Tag (no fusion to R4) Hu_FABP7_His Length = 57 |
| 1 MVDAFCATWK LTDSQNFDEY MKALGVGFAT RQVGNVTKPT VIISQEGGKV<br>51 VIRTQCTFKN TEINFQLGEE FEETSIDDRN CKSVVRLDGD KLIHVQKWDG<br>101 KETNCTREIK DGKMVVTLTF GDIVAVRCYE KA<br>(SEQ ID NO: 34) | MOUSE FABP7: *Mus musculus* fatty acid binding protein 7, brain, mRNA (cDNA clone MGC:61214 IMAGE:5700428) Accession: BC057090<br>Mouse FABP7 polypeptide sequence: 132 amino acids |
| 1 ATGGTAGATG CTTTCTGCGC AACCTGGAAG CTGACAGACA GTCAGAATTT TGATGAGTAC<br>61 ATGAAAGCTC TGGGCGTGGG CTTTGCCACT AGGCAAGTGG GAAACGTGAC CAAACCAACT<br>121 GTGATTATCA GTCAGGAAGG TGGCAAAGTG GTGATCCGGA CACAATGCAC ATTCAAGAAC | Mouse FABP7 (Fatty acid binding protein 7) cDNA (coding sequence only): |

TABLE 9-continued

SUMMARY OF SEQUENCES

| Sequence with SEQ ID NO. | Comments or Notes |
| --- | --- |
| 181 ACAGAGATCA ATTTCCAGCT GGGAGAAGAG TTTGAAGAAA CCAGCATAGA TGACAGAAAC<br>241 TGTAAGTCTG TGGTTCGGTT GGATGGAGAC AAGCTCATTC ATGTGCAGAA GTGGGATGGC<br>301 AAAGAAACAA ATTGTACCAG AGAAATTAAG GATGGCAAGA TGGTCGTGAC TCTTACCTTT<br>361 GGGGATATCG TTGCTGTTCC CTGTTATGAA AAGGCATAG<br>(SEQ ID NO: 35) | |
| GGCCGCATCTCGAGGTAGATGCTTTCTGCGCAACCTG<br>(SEQ ID NO: 36) | Mouse FABP7 PCR primers:<br>Underlines sequences are clamps, bolded are added restriction sites we introduce to facilitate cloning.<br>Mu_FABP7-F1 Length = 38 |
| GGCCGCATGAATTCTGCCTTTTCATAACAGCGAACAGC<br>(SEQ ID NO: 37) | Mu_FABP7-R1 |
| CCGCATGTCGACTCAATGGTGATGGTGATGATGTGCCTTTTCATAACAGCGAACAGC<br>(SEQ ID NO: 38) | This primer introduces a 6xHis Tag (no fusion to R4)<br>Mu_FABP7_His Length = 54 |
| CTCGAGCATTCTTTGGGAAAATGGCTAGGACATCCCGACAAGTTTGAATTC<br>(SEQ ID NO: 39) | Mouse PLP peptide cDNA with flanking restriction sites:<br>Bolded sequences denote flanking restriction sites. |
| VHFFKNIVTPRTP<br>(SEQ ID NO: 40) | Myelin basis protein (MBP) peptide: |
| 1 CTCGAGCATT CTTTGGGAAA ATGGCTAGGA CATCCCGACA AGTTTGGTAC CATTCTTTG<br>61 GGAAAATGGC TAGGACATCC CGACAAGTTT GAATTC<br>(SEQ ID NO: 41) | PLP-PLP: (Tandem PLP peptides):<br>Bolded residues indicate internal in-frame restriction site that gets translated PLP-PLP cDNA. Flanking and internal restriction sites are bolded. |
| GGTACC GTCCACTTCT TCAAGAACAT TGTGACGCCT CGCACACCAG AATTC<br>(SEQ ID NO: 42) | Myelin basis protein (MBP) peptide: MBP cDNA. Flanking restriction sites are bolded. |
| HSLGKWLGHPDKFGTHSLGKWLGHPDKF<br>(SEQ ID NO: 43) | PLP-PLP: (Tandem PLP peptides):<br>Bolded residues indicate internal in-frame restriction site that gets translated |
| 1 GGATCCATGG AGTTTGGGCT GAGCTGGGTT TTCCTTGTTG CTATTTTAAA AGGTGTCCAG<br>61 TGTCTCGAG<br>(SEQ ID NO: 44) | PLP-MBP peptide cDNA: Flanking and internal restriction sites are bolded. |
| MEFGLSWVFLVAILKGVQCLE<br>(SEQ ID NO: 45) | IgG1 leader sequence. The IgG leader sequence is used to direct secretion of expressed protein to the medium, from which it can be easily purified. We use the IgG leader sequence on any protein that isn't already secreted. We used the IgG leader sequence on the Hc, HcC, HcN, FABP7, PLP, MPB, PLP-PLP, PLP-MBP fusions to R4. |
| 1 GGATCCATGG AGTTTGGGCT GAGCTGGGTT TTCCTTGTTG CTATTTTAAA AGGTGTCCAG<br>61 TGTCTCGAG<br>(SEQ ID NO: 46) | IgG1 leader sequence cDNA:<br>Flanking restriction sites are bolded. |
| 511            EPKSCDKTHT CPPCPAPELL GGPSVFLFPP KPKDTLMISR<br>551 TPEVTCVVVD VSHEDPEVKF NWYVDGVEVH NAKTKPREEQ YNSTYRVVSV<br>601 LTVLHQDWLN GKEYKCKVSN KALPAPIEKT ISKAKGQPRE PQVYTLPPSR<br>651 EEMTKNQVSL TCLVKGFYPS DIAVEWESNG QPENNYKTTP PVLDSDGSFF<br>701 LYSKLTVDKS RWQQGNVFSC SVMHEALHNH YTQKSLSLSP GK<br>(SEQ ID NO: 47) | An Fc region of human IgG1; this example is the Fc portion of SEQ ID 13, residues 511-742. |
| 698                                                                                   EL<br>701 KTPLGDTTHT CPRCPEPKSC DTPPPCPRCP EPKSCDTPPP CPRCPEPKSC<br>751 DTPPPCPRCP APELLGGPSV FLFPPKPKDT LMISRTPEVT CVVVDVSHED<br>801 PEVQFKWYVD GVEVHNAKTK PREEQYNSTF RVVSVLTVLH QDWLNGKEYK | An Fc region of human IgG3; this example is the Fc portion of SEQ ID 14, residues 699-977. |

TABLE 9-continued

SUMMARY OF SEQUENCES

| Sequence with SEQ ID NO. | | | | | Comments or Notes |
|---|---|---|---|---|---|
| 851 CKVSNKALPA PIEKTISKTK GQPREPQVYT LPPSREEMTK NQVSLTCLVK<br>901 GFYPSDIAVE WESSGQPENN YNTTPPMLDS DGSFFLYSKL TVDKSRWQQG<br>951 NIFSCSVMHE ALHNRFTQKS LSLSPGK<br>(SEQ ID NO: 48) | | | | | |
| HSLGKWLGHPDKF<br>(SEQ ID NO: 49) | | | | | PLP peptide |
| 305-311 ELLGGPS<br>(SEQ ID NO: 50) | | | | | Hinge proximal HC2 region from human IgG3 from Accession # BC089421. Numbering is from Accession # BC089421 |
| 241 ELKTPLGDTT HTCPRCPEPK SCDTPPPCPR CPEPKSCDTP PPCPRCPEPK<br>291 SCDTPPPCPR CPAPELLGGP SVFLFPPKPK DTLMISRTPE VTCVVVDVSH<br>341 EDPEVQFKWY VDGVEVHNAK TKPREEQYNS TFRVVSVLTV LHQDWLNGKE<br>391 YKCKVSNKAL PAPIEKTISK TK<br>(SEQ ID NO: 51) | | | | | HCH2 region of human IgG3 from Accession # BC089421: amino acid residues 241-412 (with original cyteines). Numbering is from accession # BC089421 |

REFERENCES

The following may be relevant to the instant application.
U.S. Pat. No. 5,455,165
U.S. Pat. No. 4,196,265
U.S. Pat. No. 4,340,535
U.S. Pat. No. 4,554,101
U.S. Pat. No. 4,559,231
U.S. Pat. No. 4,559,230
U.S. Pat. No. 4,578,770
U.S. Pat. No. 4,596,792
U.S. Pat. No. 4,601,903
U.S. Pat. No. 4,608,251
U.S. Pat. No. 4,658,019
U.S. Pat. No. 5,440,013
U.S. Pat. No. 5,446,128
U.S. Pat. No. 5,475,085
U.S. Pat. No. 5,618,914
U.S. Pat. No. 5,670,155
U.S. Pat. No. 5,672,681
U.S. Pat. No. 5,674,976
U.S. Pat. No. 5,679,354
U.S. Pat. No. 5,710,245
U.S. Pat. No. 5,714,147
U.S. Pat. No. 5,830,731
U.S. Pat. No. 5,840,833
U.S. Pat. No. 5,859,184
U.S. Pat. No. 5,922,845
U.S. Pat. No. 5,929,237
U.S. Pat. No. 5,998,166
U.S. Pat. No. 6,046,310
U.S. Pat. No. 6,262,029
Achiron et al., *Neurology,* 50:398-402, 1998.
Alcover et al., *Mol. Immunol.,* 30:55-67, 1993.
Anegon et al., *J. Exp. Med.,* 167:452-72, 1998.
Antel et al., *Clin. Exp. Immunol.,* 43:351-6, 1981.
Antibodies: A Laboratory Manual, Cold Spring Harbor Laboratory, 1988.
Asghar, In: *Pharmacological Manipulation of the complement system in human diseases,* Front. Bioscience (On Line) 1, e15-26, 1996.
Ashkenazi and Chamow, *Curr. Opin. Immunol.,* 9:195-200, 1997.
Berger et al., *Eur. J. Immunol.,* 27:2994-3000, 1997.
Bolhuis et al., *Int. J. Cancer Suppl.,* 7:78-81, 1992.
Brittenden et al., *Cancer,* 77:1226-1243, 1996.
Brumeanu et al., *Immunotechnology,* 2:85-95, 1996.
Brumeanu et al., *J. Exp. Med.,* 178:1795-1799, 1993.
Capon et al., *Nature,* 337:525-31, 1989.
Cartron et al., *Blood,* 99:754-758, 2002.
Chamow and Ashkenazi, *Trends Biotechnol.,* 14:52-60, 1996.
Chomczynski and Sacchi, *Anal. Biochem.,* 162:156-159, 1987.
Clark et al., *Int. J. Cancer Suppl.,* 2:15-7, 1988.
Clarkson et al. *N. Engl. J. Med.,* 314(19):1236-9, 1986.
Clynes et al., *Nat. Med.,* 6:443-446, 2000.
Clynes et al., *Science,* 279:1052-4, 1998.
Curnow, *Cancer Immunol Immunother.,* 45(3-4):210-5, 1997.
Daeron, *Annu. Rev. Immunol.,* 15:203-234, 1997.
Davis et al., *Science,* 213:1385-8, 1981.
Devereux et al., *Nucl. Acids Res.,* 12:387-395, 1984.
Dillman et al., *Cancer Res.,* 48:6097-102, 1988.
Dong et al., *J. Immunol.,* 163:5427-5434, 1999.
Duncan et al., *Nature,* 332:563-4, 1988.
Durandy et al., *J. Clin. Invest.,* 67:867-77, 1981.
Dwyer, *New Engl. J. Med.,* 326:107-16, 1992.
Edberg and Kimberly, *J. Immunol.,* 159:3849-57, 1997.
Edberg et al., *Exp. Clin. Immunogenet.,* 14:183-95, 1997.
Edwards et al., *Ann. Rheum. Dis.,* 46:773-6, 1987.
Eilat et al., *Proc. Natl. Acad. Sci. USA,* 89:6871-5, 1992.
EP 44167
Fanger et al., *Crit. Rev. Immunol.,* 12:101-24, 1992.
Fazekas et al., *Lancet,* 349:589-93, 1997.
Ferreri et al., *J. Immunol.,* 136:4188-93, 1986.
Fortis et al., *Eur. J. Immunol.,* 29:3654-3662, 1999.
Galfre et al., *Methods Enzymol.,* 73:3-46, 1981.
Galon et al., *Eur. J. Immunol.,* 27:1928-32, 1997.
Geha and Rosen, In: *Therapeutic Immunology* (Eds. Austen et al.) Blackwell Science, Cambridge, Mass., 280-296, 1996.
Gessner et al., *Ann. Hematol.,* 76:231-48, 1998.
Getahun et al., *J. Immunol.,* 172:5269-5276, 2004.
Ghose et al., *Cancer Immunol. Immunother.,* 13:185-9, 1982.
Ghose et al., *Crit. Rev. Ther. Drug Carrier Syst.,* 3:263-359, 1987.
Glennie et al., *J. Immunol.,* 139:2367-75, 1987.
Goldstein, *Transplant Proc.,* 19:1-6, 1987.
Gomez-Guerrero et al., *J. Immunol.,* 164:2092-101, 2000.
Gosselin et al., *J. Immunol.,* 149:3477-3481, 1992.
Gray et al., *J. Exp. Med.,* 180:1937-42, 1994.

Gribskov et al., *Nucl. Acids Res.*, 14:6745-6763, 1986.
Greenwood et al. *Eur. J. Immunol.*, 23(5):1098-104, 1993.
Guyre et al., *Cancer Immunol. Immunother.*, 45:146-8, 1997.
Harjunpaa et al., *Scand. J. Immunol.*, 51(6):634-41, 2000.
Harris et al., *J. Immunol.*, 143:2401-6, 1989
Hayes et al., *Crit. Rev. Oncology/Hematology*, 39:31-42, 2001.
Heijnen et al., *J. Clin. Invest.*, 97:331-338, 1996.
Hinton et al., *J. Immunol.*, 176: 346-356, 2006.
Hulett and Hogarth, *Adv. in Immunol.*, 57:1-127, 1994.
Ismaili et al., *J. Immunol.*, 168:926-932, 2002.
Jarvis et al., *Protein Exp. Purif,* 8:191-203, 1996.
Johannesson et al., *J. Med. Chem.*, 42:601-608, 1999.
Johnson and Glennie, *Brit. J Cancer*, 85:1619-1623, 2001.
Johnson et al., In: *Biotechnology and Pharmacy*, Pezzuto et al., eds., Chapman and Hall, New York, 1993.
Keler et al., *J Immunol.*, 165:6738-42, 2000.
Keler et al., *J. Immunol.*, 165:6738-6742, 2000.
Kenney et al., *J. Immunol. Methods*, 121:157-166, 1989.
Kimberly, *Rheum. Dis. Clin. North Am.*, 14(1):203-21, 1988.
Kimura et al., *Jpn J. Clin. Oncol.*, 13(2):425-33, 1983.
Kroesen et al., *Cancer Immunol. Immunother.*, 45:203-6, 1997.
Kurosaki et al., *Proc. Natl. Acad. Sci. USA*, 88:3837-41, 1991.
Kyte and Doolittle, *J. Mol. Biol.*, 157(1):105-132, 1982.
Laemmli, *Nature*, 227:680-5, 1970.
Lanier et al., *J. Immunol.*, 146:4421-6, 1991.
Lanier et al., *Nature*, 342:803-5, 1989.
LaSalle et al., *Faseb J.*, 8:601-8, 1994.
Legge et al., *J. Exp. Med.*, 191:2039-52, 2000.
Liao et al., *Proc. Natl. Acad. Sci. USA*, 89:3659-3663, 1992.
Lieberman, *Rheum. Dis. Clin. North. Am.*, 14:223-243, 1988.
Liu et al., *Cell Immunol.*, 167:188-94, 1996.
Liu et al., *J. Clin. Invest.*, 98:2001-7, 1996.
Lord et al., *Biochem. Soc. Trans.*, 20:734-8, 1992.
Lord et al., *Targeted Diagn. Ther.*, 7:183-90, 1992.
Lubbe et al., *Lancet*, 1361-1363, 1983.
Lund et al., *J. Immunol.*, 147:2657-62, 1991.
Majeau et al., *J. Immunol.*, 152:2753-67, 1994.
Manabe et al., *J. Lab. Clin. Med.*, 104:445-54, 1984.
Manca et al., *J. Exp. Med.*, 173:37-48, 1991.
Marks et al., *J. Mol. Biol.*, 222:581-97, 1991.
Martin et al., *Infect. Immun.*, 71:2498-2507, 2003.
Martin et al., *J. Immunol. Methods*, 212: 187-192, 1998.
Marusic-Galesic et al., *Immunology*, 72:526-531, 1991.
Marusic-Galesic et al., *Immunology*, 75:325-329, 1992.
McCarroll and King, *Curr. Opin. Biotechnol.*, 8:590-4, 1997.
McLean et al., *Mol. Immunol.*, 37:837-845, 2000.
Menard et al., *Int. J. Biol. Markers*, 4:131-4, 1989.
Meyerson et al., *J. Immunol.*, 156:574-84, 1996.
Miller, *Curr. Opin. Rheum.*, 4:693-699, 1992.
Minghetti et al., *J. Biol. Chem.*, 261:6747-6757, 1986.
Miyagi et al., *J. Neuroimmunol.*, 78:127-31, 1997.
Moingeon et al., *Proc. Natl. Acad. Sci. USA*, 89:1492-6, 1992.
Morgan et al., *Immunology*, 86:319-24, 1995.
Nagler et al., *J. Exp. Med.* 171:1527-33, 1990.
Needleman, *J. Mol. Biol.*, 48:443-453, 1970.
Nelson, *Cancer Cells*, 3:163-72, 1991.
Nitta et al., *J. Neurosurg.*, 72:476-81, 190.
Nolan et al., *Biochim. Biophys. Acta*, 1040:1-11, 1990.
Norderhaug et al., *J. Immun. Meth.*, 204:77-87, 1997.
Ohtsuka et al., *J. Immunol.*, 160:2539-45, 1998.
Oi and Morrison, *Mt Sinai J. Med.*, 53(3):175-80, 1986.
Paoletti and McInnes, In: *Vaccines: From concept to clinic*, CRC Press, 1999.
Passwell et al., *J. Immunol.*, 123:115-20, 1979.
PCT Appln. WO 9942077
Perez et al., *J. Immunol.*, 137:2069-72, 1986.
Perez et al., *Nature*, 316:354-6, 1985.
Pfeifer, *Curr. Opin. Biotechnol.*, 9:518-21, 1998.
Pietersz et al., *Cancer Res.*, 48:926-31, 1988.
Pietersz et al., *Immunol. Cell Biol.*, 66:43-9, 1988.
Plotkin and Orenstein, In: *Vaccines*, 4$^{th}$ Ed., Saunders press, 2004.
Ptak et al., *Scand. J. Immunol.*, 51:479-84, 2000.
Raghavan and Bjorkman, *Ann. Rev. Cell. Dev. Biol.*, 12:181-220, 1996.
Regnault et al., *J. Exp. Med.*, 189:371-380, 1999.
Remington's Pharmaceutical Sciences, 15$^{th}$ ed., pages 1035-1038 and 1570-1580, Mack Publishing Company, Easton, Pa., 1980.
Remington's Pharmaceutical Sciences, 18th Ed. Mack Printing Company, 1990.
Rosenstein et al., *Cancer Res.*, 44:1949-1953, 1984.
Schwartz and Dayhoff, In: *Atlas of Protein Sequence and Structure*, National Biomedical Research Foundation, 353 358, 1979.
Segal et al., *Immunobiology*, 185(2-4):390-402, 1992.
Semple et al. *Blood,* 78(10):2619-2625, 1991.
Shields et al., *J. Biol. Chem.*, 276:6591-6604, 2001.
Silman et al., *Ann. Rheum. Dis.*, 47:988-92, 1988.
Smith and Morrison, *Biotechnology* (N Y). 12(7):683-8, 1994.
Snider et al., *J. Exp. Med.*, 171:1957-1963, 1990.
Sondermann et al., *Nature*, 406:267-273, 2000.
Sorensen et al., *Neurology*, 50:1273-81, 1998.
Staerz et al., *Nature*, 314:628-31, 1985.
Steinberg and Steinber, *Arthritis. Rheum.*, 34:945-950, 1991.
Stevenson et al., *Infect Immun.*, 58(10):3225-32, 1990.
Swain et al., *Immunol. Rev.*, 102:77-105, 1988.
Ting et al., *J. Immunol.*, 141:741-8, 1988.
Traunecker et al., *Nature*, 339:68-70, 1989.
Trombetta and Mellman, *Annu. Rev. Immunol.*, 23:975-1028, 2005.
Vaickus et al., *Cancer Invest.*, 9:195-209, 1991.
Venables, *British Medical J.*, 307:663-666, 1993.
Vita et al., *Biopolymers*, 47:93-100, 1998.
Vivier et al., *Eur. J. Immunol.*, 21:1077-80, 1991.
Vyse and Walport, *Br. F Hosp. Med.*, 50:121-132, 1993.
Wallace et al., *Lupus* 2 Suppl 1, S13-5, 1993.
Weisshoff et al., *Eur. J. Biochem.*, 259:776-788, 1999.
Wernersson et al., *J. Immunol.*, 163:618-622, 1999.
Wemersson et al., *Scand. J. Immunol.*, 52:563-569, 2000.
White et al., *Protein Expression and Purification*, 21:446-455, 2001.
Wiesenhutter et al., *J. Clin. Immunol.*, 4:124-33, 1984.
Wilke et al., *Clin. Exp. Rheumatol.*, 9:581-587, 1991.
Winter et al., *Nature*, 349:293-9, 1991.
Wu et al., *J. Clin. Invest.*, 100:1059-70, 1997.
Wunderlich et al., *Int. J. Clin. Lab. Res.*, 22:17-20, 1992.
Young, et al., *Genes Develop.*, 8:1043-1057, 1994.
Zaghouani et al., *Science*, 259:224-227, 1993.
Zaghouani et al., *Science*, 259:224-7, 1993.
Zanetti et al., *Immunol. Rev.*, 130:125-50, 1992.

What is claimed is:

1. A method for inducing an immune response in an animal comprising one or more administrations of one or more compositions comprising a polypeptide where the compositions may be the same or different if there is more than one administration and the polypeptide consists of an Fc region linked to two arms;

wherein the Fc region consists of two Fc amino acid chains;

each Fc amino acid chain is linked to one of the two arms;
each arm consists of an HCH2 polymer linked to an antigen portion;
the HCH2 polymer consists of two to six linear copies of an HCH2 monomer;

the HCH2 monomer consists of at least a fragment of an HCH2 region, wherein the at least a fragment of an HCH2 region includes a hinge region; and at least one hinge region cysteine of the HCH2 monomer is mutated to serine.

2. The method of claim 1, wherein the Fc amino acid chains of the polypeptide are selected from the group consisting of: an amino acid chain of the IgG1 Fc region, an amino acid chain of the IgG3 Fc region, an amino acid chain of the IgG2a Fc region, and fragments thereof.

3. The method of claim 1, wherein the HCH2 region of the polypeptide is selected from the group consisting of: a human IgG1 HCH2 region, a human IgG3 HCH2 region, a mouse IgG2a, and fragments thereof.

4. The method of claim 1, wherein three hinge region cysteines of the HCH2 monomer of the polypeptide are mutated to serine.

5. The method of claim 1, wherein the antigen portion of the polypeptide is an antigen or an epitope.

6. The method of claim 1, wherein the antigen portion of the polypeptide is selected from the group consisting of: BoNT/A Hc (SEQ ID NO: 23), BoNT/A HcN (SEQ ID NO: 25), BoNT/A HcC (SEQ ID NO: 27), HAS1 (SEQ ID NO: 53), CD8α, FABP7 (SEQ ID NO: 29), PLP (SEQ ID NO: 49), MBP (SEQ ID NO: 40), PLP-MBP (SEQ ID NO: 52), PLP-PLP (SEQ ID NO: 43), and fragments thereof.

7. The method of claim 1, wherein the polypeptide is capable of binding at least one recombinant FcγR without being aggregated or presented in the form of an immune complex.

8. The method of claim 1, wherein the composition further comprises a carrier or an adjuvant.

9. The method of claim 1, wherein the composition further comprises a carrier or an adjuvant selected from the group consisting of: squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, and cell wall skeleton.

10. The method of claim 1, wherein the composition further comprises IL-2 or monophosphoryl lipid A.

11. The method of claim 1, wherein the administration comprises a parenteral administration or a mucosal administration.

12. The method of claim 1, wherein administration comprises intravenous administration, subcutaneous administration, topical administration, intradermal administration, oral administration, sublingual administration, intranasal administration, or intramuscular administration.

13. The method of claim 1, wherein the animal is a mouse or a human.

14. The method of claim 1, wherein if there is more than one administration at least one composition used for at least one administration is different from the composition of at least one other administration.

15. A method for providing a subject with a polypeptide comprising one or more administrations of one or more compositions comprising the polypeptide where the compositions may be the same or different if there is more than one administration and the polypeptide consists of an Fc region linked to two arms;

wherein the Fc region consists of two Fc amino acid chains;

each Fc amino acid chain is linked to one of the two arms;

each arm consists of an HCH2 polymer linked to an antigen portion;

the HCH2 polymer consists of two to six linear copies of an HCH2 monomer;

the HCH2 monomer consists of at least a fragment of an HCH2 region, wherein the at least a fragment of an HCH2 region includes a hinge region; and at least one hinge region cysteine of the HCH2 monomer is mutated to serine.

16. The method of claim 15, wherein the Fc amino acid chains of the polypeptide are selected from the group consisting of: an amino acid chain of the IgG1 Fc region, an amino acid chain of the IgG3 Fc region, an amino acid chain of the IgG2a Fc region, and fragments thereof.

17. The method of claim 15, wherein the HCH2 region of the polypeptide is selected from the group consisting of: a human IgG1 HCH2 region, a human IgG3 HCH2 region, a mouse IgG2a, and fragments thereof.

18. The method of claim 15, wherein three hinge region cysteines of the HCH2 monomer of the polypeptide are mutated to serine.

19. The method of claim 15, wherein the antigen portion of the polypeptide is an antigen or an epitope.

20. The method of claim 15, wherein the antigen portion of the polypeptide is selected from the group consisting of: BoNT/A Hc (SEQ ID NO: 23), BoNT/A HcN (SEQ ID NO: 25), BoNT/A HcC (SEQ ID NO: 27), HAS1 (SEQ ID NO: 53), CD8α, FABP7 (SEQ ID NO: 29), PLP (SEQ ID NO: 49), MBP (SEQ ID NO: 40), PLP-MBP (SEQ ID NO: 52), PLP-PLP (SEQ ID NO: 43), and fragments thereof.

21. The method of claim 15, wherein the polypeptide is capable of binding at least one recombinant FcγR without being aggregated or presented in the form of an immune complex.

22. The method of claim 15, wherein the composition further comprises a carrier or an adjuvant.

23. The method of claim 15, wherein the composition further comprises a carrier or an adjuvant selected from the group consisting of: squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, and cell wall skeleton.

24. The method of claim 15, wherein the composition further comprises IL-2 or monophosphoryl lipid A.

25. The method of claim 15, wherein the administration comprises a parenteral administration or a mucosal administration.

26. The method of claim 15, wherein administration comprises intravenous administration, subcutaneous administration, topical administration, intradermal administration, oral administration, sublingual administration, intranasal administration, or intramuscular administration.

27. The method of claim 15, wherein if there is more than one administration at least one composition used for at least one administration is different from the composition of at least one other administration.

28. The method of claim 15, wherein the subject is a cell.

29. The method of claim 15, wherein the subject is an animal.

30. The method of claim 15, wherein the subject is a mouse or a human.

31. A method for inducing an antibody production in a subject comprising
one or more administrations of one or more compositions comprising a polypeptide, and
the one or more administrations inducing an immune response to the antigen portion in the subject;
where the compositions may be the same or different if there is more than one administration and the polypeptide consisting of an Fc region linked to two arms;
wherein
the Fc region consists of two Fc amino acid chains;
each Fc amino acid chain is linked to one of the two arms;
each arm consists of an HCH2 polymer linked to an antigen portion;
the HCH2 polymer consists of two to six linear copies of an HCH2 monomer;
the HCH2 monomer consists of at least a fragment of an HCH2 region, wherein the at least a fragment of an HCH2 region includes a hinge region; and
at least one hinge region cysteine of the HCH2 monomer is mutated to serine.

32. The method of claim 31, wherein the Fc amino acid chains of the polypeptide are selected from the group consisting of: an amino acid chain of the IgG1 Fc region, an amino acid chain of the IgG3 Fc region, an amino acid chain of the IgG2a Fc region, and fragments thereof.

33. The method of claim 31, wherein the HCH2 region of the polypeptide is selected from the group consisting of: a human IgG1 HCH2 region, a human IgG3 HCH2 region, a mouse IgG2a, and fragments thereof.

34. The method of claim 31, wherein three hinge region cysteines of the HCH2 monomer of the polypeptide are mutated to serine.

35. The method of claim 31, wherein the antigen portion of the polypeptide is an antigen or an epitope.

36. The method of claim 31, wherein the antigen portion of the polypeptide is selected from the group consisting of: BoNT/A Hc (SEQ ID NO: 23), BoNT/A HcN (SEQ ID NO: 25), BoNT/A HcC (SEQ ID NO: 27), HAS1 (SEQ ID NO: 53), CD8α, FABP7 (SEQ ID NO: 29), PLP (SEQ ID NO: 49), MBP (SEQ ID NO: 40), PLP-MBP (SEQ ID NO: 52), PLP-PLP (SEQ ID NO: 43), and fragments thereof.

37. The method of claim 31, wherein the polypeptide is capable of binding at least one recombinant FcγR without being aggregated or presented in the form of an immune complex.

38. The method of claim 31, wherein the composition further comprises a carrier or an adjuvant.

39. The method of claim 31, wherein the composition further comprises a carrier or an adjuvant selected from the group consisting of: squalene, IL-2, RIBI adjuvant system, QS21, GM-CSF, alum hydro gel, monophosphoryl lipid A, trehalose dimycolate, Toll-like receptor ligands, Toll-like receptor agonists, CpG oligodeoxynucleotides, and cell wall skeleton.

40. The method of claim 31, wherein the composition further comprises IL-2 or monophosphoryl lipid A.

41. The method of claim 31, wherein the administration comprises a parenteral administration or a mucosal administration.

42. The method of claim 31, wherein administration comprises intravenous administration, subcutaneous administration, topical administration, intradermal administration, oral administration, sublingual administration, intranasal administration, or intramuscular administration.

43. The method of claim 31, wherein if there is more than one administration at least one composition used for at least one administration is different from the composition of at least one other administration.

44. The method of claim 31, wherein the subject is a cell.

45. The method of claim 31, wherein the subject is an animal.

46. The method of claim 31, wherein the subject is a mouse or a human.

47. The method of claim 1, wherein the antigen portion is a Botulinum neurotoxin protein or fragment thereof.

48. The method of claim 1, wherein the antigen portion is selected from the group consisting of: BoNT/A (SEQ ID NO: 54), BoNT/B (SEQ ID NO: 55), BoNT/C (SEQ ID NO: 56), BoNT/D (SEQ ID NO: 57), BoNT/E (SEQ ID NO: 58), BoNT/F (SEQ ID NO: 59), BoNT/G (SEQ ID NO: 60), and fragments thereof.

49. The method of claim 1, wherein the antigen portion is a sequence selected from the group consisting of: SEQ ID NO: 23, SEQ ID NO: 25, SEQ ID NO: 27, SEQ ID NO: 29, SEQ ID NO: 34, SEQ ID NO: 40, and SEQ ID NO: 43.

50. The method of claim 1, wherein the antigen portion comprises at least one antigen or epitope selected from the group consisting of: an infectious agent, microorganism, tumor antigen, and self protein thereof.

51. The method of claim 1, wherein the antigen portion is a cancer antigen.

52. The method of claim 1, wherein the antigen portion is a cancer antigen, where the cancer is selected from the group consisting of: sarcoma, lymphoma, leukemia, melanoma, carcinoma of the breast, colon carcinoma, carcinoma of the lung, glioblastoma, astrocytoma, carcinoma of the cervix, uterine carcinoma, carcinoma of the prostate, and ovarian carcinoma.

53. The method of claim 1, wherein the antigen portion is an antigen or epitope of an infectious agent.

54. The method of claim 1, wherein the antigen portion is an antigen or epitope of a virus.

55. The method of claim 1, wherein the antigen portion is an antigen or epitope of a virus, wherein the virus is selected from the group consisting of: papilloma virus, Epstein Barr virus, herpes virus, retrovirus, hepatitis virus, influenza virus, herpes zoster virus, herpes simplex virus, human immunodeficiency virus 1, human immunodeficiency virus 2, adenovirus, cytomegalovirus, respiratory syncytial virus, and rhinovirus.

56. The method of claim 1, wherein the antigen portion is an antigen or epitope of a bacterium.

57. The method of claim 1, wherein the antigen portion is an antigen or epitope of a bacterium, wherein the bacterium is selected from the group consisting of:
Salmonella, Staphylococcus, Streptococcus, Enterococcus, Clostridium, Escherichia, Kiebsiella, Vibrio, Mycobacterium, and Mycoplasma pneumoniae.

58. The method of claim 1, wherein the antigen portion is a toxin polypeptide.

59. The method of claim 1, wherein the antigen portion is a toxin polypeptide, wherein the toxin polypeptide is abrin, a conotoxin, diacetoxyscirpenol, ricin, saxitoxin, a Shiga-like ribosome inactivating protein, flexal, guanarito, junin, machupo, sabia, tetrodotoxin, a Botulinum neurotoxin, Clostridium perfringens epsilon toxin, a Shigatoxin, Staphylococcal enterotoxin, T-2 toxin, Bovine spongiform encephalopathy agent, epsilon toxin, ricin toxin, Staphylococcal enterotoxin B, influenza virus hemagglutinin, or a fragment or variant thereof.

60. The method of claim 1, wherein the antigen portion is a fragment of a Botulinum neurotoxin protein.

61. The method of claim 1, wherein the antigen portion is a tumor antigen.

62. The method of claim 1, wherein the antigen portion is a tumor antigen, wherein the tumor antigen is KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA), bladder tumor oncofetal antigen, differentiation antigen such as human lung carcinoma antigen L6, L20, an antigen of fibrosarcoma, human leukemia T cell antigen-Gp37, neoglycoprotein, a sphingolipid, EGFR, EGFRvIII, FABP7, doublecortin, brevican, HER2 antigen, polymorphic epithelial mucin (PEM), malignant human lymphocyte antigen-APO-1, an I antigen, M18, M39, SSEA-1, VEP8, VEP9, Myl, VIM-D5, $D_{156-22}$, TRA-1-85, C14, F3, AH6, Y hapten, Le$^y$, TL5, EGF receptor, FC10.2, gastric adenocarcinoma antigen, CO-514, NS-10, CO-43, G49, MH2, a gastric cancer mucin, $T_{5A7}$, $R_{24}$, 4.2, $G_D3$, D1.1, OFA-1, $G_M2$, OFA-2, $G_D2$, M1:22:25:8, SSEA-3, SSEA-4, or a fragment or variant thereof.

63. The method of claim 1, wherein the polypeptide comprises a sequence selected from the group consisting of: SEQ ID NO: 9, SEQ ID NO: 10, SEQ ID NO: 13, SEQ ID NO: 14, SEQ ID NO: 23, SEQ ID NO: 25, SEQ ID NO: 27, SEQ ID NO: 29, SEQ ID NO: 34, SEQ ID NO: 40, SEQ ID NO: 43, SEQ ID NO: 45, SEQ ID NO: 47, SEQ ID NO: 48, SEQ ID NO: 49, SEQ ID NO: 50, and SEQ ID NO: 51.

64. The method of claim 15, wherein the antigen portion is a Botulinum neurotoxin protein or fragment thereof.

65. The method of claim 15, wherein the antigen portion is selected from the group consisting of: BoNT/A (SEQ ID NO: 54), BoNT/B (SEQ ID NO: 55), BoNT/C (SEQ ID NO: 56), BoNT/D (SEQ ID NO: 57), BoNT/E (SEQ ID NO: 58), BoNT/F (SEQ ID NO: 59), BoNT/G (SEQ ID NO: 60), and fragments thereof.

66. The method of claim 15, wherein the antigen portion is a sequence selected from the group consisting of: SEQ ID NO: 23, SEQ ID NO: 25, SEQ ID NO: 27, SEQ ID NO: 29, SEQ ID NO: 34, SEQ ID NO: 40, and SEQ ID NO: 43.

67. The method of claim 15, wherein the antigen portion comprises at least one antigen or epitope selected from the group consisting of: an infectious agent, microorganism, tumor antigen, and self protein thereof.

68. The method of claim 15, wherein the antigen portion is a cancer antigen.

69. The method of claim 15, wherein the antigen portion is a cancer antigen, where the cancer is selected from the group consisting of: sarcoma, lymphoma, leukemia, melanoma, carcinoma of the breast, colon carcinoma, carcinoma of the lung, glioblastoma, astrocytoma, carcinoma of the cervix, uterine carcinoma, carcinoma of the prostate, and ovarian carcinoma.

70. The method of claim 15, wherein the antigen portion is an antigen or epitope of an infectious agent.

71. The method of claim 15, wherein the antigen portion is an antigen or epitope of a virus.

72. The method of claim 15, wherein the antigen portion is an antigen or epitope of a virus, wherein the virus is selected from the group consisting of: papilloma virus, Epstein Barr virus, herpes virus, retrovirus, hepatitis virus, influenza virus, herpes zoster virus, herpes simplex virus, human immunodeficiency virus 1, human immunodeficiency virus 2, adenovirus, cytomegalovirus, respiratory syncytial virus, and rhinovirus.

73. The method of claim 15, wherein the antigen portion is an antigen or epitope of a bacterium.

74. The method of claim 15, wherein the antigen portion is an antigen or epitope of a bacterium, wherein the bacterium is selected from the group consisting of:
Salmonella, Staphylococcus, Streptococcus, Enterococcus, Clostridium, Escherichia, Kiebsiella, Vibrio, Mycobacterium, and Mycoplasma pneumoniae.

75. The method of claim 15, wherein the antigen portion is a toxin polypeptide.

76. The method of claim 15, wherein the antigen portion is a toxin polypeptide, wherein the toxin polypeptide is abrin, a conotoxin, diacetoxyscirpenol, ricin, saxitoxin, a Shiga-like ribosome inactivating protein, flexal, guanarito, junin, machupo, sabia, tetrodotoxin, a Botulinum neurotoxin, Clostridium perfringens epsilon toxin, a Shigatoxin, Staphylococcal enterotoxin, T-2 toxin, Bovine spongiform encephalopathy agent, epsilon toxin, ricin toxin, Staphylococcal enterotoxin B, influenza virus hemagglutinin, or a fragment or variant thereof.

77. The method of claim 15, wherein the antigen portion is a fragment of a Botulinum neurotoxin protein.

78. The method of claim 15, wherein the antigen portion is a tumor antigen.

79. The method of claim 15, wherein the antigen portion is a tumor antigen, wherein the tumor antigen is KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA), bladder tumor oncofetal antigen, differentiation antigen such as human lung carcinoma antigen L6, L20, an antigen of fibrosarcoma, human leukemia T cell antigen-Gp37, neoglycoprotein, a sphingolipid, EGFR, EGFRvIII, FABP7, doublecortin, brevican, HER2 antigen, polymorphic epithelial mucin (PEM), malignant human lymphocyte antigen-APO-1, an I antigen, M18, M39, SSEA-1, VEP8, VEP9, Myl, VIM-D5, $D_{156-22}$, TRA-1-85, C14, F3, AH6, Y hapten, $Le^y$, TL5, EGF receptor, FC10.2, gastric adenocarcinoma antigen, CO-514, NS-10, CO-43, G49, MH2, a gastric cancer mucin, $T_{5A7}$, $R_{24}$, 4.2, $G_D3$, D1.1, OFA-1, $G_M2$, OFA-2, $G_D2$, M1:22:25:8, SSEA-3, SSEA-4, or a fragment or variant thereof.

80. The method of claim 15, wherein the polypeptide comprises a sequence selected from the group consisting of: SEQ ID NO: 9, SEQ ID NO: 10, SEQ ID NO: 13, SEQ ID NO: 14, SEQ ID NO: 23, SEQ ID NO: 25, SEQ ID NO: 27, SEQ ID NO: 29, SEQ ID NO: 34, SEQ ID NO: 40, SEQ ID NO: 43, SEQ ID NO: 45, SEQ ID NO: 47, SEQ ID NO: 48, SEQ ID NO: 49, SEQ ID NO: 50, and SEQ ID NO: 51.

81. The method of claim 31, wherein the antigen portion is a Botulinum neurotoxin protein or fragment thereof.

82. The method of claim 31, wherein the antigen portion is selected from the group consisting of: BoNT/A (SEQ ID NO: 54), BoNT/B (SEQ ID NO: 55), BoNT/C (SEQ ID NO: 56), BoNT/D (SEQ ID NO: 57), BoNT/E (SEQ ID NO: 58), BoNT/F (SEQ ID NO: 59), BoNT/G (SEQ ID NO: 60), and fragments thereof.

83. The method of claim 31, wherein the antigen portion is a sequence selected from the group consisting of: SEQ ID NO: 23, SEQ ID NO: 25, SEQ ID NO: 27, SEQ ID NO: 29, SEQ ID NO: 34, SEQ ID NO: 40, and SEQ ID NO: 43.

84. The method of claim 31, wherein the antigen portion comprises at least one antigen or epitope selected from the group consisting of: an infectious agent, microorganism, tumor antigen, and self protein thereof.

85. The method of claim 31, wherein the antigen portion is a cancer antigen.

86. The method of claim 31, wherein the antigen portion is a cancer antigen, where the cancer is selected from the group consisting of: sarcoma, lymphoma, leukemia, melanoma, carcinoma of the breast, colon carcinoma, carcinoma of the lung, glioblastoma, astrocytoma, carcinoma of the cervix, uterine carcinoma, carcinoma of the prostate, and ovarian carcinoma.

87. The method of claim 31, wherein the antigen portion is an antigen or epitope of an infectious agent.

88. The method of claim 31, wherein the antigen portion is an antigen or epitope of a virus.

89. The method of claim 31, wherein the antigen portion is an antigen or epitope of a virus, wherein the virus is selected from the group consisting of: papilloma virus, Epstein Barr virus, herpes virus, retrovirus, hepatitis virus, influenza virus, herpes zoster virus, herpes simplex virus, human immunodeficiency virus 1, human immunodeficiency virus 2, adenovirus, cytomegalovirus, respiratory syncytial virus, and rhinovirus.

90. The method of claim 31, wherein the antigen portion is an antigen or epitope of a bacterium.

91. The method of claim 31, wherein the antigen portion is an antigen or epitope of a bacterium, wherein the bacterium is selected from the group consisting of:

*Salmonella, Staphylococcus, Streptococcus, Enterococcus, Clostridium, Escherichia, Kiebsiella, Vibrio, Mycobacterium*, and *Mycoplasma pneumoniae.*

92. The method of claim 31, wherein the antigen portion is a toxin polypeptide.

93. The method of claim 31, wherein the antigen portion is a toxin polypeptide, wherein the toxin polypeptide is abrin, a conotoxin, diacetoxyscirpenol, ricin, saxitoxin, a Shiga-like ribosome inactivating protein, flexal, guanarito, junin, machupo, sabia, tetrodotoxin, a Botulinum neurotoxin, Clostridium perfringens epsilon toxin, a Shigatoxin, Staphylococcal enterotoxin, T-2 toxin, Bovine spongiform encephalopathy agent, epsilon toxin, ricin toxin, Staphylococcal enterotoxin B, influenza virus hemagglutinin, or a fragment or variant thereof.

94. The method of claim 31, wherein the antigen portion is a fragment of a Botulinum neurotoxin protein.

95. The method of claim 31, wherein the antigen portion is a tumor antigen.

96. The method of claim 31, wherein the antigen portion is a tumor antigen, wherein the tumor antigen is KS ¼ pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, carcinoembryonic antigen (CEA), polymorphic epithelial mucin antigen, human milk fat globule antigen, colorectal tumor-associated antigens such as: CEA, TAG-72, CO17-1A; GICA 19-9, CTA-1 and LEA, Burkitt's lymphoma antigen-38.13, CD19, human B-lymphoma antigen-CD20, CD33, melanoma specific antigens such as ganglioside GD2, ganglioside GD3, ganglioside GM2, ganglioside GM3, tumor-specific transplantation type of cell-surface antigen (TSTA), bladder tumor oncofetal antigen, differentiation antigen such as human lung carcinoma antigen L6, L20, an antigen of fibrosarcoma, human leukemia T cell antigen-Gp37, neoglycoprotein, a sphingolipid, EGFR, EGFRvIII, FABP7, doublecortin, brevican, HER2 antigen, polymorphic epithelial mucin (PEM), malignant human lymphocyte antigen-APO-1, an I antigen, M18, M39, SSEA-1, VEP8, VEP9, Myl, VIM-D5, $D_{156-22}$, TRA-1-85, C14, F3, AH6, Y hapten, $Le^y$, TLS, EGF receptor, FC10.2, gastric adenocarcinoma antigen, CO-514, NS-10, CO-43, G49, MH2, a gastric cancer mucin, $T_{5A7}$, $R_{24}$, 4.2, $G_D3$, D1.1, OFA-1, $G_M2$, OFA-2, $G_D2$, M1:22:25:8, SSEA-3, SSEA-4, or a fragment or variant thereof.

97. The method of claim 31, wherein the polypeptide comprises a sequence selected from the group consisting of: SEQ ID NO: 9, SEQ ID NO: 10, SEQ ID NO: 13, SEQ ID NO: 14, SEQ ID NO: 23, SEQ ID NO: 25, SEQ ID NO: 27, SEQ ID NO: 29, SEQ ID NO: 34, SEQ ID NO: 40, SEQ ID NO: 43, SEQ ID NO: 45, SEQ ID NO: 47, SEQ ID NO: 48, SEQ ID NO: 49, SEQ ID NO: 50, and SEQ ID NO: 51.

* * * * *

SEQUENCE LISTING

<160> NUMBER OF SEQ ID NOS: 60

<210> SEQ ID NO 1
<211> LENGTH: 39
<212> TYPE: DNA
<213> ORGANISM: Artificial Sequence
<220> FEATURE:
<223> OTHER INFORMATION: primer

<400> SEQUENCE: 1
ggccgctaaa gcttgagccc aaatcttgtg acaaaactc                   39

<210> SEQ ID NO 2
<211> LENGTH: 38
<212> TYPE: DNA
<213> ORGANISM: Artificial Sequence
<220> FEATURE:
<223> OTHER INFORMATION: primer

<400> SEQUENCE: 2
ggccgctagt cgactcattt acccggagac agggagag                    38

<210> SEQ ID NO 3
<211> LENGTH: 57
<212> TYPE: DNA
<213> ORGANISM: Artificial Sequence
<220> FEATURE:
<223> OTHER INFORMATION: primer

<400> SEQUENCE: 3
cccgtagaat tcgagcccaa atcttctgac aaaactcaca catccccacc gtccca    57

<210> SEQ ID NO 4
<211> LENGTH: 50
<212> TYPE: DNA
<213> ORGANISM: Artificial Sequence
<220> FEATURE:
<223> OTHER INFORMATION: primer

<400> SEQUENCE: 4
ggccgcataa gcttggagcc tcgcgatttg gctttggaga tggttttctc        50

<210> SEQ ID NO 5
<211> LENGTH: 38
<212> TYPE: DNA
<213> ORGANISM: Artificial Sequence
<220> FEATURE:
<223> OTHER INFORMATION: primer

<400> SEQUENCE: 5
ggccgcatcc cggggagccc aaatcttctg acaaaact                    38

<210> SEQ ID NO 6
<211> LENGTH: 38
<212> TYPE: DNA
<213> ORGANISM: Artificial Sequence
<220> FEATURE:
<223> OTHER INFORMATION: primer

<400> SEQUENCE: 6
ggccgcataa gcttttggc tttggagatg gttttctc                     38

<210> SEQ ID NO 7
<211> LENGTH: 38
<212> TYPE: DNA

```
<213> ORGANISM: Artificial Sequence
<220> FEATURE:
<223> OTHER INFORMATION: primer

<400> SEQUENCE: 7
ggccgctact cgagatggcc ttaccagtga ccgccttg                              38

<210> SEQ ID NO 8
<211> LENGTH: 38
<212> TYPE: DNA
<213> ORGANISM: Artificial Sequence
<220> FEATURE:
<223> OTHER INFORMATION: primer

<400> SEQUENCE: 8
ggccgctaga attccgtcgt ggtgggcttc gctggcag                              38

<210> SEQ ID NO 9
<211> LENGTH: 7
<212> TYPE: PRT
<213> ORGANISM: Artificial Sequence
<220> FEATURE:
<223> OTHER INFORMATION: used to construct fusion protein

<400> SEQUENCE: 9

Glu Leu Leu Gly Gly Pro Ser
1               5

<210> SEQ ID NO 10
<211> LENGTH: 125
<212> TYPE: PRT
<213> ORGANISM: Artificial Sequence
<220> FEATURE:
<223> OTHER INFORMATION: used to construct fusion protein

<400> SEQUENCE: 10

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys
        115                 120                 125

<210> SEQ ID NO 11
<211> LENGTH: 38
<212> TYPE: DNA
<213> ORGANISM: Artificial Sequence
<220> FEATURE:
<223> OTHER INFORMATION: primer

<400> SEQUENCE: 11
ggccgcatct cgagatgaag tgggtaacct ttatttcc                              38
```

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
ccgcatgaat tctctctgtt tggcagacga agcctt                                    36

<210> SEQ ID NO 13
<211> LENGTH: 742
<212> TYPE: PRT
<213> ORGANISM: Artificial Sequence
<220> FEATURE:
<223> OTHER INFORMATION: used to construct fusion protein

<400> SEQUENCE: 13

Glu Phe Glu Pro Lys Ser Ser Asp Lys Thr His Thr Ser Pro Pro Ser
1               5                   10                  15

Pro Ala Pro Glu Leu Leu Gly Gly Pro Ser Val Phe Leu Phe Pro Pro
            20                  25                  30

Lys Pro Lys Asp Thr Leu Met Ile Ser Arg Thr Pro Glu Val Thr Cys
        35                  40                  45

Val Val Val Asp Val Ser His Glu Asp Pro Glu Val Lys Phe Asn Trp
    50                  55                  60

Tyr Val Asp Gly Val Glu Val His Asn Ala Lys Thr Lys Pro Arg Glu
65                  70                  75                  80

Glu Gln Tyr Asn Ser Thr Tyr Arg Val Val Ser Val Leu Thr Val Leu
                85                  90                  95

His Gln Asp Trp Leu Asn Gly Lys Glu Tyr Lys Cys Lys Val Ser Asn
            100                 105                 110

Lys Ala Leu Pro Ala Pro Ile Glu Lys Thr Ile Ser Lys Ala Lys Ser
        115                 120                 125

Gly Glu Pro Lys Ser Ser Asp Lys Thr His Thr Ser Pro Pro Ser Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Ser Gly
                245                 250                 255

Glu Pro Lys Ser Ser Asp Lys Thr His Thr Ser Pro Ser Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

```
Asp Gly Val Glu Val His Asn Ala Lys Thr Lys Pro Arg Glu Glu Gln
            325                 330                 335
Tyr Asn Ser Thr Tyr Arg Val Val Ser Val Leu Thr Val Leu His Gln
            340                 345                 350
Asp Trp Leu Asn Gly Lys Glu Tyr Lys Cys Lys Val Ser Asn Lys Ala
            355                 360                 365
Leu Pro Ala Pro Ile Glu Lys Thr Ile Ser Lys Ala Lys Ser Gly Glu
            370                 375                 380
Pro Lys Ser Ser Asp Lys Thr His Thr Ser Pro Pro Ser Pro Ala Pro
385                 390                 395                 400
Glu Leu Leu Gly Gly Pro Ser Val Phe Leu Phe Pro Pro Lys Pro Lys
                405                 410                 415
Asp Thr Leu Met Ile Ser Arg Thr Pro Glu Val Thr Cys Val Val Val
            420                 425                 430
Asp Val Ser His Glu Asp Pro Glu Val Lys Phe Asn Trp Tyr Val Asp
            435                 440                 445
Gly Val Glu Val His Asn Ala Lys Thr Lys Pro Arg Glu Glu Gln Tyr
450                 455                 460
Asn Ser Thr Tyr Arg Val Val Ser Val Leu Thr Val Leu His Gln Asp
465                 470                 475                 480
Trp Leu Asn Gly Lys Glu Tyr Lys Cys Lys Val Ser Asn Lys Ala Leu
                485                 490                 495
Pro Ala Pro Ile Glu Lys Thr Ile Ser Lys Ala Lys Lys Leu Glu Pro
                500                 505                 510
Lys Ser Cys Asp Lys Thr His Thr Cys Pro Pro Cys Pro Ala Pro Glu
            515                 520                 525
Leu Leu Gly Gly Pro Ser Val Phe Leu Phe Pro Pro Lys Pro Lys Asp
            530                 535                 540
Thr Leu Met Ile Ser Arg Thr Pro Glu Val Thr Cys Val Val Val Asp
545                 550                 555                 560
Val Ser His Glu Asp Pro Glu Val Lys Phe Asn Trp Tyr Val Asp Gly
                565                 570                 575
Val Glu Val His Asn Ala Lys Thr Lys Pro Arg Glu Glu Gln Tyr Asn
            580                 585                 590
Ser Thr Tyr Arg Val Val Ser Val Leu Thr Val Leu His Gln Asp Trp
            595                 600                 605
Leu Asn Gly Lys Glu Tyr Lys Cys Lys Val Ser Asn Lys Ala Leu Pro
            610                 615                 620
Ala Pro Ile Glu Lys Thr Ile Ser Lys Ala Lys Gly Gln Pro Arg Glu
625                 630                 635                 640
Pro Gln Val Tyr Thr Leu Pro Pro Ser Arg Glu Glu Met Thr Lys Asn
                645                 650                 655
Gln Val Ser Leu Thr Cys Leu Val Lys Gly Phe Tyr Pro Ser Asp Ile
                660                 665                 670
Ala Val Glu Trp Glu Ser Asn Gly Gln Pro Glu Asn Asn Tyr Lys Thr
            675                 680                 685
Thr Pro Pro Val Leu Asp Ser Asp Gly Ser Phe Phe Leu Tyr Ser Lys
            690                 695                 700
Leu Thr Val Asp Lys Ser Arg Trp Gln Gln Gly Asn Val Phe Ser Cys
705                 710                 715                 720
Ser Val Met His Glu Ala Leu His Asn His Tyr Thr Gln Lys Ser Leu
                725                 730                 735
Ser Leu Ser Pro Gly Lys
```

-continued

```
                740

<210> SEQ ID NO 14
<211> LENGTH: 977
<212> TYPE: PRT
<213> ORGANISM: Artificial Sequence
<220> FEATURE:
<223> OTHER INFORMATION: used to construct fusion protein

<400> SEQUENCE: 14

Glu Phe Glu Leu Lys Thr Pro Leu Gly Asp Thr Thr His Thr Ser Pro
1               5                   10                  15

Arg Ser Pro Glu Pro Lys Ser Ser Asp Thr Pro Pro Ser Pro Arg
            20                  25                  30

Ser Pro Glu Pro Lys Ser Ser Asp Thr Pro Pro Ser Pro Arg Ser
        35                  40                  45

Pro Glu Pro Lys Ser Ser Asp Thr Pro Pro Ser Pro Arg Ser Pro
    50                  55                  60

Ala Pro Glu Leu Leu Gly Gly Pro Ser Val Phe Leu Phe Pro Pro Lys
65                  70                  75                  80

Pro Lys Asp Thr Leu Met Ile Ser Arg Thr Pro Glu Val Thr Cys Val
                85                  90                  95

Val Val Asp Val Ser His Glu Asp Pro Glu Val Gln Phe Lys Trp Tyr
            100                 105                 110

Val Asp Gly Val Glu Val His Asn Ala Lys Thr Lys Pro Arg Glu Glu
        115                 120                 125

Gln Tyr Asn Ser Thr Phe Arg Val Val Ser Val Leu Thr Val Leu His
    130                 135                 140

Gln Asp Trp Leu Asn Gly Lys Glu Tyr Lys Cys Lys Val Ser Asn Lys
145                 150                 155                 160

Ala Leu Pro Ala Pro Ile Glu Lys Thr Ile Ser Lys Thr Lys Ser Gly
                165                 170                 175

Glu Leu Lys Thr Pro Leu Gly Asp Thr Thr His Thr Ser Pro Arg Ser
            180                 185                 190

Pro Glu Pro Lys Ser Ser Asp Thr Pro Pro Ser Pro Arg Ser Pro
        195                 200                 205

Glu Pro Lys Ser Ser Asp Thr Pro Pro Ser Pro Arg Ser Pro Glu
    210                 215                 220

Pro Lys Ser Ser Asp Thr Pro Pro Ser Pro Arg Ser Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Gln Phe Lys Trp Tyr Val Asp
        275                 280                 285

Gly Val Glu Val His Asn Ala Lys Thr Lys Pro Arg Glu Glu Gln Tyr
    290                 295                 300

Asn Ser Thr Phe Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Thr Lys Ser Gly Glu Leu
            340                 345                 350

Lys Thr Pro Leu Gly Asp Thr Thr His Thr Ser Pro Arg Ser Pro Glu
        355                 360                 365
```

```
Pro Lys Ser Ser Asp Thr Pro Pro Ser Pro Arg Ser Pro Glu Pro
        370                 375                 380

Lys Ser Ser Asp Thr Pro Pro Ser Pro Arg Ser Pro Glu Pro Lys
385                 390                 395                 400

Ser Ser Asp Thr Pro Pro Ser Pro Arg Ser Pro Ala Pro Glu Leu
                405                 410                 415

Leu Gly Gly Pro Ser Val Phe Leu Phe Pro Pro Lys Pro Lys Asp Thr
            420                 425                 430

Leu Met Ile Ser Arg Thr Pro Glu Val Thr Cys Val Val Val Asp Val
            435                 440                 445

Ser His Glu Asp Pro Glu Val Gln Phe Lys Trp Tyr Val Asp Gly Val
            450                 455                 460

Glu Val His Asn Ala Lys Thr Lys Pro Arg Glu Glu Gln Tyr Asn Ser
465                 470                 475                 480

Thr Phe Arg Val Val Ser Val Leu Thr Val Leu His Gln Asp Trp Leu
                485                 490                 495

Asn Gly Lys Glu Tyr Lys Cys Lys Val Ser Asn Lys Ala Leu Pro Ala
            500                 505                 510

Pro Ile Glu Lys Thr Ile Ser Lys Thr Lys Ser Gly Glu Leu Lys Thr
            515                 520                 525

Pro Leu Gly Asp Thr Thr His Thr Ser Pro Arg Ser Pro Glu Pro Lys
530                 535                 540

Ser Ser Asp Thr Pro Pro Ser Pro Arg Ser Pro Glu Pro Lys Ser
545                 550                 555                 560

Ser Asp Thr Pro Pro Ser Pro Arg Ser Pro Glu Pro Lys Ser Ser
                565                 570                 575

Asp Thr Pro Pro Ser Pro Arg Ser Pro Ala Pro Glu Leu Leu Gly
                580                 585                 590

Gly Pro Ser Val Phe Leu Phe Pro Pro Lys Pro Lys Asp Thr Leu Met
        595                 600                 605

Ile Ser Arg Thr Pro Glu Val Thr Cys Val Val Val Asp Val Ser His
        610                 615                 620

Glu Asp Pro Glu Val Gln Phe Lys Trp Tyr Val Asp Gly Val Glu Val
625                 630                 635                 640

His Asn Ala Lys Thr Lys Pro Arg Glu Glu Gln Tyr Asn Ser Thr Phe
                645                 650                 655

Arg Val Val Ser Val Leu Thr Val Leu His Gln Asp Trp Leu Asn Gly
                660                 665                 670

Lys Glu Tyr Lys Cys Lys Val Ser Asn Lys Ala Leu Pro Ala Pro Ile
            675                 680                 685

Glu Lys Thr Ile Ser Lys Thr Lys Lys Leu Glu Leu Lys Thr Pro Leu
            690                 695                 700

Gly Asp Thr Thr His Thr Cys Pro Arg Cys Pro Glu Pro Lys Ser Cys
705                 710                 715                 720

Asp Thr Pro Pro Cys Pro Arg Cys Pro Glu Pro Lys Ser Cys Asp
                725                 730                 735

Thr Pro Pro Cys Pro Arg Cys Pro Glu Pro Lys Ser Cys Asp Thr
                740                 745                 750

Pro Pro Cys Pro Arg Cys Pro Ala Pro Glu Leu Leu Gly Gly Pro
            755                 760                 765

Ser Val Phe Leu Phe Pro Pro Lys Pro Lys Asp Thr Leu Met Ile Ser
770                 775                 780

Arg Thr Pro Glu Val Thr Cys Val Val Val Asp Val Ser His Glu Asp
```

-continued

```
              785                 790                 795                 800
Pro Glu Val Gln Phe Lys Trp Tyr Val Asp Gly Val Glu Val His Asn
                805                 810                 815
Ala Lys Thr Lys Pro Arg Glu Glu Gln Tyr Asn Ser Thr Phe Arg Val
                820                 825                 830
Val Ser Val Leu Thr Val Leu His Gln Asp Trp Leu Asn Gly Lys Glu
                835                 840                 845
Tyr Lys Cys Lys Val Ser Asn Lys Ala Leu Pro Ala Pro Ile Glu Lys
                850                 855                 860
Thr Ile Ser Lys Thr Lys Gly Gln Pro Arg Glu Pro Gln Val Tyr Thr
865                 870                 875                 880
Leu Pro Pro Ser Arg Glu Glu Met Thr Lys Asn Gln Val Ser Leu Thr
                885                 890                 895
Cys Leu Val Lys Gly Phe Tyr Pro Ser Asp Ile Ala Val Glu Trp Glu
                900                 905                 910
Ser Ser Gly Gln Pro Glu Asn Asn Tyr Asn Thr Thr Pro Pro Met Leu
                915                 920                 925
Asp Ser Asp Gly Ser Phe Phe Leu Tyr Ser Lys Leu Thr Val Asp Lys
                930                 935                 940
Ser Arg Trp Gln Gln Gly Asn Ile Phe Ser Cys Ser Val Met His Glu
945                 950                 955                 960
Ala Leu His Asn Arg Phe Thr Gln Lys Ser Leu Ser Leu Ser Pro Gly
                965                 970                 975
Lys

<210> SEQ ID NO 15
<211> LENGTH: 60
<212> TYPE: DNA
<213> ORGANISM: Artificial Sequence
<220> FEATURE:
<223> OTHER INFORMATION: primer

<400> SEQUENCE: 15
ccgctagaat tcgagcccag agggcccaca atcaagccct ctcctccatc caaatcccca    60

<210> SEQ ID NO 16
<211> LENGTH: 50
<212> TYPE: DNA
<213> ORGANISM: Artificial Sequence
<220> FEATURE:
<223> OTHER INFORMATION: primer

<400> SEQUENCE: 16
ggccgcataa gcttggagcc tcgcgatttg ggttttgaga tggttctctc                50

<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
ccgcattcta gacccgggga gcccagaggg cccacaatca ag                       42

<210> SEQ ID NO 18
<211> LENGTH: 38
<212> TYPE: DNA
<213> ORGANISM: Artificial Sequence
<220> FEATURE:
<223> OTHER INFORMATION: primer
```

```
<400> SEQUENCE: 18
ggccgcataa gcttttggg ttttgagatg gttctctc                              38

<210> SEQ ID NO 19
<211> LENGTH: 38
<212> TYPE: DNA
<213> ORGANISM: Artificial Sequence
<220> FEATURE:
<223> OTHER INFORMATION: primer

<400> SEQUENCE: 19
ggccgctaaa gcttgagccc agagggccca caatcaag                             38

<210> SEQ ID NO 20
<211> LENGTH: 39
<212> TYPE: DNA
<213> ORGANISM: Artificial Sequence
<220> FEATURE:
<223> OTHER INFORMATION: primer

<400> SEQUENCE: 20
ggccgctagt cgactcattt acccggagtc cgggagaag                            39

<210> SEQ ID NO 21
<211> LENGTH: 38
<212> TYPE: DNA
<213> ORGANISM: Artificial Sequence
<220> FEATURE:
<223> OTHER INFORMATION: primer

<400> SEQUENCE: 21
ggccgcatgg atccaaaatg aagtgggtaa cctttctc                             38

<210> SEQ ID NO 22
<211> LENGTH: 34
<212> TYPE: DNA
<213> ORGANISM: Artificial Sequence
<220> FEATURE:
<223> OTHER INFORMATION: primer

<400> SEQUENCE: 22
ccgcatgaat tctctctgac ggacagatga gacc                                 34

<210> SEQ ID NO 23
<211> LENGTH: 440
<212> TYPE: PRT
<213> ORGANISM: Artificial Sequence
<220> FEATURE:
<223> OTHER INFORMATION: used to construct fusion protein

<400> SEQUENCE: 23

Val Asp Asn Gln Arg Leu Leu Ser Thr Phe Thr Glu Tyr Ile Lys Asn
 1               5                  10                  15

Ile Ile Asn Thr Ser Ile Leu Asn Leu Arg Tyr Glu Ser Asn His Leu
                20                  25                  30

Ile Asp Leu Ser Arg Tyr Ala Ser Lys Ile Asn Ile Gly Ser Lys Val
            35                  40                  45

Asn Phe Asp Pro Ile Asp Lys Asn Gln Ile Gln Leu Phe Asn Leu Glu
        50                  55                  60

Ser Ser Lys Ile Glu Val Ile Leu Lys Asn Ala Ile Val Tyr Asn Ser
65                  70                  75                  80

Met Tyr Glu Asn Phe Ser Thr Ser Phe Trp Ile Arg Ile Pro Lys Tyr
                85                  90                  95
```

```
Phe Asn Ser Ile Ser Leu Asn Asn Glu Tyr Thr Ile Ile Asn Cys Met
                100                 105                 110
Glu Asn Asn Ser Gly Trp Lys Val Ser Leu Asn Tyr Gly Glu Ile Ile
            115                 120                 125
Trp Thr Leu Gln Asp Thr Gln Glu Ile Lys Gln Arg Val Val Phe Lys
130                 135                 140
Tyr Ser Gln Met Ile Asn Ile Ser Asp Tyr Ile Asn Arg Trp Ile Phe
145                 150                 155                 160
Val Thr Ile Thr Asn Asn Arg Leu Asn Asn Ser Lys Ile Tyr Ile Asn
                165                 170                 175
Gly Arg Leu Ile Asp Gln Lys Pro Ile Ser Asn Leu Gly Asn Ile His
            180                 185                 190
Ala Ser Asn Asn Ile Met Phe Lys Leu Asp Gly Cys Arg Asp Thr His
        195                 200                 205
Arg Tyr Ile Trp Ile Lys Tyr Phe Asn Leu Phe Asp Lys Glu Leu Asn
    210                 215                 220
Glu Lys Glu Ile Lys Asp Leu Tyr Asp Asn Gln Ser Asn Ser Gly Ile
225                 230                 235                 240
Leu Lys Asp Phe Trp Gly Asp Tyr Leu Gln Tyr Asp Lys Pro Tyr Tyr
                245                 250                 255
Met Leu Asn Leu Tyr Asp Pro Asn Lys Tyr Val Asp Val Asn Asn Val
            260                 265                 270
Gly Ile Arg Gly Tyr Met Tyr Leu Lys Gly Pro Arg Gly Ser Val Met
        275                 280                 285
Thr Thr Asn Ile Tyr Leu Asn Ser Ser Leu Tyr Arg Gly Thr Lys Phe
    290                 295                 300
Ile Ile Lys Lys Tyr Ala Ser Gly Asn Lys Asp Asn Ile Val Arg Asn
305                 310                 315                 320
Asn Asp Arg Val Tyr Ile Asn Val Val Val Lys Asn Lys Glu Tyr Arg
                325                 330                 335
Leu Ala Thr Asn Ala Ser Gln Ala Gly Val Glu Lys Ile Leu Ser Ala
            340                 345                 350
Leu Glu Ile Pro Asp Val Gly Asn Leu Ser Gln Val Val Val Met Lys
        355                 360                 365
Ser Lys Asn Asp Gln Gly Ile Thr Asn Lys Cys Lys Met Asn Leu Gln
    370                 375                 380
Asp Asn Asn Gly Asn Asp Ile Gly Phe Ile Gly Phe His Gln Phe Asn
385                 390                 395                 400
Asn Ile Ala Lys Leu Val Ala Ser Asn Trp Tyr Asn Arg Gln Ile Glu
                405                 410                 415
Arg Ser Ser Arg Thr Leu Gly Cys Ser Trp Glu Phe Ile Pro Val Asp
            420                 425                 430
Asp Gly Trp Gly Glu Arg Pro Leu
        435                 440

<210> SEQ ID NO 24
<211> LENGTH: 1332
<212> TYPE: DNA
<213> ORGANISM: Artificial Sequence
<220> FEATURE:
<223> OTHER INFORMATION: used to construct fusion protein

<400> SEQUENCE: 24
ctcgaggttg ataatcagcg tctcctgagt acatttacag agtacatcaa gaacatcatc      60
aatacttcca tcctgaacct gcgctacgag tcaaatcacc tcatcgatct gtccaggtac     120
```

```
gcttccaaga tcaacatcgg cagcaaggtg aacttcgacc ccatcgataa aaatcagata    180
caactgttca atttggaaag cagcaaaatc gaggtgatcc tgaaaaacgc aatcgtgtat    240
aattcaatgt atgagaattt ttccacctct ttctggataa gaatcccaaa gtactttaac    300
tctatctccc tgaacaacga atacaccatt atcaattgca tggagaataa cagtggttgg    360
aaagtctccc tcaactacgg cgagatcatt tggacgctgc aagacaccca ggagattaag    420
cagcgtgtcg tgttcaagta cagccagatg attaacatct cagactacat aaacaggtgg    480
atatttgtaa caatcaccaa taccgtctc aataactcta agatttacat taacggtcgc    540
cttatcgacc agaagcccat ttccaacttg ggtaacattc atgccagcaa caatattatg    600
ttcaagctcg atggctgcag ggacactcac cgctacatat ggatcaagta cttcaacctg    660
ttcgacaagg aactgaacga aaaagagatc aaggatctgt acgacaacca gtcaaactcc    720
ggcattctca agacttttg gggagattac ctgcagtatg acaagccata ctacatgctc    780
aacctgtatg accctaataa gtacgttgac gtgaacaacg ttggcattcg cggttacatg    840
tacctgaagg gccctcgcgg tagcgtcatg acaactaaca tctacctgaa tagctcactg    900 tacagggta ccaagttcat tattaagaaa tacgcatctg caacaagga taatatagtg    960 aggaataacg accgtgtgta catcaacgtc gtggtgaaaa acaaggaata ccgtcttgcc   1020
accaacgctt ctcaagccgg agtagagaaa atcttgagtg cacttgagat tccagacgtc   1080
ggtaacttgt cccaggtggt agtgatgaaa tccaagaatg accagggtat cactaacaag   1140
tgcaagatga atctgcaaga caacaacgga acgacatcg gttttatcgg ttccaccaa    1200 ttcaacaata ttgctaagct cgtcgccagc aattggtata accgccagat cgaacgttct   1260
tccagaaccc tcggttgtag ctgggagttc atccccgtgg acgatggctg gggagagcgc   1320
cccttggaat tc                                                        1332
```

<210> SEQ ID NO 25
<211> LENGTH: 238
<212> TYPE: PRT
<213> ORGANISM: Artificial Sequence
<220> FEATURE:
<223> OTHER INFORMATION: used to construct fusion protein

<400> SEQUENCE: 25

```
Val Asp Asn Gln Arg Leu Leu Ser Thr Phe Thr Glu Tyr Ile Lys Asn
1               5                   10                  15

Ile Ile Asn Thr Ser Ile Leu Asn Leu Arg Tyr Glu Ser Asn His Leu
            20                  25                  30

Ile Asp Leu Ser Arg Tyr Ala Ser Lys Ile Asn Ile Gly Ser Lys Val
        35                  40                  45

Asn Phe Asp Pro Ile Asp Lys Asn Gln Ile Gln Leu Phe Asn Leu Glu
    50                  55                  60

Ser Ser Lys Ile Glu Val Ile Leu Lys Asn Ala Ile Val Tyr Asn Ser
65                  70                  75                  80

Met Tyr Glu Asn Phe Ser Thr Ser Phe Trp Ile Arg Ile Pro Lys Tyr
                85                  90                  95

Phe Asn Ser Ile Ser Leu Asn Asn Glu Tyr Thr Ile Ile Asn Cys Met
            100                 105                 110

Glu Asn Asn Ser Gly Trp Lys Val Ser Leu Asn Tyr Gly Glu Ile Ile
        115                 120                 125

Trp Thr Leu Gln Asp Thr Gln Glu Ile Lys Gln Arg Val Val Phe Lys
    130                 135                 140
```

```
Tyr Ser Gln Met Ile Asn Ile Ser Asp Tyr Ile Asn Arg Trp Ile Phe
145                 150                 155                 160

Val Thr Ile Thr Asn Asn Arg Leu Asn Ser Lys Ile Tyr Ile Asn
            165                 170                 175

Gly Arg Leu Ile Asp Gln Lys Pro Ile Ser Asn Leu Gly Asn Ile His
            180                 185                 190

Ala Ser Asn Asn Ile Met Phe Lys Leu Asp Gly Cys Arg Asp Thr His
            195                 200                 205

Arg Tyr Ile Trp Ile Lys Tyr Phe Asn Leu Phe Asp Lys Glu Leu Asn
            210                 215                 220

Glu Lys Glu Ile Lys Asp Leu Tyr Asp Asn Gln Ser Asn Ser
225                 230                 235

<210> SEQ ID NO 26
<211> LENGTH: 726
<212> TYPE: DNA
<213> ORGANISM: Artificial Sequence
<220> FEATURE:
<223> OTHER INFORMATION: used to construct fusion protein

<400> SEQUENCE: 26
ctcgaggttg ataatcagcg tctcctgagt acatttacag agtacatcaa gaacatcatc      60
aatacttcca tcctgaacct gcgctacgag tcaaatcacc tcatcgatct gtccaggtac     120
gcttccaaga tcaacatcgg cagcaaggtg aacttcgacc ccatcgataa aaatcagata     180
caactgttca atttggaaag cagcaaaatc gaggtgatcc tgaaaaacgc aatcgtgtat     240
aattcaatgt atgagaattt ttccacctct ttctggataa gaatcccaaa gtactttaac     300
tctatctccc tgaacaacga atacaccatt atcaattgca tggagaataa cagtggttgg     360
aaagtctccc tcaactacgg cgagatcatt tggacgctgc aagacaccca ggagattaag     420
cagcgtgtcg tgttcaagta cagccagatg attaacatct cagactacat aaacaggtgg     480
atatttgtaa caatcaccaa taccgtctc aataactcta agatttacat taacggtcgc     540
cttatcgacc agaagcccat tccaacttg ggtaacattc atgccagcaa caatattatg     600
ttcaagctcg atggctgcag ggacactcac cgctacatat ggattaagta cttcaacttg     660
ttcgataagg agctgaacga aggaaaatc aaagacttgt atgacaacca gagcaactct     720
gaattc                                                                726

<210> SEQ ID NO 27
<211> LENGTH: 231
<212> TYPE: PRT
<213> ORGANISM: Artificial Sequence
<220> FEATURE:
<223> OTHER INFORMATION: used to construct fusion protein

<400> SEQUENCE: 27

Tyr Ile Trp Ile Lys Tyr Phe Asn Leu Phe Asp Lys Glu Leu Asn Glu
1               5                   10                  15

Lys Glu Ile Lys Asp Leu Tyr Asp Asn Gln Ser Asn Ser Gly Ile Leu
            20                  25                  30

Lys Asp Phe Trp Gly Asp Tyr Leu Gln Tyr Asp Lys Pro Tyr Tyr Met
            35                  40                  45

Leu Asn Leu Tyr Asp Pro Asn Lys Tyr Val Asp Val Asn Asn Val Gly
            50                  55                  60

Ile Arg Gly Tyr Met Tyr Leu Lys Gly Pro Arg Gly Ser Val Met Thr
65                  70                  75                  80

Thr Asn Ile Tyr Leu Asn Ser Ser Leu Tyr Arg Gly Thr Lys Phe Ile
```

```
                    85                  90                  95
Ile Lys Lys Tyr Ala Ser Gly Asn Lys Asp Asn Ile Val Arg Asn Asn
            100                 105                 110

Asp Arg Val Tyr Ile Asn Val Val Lys Asn Lys Glu Tyr Arg Leu
            115                 120                 125

Ala Thr Asn Ala Ser Gln Ala Gly Val Glu Lys Ile Leu Ser Ala Leu
            130                 135                 140

Glu Ile Pro Asp Val Gly Asn Leu Ser Gln Val Val Met Lys Ser
145                 150                 155                 160

Lys Asn Asp Gln Gly Ile Thr Asn Lys Cys Lys Met Asn Leu Gln Asp
                165                 170                 175

Asn Asn Gly Asn Asp Ile Gly Phe Ile Gly Phe His Gln Phe Asn Asn
            180                 185                 190

Ile Ala Lys Leu Val Ala Ser Asn Trp Tyr Asn Arg Gln Ile Glu Arg
                195                 200                 205

Ser Ser Arg Thr Leu Gly Cys Ser Trp Glu Phe Ile Pro Val Asp Asp
            210                 215                 220

Gly Trp Gly Glu Arg Pro Leu
225                 230

<210> SEQ ID NO 28
<211> LENGTH: 705
<212> TYPE: DNA
<213> ORGANISM: Artificial Sequence
<220> FEATURE:
<223> OTHER INFORMATION: used to construct fusion protein

<400> SEQUENCE: 28
ctcgagtaca tatggatcaa gtacttcaac ctgttcgaca aggaactgaa cgaaaaagag        60
atcaaggatc tgtacgacaa ccagtcaaac tccggcattc tcaaagactt tggggagat       120 tacctgcagt atgacaagcc atactacatg ctcaacctgt atgaccctaa taagtacgtt       180
gacgtgaaca acgttggcat cgcggttac atgtacctga agggccctcg cggtagcgtc       240
atgacaacta acatctacct gaatagctca ctgtacaggg gtaccaagtt cattattaag       300
aaatacgcat ctggcaacaa ggataatata gtgaggaata cgaccgtgt gtacatcaac       360 gtcgtggtga aaaacaagga ataccgtctt gccaccaacg cttctcaagc cggagtagag       420
aaaatcttga gtgcacttga gattccagac gtcggtaact tgtcccaggt ggtagtgatg       480
aaatccaaga tgaccaggg tatcactaac aagtgcaaga tgaatctgca agacaacaac       540
ggaaacgaca tcggttttat cggtttccac caattcaaca atattgctaa gctcgtcgcc       600
agcaattggt ataaccgcca gatcgaacgt tcttccagaa ccctcggttg tagctgggag       660
ttcatccccg tggacgatgg ctggggagag cgccccttgg aattc                      705

<210> SEQ ID NO 29
<211> LENGTH: 132
<212> TYPE: PRT
<213> ORGANISM: Artificial Sequence
<220> FEATURE:
<223> OTHER INFORMATION: used to construct fusion protein

<400> SEQUENCE: 29

Met Val Glu Ala Phe Cys Ala Thr Trp Lys Leu Thr Asn Ser Gln Asn
1               5                   10                  15

Phe Asp Glu Tyr Met Lys Ala Leu Gly Val Gly Phe Ala Thr Arg Gln
                20                  25                  30

Val Gly Asn Val Thr Lys Pro Thr Val Ile Ile Ser Gln Glu Gly Asp
```

```
                35                  40                  45
Lys Val Val Ile Arg Thr Leu Ser Thr Phe Lys Asn Thr Glu Ile Ser
 50                  55                  60

Phe Gln Leu Gly Glu Glu Phe Asp Glu Thr Thr Ala Asp Asp Arg Asn
 65                  70                  75                  80

Cys Lys Ser Val Val Ser Leu Asp Gly Asp Lys Leu Val His Ile Gln
                 85                  90                  95

Lys Trp Asp Gly Lys Glu Thr Asn Phe Val Arg Glu Ile Lys Asp Gly
            100                 105                 110

Lys Met Val Met Thr Leu Thr Phe Gly Asp Val Val Ala Val Arg His
        115                 120                 125

Tyr Glu Lys Ala
    130
```

<210> SEQ ID NO 30
<211> LENGTH: 399
<212> TYPE: DNA
<213> ORGANISM: Artificial Sequence
<220> FEATURE:
<223> OTHER INFORMATION: used to construct fusion protein

<400> SEQUENCE: 30

```
atggtggagg ctttctgtgc tacctggaag ctgaccaaca gtcagaactt tgatgagtac      60
atgaaggctc taggcgtggg ctttgccact aggcaggtgg gaaatgtgac caaaccaacg     120
gtaattatca gtcaagaagg agacaaagtg gtcatcagga ctctcagcac attcaagaac     180
acggagatta gtttccagct gggagaagag tttgatgaaa ccactgcaga tgatagaaac     240
tgtaagtctg ttgttagcct ggatggagac aaacttgttc acatacagaa atgggatggc     300
aaagaaacaa attttgtaag agaaattaag gatggcaaaa tggttatgac ccttactttt     360
ggtgatgtgg ttgctgttcg ccactatgag aaggcataa                            399
```

<210> SEQ ID NO 31
<211> LENGTH: 38
<212> TYPE: DNA
<213> ORGANISM: Artificial Sequence
<220> FEATURE:
<223> OTHER INFORMATION: primer

<400> SEQUENCE: 31

```
ggccgcatct cgaggtggag ctttctgtg ctacctgg                               38
```

<210> SEQ ID NO 32
<211> LENGTH: 38
<212> TYPE: DNA
<213> ORGANISM: Artificial Sequence
<220> FEATURE:
<223> OTHER INFORMATION: primer

<400> SEQUENCE: 32

```
ggccgcatga attctgcctt ctcatagtgg cgaacagc                              38
```

<210> SEQ ID NO 33
<211> LENGTH: 57
<212> TYPE: DNA
<213> ORGANISM: Artificial Sequence
<220> FEATURE:
<223> OTHER INFORMATION: primer

<400> SEQUENCE: 33

```
ccgcataagc tttcaatggt gatggtgatg atgtgccttc tcatagtggc gaacagc         57
```

```
<210> SEQ ID NO 34
<211> LENGTH: 132
<212> TYPE: PRT
<213> ORGANISM: Artificial Sequence
<220> FEATURE:
<223> OTHER INFORMATION: used to construct fusion protein

<400> SEQUENCE: 34

Met Val Asp Ala Phe Cys Ala Thr Trp Lys Leu Thr Asp Ser Gln Asn
1               5                   10                  15

Phe Asp Glu Tyr Met Lys Ala Leu Gly Val Gly Phe Ala Thr Arg Gln
                20                  25                  30

Val Gly Asn Val Thr Lys Pro Thr Val Ile Ile Ser Gln Glu Gly Gly
            35                  40                  45

Lys Val Val Ile Arg Thr Gln Cys Thr Phe Lys Asn Thr Glu Ile Asn
    50                  55                  60

Phe Gln Leu Gly Glu Glu Phe Glu Glu Thr Ser Ile Asp Asp Arg Asn
65                  70                  75                  80

Cys Lys Ser Val Val Arg Leu Asp Gly Asp Lys Leu Ile His Val Gln
                85                  90                  95

Lys Trp Asp Gly Lys Glu Thr Asn Cys Thr Arg Glu Ile Lys Asp Gly
                100                 105                 110

Lys Met Val Val Thr Leu Thr Phe Gly Asp Ile Val Ala Val Arg Cys
            115                 120                 125

Tyr Glu Lys Ala
        130

<210> SEQ ID NO 35
<211> LENGTH: 399
<212> TYPE: DNA
<213> ORGANISM: Artificial Sequence
<220> FEATURE:
<223> OTHER INFORMATION: used to construct fusion protein

<400> SEQUENCE: 35
atggtagatg ctttctgcgc aacctggaag ctgacagaca gtcagaattt tgatgagtac      60
atgaaagctc tgggcgtggg ctttgccact aggcaagtgg gaaacgtgac caaaccaact     120
gtgattatca gtcaggaagg tggcaaagtg gtgatccgga cacaatgcac attcaagaac     180
acagagatca atttccagct gggagaagag tttgaagaaa ccagcataga tgacagaaac     240
tgtaagtctg tggttcggtt ggatggagac aagctcattc atgtgcagaa gtgggatggc     300
aaagaaacaa attgtaccag agaaattaag gatggcaaga tggtcgtgac tcttaccttt     360
ggggatatcg ttgctgttcg ctgttatgaa aaggcatag                            399

<210> SEQ ID NO 36
<211> LENGTH: 37
<212> TYPE: DNA
<213> ORGANISM: Artificial Sequence
<220> FEATURE:
<223> OTHER INFORMATION: primer

<400> SEQUENCE: 36
ggccgcatct cgaggtagat gctttctgcg caacctg                               37

<210> SEQ ID NO 37
<211> LENGTH: 38
<212> TYPE: DNA
<213> ORGANISM: Artificial Sequence
<220> FEATURE:
<223> OTHER INFORMATION: primer
```

-continued

<400> SEQUENCE: 37
ggccgcatga attctgcctt ttcataacag cgaacagc                              38

<210> SEQ ID NO 38
<211> LENGTH: 57
<212> TYPE: DNA
<213> ORGANISM: Artificial Sequence
<220> FEATURE:
<223> OTHER INFORMATION: primer

<400> SEQUENCE: 38
ccgcatgtcg actcaatggt gatggtgatg atgtgccttt tcataacagc gaacagc        57

<210> SEQ ID NO 39
<211> LENGTH: 51
<212> TYPE: DNA
<213> ORGANISM: Artificial Sequence
<220> FEATURE:
<223> OTHER INFORMATION: used to construct fusion protein

<400> SEQUENCE: 39
ctcgagcatt ctttgggaaa atggctagga catcccgaca agtttgaatt c              51

<210> SEQ ID NO 40
<211> LENGTH: 13
<212> TYPE: PRT
<213> ORGANISM: Artificial Sequence
<220> FEATURE:
<223> OTHER INFORMATION: used to construct fusion protein

<400> SEQUENCE: 40

Val His Phe Phe Lys Asn Ile Val Thr Pro Arg Thr Pro
1               5                   10

<210> SEQ ID NO 41
<211> LENGTH: 96
<212> TYPE: DNA
<213> ORGANISM: Artificial Sequence
<220> FEATURE:
<223> OTHER INFORMATION: used to construct fusion protein

<400> SEQUENCE: 41
ctcgagcatt ctttgggaaa atggctagga catcccgaca agtttggtac ccattctttg     60
ggaaaatggc taggacatcc cgacaagttt gaattc                               96

<210> SEQ ID NO 42
<211> LENGTH: 51
<212> TYPE: DNA
<213> ORGANISM: Artificial Sequence
<220> FEATURE:
<223> OTHER INFORMATION: used to construct fusion protein

<400> SEQUENCE: 42
ggtaccgtcc acttcttcaa gaacattgtg acgcctcgca caccagaatt c              51

<210> SEQ ID NO 43
<211> LENGTH: 28
<212> TYPE: PRT
<213> ORGANISM: Artificial Sequence
<220> FEATURE:
<223> OTHER INFORMATION: used to construct fusion protein

<400> SEQUENCE: 43

His Ser Leu Gly Lys Trp Leu Gly His Pro Asp Lys Phe Gly Thr His
1               5                   10                  15

```
Ser Leu Gly Lys Trp Leu Gly His Pro Asp Lys Phe
            20                  25
```

<210> SEQ ID NO 44
<211> LENGTH: 69
<212> TYPE: DNA
<213> ORGANISM: Artificial Sequence
<220> FEATURE:
<223> OTHER INFORMATION: used to construct fusion protein

<400> SEQUENCE: 44

```
ggatccatgg agtttgggct gagctgggtt ttccttgttg ctattttaaa aggtgtccag    60
tgtctcgag                                                           69
```

<210> SEQ ID NO 45
<211> LENGTH: 21
<212> TYPE: PRT
<213> ORGANISM: Artificial Sequence
<220> FEATURE:
<223> OTHER INFORMATION: leader

<400> SEQUENCE: 45

```
Met Glu Phe Gly Leu Ser Trp Val Phe Leu Val Ala Ile Leu Lys Gly
1               5                   10                  15

Val Gln Cys Leu Glu
            20
```

<210> SEQ ID NO 46
<211> LENGTH: 69
<212> TYPE: DNA
<213> ORGANISM: Artificial Sequence
<220> FEATURE:
<223> OTHER INFORMATION: leader

<400> SEQUENCE: 46

```
ggatccatgg agtttgggct gagctgggtt ttccttgttg ctattttaaa aggtgtccag    60
tgtctcgag                                                           69
```

<210> SEQ ID NO 47
<211> LENGTH: 232
<212> TYPE: PRT
<213> ORGANISM: Artificial Sequence
<220> FEATURE:
<223> OTHER INFORMATION: used to construct fusion protein

<400> SEQUENCE: 47

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
```

```
                   115                 120                 125
Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
        210                 215                 220

Ser Leu Ser Leu Ser Pro Gly Lys
225                 230

<210> SEQ ID NO 48
<211> LENGTH: 277
<212> TYPE: PRT
<213> ORGANISM: Artificial Sequence
<220> FEATURE:
<223> OTHER INFORMATION: used to construct fusion protein

<400> SEQUENCE: 48

Lys Thr Pro Leu Gly Asp Thr Thr His Thr Cys Pro Arg Cys Pro Glu
1               5                   10                  15

Pro Lys Ser Cys Asp Thr Pro Pro Cys Pro Arg Cys Pro Glu Pro
                20                  25                  30

Lys Ser Cys Asp Thr Pro Pro Cys Pro Arg Cys Pro Glu Pro Lys
            35                  40                  45

Ser Cys Asp Thr Pro Pro Cys Pro Arg Cys Pro Ala Pro Glu Leu
        50                  55                  60

Leu Gly Gly Pro Ser Val Phe Leu Phe Pro Pro Lys Pro Lys Asp Thr
65                  70                  75                  80

Leu Met Ile Ser Arg Thr Pro Glu Val Thr Cys Val Val Val Asp Val
                85                  90                  95

Ser His Glu Asp Pro Glu Val Gln Phe Lys Trp Tyr Val Asp Gly Val
            100                 105                 110

Glu Val His Asn Ala Lys Thr Lys Pro Arg Glu Glu Gln Tyr Asn Ser
        115                 120                 125

Thr Phe Arg Val Val Ser Val Leu Thr Val Leu His Gln Asp Trp Leu
    130                 135                 140

Asn Gly Lys Glu Tyr Lys Cys Lys Val Ser Asn Lys Ala Leu Pro Ala
145                 150                 155                 160

Pro Ile Glu Lys Thr Ile Ser Lys Thr Lys Gly Gln Pro Arg Glu Pro
                165                 170                 175

Gln Val Tyr Thr Leu Pro Pro Ser Arg Glu Glu Met Thr Lys Asn Gln
            180                 185                 190

Val Ser Leu Thr Cys Leu Val Lys Gly Phe Tyr Pro Ser Asp Ile Ala
        195                 200                 205

Val Glu Trp Glu Ser Ser Gly Gln Pro Glu Asn Asn Tyr Asn Thr Thr
    210                 215                 220

Pro Pro Met Leu Asp Ser Asp Gly Ser Phe Phe Leu Tyr Ser Lys Leu
225                 230                 235                 240

Thr Val Asp Lys Ser Arg Trp Gln Gln Gly Asn Ile Phe Ser Cys Ser
                245                 250                 255
```

```
Val Met His Glu Ala Leu His Asn Arg Phe Thr Gln Lys Ser Leu Ser
            260                 265                 270

Leu Ser Pro Gly Lys
        275

<210> SEQ ID NO 49
<211> LENGTH: 13
<212> TYPE: PRT
<213> ORGANISM: Artificial Sequence
<220> FEATURE:
<223> OTHER INFORMATION: used to construct fusion protein

<400> SEQUENCE: 49

His Ser Leu Gly Lys Trp Leu Gly His Pro Asp Lys Phe
1               5                   10

<210> SEQ ID NO 50
<211> LENGTH: 7
<212> TYPE: PRT
<213> ORGANISM: Artificial Sequence
<220> FEATURE:
<223> OTHER INFORMATION: used to construct fusion protein

<400> SEQUENCE: 50

Glu Leu Leu Gly Gly Pro Ser
1               5

<210> SEQ ID NO 51
<211> LENGTH: 172
<212> TYPE: PRT
<213> ORGANISM: Artificial Sequence
<220> FEATURE:
<223> OTHER INFORMATION: used to construct fusion protein

<400> SEQUENCE: 51

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys
                165                 170

<210> SEQ ID NO 52
<211> LENGTH: 28
<212> TYPE: PRT
```

-continued

```
<213> ORGANISM: Artificial Sequence
<220> FEATURE:
<223> OTHER INFORMATION: used to construct fusion protein

<400> SEQUENCE: 52

His Ser Leu Gly Lys Trp Leu Gly His Pro Asp Lys Phe Gly Thr Val
1               5                   10                  15

His Phe Phe Lys Asn Ile Val Thr Pro Arg Thr Pro
            20                  25

<210> SEQ ID NO 53
<211> LENGTH: 197
<212> TYPE: PRT
<213> ORGANISM: Artificial Sequence
<220> FEATURE:
<223> OTHER INFORMATION: used to construct fusion protein

<400> SEQUENCE: 53

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg
        195

<210> SEQ ID NO 54
<211> LENGTH: 1296
<212> TYPE: PRT
<213> ORGANISM: Artificial Sequence
<220> FEATURE:
<223> OTHER INFORMATION: used to construct fusion protein

<400> SEQUENCE: 54

Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45
```

```
Asp Thr Phe Thr Asn Pro Glu Glu Gly Asp Leu Asn Pro Pro Glu
 50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480
```

```
Ile Thr Ser Asp Thr Asn Ile Glu Ala Ala Glu Asn Ile Ser Leu
            485                 490                 495

Asp Leu Ile Gln Gln Tyr Tyr Leu Thr Phe Asn Phe Asp Asn Glu Pro
        500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
        770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
                820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
```

```
            900             905             910
Gln Ile Gln Leu Phe Asn Leu Glu Ser Ser Lys Ile Glu Val Ile Leu
    915             920             925

Lys Asn Ala Ile Val Tyr Asn Ser Met Tyr Glu Asn Phe Ser Thr Ser
    930             935             940

Phe Trp Ile Arg Ile Pro Lys Tyr Phe Asn Ser Ile Ser Leu Asn Asn
945             950             955             960

Glu Tyr Thr Ile Ile Asn Cys Met Glu Asn Asn Ser Gly Trp Lys Val
                965             970             975

Ser Leu Asn Tyr Gly Glu Ile Ile Trp Thr Leu Gln Asp Thr Gln Glu
            980             985             990

Ile Lys Gln Arg Val Val Phe Lys Tyr Ser Gln Met Ile Asn Ile Ser
        995             1000            1005

Asp Tyr Ile Asn Arg Trp Ile Phe Val Thr Ile Thr Asn Asn Arg
    1010            1015            1020

Leu Asn Asn Ser Lys Ile Tyr Ile Asn Gly Arg Leu Ile Asp Gln
    1025            1030            1035

Lys Pro Ile Ser Asn Leu Gly Asn Ile His Ala Ser Asn Asn Ile
    1040            1045            1050

Met Phe Lys Leu Asp Gly Cys Arg Asp Thr His Arg Tyr Ile Trp
    1055            1060            1065

Ile Lys Tyr Phe Asn Leu Phe Asp Lys Glu Leu Asn Glu Lys Glu
    1070            1075            1080

Ile Lys Asp Leu Tyr Asp Asn Gln Ser Asn Ser Gly Ile Leu Lys
    1085            1090            1095

Asp Phe Trp Gly Asp Tyr Leu Gln Tyr Asp Lys Pro Tyr Tyr Met
    1100            1105            1110

Leu Asn Leu Tyr Asp Pro Asn Lys Tyr Val Asp Val Asn Asn Val
    1115            1120            1125

Gly Ile Arg Gly Tyr Met Tyr Leu Lys Gly Pro Arg Gly Ser Val
    1130            1135            1140

Met Thr Thr Asn Ile Tyr Leu Asn Ser Ser Leu Tyr Arg Gly Thr
    1145            1150            1155

Lys Phe Ile Ile Lys Lys Tyr Ala Ser Gly Asn Lys Asp Asn Ile
    1160            1165            1170

Val Arg Asn Asn Asp Arg Val Tyr Ile Asn Val Val Val Lys Asn
    1175            1180            1185

Lys Glu Tyr Arg Leu Ala Thr Asn Ala Ser Gln Ala Gly Val Glu
    1190            1195            1200

Lys Ile Leu Ser Ala Leu Glu Ile Pro Asp Val Gly Asn Leu Ser
    1205            1210            1215

Gln Val Val Val Met Lys Ser Lys Asn Asp Gln Gly Ile Thr Asn
    1220            1225            1230

Lys Cys Lys Met Asn Leu Gln Asp Asn Asn Gly Asn Asp Ile Gly
    1235            1240            1245

Phe Ile Gly Phe His Gln Phe Asn Asn Ile Ala Lys Leu Val Ala
    1250            1255            1260

Ser Asn Trp Tyr Asn Arg Gln Ile Glu Arg Ser Ser Arg Thr Leu
    1265            1270            1275

Gly Cys Ser Trp Glu Phe Ile Pro Val Asp Asp Gly Trp Gly Glu
    1280            1285            1290

Arg Pro Leu
    1295
```

```
<210> SEQ ID NO 55
<211> LENGTH: 1291
<212> TYPE: PRT
<213> ORGANISM: Artificial Sequence
<220> FEATURE:
<223> OTHER INFORMATION: used to construct fusion protein

<400> SEQUENCE: 55

Met Ser Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asn Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Ser Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
```

```
                370            375            380
Asn Leu Leu Asp Asn Glu Ile Tyr Thr Ile Glu Glu Gly Phe Asn Ile
385                 390                 395                 400

Ser Asp Lys Asn Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
                420                 425                 430

Lys Ile Gln Met Cys Lys Ser Val Lys Ala Pro Gly Ile Cys Ile Asp
                435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Ala Tyr Asn Thr Gln Asn Asn
465                 470                 475                 480

Tyr Ile Asp Asn Asp Phe Ser Ile Asn Glu Leu Ile Leu Asp Thr Asp
                485                 490                 495

Leu Ile Ser Lys Ile Glu Leu Pro Ser Glu Asn Thr Glu Ser Leu Thr
                500                 505                 510

Asp Phe Asn Val Tyr Val Pro Glu Tyr Lys Lys Gln Pro Ala Ile Lys
                515                 520                 525

Lys Ile Phe Thr Asp Glu Asn Thr Ile Phe Gln Tyr Leu Tyr Ser Gln
                530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
                580                 585                 590

Trp Val Lys Gln Ile Val Asp Asp Phe Val Ile Glu Ala Asn Lys Ser
                595                 600                 605

Ser Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asn Ser Ala Leu Thr Lys
                675                 680                 685

Arg Asp Glu Lys Trp Ile Asp Met Tyr Gly Leu Ile Val Ala Gln Trp
690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Lys Tyr Asn Ile Tyr Ser Glu Lys Glu Arg Ser Asn Ile Asn Ile Asp
                740                 745                 750

Phe Asn Asp Val Asn Ser Lys Leu Asn Glu Gly Ile Asn Gln Ala Ile
                755                 760                 765

Asp Asn Ile Asn Asn Phe Ile Asn Glu Cys Ser Val Ser Tyr Leu Met
                770                 775                 780

Lys Lys Met Ile Pro Leu Ala Val Glu Lys Leu Leu Asp Phe Asp Asn
785                 790                 795                 800
```

```
Thr Leu Arg Lys Asn Leu Leu Asn Tyr Ile Asp Glu Asn Lys Leu Tyr
                805                 810                 815

Leu Ile Gly Ser Ala Glu Tyr Glu Lys Ser Lys Val Asp Lys Tyr Leu
                820                 825                 830

Lys Thr Ser Ile Pro Phe Asp Leu Ser Thr Tyr Thr Asn Asn Thr Ile
                835                 840                 845

Leu Ile Glu Ile Phe Asn Lys Tyr Asn Ser Asp Ile Leu Asn Asn Ile
            850                 855                 860

Ile Leu Asn Leu Arg Tyr Arg Asp Asn Lys Leu Ile Asp Leu Ser Gly
865                 870                 875                 880

Tyr Gly Ala Lys Val Glu Val Tyr Asp Gly Val Lys Leu Asn Asp Lys
                885                 890                 895

Asn Gln Phe Lys Leu Thr Ser Ser Ala Asn Ser Lys Ile Arg Val Ile
                900                 905                 910

Gln Asn Gln Asn Ile Ile Phe Asn Ser Met Phe Leu Asp Phe Ser Val
                915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Met Ile Ile Trp Thr Leu Ile
                965                 970                 975

Asp Ile Asn Gly Lys Ile Lys Ser Val Phe Phe Glu Tyr Ser Ile Lys
                980                 985                 990

Glu Asp Ile Ser Glu Tyr Ile Asn Arg Trp Phe Phe Val Thr Ile Thr
                995                 1000                1005

Asn Asn Ser Asp Asn Ala Lys Ile Tyr Ile Asn Gly Lys Leu Glu
            1010                1015                1020

Ser His Ile Asp Ile Arg Asp Ile Arg Glu Val Ile Ala Asn Asp
        1025                1030                1035

Glu Ile Ile Phe Lys Leu Asp Gly Asn Ile Asp Arg Thr Gln Phe
        1040                1045                1050

Ile Trp Met Lys Tyr Phe Ser Ile Phe Asn Thr Glu Leu Ser Gln
        1055                1060                1065

Ser Asn Ile Glu Glu Ile Tyr Lys Ile Gln Ser Tyr Ser Glu Tyr
        1070                1075                1080

Leu Lys Asp Phe Trp Gly Asn Pro Leu Met Tyr Asn Lys Glu Tyr
        1085                1090                1095

Tyr Met Phe Asn Ala Gly Asn Lys Asn Ser Tyr Ile Lys Leu Lys
        1100                1105                1110

Lys Asp Ser Pro Val Gly Glu Ile Leu Thr Arg Ser Lys Tyr Asn
        1115                1120                1125

Gln Asn Ser Lys Tyr Ile Asn Tyr Arg Asp Leu Tyr Ile Gly Glu
        1130                1135                1140

Lys Phe Ile Ile Arg Arg Lys Ser Asn Ser Gln Ser Ile Asn Asp
        1145                1150                1155

Asp Ile Val Arg Lys Glu Asp Tyr Ile Tyr Leu Asp Phe Phe Asn
        1160                1165                1170

Leu Asn Gln Glu Trp Arg Val Tyr Ile Tyr Lys Tyr Phe Lys Lys
        1175                1180                1185

Glu Glu Glu Lys Leu Phe Leu Ala Pro Ile Ser Asp Ser Asp Glu
        1190                1195                1200

Phe Tyr Asn Thr Ile Gln Ile Lys Glu Tyr Asp Glu Gln Pro Thr
        1205                1210                1215
```

Tyr Ser Cys Gln Leu Leu Phe Lys Lys Asp Glu Ser Thr Asp
1220                    1225                1230

Glu Ile Gly Leu Ile Gly Ile His Arg Phe Tyr Glu Ser Gly Ile
1235                1240                1245

Val Phe Lys Glu Tyr Lys Asp Tyr Phe Cys Ile Ser Lys Trp Tyr
1250                    1255                1260

Leu Lys Glu Val Lys Arg Lys Pro Tyr Asn Ser Lys Leu Gly Cys
1265                    1270                1275

Asn Trp Gln Phe Ile Pro Lys Asp Glu Gly Trp Thr Glu
1280                    1285                1290

<210> SEQ ID NO 56
<211> LENGTH: 1280
<212> TYPE: PRT
<213> ORGANISM: Artificial Sequence
<220> FEATURE:
<223> OTHER INFORMATION: used to construct fusion protein

<400> SEQUENCE: 56

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
    210                 215                 220

Leu Ile Leu Met His Glu Leu Asn His Thr Met His Asn Leu Tyr Gly
225                 230                 235                 240

Ile Ala Ile Pro Asn Asp Gln Arg Ile Ser Ser Val Thr Ser Asn Ile
                245                 250                 255

Phe Tyr Ser Gln Tyr Lys Val Lys Leu Glu Tyr Ala Glu Ile Tyr Ala
            260                 265                 270

Phe Gly Gly Pro Thr Ile Asp Leu Ile Pro Lys Ser Gly Arg Lys Tyr
        275                 280                 285

-continued

```
Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Ala Val Asp Arg Asn Lys Phe Ala Glu Leu Tyr Lys
                340                 345                 350

Glu Leu Thr Gln Ile Phe Thr Glu Phe Asn Tyr Ala Lys Ile Tyr Asn
                355                 360                 365

Val Gln Asn Arg Lys Ile Tyr Leu Ser Asn Val Tyr Thr Pro Val Thr
    370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
    435                 440                 445

Lys Thr Leu Asp Cys Arg Glu Leu Leu Val Lys Asn Thr Asp Leu Pro
    450                 455                 460

Phe Ile Gly Asp Ile Ser Asp Ile Lys Thr Asp Ile Phe Leu Ser Lys
465                 470                 475                 480

Asp Ile Asn Val Glu Thr Glu Val Ile Asp Tyr Pro Asp Asn Val Ser
                485                 490                 495

Val Asp Gln Val Ile Leu Ser Lys Asn Thr Ser Glu His Gly Gln Leu
                500                 505                 510

Asp Leu Leu Tyr Pro Ile Ile Glu Gly Glu Ser Gln Val Leu Pro Gly
                515                 520                 525

Glu Asn Gln Val Phe Tyr Asp Asn Arg Thr Gln Asn Val Asp Tyr Leu
                530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
                565                 570                 575

Lys Val Tyr Thr Tyr Phe Pro Lys Leu Ala Asp Lys Val Asn Thr Gly
                580                 585                 590

Val Gln Gly Gly Leu Phe Leu Met Trp Ala Asn Asp Val Val Glu Asp
                595                 600                 605

Phe Thr Thr Asn Ile Leu Arg Lys Asp Thr Leu Asp Lys Ile Ser Asp
    610                 615                 620

Val Ser Ala Ile Ile Pro Tyr Ile Gly Pro Ala Leu Asn Ile Ser Asn
625                 630                 635                 640

Ser Val Arg Arg Glu Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
                660                 665                 670

Ala Phe Val Ile Tyr Ser Lys Val Gln Glu Arg Asn Glu Ile Ile Lys
                675                 680                 685

Thr Ile Asp Asn Cys Leu Glu Gln Arg Ile Lys Arg Trp Lys Asp Ser
    690                 695                 700

Tyr Glu Trp Met Ile Gly Thr Trp Leu Ser Arg Ile Thr Thr Gln Phe
705                 710                 715                 720
```

```
Asn Asn Ile Ser Tyr Gln Met Tyr Asp Ser Leu Asn Tyr Gln Ala Asp
                725                 730                 735

Ala Ile Lys Asp Lys Ile Asp Leu Glu Tyr Lys Lys Tyr Ser Gly Ser
                740                 745                 750

Asp Lys Glu Asn Ile Lys Ser Gln Val Glu Asn Leu Lys Asn Ser Leu
                755                 760                 765

Asp Ile Lys Ile Ser Glu Ala Met Asn Asn Ile Asn Lys Phe Ile Arg
                770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
                820                 825                 830

Lys Ala Lys Val Asn Glu Ser Phe Glu Asn Thr Ile Pro Phe Asn Ile
                835                 840                 845

Phe Ser Tyr Thr Asn Asn Ser Leu Leu Lys Asp Ile Ile Asn Glu Tyr
                850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
                900                 905                 910

Ser Ser Gly Asp Lys Ile Ile Val Asn Leu Asn Asn Asn Ile Leu Tyr
                915                 920                 925

Ser Ala Ile Tyr Glu Asn Ser Ser Val Ser Phe Trp Ile Lys Ile Ser
                930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
                980                 985                 990

Tyr Ser Glu Ser Leu Ser His Thr Gly Tyr Thr Asn Lys Trp Phe Phe
                995                1000                1005

Val Thr Ile Thr Asn Asn Ile Met Gly Tyr Met Lys Leu Tyr Ile
   1010                1015                1020

Asn Gly Glu Leu Lys Gln Ser Glu Arg Ile Glu Asp Leu Asn Glu
   1025                1030                1035

Val Lys Leu Asp Lys Thr Ile Val Phe Gly Ile Asp Glu Asn Ile
   1040                1045                1050

Asp Glu Asn Gln Met Leu Trp Ile Arg Asp Phe Asn Ile Phe Ser
   1055                1060                1065

Lys Glu Leu Ser Asn Glu Asp Ile Asn Ile Val Tyr Glu Gly Gln
   1070                1075                1080

Ile Leu Arg Asn Val Ile Lys Asp Tyr Trp Gly Asn Pro Leu Lys
   1085                1090                1095

Phe Asp Thr Glu Tyr Tyr Ile Ile Asn Asp Asn Tyr Ile Asp Arg
   1100                1105                1110

Tyr Ile Ala Pro Lys Ser Asn Ile Leu Val Leu Val Gln Tyr Pro
   1115                1120                1125

Asp Arg Ser Lys Leu Tyr Thr Gly Asn Pro Ile Thr Ile Lys Ser
```

-continued

```
           1130                1135                1140

Val Ser Asp Lys Asn Pro Tyr Ser Arg Ile Leu Asn Gly Asp Asn
    1145                1150                1155

Ile Met Phe His Met Leu Tyr Asn Ser Gly Lys Tyr Met Ile Ile
    1160                1165                1170

Arg Asp Thr Asp Thr Ile Tyr Ala Ile Glu Gly Arg Glu Cys Ser
    1175                1180                1185

Lys Asn Cys Val Tyr Ala Leu Lys Leu Gln Ser Asn Leu Gly Asn
    1190                1195                1200

Tyr Gly Ile Gly Ile Phe Ser Ile Lys Asn Ile Val Ser Gln Asn
    1205                1210                1215

Lys Tyr Cys Ser Gln Ile Phe Ser Ser Phe Met Lys Asn Thr Met
    1220                1225                1230

Leu Leu Ala Asp Ile Tyr Lys Pro Trp Arg Phe Ser Phe Glu Asn
    1235                1240                1245

Ala Tyr Thr Pro Val Ala Val Thr Asn Tyr Glu Thr Lys Leu Leu
    1250                1255                1260

Ser Thr Ser Ser Phe Trp Lys Phe Ile Ser Arg Asp Pro Gly Trp
    1265                1270                1275

Val Glu
    1280

<210> SEQ ID NO 57
<211> LENGTH: 1276
<212> TYPE: PRT
<213> ORGANISM: Artificial Sequence
<220> FEATURE:
<223> OTHER INFORMATION: used to construct fusion protein

<400> SEQUENCE: 57

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205
```

-continued

```
Gln Ser Ser Ala Val Leu Gly Lys Ser Ile Phe Cys Met Asp Pro Val
    210                 215                 220
Ile Ala Leu Met His Glu Leu Thr His Ser Leu His Gln Leu Tyr Gly
225                 230                 235                 240
Ile Asn Ile Pro Ser Asp Lys Arg Ile Arg Pro Gln Val Ser Glu Gly
                245                 250                 255
Phe Phe Ser Gln Asp Gly Pro Asn Val Gln Phe Glu Glu Leu Tyr Thr
            260                 265                 270
Phe Gly Gly Leu Asp Val Glu Ile Ile Pro Gln Ile Glu Arg Ser Gln
        275                 280                 285
Leu Arg Glu Lys Ala Leu Gly His Tyr Lys Asp Ile Ala Lys Arg Leu
    290                 295                 300
Asn Asn Ile Asn Lys Thr Ile Pro Ser Ser Trp Ile Ser Asn Ile Asp
305                 310                 315                 320
Lys Tyr Lys Lys Ile Phe Ser Glu Lys Tyr Asn Phe Asp Lys Asp Asn
                325                 330                 335
Thr Gly Asn Phe Val Val Asn Ile Asp Lys Phe Asn Ser Leu Tyr Ser
            340                 345                 350
Asp Leu Thr Asn Val Met Ser Glu Val Val Tyr Ser Ser Gln Tyr Asn
        355                 360                 365
Val Lys Asn Arg Thr His Tyr Phe Ser Arg His Tyr Leu Pro Val Phe
    370                 375                 380
Ala Asn Ile Leu Asp Asp Asn Ile Tyr Thr Ile Arg Asp Gly Phe Asn
385                 390                 395                 400
Leu Thr Asn Lys Gly Phe Asn Ile Glu Asn Ser Gly Gln Asn Ile Glu
                405                 410                 415
Arg Asn Pro Ala Leu Gln Lys Leu Ser Ser Glu Ser Val Val Asp Leu
            420                 425                 430
Phe Thr Lys Val Cys Leu Arg Leu Thr Lys Asn Ser Arg Asp Asp Ser
        435                 440                 445
Thr Cys Ile Lys Val Lys Asn Asn Arg Leu Pro Tyr Val Ala Asp Lys
    450                 455                 460
Asp Ser Ile Ser Gln Glu Ile Phe Glu Asn Lys Ile Ile Thr Asp Glu
465                 470                 475                 480
Thr Asn Val Gln Asn Tyr Ser Asp Lys Phe Ser Leu Asp Glu Ser Ile
                485                 490                 495
Leu Asp Gly Gln Val Pro Ile Asn Pro Glu Ile Val Asp Pro Leu Leu
            500                 505                 510
Pro Asn Val Asn Met Glu Pro Leu Asn Leu Pro Gly Glu Glu Ile Val
        515                 520                 525
Phe Tyr Asp Asp Ile Thr Lys Tyr Val Asp Tyr Leu Asn Ser Tyr Tyr
    530                 535                 540
Tyr Leu Glu Ser Gln Lys Leu Ser Asn Asn Val Glu Asn Ile Thr Leu
545                 550                 555                 560
Thr Thr Ser Val Glu Glu Ala Leu Gly Tyr Ser Asn Lys Ile Tyr Thr
                565                 570                 575
Phe Leu Pro Ser Leu Ala Glu Lys Val Asn Lys Gly Val Gln Ala Gly
            580                 585                 590
Leu Phe Leu Asn Trp Ala Asn Glu Val Val Glu Asp Phe Thr Thr Asn
        595                 600                 605
Ile Met Lys Lys Asp Thr Leu Asp Lys Ile Ser Asp Val Ser Val Ile
    610                 615                 620
Ile Pro Tyr Ile Gly Pro Ala Leu Asn Ile Gly Asn Ser Ala Leu Arg
```

-continued

```
            625                 630                 635                 640
Gly Asn Phe Asn Gln Ala Phe Ala Thr Ala Gly Val Ala Phe Leu Leu
                    645                 650                 655
Glu Gly Phe Pro Glu Phe Thr Ile Pro Ala Leu Gly Val Phe Thr Phe
                660                 665                 670
Tyr Ser Ser Ile Gln Glu Arg Glu Lys Ile Ile Lys Thr Ile Glu Asn
            675                 680                 685
Cys Leu Glu Gln Arg Val Lys Arg Trp Lys Asp Ser Tyr Gln Trp Met
690                 695                 700
Val Ser Asn Trp Leu Ser Arg Ile Thr Thr Gln Phe Asn His Ile Asn
705                 710                 715                 720
Tyr Gln Met Tyr Asp Ser Leu Ser Tyr Gln Ala Asp Ala Ile Lys Ala
                    725                 730                 735
Lys Ile Asp Leu Glu Tyr Lys Lys Tyr Ser Gly Ser Asp Lys Glu Asn
                740                 745                 750
Ile Lys Ser Gln Val Glu Asn Leu Lys Asn Ser Leu Asp Val Lys Ile
            755                 760                 765
Ser Glu Ala Met Asn Asn Ile Asn Lys Phe Ile Arg Glu Cys Ser Val
770                 775                 780
Thr Tyr Leu Phe Lys Asn Met Leu Pro Lys Val Ile Asp Glu Leu Asn
785                 790                 795                 800
Lys Phe Asp Leu Arg Thr Lys Thr Glu Leu Ile Asn Leu Ile Asp Ser
                    805                 810                 815
His Asn Ile Ile Leu Val Gly Glu Val Asp Arg Leu Lys Ala Lys Val
                820                 825                 830
Asn Glu Ser Phe Glu Asn Thr Met Pro Phe Asn Ile Phe Ser Tyr Thr
            835                 840                 845
Asn Asn Ser Leu Leu Lys Asp Ile Ile Asn Glu Tyr Phe Asn Ser Ile
850                 855                 860
Asn Asp Ser Lys Ile Leu Ser Leu Gln Asn Lys Lys Asn Ala Leu Val
865                 870                 875                 880
Asp Thr Ser Gly Tyr Asn Ala Glu Val Arg Val Gly Asp Asn Val Gln
                    885                 890                 895
Leu Asn Thr Ile Tyr Thr Asn Asp Phe Lys Leu Ser Ser Ser Gly Asp
                900                 905                 910
Lys Ile Ile Val Asn Leu Asn Asn Ile Leu Tyr Ser Ala Ile Tyr
            915                 920                 925
Glu Asn Ser Ser Val Ser Phe Trp Ile Lys Ile Ser Lys Asp Leu Thr
            930                 935                 940
Asn Ser His Asn Glu Tyr Thr Ile Ile Asn Ser Ile Glu Gln Asn Ser
945                 950                 955                 960
Gly Trp Lys Leu Cys Ile Arg Asn Gly Asn Ile Glu Trp Ile Leu Gln
                    965                 970                 975
Asp Val Asn Arg Lys Tyr Lys Ser Leu Ile Phe Asp Tyr Ser Glu Ser
                980                 985                 990
Leu Ser His Thr Gly Tyr Thr Asn  Lys Trp Phe Phe Val  Thr Ile Thr
            995                 1000                1005
Asn Asn  Ile Met Gly Tyr Met  Lys Leu Tyr Ile Asn  Gly Glu Leu
       1010                1015                1020
Lys Gln  Ser Gln Lys Ile Glu  Asp Leu Asp Glu Val  Lys Leu Asp
       1025                1030                1035
Lys Thr  Ile Val Phe Gly Ile  Asp Glu Asn Ile Asp  Glu Asn Gln
       1040                1045                1050
```

```
Met Leu Trp Ile Arg Asp Phe Asn Ile Phe Ser Lys Glu Leu Ser
    1055                1060                1065

Asn Glu Asp Ile Asn Ile Val Tyr Glu Gly Gln Ile Leu Arg Asn
    1070                1075                1080

Val Ile Lys Asp Tyr Trp Gly Asn Pro Leu Lys Phe Asp Thr Glu
    1085                1090                1095

Tyr Tyr Ile Ile Asn Asp Asn Tyr Ile Asp Arg Tyr Ile Ala Pro
    1100                1105                1110

Glu Ser Asn Val Leu Val Leu Val Gln Tyr Pro Asp Arg Ser Lys
    1115                1120                1125

Leu Tyr Thr Gly Asn Pro Ile Thr Ile Lys Ser Val Ser Asp Lys
    1130                1135                1140

Asn Pro Tyr Ser Arg Ile Leu Asn Gly Asp Asn Ile Ile Leu His
    1145                1150                1155

Met Leu Tyr Asn Ser Arg Lys Tyr Met Ile Ile Arg Asp Thr Asp
    1160                1165                1170

Thr Ile Tyr Ala Thr Gln Gly Gly Glu Cys Ser Gln Asn Cys Val
    1175                1180                1185

Tyr Ala Leu Lys Leu Gln Ser Asn Leu Gly Asn Tyr Gly Ile Gly
    1190                1195                1200

Ile Phe Ser Ile Lys Asn Ile Val Ser Lys Asn Lys Tyr Cys Ser
    1205                1210                1215

Gln Ile Phe Ser Ser Phe Arg Glu Asn Thr Met Leu Leu Ala Asp
    1220                1225                1230

Ile Tyr Lys Pro Trp Arg Phe Ser Phe Lys Asn Ala Tyr Thr Pro
    1235                1240                1245

Val Ala Val Thr Asn Tyr Glu Thr Lys Leu Leu Ser Thr Ser Ser
    1250                1255                1260

Phe Trp Lys Phe Ile Ser Arg Asp Pro Gly Trp Val Glu
    1265                1270                1275

<210> SEQ ID NO 58
<211> LENGTH: 1252
<212> TYPE: PRT
<213> ORGANISM: Artificial Sequence
<220> FEATURE:
<223> OTHER INFORMATION: used to construct fusion protein

<400> SEQUENCE: 58

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
```

-continued

```
            130                 135                 140
Leu Pro Asn Val Ile Ile Met Gly Ala Glu Pro Asp Leu Phe Glu Thr
145                 150                 155                 160

Asn Ser Ser Asn Ile Ser Leu Arg Asn Tyr Met Pro Ser Asn His
                165                 170                 175

Gly Phe Gly Ser Ile Ala Ile Val Thr Phe Ser Pro Glu Tyr Ser Phe
                180                 185                 190

Arg Phe Asn Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
                370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
                435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
                515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560
```

```
Asn Asn Val Asn Lys Pro Val Gln Ala Ala Leu Phe Val Ser Trp Ile
            565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
            595                 600                 605
Ala Leu Asn Ile Gly Asn Glu Ala Gln Lys Gly Asn Phe Lys Asp Ala
            610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                    645                 650                 655
Ser Asp Asn Lys Asn Lys Val Ile Lys Ala Ile Asn Asn Ala Leu Lys
                    660                 665                 670
Glu Arg Asp Glu Lys Trp Lys Glu Val Tyr Ser Phe Ile Val Ser Asn
                    675                 680                 685
Trp Met Thr Lys Ile Asn Thr Gln Phe Asn Lys Arg Lys Glu Gln Met
690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                    725                 730                 735
Lys Tyr Asp Ile Lys Gln Ile Glu Asn Glu Leu Asn Gln Lys Val Ser
                    740                 745                 750
Ile Ala Met Asn Asn Ile Asp Arg Phe Leu Thr Glu Ser Ser Ile Ser
                    755                 760                 765
Tyr Leu Met Lys Leu Ile Asn Glu Val Lys Ile Asn Lys Leu Arg Glu
770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                    805                 810                 815
Asp Thr Leu Asn Asn Ser Ile Pro Phe Lys Leu Ser Ser Tyr Thr Asp
                    820                 825                 830
Asp Lys Ile Leu Ile Ser Tyr Phe Asn Lys Phe Phe Lys Arg Ile Lys
                    835                 840                 845
Ser Ser Ser Val Leu Asn Met Arg Tyr Lys Asn Asp Lys Tyr Val Asp
850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                    885                 890                 895
Glu Val Asn Ile Ser Gln Asn Asp Tyr Ile Ile Tyr Asp Asn Lys Tyr
                    900                 905                 910
Lys Asn Phe Ser Ile Ser Phe Trp Val Arg Ile Pro Asn Tyr Asp Asn
                    915                 920                 925
Lys Ile Val Asn Val Asn Asn Glu Tyr Thr Ile Ile Asn Cys Met Arg
930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Ala Phe Asn
                    965                 970                 975
Tyr Gly Asn Ala Asn Gly Ile Ser Asp Tyr Ile Asn Lys Trp Ile Phe
                    980                 985                 990
```

```
Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu
    1040                1045                1050

Leu Asp Glu Thr Glu Ile Gln Thr Leu Tyr Ser Asn Glu Pro Asn
    1055                1060                1065

Thr Asn Ile Leu Lys Asp Phe Trp Gly Asn Tyr Leu Leu Tyr Asp
    1070                1075                1080

Lys Glu Tyr Tyr Leu Leu Asn Val Leu Lys Pro Asn Asn Phe Ile
    1085                1090                1095

Asp Arg Arg Lys Asp Ser Thr Leu Ser Ile Asn Asn Ile Arg Ser
    1100                1105                1110

Thr Ile Leu Leu Ala Asn Arg Leu Tyr Ser Gly Ile Lys Val Lys
    1115                1120                1125

Ile Gln Arg Val Asn Asn Ser Ser Thr Asn Asp Asn Leu Val Arg
    1130                1135                1140

Lys Asn Asp Gln Val Tyr Ile Asn Phe Val Ala Ser Lys Thr His
    1145                1150                1155

Leu Phe Pro Leu Tyr Ala Asp Thr Ala Thr Thr Asn Lys Glu Lys
    1160                1165                1170

Thr Ile Lys Ile Ser Ser Ser Gly Asn Arg Phe Asn Gln Val Val
    1175                1180                1185

Val Met Asn Ser Val Gly Asn Asn Cys Thr Met Asn Phe Lys Asn
    1190                1195                1200

Asn Asn Gly Asn Asn Ile Gly Leu Leu Gly Phe Lys Ala Asp Thr
    1205                1210                1215

Val Val Ala Ser Thr Trp Tyr Tyr Thr His Met Arg Asp His Thr
    1220                1225                1230

Asn Ser Asn Gly Cys Phe Trp Asn Phe Ile Ser Glu Glu His Gly
    1235                1240                1245

Trp Gln Glu Lys
    1250

<210> SEQ ID NO 59
<211> LENGTH: 1274
<212> TYPE: PRT
<213> ORGANISM: Artificial Sequence
<220> FEATURE:
<223> OTHER INFORMATION: used to construct fusion protein

<400> SEQUENCE: 59

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80
```

-continued

```
Asp Ala Glu Lys Asp Arg Tyr Leu Lys Thr Thr Ile Lys Leu Phe Lys
             85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445

Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
            500                 505                 510
```

-continued

```
Asp Asn Ser Tyr Val Pro Arg Tyr Asp Ser Asn Gly Thr Ser Glu Ile
        515                 520                 525
Glu Glu Tyr Asp Val Val Asp Phe Asn Val Phe Phe Tyr Leu His Ala
        530                 535                 540
Gln Lys Val Pro Glu Gly Glu Thr Asn Ile Ser Leu Thr Ser Ser Ile
545                 550                 555                 560
Asp Thr Ala Leu Leu Glu Glu Ser Lys Asp Ile Phe Phe Ser Ser Glu
                565                 570                 575
Phe Ile Asp Thr Ile Asn Lys Pro Val Asn Ala Ala Leu Phe Ile Asp
            580                 585                 590
Trp Ile Ser Lys Val Ile Arg Asp Phe Thr Thr Glu Ala Thr Gln Lys
            595                 600                 605
Ser Thr Val Asp Lys Ile Ala Asp Ile Ser Leu Ile Val Pro Tyr Val
        610                 615                 620
Gly Leu Ala Leu Asn Ile Ile Ile Glu Ala Glu Lys Gly Asn Phe Glu
625                 630                 635                 640
Glu Ala Phe Glu Leu Leu Gly Val Gly Ile Leu Leu Glu Phe Val Pro
                645                 650                 655
Glu Leu Thr Ile Pro Val Ile Leu Val Phe Thr Ile Lys Ser Tyr Ile
            660                 665                 670
Asp Ser Tyr Glu Asn Lys Asn Lys Ala Ile Lys Ala Ile Asn Asn Ser
        675                 680                 685
Leu Ile Glu Arg Glu Ala Lys Trp Lys Glu Ile Tyr Ser Trp Ile Val
        690                 695                 700
Ser Asn Trp Leu Thr Arg Ile Asn Thr Gln Phe Asn Lys Arg Lys Glu
705                 710                 715                 720
Gln Met Tyr Gln Ala Leu Gln Asn Gln Val Asp Ala Ile Lys Thr Ala
                725                 730                 735
Ile Glu Tyr Lys Tyr Asn Asn Tyr Thr Ser Asp Glu Lys Asn Arg Leu
            740                 745                 750
Glu Ser Glu Tyr Asn Ile Asn Asn Ile Glu Glu Leu Asn Lys Lys
        755                 760                 765
Val Ser Leu Ala Met Lys Asn Ile Glu Arg Phe Met Thr Glu Ser Ser
770                 775                 780
Ile Ser Tyr Leu Met Lys Leu Ile Asn Glu Ala Lys Val Gly Lys Leu
785                 790                 795                 800
Lys Lys Tyr Asp Asn His Val Lys Ser Asp Leu Leu Asn Tyr Ile Leu
                805                 810                 815
Asp His Arg Ser Ile Leu Gly Glu Gln Thr Asn Glu Leu Ser Asp Leu
            820                 825                 830
Val Thr Ser Thr Leu Asn Ser Ser Ile Pro Phe Glu Leu Ser Ser Tyr
            835                 840                 845
Thr Asn Asp Lys Ile Leu Ile Ile Tyr Phe Asn Arg Leu Tyr Lys Lys
        850                 855                 860
Ile Lys Asp Ser Ser Ile Leu Asp Met Arg Tyr Glu Asn Asn Lys Phe
865                 870                 875                 880
Ile Asp Ile Ser Gly Tyr Gly Ser Asn Ile Ser Ile Asn Gly Asn Val
                885                 890                 895
Tyr Ile Tyr Ser Thr Asn Arg Asn Gln Phe Gly Ile Tyr Asn Ser Arg
            900                 905                 910
Leu Ser Glu Val Asn Ile Ala Gln Asn Asn Asp Ile Ile Tyr Asn Ser
        915                 920                 925
Arg Tyr Gln Asn Phe Ser Ile Ser Phe Trp Val Arg Ile Pro Lys His
```

```
                    930             935             940
Tyr Lys Pro Met Asn His Asn Arg Glu Tyr Thr Ile Ile Asn Cys Met
945                 950             955                 960

Gly Asn Asn Asn Ser Gly Trp Lys Ile Ser Leu Arg Thr Val Arg Asp
            965             970                 975

Cys Glu Ile Ile Trp Thr Leu Gln Asp Thr Ser Gly Asn Lys Glu Asn
            980             985                 990

Leu Ile Phe Arg Tyr Glu Glu Leu  Asn Arg Ile Ser Asn  Tyr Ile Asn
            995             1000                 1005

Lys Trp  Ile Phe Val Thr Ile  Thr Asn Asn Arg Leu  Gly Asn Ser
    1010              1015                 1020

Arg Ile  Tyr Ile Asn Gly Asn  Leu Ile Val Glu Lys  Ser Ile Ser
    1025              1030                 1035

Asn Leu  Gly Asp Ile His Val  Ser Asp Asn Ile Leu  Phe Lys Ile
    1040              1045                 1050

Val Gly  Cys Asp Asp Glu Thr  Tyr Val Gly Ile Arg  Tyr Phe Lys
    1055              1060                 1065

Val Phe  Asn Thr Glu Leu Asp  Lys Thr Glu Ile Glu  Thr Leu Tyr
    1070              1075                 1080

Ser Asn  Glu Pro Asp Pro Ser  Ile Leu Lys Asn Tyr  Trp Gly Asn
    1085              1090                 1095

Tyr Leu  Leu Tyr Asn Lys Lys  Tyr Tyr Leu Phe Asn  Leu Leu Arg
    1100              1105                 1110

Lys Asp  Lys Tyr Ile Thr Leu  Asn Ser Gly Ile Leu  Asn Ile Asn
    1115              1120                 1125

Gln Gln  Arg Gly Val Thr Glu  Gly Ser Val Phe Leu  Asn Tyr Lys
    1130              1135                 1140

Leu Tyr  Glu Gly Val Glu Val  Ile Ile Arg Lys Asn  Gly Pro Ile
    1145              1150                 1155

Asp Ile  Ser Asn Thr Asp Asn  Phe Val Arg Lys Asn  Asp Leu Ala
    1160              1165                 1170

Tyr Ile  Asn Val Val Asp Arg  Gly Val Glu Tyr Arg  Leu Tyr Ala
    1175              1180                 1185

Asp Thr  Lys Ser Glu Lys Glu  Lys Ile Ile Arg Thr  Ser Asn Leu
    1190              1195                 1200

Asn Asp  Ser Leu Gly Gln Ile  Ile Val Met Asp Ser  Ile Gly Asn
    1205              1210                 1215

Asn Cys  Thr Met Asn Phe Gln  Asn Asn Asn Gly Ser  Asn Ile Gly
    1220              1225                 1230

Leu Leu  Gly Phe His Ser Asn  Leu Val Ala Ser  Ser Trp Tyr
    1235              1240                 1245

Tyr Asn  Asn Ile Arg Arg Asn  Thr Ser Ser Asn Gly  Cys Phe Trp
    1250              1255                 1260

Ser Ser  Ile Ser Lys Glu Asn  Gly Trp Lys Glu
    1265              1270

<210> SEQ ID NO 60
<211> LENGTH: 1297
<212> TYPE: PRT
<213> ORGANISM: Artificial Sequence
<220> FEATURE:
<223> OTHER INFORMATION: used to construct fusion protei

<400> SEQUENCE: 60

Met Pro Val Asn Ile Lys Asn Phe Asn Tyr Asn Asp Pro Ile Asn Asn
1               5                   10                  15
```

```
Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
            115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
            195                 200                 205

Asn Lys Asp Thr Ser Ile Phe Ser Arg Arg Ala Tyr Phe Ala Asp Pro
            210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
            275                 280                 285

Tyr Asn Lys Ala Leu Gln Asn Phe Gln Asp Ile Ala Asn Arg Leu Asn
            290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
            355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
```

```
            435                 440                 445
Gln Cys Ile Ile Val Asn Asn Glu Asp Leu Phe Phe Ile Ala Asn Lys
450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
                500                 505                 510
Glu Pro Phe Thr Asn Phe Asp Asp Ile Asp Ile Pro Val Tyr Ile Lys
                515                 520                 525
Gln Ser Ala Leu Lys Lys Ile Phe Val Asp Gly Asp Ser Leu Phe Glu
530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
                580                 585                 590
Ser Leu Phe Val Asn Trp Val Lys Gly Val Ile Asp Asp Phe Thr Ser
                595                 600                 605
Glu Ser Thr Gln Lys Ser Thr Ile Asp Lys Val Ser Asp Val Ser Ile
                610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
                660                 665                 670
Leu Glu Ser Tyr Val Gly Asn Lys Gly His Ile Ile Met Thr Ile Ser
                675                 680                 685
Asn Ala Leu Lys Lys Arg Asp Gln Lys Trp Thr Asp Met Tyr Gly Leu
690                 695                 700
Ile Val Ser Gln Trp Leu Ser Thr Val Asn Thr Gln Phe Tyr Thr Ile
705                 710                 715                 720
Lys Glu Arg Met Tyr Asn Ala Leu Asn Asn Gln Ser Gln Ala Ile Glu
                725                 730                 735
Lys Ile Ile Glu Asp Gln Tyr Asn Arg Tyr Ser Glu Glu Asp Lys Met
                740                 745                 750
Asn Ile Asn Ile Asp Phe Asn Asp Ile Asp Phe Lys Leu Asn Gln Ser
                755                 760                 765
Ile Asn Leu Ala Ile Asn Asn Ile Asp Asp Phe Ile Asn Gln Cys Ser
                770                 775                 780
Ile Ser Tyr Leu Met Asn Arg Met Ile Pro Leu Ala Val Lys Lys Leu
785                 790                 795                 800
Lys Asp Phe Asp Asp Asn Leu Lys Arg Asp Leu Leu Glu Tyr Ile Asp
                805                 810                 815
Thr Asn Glu Leu Tyr Leu Leu Asp Glu Val Asn Ile Leu Lys Ser Lys
                820                 825                 830
Val Asn Arg His Leu Lys Asp Ser Ile Pro Phe Asp Leu Ser Leu Tyr
                835                 840                 845
Thr Lys Asp Thr Ile Leu Ile Gln Val Phe Asn Asn Tyr Ile Ser Asn
850                 855                 860
```

```
Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
                900                 905                 910

Asn Ser Asn Ile Thr Ala His Gln Ser Lys Phe Val Val Tyr Asp Ser
                915                 920                 925

Met Phe Asp Asn Phe Ser Ile Asn Phe Trp Val Arg Thr Pro Lys Tyr
                930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
                980                 985                 990

Phe Phe Glu Tyr Ser Ile Lys Asp Asn Ile Ser Asp Tyr Ile Asn Lys
                995                 1000                1005

Trp Phe Ser Ile Thr Ile Thr Asn Asp Arg Leu Gly Asn Ala Asn
                1010                1015                1020

Ile Tyr Ile Asn Gly Ser Leu Lys Lys Ser Glu Lys Ile Leu Asn
                1025                1030                1035

Leu Asp Arg Ile Asn Ser Ser Asn Asp Ile Asp Phe Lys Leu Ile
                1040                1045                1050

Asn Cys Thr Asp Thr Thr Lys Phe Val Trp Ile Lys Asp Phe Asn
                1055                1060                1065

Ile Phe Gly Arg Glu Leu Asn Ala Thr Glu Val Ser Ser Leu Tyr
                1070                1075                1080

Trp Ile Gln Ser Ser Thr Asn Thr Leu Lys Asp Phe Trp Gly Asn
                1085                1090                1095

Pro Leu Arg Tyr Asp Thr Gln Tyr Tyr Leu Phe Asn Gln Gly Met
                1100                1105                1110

Gln Asn Ile Tyr Ile Lys Tyr Phe Ser Lys Ala Ser Met Gly Glu
                1115                1120                1125

Thr Ala Pro Arg Thr Asn Phe Asn Asn Ala Ala Ile Asn Tyr Gln
                1130                1135                1140

Asn Leu Tyr Leu Gly Leu Arg Phe Ile Ile Lys Lys Ala Ser Asn
                1145                1150                1155

Ser Arg Asn Ile Asn Asn Asp Asn Ile Val Arg Glu Gly Asp Tyr
                1160                1165                1170

Ile Tyr Leu Asn Ile Asp Asn Ile Ser Asp Glu Ser Tyr Arg Val
                1175                1180                1185

Tyr Val Leu Val Asn Ser Lys Glu Ile Gln Thr Gln Leu Phe Leu
                1190                1195                1200

Ala Pro Ile Asn Asp Asp Pro Thr Phe Tyr Asp Val Leu Gln Ile
                1205                1210                1215

Lys Lys Tyr Tyr Glu Lys Thr Thr Tyr Asn Cys Gln Ile Leu Cys
                1220                1225                1230

Glu Lys Asp Thr Lys Thr Phe Gly Leu Phe Gly Ile Gly Lys Phe
                1235                1240                1245

Val Lys Asp Tyr Gly Tyr Val Trp Asp Thr Tyr Asp Asn Tyr Phe
                1250                1255                1260

Cys Ile Ser Gln Trp Tyr Leu Arg Arg Ile Ser Glu Asn Ile Asn
                1265                1270                1275
```

-continued

```
Lys Leu  Arg Leu Gly Cys Asn  Trp Gln Phe Ile Pro  Val Asp Glu
    1280                1285                1290

Gly Trp  Thr Glu
    1295
```